United States Patent
Ahearn et al.

(10) Patent No.: US 8,993,756 B2
(45) Date of Patent: Mar. 31, 2015

(54) PYRROLOPYRIMIDINES AS JANUS KINASE INHIBITORS

(71) Applicant: Merck Sharp & Dohme Corp., Rahway, NJ (US)

(72) Inventors: Sean P. Ahearn, Somerville, MA (US); Matthew Christopher, Brookline, MA (US); Christopher Dinsmore, Newton, MA (US); Joon Jung, Natick, MA (US); Qinglin Pu, Melrose, MA (US); Alexey Rivkin, San Francisco, CA (US); Mark E. Scott, Andover, MA (US); David J. Witter, Norfolk, MA (US); Hyun Chong Woo, Natick, MA (US); Brandon Cash, Framingham, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/363,097

(22) PCT Filed: Nov. 30, 2012

(86) PCT No.: PCT/US2012/067152
§ 371 (c)(1),
(2) Date: Jun. 5, 2014

(87) PCT Pub. No.: WO2013/085802
PCT Pub. Date: Jun. 13, 2013

(65) Prior Publication Data
US 2014/0349998 A1  Nov. 27, 2014

Related U.S. Application Data

(60) Provisional application No. 61/567,384, filed on Dec. 6, 2011.

(51) Int. Cl.
| | | |
|---|---|---|
| C07D 487/04 | (2006.01) |
| C07D 417/04 | (2006.01) |
| C07D 413/04 | (2006.01) |
| A61K 31/519 | (2006.01) |
| A61P 19/02 | (2006.01) |
| C07D 519/00 | (2006.01) |
| C07D 471/04 | (2006.01) |

(52) U.S. Cl.
CPC ............ *C07D 487/04* (2013.01); *C07D 519/00* (2013.01); *C07D 471/04* (2013.01)
USPC ........................................ 544/280; 514/265.1

(58) Field of Classification Search
USPC ........................................ 544/280; 514/265.1
See application file for complete search history.

(56) References Cited

U.S. PATENT DOCUMENTS

| 6,627,754 | B2 * | 9/2003 | Blumenkopf et al. | ........ 544/280 |
| 6,635,762 | B1 * | 10/2003 | Blumenkopf et al. | ........ 544/280 |
| 7,569,569 | B2 * | 8/2009 | Blumenkopf et al. | ..... 514/258.1 |
| 2004/0058922 | A1 | 3/2004 | Blumenkopf et al. | |
| 2006/0241131 | A1 | 10/2006 | Blumenkopf et al. | |
| 2011/0288297 | A1 | 11/2011 | Gut Ruggeri et al. | |
| 2011/0294826 | A1 | 12/2011 | Xie et al. | |

FOREIGN PATENT DOCUMENTS

WO     9965909     12/1999

OTHER PUBLICATIONS

Verstovsek S., American Society of Hematology, 636-642, 2009.*
Cornejo et al., Int J Biochem Cell Biol. 41 (12): 2376-2379, 2009.*
Mass, R. D., Int. J. Radiation Oncology Bio. Phys.vol. 58(3): 932-940, 2004.*
Fabbro et al. Pharmacology & therapeutics 93, 79-98, 2002.*
Cohen et al., Current Opinion in Chemical Biology, 3,459-465, 1999.*
Freshney et al.,Culture of Animal Cells, A Manual of Basic Technique, Alan R. Liss, Inc., 1983, New York, pz.*
Dermer et al., Bio/Technology, 1994, 12:320.*
Golub et al., Science, 286, 531-537, 1999.*
Cecil Textbook of Medicine, edited by Bennet, J.C., and Plum F., 20th edition,vol. 1, 1004-101 O, 1996.*
PCT/US2012/067152 Search Report.

* cited by examiner

*Primary Examiner* — Venkataraman Balasubramanian
(74) *Attorney, Agent, or Firm* — Patricia A. Shatynski; Laura M. Ginkel

(57) ABSTRACT

The instant invention provides compounds of formula I which are JAK3 inhibitors. Specifically, the compounds of formula I are pyrrolo[2,3-d]pyrimidine derivative compounds. The instant invention also provides methods of treating JAK-mediated diseases such as rheumatoid arthritis, asthma, COPD and cancer, by administering the pyrrolo[2,3-d]pyrimidine-derivative compounds of formula I.

3 Claims, No Drawings

PYRROLOPYRIMIDINES AS JANUS KINASE INHIBITORS

CROSS REFERENCE TO RELATED APPLICATIONS

This application is a U.S. National Phase application under 35 U.S.C. §371 of PCT Application No. PCT/US2012/067152, filed Nov. 30, 2012, which claims priority under 35 U.S.C. §119(e) from U.S. Provisional Application Ser. No. 61/567,384, filed Dec. 6, 2011.

BACKGROUND OF THE INVENTION

Studies of interferon (IFN)-induced receptor mediated gene expression led to the initial discovery of a Janus kinase (JAK) signaling pathway, which has been shown to be a common signaling pathway used by many cytokines and growth factors. The mammalian JAK family of intracellular tyrosine kinases, has four members; JAK1, JAK2, JAK3 and Tyk2. JAKs range in size from 120 to 140 kDa and contain seven conserved JAK homology (JH) domains which define this kinase super family.

Prototypically, the binding of a cytokine to its cell surface receptor results in receptor dimerization and subsequent activationphosphorylation of JAK tyrosine kinases which are constitutively associated with the receptor. Specific tyrosine residues on the receptor are then phosphorylated by activated JAKs and serve as docking sites for a family of latent cytoplasmic transcription factors known as Signal Transducers and Activators of Transcription (STATS). STATS are phosphorylated by JAKs, dimerize, then translocate to the nucleus where they bind specific DNA elements and activate gene transcription.

Many pro-inflammatory cytokines (IL-6, IL-12, IL-15, IL-23, GM-CSF and IFN-γ) which are implicated in autoimmune diseases mediate their activity through the JAK kinases. As a consequence, these enzymes have long been considered attractive drug targets. The essential role of JAKs in mediating the biological effects of cytokines has been confirmed by natural mutations in humans and targeted disruption in mice. Humans with a genetic loss of JAK3 have a severe combined immunodefiency (SCID) phenotype due to a developmental block in T and NK cell development and nonfunctional B-cells. Humans lacking Tyk2 are susceptible to microbial infection, have a Th2 bias with Hyper-IgE syndrome and defective cytokine signaling (IL-6, 10, 12 and 23). Signaling can be restored by transfection of the wild type kinase.

Animal KO models of the JAK family of kinases have demonstrated significant phenotypes. JAK1 KO animals exhibit defective responses to class 2 cytokines (IL-10 family), those utilizing the common gamma chain $\gamma_c$ (IL-2, IL-4 etc) and gp130 receptor subunits (IL-6, LIF, OSM), resulting in perinatal lethality due to developmental, neurological and lymphoid defects. JAK2 KO mice exhibit defective erythropoiesis caused by a block in EPO signaling, resulting in embryonic lethality. JAK3 KO mice are viable but exhibit a SCID phenotype with nonfunctional T-cells and a lack of B and NK-cells (similar to human mutation). Tyk2 KO animals manifest modest viral susceptibility, reduced IL-12 responses, resistance to arthritis and enhanced Th2 cell-mediated allergic inflammation.

A considerable body of literature has accumulated that link the JAK/STAT pathway to various diseases and disorders including hyperproliferative disorders and cancer such as leukemia and lymphomas, immunological and inflammatory disorders such as transplant rejection, asthma, chronic obstructive pulmonary disease, allergies, rheumatoid arthritis, type I diabetes, amyotropic lateral sclerosis and multiple sclerosis.

SUMMARY OF THE INVENTION

The present invention provides novel compounds which are inhibitors of JAKs, in particular JAK3. The invention also provides a method for the treatment and prevention of JAK-mediated diseases and disorders using the novel compounds, as well as pharmaceutical compositions containing the compounds.

DETAILED DESCRIPTION OF THE INVENTION

The present invention provides compounds of formula I and pharmaceutically acceptable salts thereof:

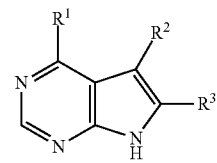

I wherein X is N and $CR^5$; wherein the ring can have up to a total of 4 nitrogen atoms in the ring;

$R^1$ is $(C_{1-10})$ alkyl; $(C_{1-10})$ heteroalkyl containing 1, 2, or 3 atoms independently selected from N, O or S; a 3-15-membered saturated, unsaturated or partially saturated monocyclic or bicyclic ring system containing 0, 1, 2, 3, or 4 atoms independently selected from N, O or S;

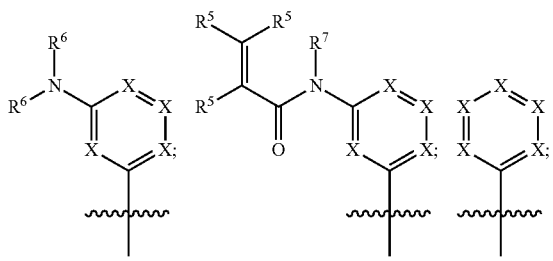

additionally, $R^1$ may be substituted with 0, 1, 2, or 3 independently chosen $R^5$;

$R^2$ is $-C=O(OR^4)$; $-C=ON(R^7)_2$; $(C_{1-10})$ alkyl; $(C_{1-10})$ heteroalkyl containing 1, 2, or 3 atoms independently selected from N, O or S; a 3-15-membered saturated, unsaturated or partially saturated monocyclic or bicyclic ring system containing 0, 1, 2, 3, or 4 atoms independently selected from N, O, or S;

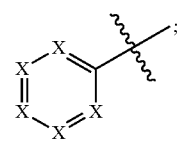

additionally, $R^2$ may be substituted with 0, 1, 2, or 3 independently chosen $R^5$;

$R^3$ is hydrogen halogen, and $-C_{1-3}$alkyl;
$R^4$ is hydrogen; $-C_{1-10}$ alkyl, $-C_{2-10}$ alkenyl, $-(C_{1-6}$ alkyl) $C_{3-8}$ cycloalkyl; $-(C_{1-6}$ alkyl) aryl;
each optionally substituted with halogen, cyano, oxo, C1-6 alkoxy, amino, alkylamino, dialkylamino;
$R^5$ is:
hydrogen,
halogen,
amino,
cyano,
—COOH,
$C_{1-10}$alkyl,
$C_{1-10}$alkoxy,
$C_{0-10}$alkylcarbamoyl,
$C_{0-10}$alkoxycarbamoyl,
hydroxy,
hydroxy $C_{0-10}$alkyl,
$C_{1-6}$haloalkyl,
$C_{1-10}$ alkylsulfonyl,
$(C_{0-10}$ alkyl)sulfonylamino,
aryl $C_{1-10}$ alkylsulfonylamino,
$C_{3-8}$ heterocyclyl $C_{1-10}$ alkylsulfonylamino,
$C_{3-8}$ heterocycloalkyl $C_{1-10}$ alkylsulfonylamino,
$C_{3-8}$ cycloalkyl $C_{1-10}$ alkylsulfonylamino,
$(C_{0-10}$ alkyl$)_{1-2}$aminosulfonyl,
$C_{1-10}$ alkyl(oxy$)_{0-1}$ $C_{0-10}$ alkyl,
$C_{2-10}$ alkenyl(oxy$)_{0-1}$ $C_{0-10}$ alkyl,
$C_{2-10}$ alkynyl(oxy$)_{0-1}$$C_{0-10}$ alkyl,
aryl$C_{0-10}$ alkyl(oxy$)_{0-1}$$C_{0-10}$ alkyl,
$(C_{3-8})$heteroaryl$C_{0-10}$ alkyl(oxy$)_{0-1}$$C_{0-10}$ alkyl,
$C_{3-8}$ cycloalkyl$C_{0-10}$ alkyl(oxy$)_{0-1}$$C_{0-10}$ alkyl,
$(C_{3-8})$heterocycloalkyl$C_{0-10}$ alkyl(oxy$)_{0-1}$$C_{0-10}$ alkyl,
$(C_{1-10})$heteroalkyl$C_{0-10}$ alkyl(oxy$)_{0-1}$ $C_{0-10}$ alkyl,
(carbonyl$)_{0-1}$$C_{1-10}$ alkyl,
(carbonyl$)_{0-1}$$C_{2-10}$ alkenyl,
(carbonyl$)_{0-1}$$C_{2-10}$ alkynyl,
$C_{0-10}$ alkylcarbonyl(oxy$)_{0-1}$$C_{0-10}$ alkyl,
$C_{1-10}$ alkyl(oxy$)_{0-1}$carbonyl$C_{0-10}$ alkyl,
$C_{2-10}$ alkenylcarbonyl,
$C_{2-10}$ alkynylcarbonyl,
$C_{0-10}$ alkyl(oxy$)_{0-1}$$C_{1-10}$ alkyloxy$C_{0-10}$ alkyl,
$C_{0-10}$ alkyl(oxy$)_{0-1}$$C_{0-10}$ alkylaminocarbonyl$C_{0-10}$ alkyl,
$C_{0-10}$ alkylaminocarbonylaryl$C_{0-10}$ alkyl,
$C_{0-10}$ alkylaminocarbonyl$C_{1-10}$ heteroalkyl,
$C_{0-10}$ alkylaminocarbonyl$(C_{3-8})$heterocycloalkyl$C_{0-10}$ alkyl,
$C_{0-10}$ alkylaminocarbonyl$(C_{3-8})$heteroaryl$C_{0-10}$ alkyl,
$C_{0-10}$ alkylaminocarbonyl$(C_{3-8})$cycloalkyl$C_{0-10}$ alkyl,
$(C_{0-10}$ alkyl$)_{1-2}$amino$C_{1-10}$ alkyloxy$C_{0-10}$ alkyl,
$(C_{0-10}$ alkyl$)_{1-2}$aminocarbonyl$C_{0-10}$ alkyl,
$C_{1-10}$ heteroalkyl$C_{0-10}$ alkylaminocarbonyl$C_{0-10}$ alkyl,
$(C_{3-8})$heterocycloalkyl$C_{0-10}$ alkylaminocarbonyl$C_{0-10}$ alkyl,
$(C_{3-8})$heteroaryl $C_{0-10}$ alkylaminocarbonyl$C_{0-10}$ alkyl,
$C_{3-8}$ cycloalkyl $C_{0-10}$ alkylaminocarbonyl$C_{0-10}$ alkyl,
aryl $C_{0-10}$ alkylaminocarbonyl$C_{0-10}$ alkyl,
$(C_{3-8})$heterocycloalkyl$C_{0-10}$ alkylcarbonyl$C_{0-10}$ alkyl,
$C_{1-10}$ alkyl(oxy$)_{0-1}$$C_{0-10}$ alkyl carbonylamino$C_{0-10}$ alkyl,
$C_{1-10}$ alkenyl(oxy$)_{0-1}$$C_{0-10}$ alkyl carbonylamino$C_{0-10}$ alkyl,
$C_{1-10}$ heteroalkyl(oxy$)_{0-1}$carbonylamino$C_{0-10}$ alkyl,
$C_{3-8}$ cycloalkyl$C_{0-10}$ alkyl(oxy$)_{0-1}$carbonylamino$C_{0-10}$ alkyl,
aryl $C_{0-10}$ alkyl(oxy$)_{0-1}$carbonylamino$C_{0-10}$ alkyl,
$(C_{3-8})$heteroaryl $C_{0-10}$ alkyl(oxy$)_{0-1}$carbonylamino$C_{0-10}$ alkyl,
$(C_{3-8})$heterocycloalkyl $C_{0-10}$ alkyl(oxy$)_{0-1}$carbonylamino $C_{0-10}$ alkyl,
$C_{0-10}$ alkylureylenyl,
$C_{1-4}$acylamino $C_{0-10}$ alkyl,
$C_{0-10}$ alkylamino $C_{0-10}$ alkyl,
aryl$C_{0-10}$ alkylamino $C_{0-10}$ alkyl,
$C_{3-8}$ cycloalkyl $C_{0-10}$ alkylamino $C_{0-10}$ alkyl,
$C_{3-8}$ heterocyclyl $C_{0-10}$ alkylamino $C_{0-10}$ alkyl,
$C_{3-8}$ heterocycloalkyl $C_{0-10}$ alkylamino $C_{0-10}$ alkyl,
$(C_{1-10}$ alkyl$)_2$aminocarbonyloxy,
nitro,
aryl,
acrylamido,
acryloylamino,
halo-aryl,
halo-heterocyclyl,
cyano-aryl,
cyano-heteroaryl,
cyano-heterocyclyl,
oxo, and
perfluoro$C_{1-6}$alkoxy;
$R^6$ and $R^7$ are each independently:
hydrogen,
$C_{1-10}$ alkyl,
(carbonyl$)_{0-1}$$C_{1-10}$ alkyl,
(carbonyl$)_{0-1}$$C_{2-10}$ alkenyl,
(carbonyl$)_{0-1}$$C_{2-10}$ alkynyl,
$C_{0-10}$ alkylcarbonyl(oxy$)_{0-1}$$C_{0-10}$ alkyl,
$C_{1-10}$ alkyl(oxy$)_{0-1}$carbonyl$C_{0-10}$ alkyl,
aryl$C_{0-10}$ alkyl(oxy$)_{0-1}$carbonyl$C_{0-10}$ alkyl,
$(C_{3-8})$heteroaryl$C_{0-10}$ alkyl(oxy$)_{0-1}$carbonyl$C_{0-10}$ alkyl,
$C_{3-8}$ cycloalkyl$C_{0-10}$ alkyl(oxy$)_{0-1}$carbonyl$C_{0-10}$ alkyl,
$(C_{3-8})$heterocycloalkyl$C_{0-10}$ alkyl(oxy$)_{0-1}$carbonyl$C_{0-10}$ alkyl,
$(C_{1-10})$heteroalkyl$C_{0-10}$ alkyl(oxy$)_{0-1}$carbonyl$C_{0-10}$ alkyl,
$C_{2-10}$ alkenylcarbonyl,
$C_{2-10}$ alkynylcarbonyl,
$(C_{1-10})$alkyl(oxy$)_{0-1}$$C_{0-10}$ alkyl,
aryl(oxy$)_{0-1}$$C_{0-10}$ alkyl,
$(C_{3-8})$heteroaryl(oxy$)_{0-1}$$C_{0-10}$ alkyl,
$C_{3-8}$ cycloalkyl(oxy$)_{0-1}$$C_{0-10}$ alkyl,
$(C_{3-8})$heterocycloalkyl(oxy$)_{0-1}$$C_{0-10}$ alkyl,
$(C_{1-10})$heteroalkyl(oxy$)_{0-1}$$C_{0-10}$ alkyl,
$C_{0-10}$ alkyl(oxy$)_{0-1}$$C_{0-10}$ alkylaminocarbonyl$C_{0-10}$ alkyl,
$C_{0-10}$ alkylaminocarbonyl$C_{1-10}$ heteroalkyl,
$C_{0-10}$ alkylaminocarbonyl$(C_{3-8})$heterocycloalkyl$C_{0-10}$ alkyl,
$C_{0-10}$ alkylaminocarbonyl$(C_{3-8})$heteroaryl$C_{0-10}$ alkyl,
$C_{0-10}$ alkylaminocarbonyl$(C_{3-8})$cycloalkyl$C_{0-10}$ alkyl,
$C_{0-10}$ alkylaminocarbonylaryl$C_{0-10}$ alkyl,
hydroxy $C_{0-10}$ alkyl,
$C_{0-10}$ alkylsulfonyl,
aryl $C_{1-10}$ alkylsulfonyl,
$C_{3-8}$ heterocyclyl $C_{1-10}$ alkylsulfonyl,
$C_{3-8}$ heterocycloalkyl $C_{1-10}$ alkylsulfonyl,
$C_{3-8}$ cycloalkyl $C_{1-10}$ alkylsulfonyl, and
$C_{1-6}$haloalkyl;
wherein $R^5$, $R^6$ and $R^7$ are each additionally independently substituted with 0, 1, 2, or 3 substituents chosen from:
halogen, $C_1$-$C_{10}$ alkyl, $CF_3$, $NH_2$, $N(C_1$-$C_6$ alkyl$)_2$, $NO_2$, $-(C_{0-6})$alkylCN, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl)$S(O)_{0-2}$—, ($C_0$-$C_6$ alkyl)$S(O)_{0-2}$($C_0$-$C_6$ alkyl)-, ($C_0$-$C_6$ alkyl)C(O)NH—, $H_2$N—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$ alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, —NH($C_1$-$C_6$ alkyl)NHC(O)NH($C_1$-$C_6$ alkyl), NHC(O)O$C_1$-$C_6$ alkyl, —NH($C_1$-$C_6$ alkyl)NHSO$_2$($C_1$-$C_6$ alkyl), —($C_0$-$C_6$ alkyl)NHSO$_2$($C_1$-$C_6$ alkyl), $C_{1-10}$alkoxy, —$CO_2$($C_{0-10}$ alkyl), Oxo (=O), trifluoromethyl, trifluoroethyl, $C_{1-10}$ alkylsulfonyl, —$SO_2N(C_{1-6}$alkyl$)_{1-2}$, —$SO_2CF_3$, —$SO_2CF_2H$, —C$_{1-10}$ alkylsulfinyl, —O$_{(0-1)}$(C$_{1-10}$)haloalkyl, aryl, heteroaryl, heterocyclyl, halo-aryl, halo-heterocyclyl, cyano-aryl, cyano-heteroaryl, and cyano-heterocyclyl.

The present invention provides compounds of formula II and pharmaceutically acceptable salts thereof:

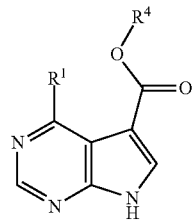

II wherein R$^1$, R$^4$, R$^5$, R$^6$ and R$^7$ are the substituents described hereinabove for the compound of formula I.

The present invention provides compounds of formula III and pharmaceutically acceptable salts thereof:

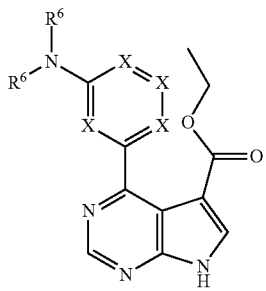

III wherein X, and R$^6$ are the substituents described hereinabove for the compound of formula I.

The present invention provides compounds of formula IV and pharmaceutically acceptable salts thereof:

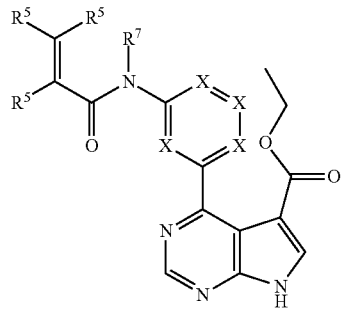

IV wherein X, R$^5$ and R$^7$ are the substituents described hereinabove for the compound of formula I.

The present invention provides compounds of formula V and pharmaceutically acceptable salts thereof:

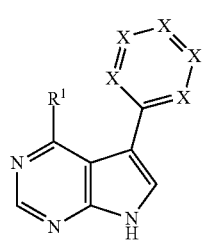

V wherein X and R$^1$, R$^5$, R$^6$ and R$^7$ are the substituents described hereinabove for the compound of formula I.

The present invention provides compounds of formula VI and pharmaceutically acceptable salts thereof:

VI wherein X, R$^5$, R$^6$ and R$^7$ are the substituents described hereinabove for the compound of formula I.

Representative compounds of the instant invention include, but are not limited to, the compounds set forth in the Examples and Tables 1-14 and their pharmaceutically acceptable salts. The preferred embodiments include, but are not limited to, the following compounds and their pharmaceutically acceptable salts and stereoisomers thereof:

ethyl 4-phenyl-7H-pyrrolo[2,3-d]pyrimidine-5-carboxylate;

ethyl 4-(4-chlorophenyl)-7H-pyrrolo[2,3-d]pyrimidine-5-carboxylate;

ethyl 4-(3-aminophenyl)-7H-pyrrolo[2,3-d]pyrimidine-5-carboxylate;

prop-2-en-1-yl-4-(2-methyl-2H-indazol-6-yl)-7H-pyrrolo[2,3-d]pyrimidine-5-carboxylate;

ethyl 4-(2-methyl-2H-indazol-6-yl)-7H-pyrrolo[2,3-d]pyrimidine-5-carboxylate;

ethyl 4-(3-cyanophenyl)-7H-pyrrolo[2,3-d]pyrimidine-5-carboxylate;

ethyl 4-(4-carbamoylphenyl)-7H-pyrrolo[2,3-d]pyrimidine-5-carboxylate;

ethyl 4-[3-(methoxycarbonyl)phenyl]-7H-pyrrolo[2,3-d]pyrimidine-5-carboxylate;

ethyl 4-[4-(methoxycarbonyl)phenyl]-7H-pyrrolo[2,3-d]pyrimidine-5-carboxylate;

ethyl 4-(4-cyanophenyl)-7H-pyrrolo[2,3-d]pyrimidine-5-carboxylate;

ethyl 4-[4-(methylsulfonyl)phenyl]-7H-pyrrolo[2,3-d]pyrimidine-5-carboxylate;

ethyl 4-(3-carbamoylphenyl)-7H-pyrrolo[2,3-d]pyrimidine-5-carboxylate;

ethyl 4-[4-(dimethylcarbamoyl)phenyl]-7H-pyrrolo[2,3-d]pyrimidine-5-carboxylate;

ethyl 4-pyridin-4-yl-7H-pyrrolo[2,3-d]pyrimidine-5-carboxylate;

ethyl 4-(4-methoxyphenyl)-7H-pyrrolo[2,3-d]pyrimidine-5-carboxylate;

3-[5-(ethoxycarbonyl)-7H-pyrrolo[2,3-d]pyrimidin-4-yl]benzoic acid;

ethyl 4-(3-methoxyphenyl)-7H-pyrrolo[2,3-d]pyrimidine-5-carboxylate;

ethyl 4-[1-(tert-butoxycarbonyl)-1,2,3,6-tetrahydropyridin-4-yl]-7H-pyrrolo[2,3-d]pyrimidine-5-carboxylate;

ethyl 4-[1-(tert-butoxycarbonyl)-1,2,5,6-tetrahydropyridin-3-yl]-7H-pyrrolo[2,3-d]pyrimidine-5-carboxylate;

ethyl 4-[1-(tert-butoxycarbonyl)-2,5-dihydro-1H-pyrrol-3-yl]-7H-pyrrolo[2,3-d]pyrimidine-5-carboxylate;

ethyl 4-[3-(2,2,2-trifluoroethoxy)phenyl]-7H-pyrrolo[2,3-d]pyrimidine-5-carboxylate;

ethyl 4-(3-amino-4-methylphenyl)-7H-pyrrolo[2,3-d]pyrimidine-5-carboxylate;

ethyl 4-cyclohex-1-en-1-yl-7H-pyrrolo[2,3-d]pyrimidine-5-carboxylate;

ethyl 4-(3-amino-4-chlorophenyl)-7H-pyrrolo[2,3-d]pyrimidine-5-carboxylate;

ethyl 4-(2-methyl-1,3-benzothiazol-5-yl)-7H-pyrrolo[2,3-d]pyrimidine-5-carboxylate;

ethyl 4-[3-(trifluoromethoxy)phenyl]-7H-pyrrolo[2,3-d]pyrimidine-5-carboxylate;

ethyl 4-(1-methyl-1H-pyrazol-4-yl)-7H-pyrrolo[2,3-d]pyrimidine-5-carboxylate;

ethyl 4-pyridin-3-yl-7H-pyrrolo[2,3-d]pyrimidine-5-carboxylate;

ethyl 4-(3-fluoro-2-methyl-2H-indazol-6-yl)-7H-pyrrolo[2,3-d]pyrimidine-5-carboxylate;

ethyl 4-[3-(dimethylcarbamoyl)-2-methyl-2H-indazol-6-yl]-7H-pyrrolo[2,3-d]pyrimidine-5-carboxylate;

ethyl 4-(2,3-dihydro-1H-indol-6-yl)-7H-pyrrolo[2,3-d]pyrimidine-5-carboxylate;

ethyl 4-[3-amino-4-(hydroxymethyl)phenyl]-7H-pyrrolo[2,3-d]pyrimidine-5-carboxylate;

ethyl 4-[3-amino-4-(methoxymethyl)phenyl]-7H-pyrrolo[2,3-d]pyrimidine-5-carboxylate;

ethyl 4-(4-fluorophenyl)-7H-pyrrolo[2,3-d]pyrimidine-5-carboxylate;

ethyl 4-(4-hydroxyphenyl)-7H-pyrrolo[2,3-d]pyrimidine-5-carboxylate;

ethyl 4-[4-(trifluoromethyl)phenyl]-7H-pyrrolo[2,3-d]pyrimidine-5-carboxylate;

ethyl 4-(4-methylphenyl)-7H-pyrrolo[2,3-d]pyrimidine-5-carboxylate;

ethyl 4-(2-methylphenyl)-7H-pyrrolo[2,3-d]pyrimidine-5-carboxylate;

ethyl 4-(3-chlorophenyl)-7H-pyrrolo[2,3-d]pyrimidine-5-carboxylate;

ethyl 4-naphthalen-2-yl-7H-pyrrolo[2,3-d]pyrimidine-5-carboxylate;

ethyl 4-(2-fluorophenyl)-7H-pyrrolo[2,3-d]pyrimidine-5-carboxylate;

ethyl 4-(3-fluorophenyl)-7H-pyrrolo[2,3-d]pyrimidine-5-carboxylate;

ethyl 4-(2-chlorophenyl)-7H-pyrrolo[2,3-d]pyrimidine-5-carboxylate;

ethyl 4-biphenyl-4-yl-7H-pyrrolo[2,3-d]pyrimidine-5-carboxylate;

ethyl 4-(3-hydroxyphenyl)-7H-pyrrolo[2,3-d]pyrimidine-5-carboxylate;

ethyl 4-(3-methylphenyl)-7H-pyrrolo[2,3-d]pyrimidine-5-carboxylate;

ethyl 4-[4-(dimethylamino)phenyl]-7H-pyrrolo[2,3-d]pyrimidine-5-carboxylate;

ethyl 4-(1,3-benzodioxol-5-yl)-7H-pyrrolo[2,3-d]pyrimidine-5-carboxylate;

ethyl 4-quinolin-6-yl-7H-pyrrolo[2,3-d]pyrimidine-5-carboxylate;

ethyl 4-(1-benzothiophen-2-yl)-7H-pyrrolo[2,3-d]pyrimidine-5-carboxylate;

ethyl 4-(1H-pyrazol-4-yl)-7H-pyrrolo[2,3-d]pyrimidine-5-carboxylate;

ethyl 4-[3-(benzyloxy)phenyl]-7H-pyrrolo[2,3-d]pyrimidine-5-carboxylate;

ethyl 4-(1H-indol-5-yl)-7H-pyrrolo[2,3-d]pyrimidine-5-carboxylate;

ethyl 4-(1-benzofuran-2-yl)-7H-pyrrolo[2,3-d]pyrimidine-5-carboxylate;

ethyl 4-(2-aminophenyl)-7H-pyrrolo[2,3-d]pyrimidine-5-carboxylate;

ethyl 4-thiophen-2-yl-7H-pyrrolo[2,3-d]pyrimidine-5-carboxylate;

ethyl 4-thiophen-3-yl-7H-pyrrolo[2,3-d]pyrimidine-5-carboxylate;

ethyl 4-[6-(hydroxymethyl)pyridin-3-yl]-7H-pyrrolo[2,3-d]pyrimidine-5-carboxylate;

ethyl 4-[3-(difluoromethoxy)phenyl]-7H-pyrrolo[2,3-d]pyrimidine-5-carboxylate;

ethyl 4-[2-(hydroxymethyl)pyridin-4-yl]-7H-pyrrolo[2,3-d]pyrimidine-5-carboxylate;

ethyl 4-(1-benzothiophen-7-yl)-7H-pyrrolo[2,3-d]pyrimidine-5-carboxylate;

ethyl 4-(4,5,6,7-tetrahydropyrazolo[1,5-a]pyridin-3-yl)-7H-pyrrolo[2,3-d]pyrimidine-5-carboxylate;

ethyl 4-(1-benzofuran-3-yl)-7H-pyrrolo[2,3-d]pyrimidine-5-carboxylate;

ethyl 4-(1H-indazol-4-yl)-7H-pyrrolo[2,3-d]pyrimidine-5-carboxylate;

ethyl 4-(1-oxo-2,3-dihydro-1H-isoindol-5-yl)-7H-pyrrolo[2,3-d]pyrimidine-5-carboxylate;

ethyl 4-(1,3-dimethyl-2-oxo-2,3-dihydro-1H-benzimidazol-5-yl)-7H-pyrrolo[2,3-d]pyrimidine-5-carboxylate;

ethyl 4-(1-methyl-1H-benzotriazol-6-yl)-7H-pyrrolo[2,3-d]pyrimidine-5-carboxylate;

ethyl 4-(1-oxo-2,3,4,5-tetrahydro-1H-2-benzazepin-6-yl)-7H-pyrrolo[2,3-d]pyrimidine-5-carboxylate;

ethyl 4-(1H-indazol-5-yl)-7H-pyrrolo[2,3-d]pyrimidine-5-carboxylate;

ethyl 4-(1,3-benzodioxol-5-yl)-7H-pyrrolo[2,3-d]pyrimidine-5-carboxylate;

ethyl 4-(1-benzothiophen-3-yl)-7H-pyrrolo[2,3-d]pyrimidine-5-carboxylate;

ethyl 4-[3-(trifluoromethyl)-1H-indazol-5-yl]-7H-pyrrolo[2,3-d]pyrimidine-5-carboxylate;

ethyl 4-(1-oxo-2,3-dihydro-1H-isoindol-4-yl)-7H-pyrrolo[2,3-d]pyrimidine-5-carboxylate;

tert-butyl 6-[5-(ethoxycarbonyl)-7H-pyrrolo[2,3-d]pyrimidin-4-yl]-3,4-dihydroisoquinoline-2(1H)-carboxylate;

ethyl 4-(3-oxo-2,3-dihydro-1H-isoindol-5-yl)-7H-pyrrolo[2,3-d]pyrimidine-5-carboxylate;

ethyl 4-(1H-indazol-6-yl)-7H-pyrrolo[2,3-d]pyrimidine-5-carboxylate;

ethyl 4-[2-(tert-butoxycarbonyl)-1-oxo-2,3-dihydro-1H-isoindol-5-yl]-7H-pyrrolo[2,3-d]pyrimidine-5-carboxylate;

tert-butyl 7-[5-(ethoxycarbonyl)-7H-pyrrolo[2,3-d]pyrimidin-4-yl]-3,4-dihydroisoquinoline-2(1H)-carboxylate;

tert-butyl 7-[5-(ethoxycarbonyl)-7H-pyrrolo[2,3-d]pyrimidin-4-yl]-2,3-dihydro-1,4-benzoxazepine-4(5H)-carboxylate;

ethyl 4-(4-aminophenyl)-7H-pyrrolo[2,3-d]pyrimidine-5-carboxylate;

ethyl 4-(1H-pyrazol-5-yl)-7H-pyrrolo[2,3-d]pyrimidine-5-carboxylate;
ethyl 4-(1,3-benzothiazol-5-yl)-7H-pyrrolo[2,3-d]pyrimidine-5-carboxylate;
ethyl 4-(1H-indol-6-yl)-7H-pyrrolo[2,3-d]pyrimidine-5-carboxylate;
ethyl 4-(1H-pyrrolo[2,3-b]pyridin-5-yl)-7H-pyrrolo[2,3-d]pyrimidine-5-carboxylate;
ethyl 4-[4-(4-methylpiperazin-1-yl)phenyl]-7H-pyrrolo[2,3-d]pyrimidine-5-carboxylate;
ethyl 4-(4-hydroxycyclohex-1-en-1-yl)-7H-pyrrolo[2,3-d]pyrimidine-5-carboxylate;
ethyl 4-[6-(4-methylpiperazin-1-yl)pyridin-3-yl]-7H-pyrrolo[2,3-d]pyrimidine-5-carboxylate;
ethyl 4-(5,6-dihydro-2H-pyran-3-yl)-7H-pyrrolo[2,3-d]pyrimidine-5-carboxylate;
ethyl 4-(2-methoxypyridin-4-yl)-7H-pyrrolo[2,3-d]pyrimidine-5-carboxylate;
ethyl 4-(4-cyanocyclohex-1-en-1-yl)-7H-pyrrolo[2,3-d]pyrimidine-5-carboxylate;
ethyl 4-(2-methoxypyrimidin-5-yl)-7H-pyrrolo[2,3-d]pyrimidine-5-carboxylate;
ethyl 4-{1-[2-(methylsulfonyl)ethyl]-1H-pyrazol-4-yl}-7H-pyrrolo[2,3-d]pyrimidine-5-carboxylate;
ethyl 4-(6-methoxypyridin-3-yl)-7H-pyrrolo[2,3-d]pyrimidine-5-carboxylate;
ethyl 4-[4-(1H-pyrazol-1-yl)phenyl]-7H-pyrrolo[2,3-d]pyrimidine-5-carboxylate;
ethyl 4-[3-(1,1-dioxidothiomorpholin-4-yl)phenyl]-7H-pyrrolo[2,3-d]pyrimidine-5-carboxylate;
ethyl 4-[3-(morpholin-4-ylmethyl)phenyl]-7H-pyrrolo[2,3-d]pyrimidine-5-carboxylate;
ethyl 4-[4-(1,1-dioxidothiomorpholin-4-yl)phenyl]-7H-pyrrolo[2,3-d]pyrimidine-5-carboxylate;
ethyl 4-(3,6-dihydro-2H-pyran-4-yl)-7H-pyrrolo[2,3-d]pyrimidine-5-carboxylate;
ethyl 4-[1-(2-methoxyethyl)-1H-pyrazol-4-yl]-7H-pyrrolo[2,3-d]pyrimidine-5-carboxylate;
ethyl 4-[4-(tetrahydrofuran-3-ylcarbamoyl)phenyl]-7H-pyrrolo[2,3-d]pyrimidine-5-carboxylate;
ethyl 4-(3-oxo-2,3-dihydro-1H-isoindol-5-yl)-7H-pyrrolo[2,3-d]pyrimidine-5-carboxylate;
ethyl 4-{3-[methyl(methylsulfonyl)amino]phenyl}-7H-pyrrolo[2,3-d]pyrimidine-5-carboxylate;
ethyl 4-[3-(1H-pyrazol-1-yl)phenyl]-7H-pyrrolo[2,3-d]pyrimidine-5-carboxylate;
ethyl 4-[6-(cyanomethyl)pyridin-3-yl]-7H-pyrrolo[2,3-d]pyrimidine-5-carboxylate;
ethyl 4-[3-(1-hydroxy-1-methylethyl)phenyl]-7H-pyrrolo[2,3-d]pyrimidine-5-carboxylate;
ethyl 4-[5-(hydroxymethyl)pyridin-3-yl]-7H-pyrrolo[2,3-d]pyrimidine-5-carboxylate;
ethyl 4-[4-(1-hydroxy-1-methylethyl)phenyl]-7H-pyrrolo[2,3-d]pyrimidine-5-carboxylate;
ethyl 4-(3-amino-5-fluorophenyl)-7H-pyrrolo[2,3-d]pyrimidine-5-carboxylate;
ethyl 4-(5-amino-2-fluorophenyl)-7H-pyrrolo[2,3-d]pyrimidine-5-carboxylate;
ethyl 4-(3-amino-4-fluorophenyl)-7H-pyrrolo[2,3-d]pyrimidine-5-carboxylate;
propyl 4-(2-methyl-2H-indazol-6-yl)-7H-pyrrolo[2,3-d]pyrimidine-5-carboxylate;
prop-2-en-1-yl 4-(2-methyl-2H-indazol-6-yl)-7H-pyrrolo[2,3-d]pyrimidine-5-carboxylate;
ethyl 4-{3-[(2,2,2-trifluoroethyl)amino]phenyl}-7H-pyrrolo[2,3-d]pyrimidine-5-carboxylate;
ethyl 4-{4-methyl-3-[(2,2,2-trifluoroethyl)amino]phenyl}-7H-pyrrolo[2,3-d]pyrimidine-5-carboxylate;
ethyl 4-{3-[(2-methylacryloyl)amino]phenyl}-7H-pyrrolo[2,3-d]pyrimidine-5-carboxylate;
ethyl 4-{2-fluoro-3-[(2-methylacryloyl)amino]phenyl}-7H-pyrrolo[2,3-d]pyrimidine-5-carboxylate;
ethyl 4-{5-[(2-methylacryloyl)amino]pyridin-3-yl}-7H-pyrrolo[2,3-d]pyrimidine-5-carboxylate;
ethyl 4-{2-methoxy-6-[(2-methylacryloyl)amino]pyridin-4-yl}-7H-pyrrolo[2,3-d]pyrimidine-5-carboxylate;
ethyl 4-[3-(acryloylamino)phenyl]-7H-pyrrolo[2,3-d]pyrimidine-5-carboxylate;
ethyl 4-{3-[(2E)-but-2-enoylamino]phenyl}-7H-pyrrolo[2,3-d]pyrimidine-5-carboxylate;
ethyl 4-[3-(propanoylamino)phenyl]-7H-pyrrolo[2,3-d]pyrimidine-5-carboxylate;
ethyl 4-{3-[(2-methylidenebutanoyl)amino]phenyl}-7H-pyrrolo[2,3-d]pyrimidine-5-carboxylate;
ethyl 4-{4-chloro-3-[(2-methylacryloyl)amino]phenyl}-7H-pyrrolo[2,3-d]pyrimidine-5-carboxylate;
ethyl 4-{4-methyl-3-[(2-methylacryloyl)amino]phenyl}-7H-pyrrolo[2,3-d]pyrimidine-5-carboxylate;
ethyl 4-[3-(acryloylamino)-4-methylphenyl]-7H-pyrrolo[2,3-d]pyrimidine-5-carboxylate;
ethyl 4-[3-(acryloylamino)-2-methylphenyl]-7H-pyrrolo[2,3-d]pyrimidine-5-carboxylate;
ethyl 4-{2-methyl-3-[(2-methylacryloyl)amino]phenyl}-7H-pyrrolo[2,3-d]pyrimidine-5-carboxylate;
ethyl 4-[3-(acryloylamino)-4-chlorophenyl]-7H-pyrrolo[2,3-d]pyrimidine-5-carboxylate;
ethyl 4-[3-(acryloylamino)-4-methoxyphenyl]-7H-pyrrolo[2,3-d]pyrimidine-5-carboxylate;
ethyl 4-{4-fluoro-3-[(2-methylacryloyl)amino]phenyl}-7H-pyrrolo[2,3-d]pyrimidine-5-carboxylate;
ethyl 4-{4-methoxy-3-[(2-methylacryloyl)amino]phenyl}-7H-pyrrolo[2,3-d]pyrimidine-5-carboxylate;
ethyl 4-{2-fluoro-5-[(2-methylacryloyl)amino]phenyl}-7H-pyrrolo[2,3-d]pyrimidine-5-carboxylate;
ethyl 4-{3-fluoro-5-[(2-methylacryloyl)amino]phenyl}-7H-pyrrolo[2,3-d]pyrimidine-5-carboxylate;
ethyl 4-(1-acryloyl-2,3-dihydro-1H-indol-6-yl)-7H-pyrrolo[2,3-d]pyrimidine-5-carboxylate;
ethyl 4-[1-(2-methylacryloyl)-2,3-dihydro-1H-indol-6-yl]-7H-pyrrolo[2,3-d]pyrimidine-5-carboxylate;
ethyl 4-{2-cyano-5-[(2-methylacryloyl)amino]phenyl}-7H-pyrrolo[2,3-d]pyrimidine-5-carboxylate;
ethyl 4-[1-(2-methylacryloyl)-1H-indol-6-yl]-7H-pyrrolo[2,3-d]pyrimidine-5-carboxylate;
ethyl 4-{3-cyano-5-[(2-methylacryloyl)amino]phenyl}-7H-pyrrolo[2,3-d]pyrimidine-5-carboxylate;
ethyl 4-{4-(hydroxymethyl)-3-[(2-methylacryloyl)amino]phenyl}-7H-pyrrolo[2,3-d]pyrimidine-5-carboxylate;
ethyl 4-{3-methyl-5-[(2-methylacryloyl)amino]phenyl}-7H-pyrrolo[2,3-d]pyrimidine-5-carboxylate;
ethyl 4-{4-cyano-3-[(2-methylacryloyl)amino]phenyl}-7H-pyrrolo[2,3-d]pyrimidine-5-carboxylate;
ethyl 4-{4-(dimethylcarbamoyl)-3-[(2-methylacryloyl)amino]phenyl}-7H-pyrrolo[2,3-d]pyrimidine-5-carboxylate;
ethyl 4-{3-[(2-methylacryloyl)amino]-4-(methylsulfonyl)phenyl}-7H-pyrrolo[2,3-d]pyrimidine-5-carboxylate;
ethyl 4-{4-[(dimethylamino)methyl]-3-[(2-methylacryloyl)amino]phenyl}-7H-pyrrolo[2,3-d]pyrimidine-5-carboxylate;
ethyl 4-{4-hydroxy-3-[(2-methylacryloyl)amino]phenyl}-7H-pyrrolo[2,3-d]pyrimidine-5-carboxylate;

ethyl 4-{6-methoxy-5-[(2-methylacryloyl)amino]pyridin-3-yl}-7H-pyrrolo[2,3-d]pyrimidine-5-carboxylate;

ethyl 4-{5-[(2-methylacryloyl)amino]-6-oxo-1,6-dihydropyridin-3-yl}-7H-pyrrolo[2,3-d]pyrimidine-5-carboxylate;

ethyl 4-{1-methyl-5-[(2-methylacryloyl)amino]-6-oxo-1,6-dihydropyridin-3-yl}-7H-pyrrolo[2,3-d]pyrimidine-5-carboxylate;

ethyl 4-{2-[(2-methylacryloyl)amino]pyridin-4-yl}-7H-pyrrolo[2,3-d]pyrimidine-5-carboxylate;

ethyl 4-{3-[(2-fluoroacryloyl)amino]phenyl}-7H-pyrrolo[2,3-d]pyrimidine-5-carboxylate;

ethyl 4-{2-fluoro-5-[(2-methylacryloyl)amino]phenyl}-7H-pyrrolo[2,3-d]pyrimidine-5-carboxylate;

ethyl 4-[3-(but-2-ynoylamino)phenyl]-7H-pyrrolo[2,3-d]pyrimidine-5-carboxylate;

ethyl 4-{3-[(cyano acetyl)amino]phenyl}-7H-pyrrolo[2,3-d]pyrimidine-5-carboxylate;

ethyl 4-{3-[(2-bromoacryloyl)amino]phenyl}-7H-pyrrolo[2,3-d]pyrimidine-5-carboxylate;

ethyl 4-{3-[(2-chloroacryloyl)amino]phenyl}-7H-pyrrolo[2,3-d]pyrimidine-5-carboxylate;

ethyl 4-{3-[(4-oxopentanoyl)amino]phenyl}-7H-pyrrolo[2,3-d]pyrimidine-5-carboxylate;

ethyl 4-(3-{[(2E)-4-methoxybut-2-enoyl]amino}phenyl)-7H-pyrrolo[2,3-d]pyrimidine-5-carboxylate;

ethyl 4-{3-[(2Z)-but-2-enoylamino]phenyl}-7H-pyrrolo[2,3-d]pyrimidine-5-carboxylate;

ethyl 4-{4-fluoro-3-[(2-fluoroacryloyl)amino]phenyl}-7H-pyrrolo[2,3-d]pyrimidine-5-carboxylate;

ethyl 4-{3-[(2-fluoroacryloyl)amino]-4-methylphenyl}-7H-pyrrolo[2,3-d]pyrimidine-5-carboxylate;

ethyl 4-{3-fluoro-5-[(2-methylacryloyl)amino]phenyl}-7H-pyrrolo[2,3-d]pyrimidine-5-carboxylate;

ethyl 4-{3-[(5,6-dihydro-1,4-di oxin-2-ylcarbonyl)amino]phenyl}-7H-pyrrolo[2,3-d]pyrimidine-5-carboxylate;

ethyl 4-(3-{[(2E)-4-oxopent-2-enoyl]amino}phenyl)-7H-pyrrolo[2,3-d]pyrimidine-5-carboxylate;

ethyl 4-(3-{[(2E)-3-(1,3,5-trimethyl-1H-pyrazol-4-yl)prop-2-enoyl]amino}phenyl)-7H-pyrrolo[2,3-d]pyrimidine-5-carboxylate;

ethyl 4-(3-{[(2E)-3-pyridin-2-ylprop-2-enoyl]amino}phenyl)-7H-pyrrolo[2,3-d]pyrimidine-5-carboxylate;

ethyl 4-(3-{[(2E)-3-pyridin-4-ylprop-2-enoyl]amino}phenyl)-7H-pyrrolo[2,3-d]pyrimidine-5-carboxylate;

ethyl 4-(3-{[(2,4-dioxo-1,2,3,4-tetrahydropyrimidin-5-yl)carbonyl]amino}phenyl)-7H-pyrrolo[2,3-d]pyrimidine-5-carboxylate;

ethyl 4-(3-{[(2E)-3-(1H-indol-3-yl)prop-2-enoyl]amino}phenyl)-7H-pyrrolo[2,3-d]pyrimidine-5-carboxylate;

ethyl 4-(3-{[(2-oxo-2,3-dihydro-1H-imidazol-4-yl)carbonyl]amino}phenyl)-7H-pyrrolo[2,3-d]pyrimidine-5-carboxylate;

ethyl 4-(3-{[(2E)-3-thiophen-2-ylprop-2-enoyl]amino}phenyl)-7H-pyrrolo[2,3-d]pyrimidine-5-carboxylate;

ethyl 4-(3-{[(2E)-3-furan-3-ylprop-2-enoyl]amino}phenyl)-7H-pyrrolo[2,3-d]pyrimidine-5-carboxylate;

ethyl 4-(3-{[(2Z)-3-(2-methoxyphenyl)prop-2-enoyl]amino}phenyl)-7H-pyrrolo[2,3-d]pyrimidine-5-carboxylate;

ethyl 4-(3-{[(2E)-3-(3-methoxyphenyl)prop-2-enoyl]amino}phenyl)-7H-pyrrolo[2,3-d]pyrimidine-5-carboxylate;

ethyl 4-(3-{[(2E)-2-methylpent-2-enoyl]amino}phenyl)-7H-pyrrolo[2,3-d]pyrimidine-5-carboxylate;

ethyl 4-(3-{[(2Z)-2-fluoro-3-phenylprop-2-enoyl]amino}phenyl)-7H-pyrrolo[2,3-d]pyrimidine-5-carboxylate;

ethyl 4-{3-[(3-methylbut-2-enoyl)amino]phenyl}-7H-pyrrolo[2,3-d]pyrimidine-5-carboxylate;

ethyl 4-(3-{[(2E)-2-methyl-3-phenylprop-2-enoyl]amino}phenyl)-7H-pyrrolo[2,3-d]pyrimidine-5-carboxylate;

ethyl 4-(3-{[(2E)-3-(4-methoxyphenyl)prop-2-enoyl]amino}phenyl)-7H-pyrrolo[2,3-d]pyrimidine-5-carboxylate;

ethyl 4-(3-{[(2E)-3-pyridin-3-ylprop-2-enoyl]amino}phenyl)-7H-pyrrolo[2,3-d]pyrimidine-5-carboxylate;

ethyl 4-(3-{[(2E)-2-methylbut-2-enoyl]amino}phenyl)-7H-pyrrolo[2,3-d]pyrimidine-5-carboxylate;

ethyl 4-(3-{[(2E)-3-furan-2-ylprop-2-enoyl]amino}phenyl)-7H-pyrrolo[2,3-d]pyrimidine-5-carboxylate;

ethyl 4-{3-[(2E)-pent-2-enoylamino]phenyl}-7H-pyrrolo[2,3-d]pyrimidine-5-carboxylate;

ethyl 4-(3-{[(2Z)-4,4,4-trifluoro-3-methylbut-2-enoyl]amino}phenyl)-7H-pyrrolo[2,3-d]pyrimidine-5-carboxylate;

ethyl 4-{3-[(cyclohex-1-en-1-ylcarbonyl)amino]phenyl}-7H-pyrrolo[2,3-d]pyrimidine-5-carboxylate;

ethyl 4-(3-{[(3-oxocyclopent-1-en-1-yl)carbonyl]amino}phenyl)-7H-pyrrolo[2,3-d]pyrimidine-5-carboxylate;

ethyl 4-{3-[(cyclopentylideneacetyl)amino]phenyl}-7H-pyrrolo[2,3-d]pyrimidine-5-carboxylate;

ethyl 4-(3-{[(2E)-2-methoxybut-2-enoyl]amino}phenyl)-7H-pyrrolo[2,3-d]pyrimidine-5-carboxylate;

ethyl 4-(3-{[(2E)-3-(1,3-thiazol-2-yl)prop-2-enoyl]amino}phenyl)-7H-pyrrolo[2,3-d]pyrimidine-5-carboxylate;

ethyl 4-{3-[(4,5-dihydrofuran-3-ylcarbonyl)amino]phenyl}-7H-pyrrolo[2,3-d]pyrimidine-5-carboxylate;

ethyl 4-(3-{[2-(morpholin-4-ylmethyl)acryloyl]amino}phenyl)-7H-pyrrolo[2,3-d]pyrimidine-5-carboxylate;

ethyl 4-(3-{[(2E)-4,4,4-trifluorobut-2-enoyl]amino}phenyl)-7H-pyrrolo[2,3-d]pyrimidine-5-carboxylate;

ethyl 4-(3-{[(2E)-2-methyl-3-phenylprop-2-enoyl]amino}phenyl)-7H-pyrrolo[2,3-d]pyrimidine-5-carboxylate;

ethyl 4-[3-({(2E)-3-[4-(trifluoromethyl)phenyl]prop-2-enoyl}amino)phenyl]-7H-pyrrolo[2,3-d]pyrimidine-5-carboxylate;

ethyl 4-(3-{[2-(methoxymethyl)acryloyl]amino}phenyl)-7H-pyrrolo[2,3-d]pyrimidine-5-carboxylate;

ethyl 4-{3-[(3-chloro-1,2,4-thiadiazol-5-yl)amino]phenyl}-7H-pyrrolo[2,3-d]pyrimidine-5-carboxylate;

ethyl 4-{3-[(3-cyanopyrazin-2-yl)amino]phenyl}-7H-pyrrolo[2,3-d]pyrimidine-5-carboxylate;

ethyl 4-{3-[(4-cyano-1,3,5-triazin-2-yl)amino]phenyl}-7H-pyrrolo[2,3-d]pyrimidine-5-carboxylate;

ethyl 4-{3-[(3-cyano-1,2,4-thiadiazol-5-yl)amino]phenyl}-7H-pyrrolo[2,3-d]pyrimidine-5-carboxylate;

ethyl 4-(3-(2-cyanopyrimidin-4-yl)phenyl)-7H-pyrrolo[2,3-d]pyrimidine-5-carboxylate;

ethyl 4-(3-(3-chloro-1,2,4-thiadiazol-5-yl)phenyl)-7H-pyrrolo[2,3-d]pyrimidine-5-carboxylate;

ethyl 4-(3-(3-bromo-1,2,4-thiadiazol-5-yl)phenyl)-7H-pyrrolo[2,3-d]pyrimidine-5-carboxylate;

ethyl 4-(3-(cyano-1,2,4-thiadiazol-5-yl)phenyl)-7H-pyrrolo [2,3-d]pyrimidine-5-carboxylate;
ethyl 4-(3-(cyanomethylcarbamoyl)phenyl)-7H-pyrrolo[2,3-d]pyrimidine-5-carboxylate;
ethyl 4-(3-(3-(cyanomethyl)ureido)phenyl)-7H-pyrrolo[2,3-d]pyrimidine-5-carboxylate;
ethyl 4-(3-(3-cyanoureido)phenyl)-7H-pyrrolo[2,3-d]pyrimidine-5-carboxylate;
ethyl 4-{3-[(ethenylsulfonyl)amino]phenyl}-7H-pyrrolo[2,3-d]pyrimidine-5-carboxylate;
ethyl 4-(3-{[(1E)-prop-1-en-1-ylsulfonyl]amino}phenyl)-7H-pyrrolo[2,3-d]pyrimidine-5-carboxylate;
ethyl 4-(3-{[(1-methylethenyl)sulfonyl]amino}phenyl)-7H-pyrrolo[2,3-d]pyrimidine-5-carboxylate;
methyl 4-{4-fluoro-3-[(2-methylacryloyl)amino]phenyl}-7H-pyrrolo[2,3-d]pyrimidine-5-carboxylate;
methyl 4-{3-[(2-methylacryloyl)amino]phenyl}-7H-pyrrolo[2,3-d]pyrimidine-5-carboxylate;
ethyl 4-(3-(N-methylacrylamido)phenyl)-7H-pyrrolo[2,3-d]pyrimidine-5-carboxylate;
ethyl 4-(3-(2-(methylsulfonamidomethyl)acrylamido)phenyl)-7H-pyrrolo[2,3-d]pyrimidine-5-carboxylate;
ethyl 4-(3-(2-(aminomethyl)acrylamido)phenyl)-7H-pyrrolo[2,3-d]pyrimidine-5-carboxylate;
ethyl 4-(3-(2-(acetamidomethyl)acrylamido)phenyl)-7H-pyrrolo[2,3-d]pyrimidine-5-carboxylate;
ethyl 4-[3-({2-[(dimethylamino)methyl]acryloyl}amino) phenyl]-7H-pyrrolo[2,3-d]pyrimidine-5-carboxylate;
ethyl 4-(3-{[2-(fluoromethyl)acryloyl]amino}phenyl)-7H-pyrrolo[2,3-d]pyrimidine-5-carboxylate;
ethyl 4-(3-{[2-(hydroxymethyl)acryloyl]amino}phenyl)-7H-pyrrolo[2,3-d]pyrimidine-5-carboxylate;
ethyl 4-(3-{[(2E)-4-(dimethylamino)but-2-enoyl]amino}phenyl)-7H-pyrrolo[2,3-d]pyrimidine-5-carboxylate;
ethyl 4-(3-{[(2E)-4-(dimethylamino)-2-methylbut-2-enoyl]amino}phenyl)-7H-pyrrolo[2,3-d]pyrimidine-5-carboxylate;
ethyl 4-(3-(2-methyloxirane-2-carboxamido)phenyl)-7H-pyrrolo[2,3-d]pyrimidine-5-carboxylate;
ethyl 4-(3-(2,3-dihydroxy-2-methylpropanamido)phenyl)-7H-pyrrolo[2,3-d]pyrimidine-5-carboxylate;
N-(3-{5-[4-(aminomethyl)phenyl]-7H-pyrrolo[2,3-d]pyrimidin-4-yl}phenyl)-2-methylprop-2-enamide;
2-methyl-N-{3-[5-(3-methylphenyl)-7H-pyrrolo[2,3-d]pyrimidin-4-yl]phenyl}prop-2-enamide;
N-{3-[5-(3-fluorophenyl)-7H-pyrrolo[2,3-d]pyrimidin-4-yl]phenyl}-2-methylprop-2-enamide;
N-{3-[5-(2-fluorophenyl)-7H-pyrrolo[2,3-d]pyrimidin-4-yl]phenyl}-2-methylprop-2-enamide;
N-{3-[5-(4-fluorophenyl)-7H-pyrrolo[2,3-d]pyrimidin-4-yl]phenyl}-2-methylprop-2-enamide;
N-{3-[5-(2-chloro-3-fluorophenyl)-7H-pyrrolo[2,3-d]pyrimidin-4-yl]phenyl}-2-methylprop-2-enamide;
2-methyl-N-{3-[5-(2-methylphenyl)-7H-pyrrolo[2,3-d]pyrimidin-4-yl]phenyl}prop-2-enamide;
2-methyl-N-{3-[5-(4-methylphenyl)-7H-pyrrolo[2,3-d]pyrimidin-4-yl]phenyl}prop-2-enamide;
2-methyl-N-{3-[5-(2,4,6-trimethylphenyl)-7H-pyrrolo[2,3-d]pyrimidin-4-yl]phenyl}prop-2-enamide;
N-[3-(5-phenyl-7H-pyrrolo[2,3-d]pyrimidin-4-yl)phenyl] prop-2-enamide;
N-(3-(5-(pyridin-2-yl)-7H-pyrrolo[2,3-d]pyrimidin-4-yl) phenyl)methacrylamide;
N-(3-(5-(1H-imidazol-5-yl)-7H-pyrrolo[2,3-d]pyrimidin-4-yl)phenyl)methacrylamide;
N-(3-(5-(pyridin-4-yl)-7H-pyrrolo[2,3-d]pyrimidin-4-yl) phenyl)methacrylamide;
N-(3-(5-(pyridin-3-yl)-7H-pyrrolo[2,3-d]pyrimidin-4-yl) phenyl)methacrylamide;
N-(3-(5-(3,6-dihydro-2H-pyran-4-yl)-7H-pyrrolo[2,3-d]pyrimidin-4-yl)phenyl)methacrylamide;
N-(3-(5-(2-methylthiazol-5-yl)-7H-pyrrolo[2,3-d]pyrimidin-4-yl)phenyl)methacrylamide;
N-(3-(5-(thiazol-5-yl)-7H-pyrrolo[2,3-d]pyrimidin-4-yl) phenyl)methacrylamide;
N-(3-(5-(oxazol-2-yl)-7H-pyrrolo[2,3-d]pyrimidin-4-yl) phenyl)methacrylamide;
N-(3-(5-(tetrahydro-2H-pyran-4-yl)-7H-pyrrolo[2,3-d]pyrimidin-4-yl)phenyl)methacrylamide;
N-methyl-N-(3-(5-(tetrahydro-2H-pyran-4-yl)-7H-pyrrolo [2,3-d]pyrimidin-4-yl)phenyl)methacrylamide;
N-(3-(5-(tetrahydrofuran-2-yl)-7H-pyrrolo[2,3-d]pyrimidin-4-yl)phenyl)methacrylamide;
N-(3-(5-(5-methyl-1,3,4-oxadiazol-2-yl)-7H-pyrrolo[2,3-d]pyrimidin-4-yl)phenyl)methacrylamide;
N-(3-(5-(5-methyl-4,5-dihydro oxazol-2-yl)-7H-pyrrolo[2,3-d]pyrimidin-4-yl)phenyl)methacrylamide;
N-(3-(5-(4-methyloxazol-2-yl)-7H-pyrrolo[2,3-d]pyrimidin-4-yl)phenyl)methacrylamide;
N-(3-(5-(oxazol-5-yl)-7H-pyrrolo[2,3-d]pyrimidin-4-yl) phenyl)methacrylamide;
N-(3-(5-(thiazol-2-yl)-7H-pyrrolo[2,3-d]pyrimidin-4-yl) phenyl)methacrylamide;
5-(2-methoxypyridin-3-yl)-4-phenyl-7H-pyrrolo[2,3-d]pyrimidine;
4,5-diphenyl-7H-pyrrolo[2,3-d]pyrimidine;
methyl [4-methoxy-3-(4-phenyl-7H-pyrrolo[2,3-d]pyrimidin-5-yl)phenyl]acetate;
5-(3-methoxyphenyl)-4-phenyl-7H-pyrrolo[2,3-d]pyrimidine;
5-(3-phenoxyphenyl)-4-phenyl-7H-pyrrolo[2,3-d]pyrimidine;
5-[3-(benzyloxy)phenyl]-4-phenyl-7H-pyrrolo[2,3-d]pyrimidine;
5-(2-phenoxyphenyl)-4-phenyl-7H-pyrrolo[2,3-d]pyrimidine;
5-(2-methoxyphenyl)-4-phenyl-7H-pyrrolo[2,3-d]pyrimidine;
5-(2-methoxyphenyl)-4-(2-methyl-2H-indazol-6-yl)-7H-pyrrolo[2,3-d]pyrimidine;
5-(5-fluoro-2-methoxyphenyl)-4-phenyl-7H-pyrrolo[2,3-d]pyrimidine;
5-(2-methoxyphenyl)-4-(3-methoxyphenyl)-7H-pyrrolo[2,3-d]pyrimidine;
3-[5-(2-methoxyphenyl)-7H-pyrrolo[2,3-d]pyrimidin-4-yl]-N,N-dimethylbenzamide; and
5-(2-methoxyphenyl)-4-(1H-pyrazol-4-yl)-7H-pyrrolo[2,3-d]pyrimidine.

In one embodiment of the invention, $R^1$ is selected from $(C_{1-10})$ heteroalkyl containing 1, 2, or 3 atoms independently selected from N, O or S; a 3-15-membered saturated, unsaturated or partially saturated monocyclic or bicyclic ring system containing 0, 1, 2, 3, or 4 atoms independently selected from N, O or S;

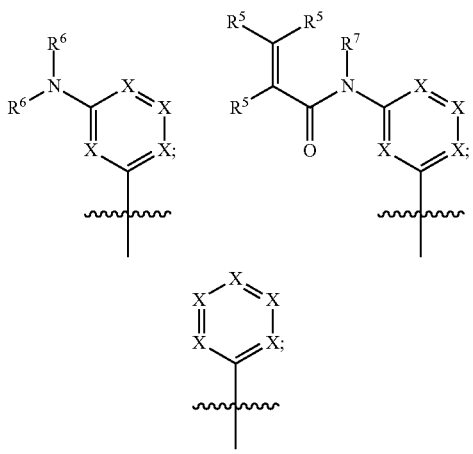

additionally, $R^1$ may be substituted with 0, 1, 2, or 3 independently chosen $R^5$.

In another embodiment of the invention, $R^1$ is a 3-15-membered saturated, unsaturated or partially saturated monocyclic or bicyclic ring system containing 0, 1, 2, 3, or 4 atoms independently selected from N, O or S;

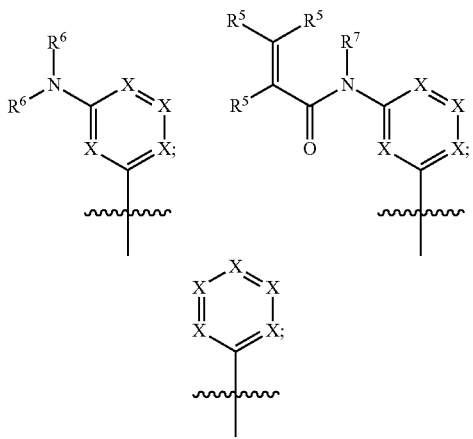

additionally, $R^1$ may be substituted with 0, 1, 2, or 3 independently chosen $R^5$.

In a variant of this embodiment, $R^1$ is selected from: phenyl, pyridinyl, indazolyl, dihydro-pyrrolyl, tetrahydropyridinyl, cyclohexenyl, benzothiazolyl, pyrazolyl, dihydro-indolyl, naphthalenyl, 1,3-benzodioxolyl, quinolinyl, benzothiphenyl, indolyl, benzofuranyl, thiophenyl, 4,5,6,7-tetrahydropyrazolo[1,5-a]pyridinyl, 2,3-dihydro-isoindolyl, 2,3-dihydro-benzimidazolyl, benzotriazolyl, 2,3,4,5-tetrahydro-benzazepinyl, benzothiophenyl, 3,4-dihydroisoquinolinyl, 2,3-dihydro-1,4-benzoazepinyl, pyrrolo[2,3-b]pyridinyl, 5,6-dihydro-pyranyl, pyrimidinyl, and 3,6-dihydro-pyranyl; additionally, $R^1$ may be substituted with 0, 1, 2, or 3 independently chosen $R^5$.

In one embodiment of the invention, $R^2$ is —C=O(OR$^4$); —C=ON(R$^7$)$_2$, a 3-15-membered saturated, unsaturated or partially saturated monocyclic or bicyclic ring system containing 0, 1, 2, 3, or 4 atoms independently selected from N, O, or S;

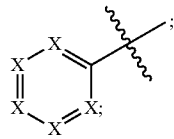

additionally, $R^2$ may be substituted with 0, 1, 2, or 3 independently chosen $R^5$.

In another embodiment, $R^2$ is selected from ethyloxycarbonyl, propyloxycarbonyl, Prop-2-en-1-yloxycarbonyl, methyloxycarbonyl, phenyl, pyridinyl, imidazolyl, 3,6-dihydro-pyranyl, thiazolyl, oxazolyl, tetrahydropyranyl, tetrahydrofuranyl, 1,3,4-oxadiazolyl, thiadiazolyl, and 4,5-dihydrooxazolyl; additionally, $R^2$ may be substituted with 0, 1, 2, or 3 independently chosen $R^5$.

In one embodiment of the invention, $R^3$ is hydrogen. In another embodiment, $R^3$ is selected from halogen, and —C$_{1-3}$ alkyl. In yet another embodiment, $R^3$ is selected from hydrogen and —C$_{1-3}$alkyl.

In one embodiment of the invention, $R^4$ is selected from hydrogen, —C$_{1-10}$ alkyl, —C$_{2-10}$ alkenyl, —(C$_{1-6}$ alkyl) C$_{3-8}$ cycloalkyl; and —(C$_{1-6}$ alkyl) aryl; $R^4$ is optionally substituted with halogen, cyano, oxo, C1-6 alkoxy, amino, alkylamino, or dialkylamino.

In another embodiment, $R^4$ is selected from hydrogen, —C$_{1-10}$ alkyl, and —C$_{2-10}$ alkenyl; $R^4$ is optionally substituted with halogen, cyano, oxo, C1-6 alkoxy, amino, alkylamino, or dialkylamino. In a variant of this embodiment, $R^4$ is selected from hydrogen, methyl, ethyl, propyl, butyl, butylenyl, and propenyl. In a variant of this embodiment, $R^4$ is selected from methyl, ethyl, propyl, and propenyl and $R^4$ is optionally substituted with halogen, cyano, oxo, C1-6 alkoxy, amino, alkylamino, or dialkylamino.

In one embodiment, $R^5$ is selected from: hydrogen, halogen, amino, cyano, —COOH, C$_{1-10}$alkyl, C$_{1-10}$alkoxy, C$_{0-10}$alkylcarbamoyl, hydroxyC$_{0-10}$alkyl, C$_{1-6}$haloalkyl, C$_{1-10}$ alkylsulfonyl, C$_{1-10}$ alkyl(oxy)$_{0-1}$C$_{0-10}$ alkyl, arylC$_{0-10}$ alkyl(oxy)$_{0-1}$C$_{0-10}$ alkyl, (C$_{3-8}$)heteroarylC$_{0-10}$ alkyl(oxy)$_{0-1}$ C$_{0-10}$ alkyl, C$_{3-8}$ cycloalkylC$_{0-10}$ alkyl(oxy)$_{04}$C$_{0-10}$ alkyl, (C$_{3-8}$) heterocycloalkylC$_{0-10}$ alkyl(oxy)$_{0-1}$C$_{0-10}$ alkyl, C$_{0-10}$ alkylcarbonyl(oxy)$_{0-1}$C$_{0-10}$ alkyl, C$_{1-10}$ alkyl(oxy)$_{0-1}$carbonylC$_{0-10}$ alkyl, C$_{2-10}$ alkenylcarbonyl, C$_{2-10}$ alkynylcarbonyl, C$_{0-10}$ alkyl(oxy)$_{0-1}$C$_{0-10}$ alkylaminocarbonylC$_{0-10}$ alkyl, (C$_{0-10}$ alkyl)$_{1-2}$aminoC$_{1-10}$ alkyloxyC$_{0-10}$ alkyl, (C$_{0-10}$ alkyl)$_{1-2}$aminocarbonylC$_{0-10}$ alkyl, C$_{1-10}$ heteroalkylC$_{0-10}$ alkylaminocarbonylC$_{0-10}$ alkyl, (C$_{3-8}$)heterocycloalkylC$_{0-10}$ alkylaminocarbonylC$_{0-10}$ alkyl, (C$_{3-8}$)heteroaryl C$_{0-10}$ alkylaminocarbonylC$_{0-10}$ alkyl, C$_{3-8}$ cycloalkyl C$_{0-10}$ alkylaminocarbonylC$_{0-10}$ alkyl, aryl C$_{0-10}$ alkylaminocarbonylC$_{0-1}$ alkyl, (C$_{3-8}$)heterocycloalkylC$_{0-10}$ alkylcarbonylC$_{0-10}$ alkyl, C$_{3-8}$ cycloalkyl C$_{0-10}$ alkyl(oxy)$_{0-1}$carbonylaminoC$_{0-10}$ alkyl, aryl C$_{0-10}$ alkyl(oxy)$_{0-1}$carbonylaminoC$_{0-10}$ alkyl, (C$_{3-8}$)heteroaryl C$_{0-10}$ alkyl(oxy)$_{0-1}$carbonylaminoC$_{0-10}$ alkyl, (C$_{3-8}$) heterocycloalkyl C$_{0-10}$ alkyl(oxy)$_{0-1}$carbonylaminoC$_{0-10}$ alkyl, C$_{0-10}$ alkylureylenyl, C$_{1-4}$ acylamino C$_{0-10}$ alkyl, C$_{0-10}$ alkylamino C$_{0-10}$ alkyl, aryl, acrylamido, acryloylamino, halo-aryl, halo-heterocyclyl, cyanoC$_{1-6}$alkyl, cyano-aryl, and perfluoroC$_{1-6}$alkoxy.

In another embodiment, $R^5$ is selected from: hydrogen, halogen, amino, cyano, C$_{1-10}$alkyl, C$_{1-10}$alkoxy, C$_{0-10}$alkylcarbamoyl, C$_{1-6}$haloalkyl, C$_{1-10}$ alkylsulfonyl, C$_{1-10}$ alkyl (oxy)$_{0-1}$C$_{0-10}$ alkyl, arylC$_{0-10}$ alkyl(oxy)$_{0-1}$C$_{0-10}$ alkyl, (C$_{3-8}$) heteroarylC$_{0-10}$ alkyl(oxy)$_{0-1}$C$_{0-10}$ alkyl, C$_{3-8}$ cycloalkyl C$_{0-10}$ alkyl(oxy)$_{0-1}$ C$_{0-10}$ alkyl, (C$_{3-8}$)heterocycloalkylC$_{0-10}$ alkyl(oxy)$_{0-1}$ C$_{0-10}$ alkyl, C$_{0-10}$ alkylcarbonyl(oxy)$_{0-1}$C$_{0-10}$ alkyl, $C_{1-10}$ alkyl(oxy)$_{0-1}$carbonyl$C_{0-10}$ alkyl, $C_{2-10}$ alkenylcarbonyl, $C_{2-10}$ alkynylcarbonyl, $C_{0-10}$ alkyl(oxy)$_{0-1}$$C_{0-10}$ alkylaminocarbonyl$C_{0-10}$ alkyl, $(C_{0-10}$ alkyl)$_{1-2}$amino$C_{1-10}$ alkyloxy$C_{0-10}$ alkyl, $(C_{0-10}$ alkyl)$_{1-2}$aminocarbonyl$C_{0-10}$ alkyl, $C_{1-10}$ heteroalkyl$C_{0-10}$ alkylaminocarbonyl$C_{0-10}$ alkyl, $(C_{3-8})$heterocycloalkyl$C_{0-10}$ alkylaminocarbonyl$C_{0-10}$ alkyl, $(C_{3-8})$heteroaryl $C_{0-10}$ alkylaminocarbonyl$C_{0-10}$ alkyl, $C_{3-8}$ cycloalkyl $C_{0-10}$ alkylaminocarbonyl$C_{0-10}$ alkyl, aryl $C_{0-10}$ alkylaminocarbonyl$C_{0-10}$ alkyl, $(C_{3-8})$heterocycloalkyl$C_{0-10}$ alkylcarbonyl$C_{0-10}$ alkyl, $C_{3-8}$ cycloalkyl $C_{0-10}$ alkyl(oxy)$_{0-1}$carbonylamino$C_{0-10}$ alkyl, aryl $C_{0-10}$ alkyl(oxy)$_{0-1}$carbonylamino$C_{0-10}$ alkyl, $(C_{3-8})$heteroaryl $C_{0-10}$ alkyl(oxy)$_{0-1}$carbonylamino$C_{0-10}$ alkyl, $(C_{3-8})$heterocycloalkyl $C_{0-10}$ alkyl (oxy)$_{0-1}$carbonylamino$C_{0-10}$ alkyl, $C_{0-10}$ alkylureylenyl, $C_{1-4}$acylamino $C_{0-10}$ alkyl, $C_{0-10}$ alkylamino $C_{0-10}$ alkyl, aryl, acrylamido, acryloylamino, halo-aryl, halo-heterocyclyl, cyano$C_{1-6}$alkyl, cyano-aryl, oxo, and perfluoro$C_{1-6}$alkoxy.

In another embodiment, $R^5$ is selected from: hydrogen, halogen, amino, methoxy, methyl, cyano, carbamoyl, methoxycarbonyl, methylsulfonyl, dimethylcarbamoyl, ethoxycarbonyl, tert-butoxycarbonyl, trifluoroethoxy, trifluoromethoxy, hydroxymethyl, methoxymethyl, hydroxyl, trifluoromethyl, phenyl, dimethylamino, benzyloxy, oxo, piperazinyl, methylsulfonyl, pyrazolyl, thiomorpholinyl, morpholinylmethyl, methoxyethyl, tetrahydrofuranylcarbamoyl, cyanomethyl, methacrylamino, acrylamino, (2E)-but-2-enoylamino, propanoylamino (ethylcarbonylamino), 2-methylidenebutanoylamino, acryloyl, methylacryloyl, dimethylcarbamoyl, dimethylamino, but-2-ynoylamino, methylcarbonylamino, ethylcarbonylamino, (5,6-dihydro-1,4-dioxin-2-ylcarbonyl)amino, acrylamino, pyridinyl, [1,2,3,4-tetrahydropyrimidinylcarbonyl]amino, indolyl, (2,3-dihydro-imidazolylcarbonyl)amino, thiophenyl, furanyl, ethyl, pyridinyl, cyclopentyl, thiazolyl, morpholinylmethyl, methoxymethyl, pyrimidinyl, thiadiazolyl, methylaminocarbonyl, methylureylenyl, ureylenyl, aminomethyl, fluoromethyl, dimethylaminomethyl, oxiranecarbonyl, 2-hydroxy-propylcarbonyl, dimethylaminocarbonyl, aminomethyl, methoxycarbonylmethyl, and phenoxy.

In another embodiment, $R^6$ and $R^7$ are each independently selected from: hydrogen, $C_{1-10}$ alkyl, (carbonyl)$_{0-1}$$C_{2-10}$ alkenyl, (carbonyl)$_{0-1}$$C_{2-10}$ alkynyl, $C_{0-10}$ alkylcarbonyl(oxy)$_{0-1}$ $C_{0-10}$ alkyl, $C_{1-10}$ alkyl(oxy)$_{0-1}$carbonyl$C_{0-10}$ alkyl, aryl $C_{0-10}$alkyl(oxy)$_{0-1}$carbonyl$C_{0-10}$alkyl, $(C_{3-8})$heteroaryl$C_{0-10}$ alkyl(oxy)$_{0-1}$carbonyl$C_{0-10}$ alkyl, $C_{3-8}$ cycloalkyl$C_{0-10}$ alkyl (oxy)$_{0-1}$carbonyl$C_{0-10}$ alkyl, $(C_{3-8})$heterocycloalkyl$C_{0-10}$ alkyl(oxy)$_{0-1}$carbonyl$C_{0-10}$ alkyl, $(C_{1-10})$heteroalkyl$C_{0-10}$ alkyl(oxy)$_{0-1}$carbonyl$C_{0-10}$ alkyl, $(C_{1-10})$alkyl(oxy)$_{0-1}$$C_{0-10}$ alkyl, aryl(oxy)$_{0-1}$$C_{0-10}$ alkyl, $(C_{3-8})$heteroaryl(oxy)$_{0-1}$ $C_{0-10}$ alkyl, $C_{3-8}$ cycloalkyl(oxy)$_{0-1}$$C_{0-10}$ alkyl, $(C_{3-8})$heterocloalkyl(oxy)$_{0-1}$ $C_{0-10}$ alkyl, $(C_{1-10})$heteroalkyl(oxy)$_{0-1}$$C_{0-10}$ alkyl, $C_{0-10}$ alkyl(oxy)$_{0-1}$$C_{0-10}$ alkylaminocarbonyl$C_{0-10}$ alkyl, $C_{0-10}$ alkylaminocarbonyl$C_{1-10}$ heteroalkyl, hydroxy $C_{0-10}$alkyl, $C_{0-10}$ alkylsulfonyl, and $C_{1-6}$haloalkyl.

In yet another embodiment, $R^6$ and $R^7$ are each independently selected from: hydrogen, $C_{1-10}$ alkyl, $C_{0-10}$ alkylcarbonyl(oxy)$_{0-1}$$C_{0-10}$ alkyl, $C_{1-10}$ alkyl(oxy)$_{0-1}$carbonyl$C_{0-10}$ alkyl, aryl$C_{0-10}$ alkyl(oxy)$_{0-1}$carbonyl$C_{0-10}$ alkyl, $(C_{3-8})$heteroaryl$C_{0-10}$ alkyl(oxy)$_{0-1}$carbonyl$C_{0-10}$ alkyl, $C_{3-8}$ cycloalkyl$C_{0-10}$ alkyl(oxy)$_{0-1}$carbonyl$C_{0-10}$ alkyl, $(C_{3-8})$heterocycloalkyl$C_{0-10}$ alkyl(oxy)$_{0-1}$carbonyl$C_{0-10}$ alkyl, $(C_{1-10})$ heteroalkyl$C_{0-10}$ alkyl(oxy)$_{0-1}$carbonyl$C_{0-10}$ alkyl, and $C_{0-10}$ alkylsulfonyl.

In a variant of this embodiment, $R^6$ and $R^7$ are each independently selected from: methyl, ethyl, cyclohexenylcarbonyl, cyclopentenylcarbonyl, (4,5-dihydrofuranyl)carbonyl, pyrazinyl, triazinyl, thiadiazolyl, and sulfonyl.

In one embodiment, $R^7$ is selected from hydrogen, $C_{1-10}$ alkyl, $C_{0-10}$ alkylcarbonyl(oxy)$_{0-1}$$C_{0-10}$ alkyl, $C_{1-10}$ alkyl (oxy)$_{0-1}$carbonyl$C_{0-10}$ alkyl, hydroxy$C_{0-10}$alkyl, and $C_{1-6}$haloalkyl. In one variant of this embodiment, $R^7$ is selected from hydrogen and $C_{1-10}$ alkyl. In another variant, $R^7$ is selected from hydrogen and methyl, ethyl, propyl, butyl, and pentyl. In yet another embodiment, $R^7$ is selected from hydrogen and methyl.

In the above described embodiments, $R^6$ and $R^7$ are each independently substituted with 0, 1, 2, or 3 substituents chosen from: halogen, $C_1$-$C_{10}$ alkyl, $CF_3$, $NH_2$, $N(C_1$-$C_6$ alkyl)$_2$, $NO_2$, —$(C_{0-6})$alkylCN, —OH, —O($C_1$-$C_6$ alkyl), $C_3$-$C_{10}$ cycloalkyl, $C_2$-$C_6$ alkenyl, $C_2$-$C_6$ alkynyl, $(C_0$-$C_6$ alkyl)S(O)$_{0-2}$-, $(C_0$-$C_6$ alkyl)S(O)$_{0-2}$($C_0$-$C_6$ alkyl)-, $(C_0$-$C_6$ alkyl) C(O)NH—, $H_2$N—C(NH)—, —O($C_1$-$C_6$ alkyl)$CF_3$, $(C_0$-$C_6$ alkyl)C(O)—, $(C_0$-$C_6$ alkyl)OC(O)—, $(C_0$-$C_6$ alkyl)O($C_1$-$C_6$ alkyl)-, $(C_0$-$C_6$ alkyl)C(O)$_{1-2}$($C_0$-$C_6$ alkyl)-, $(C_0$-$C_6$ alkyl)OC (O)NH—, —NH($C_1$-$C_6$ alkyl)NHC(O)NH($C_1$-$C_6$ alkyl), NHC(O)OC$_1$-$C_6$ alkyl, —NH($C_1$-$C_6$ alkyl)NHSO$_2$($C_1$-$C_6$ alkyl), —$(C_0$-$C_6$ alkyl)NHSO$_2$($C_1$-$C_6$ alkyl), $C_{1-10}$alkoxy, —CO$_2$($C_{0-10}$ alkyl), Oxo (=O), trifluoromethyl, trifluoroethyl, $C_{1-10}$ alkylsulfonyl, —SO$_2$N($C_{1-6}$alkyl)$_{1-2}$, —SO$_2$CF$_3$, —SO$_2$CF$_2$H, —$C_{1-10}$ alkylsulfinyl, —O$_{(0-1)}$($C_{1-10}$)haloalkyl, aryl, heteroaryl, heterocyclyl, halo-aryl, halo-heterocyclyl, cyano-aryl, cyano-heteroaryl, and cyano-heterocyclyl.

In variant of this embodiment, $R^6$ and $R^7$ are each independently substituted with 0, 1, 2, or 3 substituents chosen from: halogen, $C_1$-$C_{10}$ alkyl, $CF_3$, $NH_2$, $N(C_1$-$C_6$ alkyl)$_2$, —$(C_{0-6})$ alkylCN, —OH, —O($C_1$-$C_6$ alkyl), $C_3$-$C_{10}$ cycloalkyl, $(C_0$-$C_6$ alkyl)S(O)$_{0-2}$($C_0$-$C_6$ alkyl)-, $(C_0$-$C_6$ alkyl)C(O)NH—, —O($C_1$-$C_6$ alkyl)$CF_3$, $(C_0$-$C_6$ alkyl)C(O)—, $(C_0$-$C_6$ alkyl) OC(O)—, $(C_0$-$C_6$ alkyl)O($C_1$-$C_6$ alkyl)-, $(C_0$-$C_6$ alkyl) C(O)$_{1-2}$ $(C_0$-$C_6$ alkyl)-, $C_{1-10}$alkoxy, —CO$_2$($C_{0-10}$ alkyl), Oxo (=O), trifluoromethyl, trifluoroethyl, $C_{1-10}$ alkylsulfonyl, —SO$_2$N($C_{1-6}$ alkyl)$_{1-2}$, —SO$_2$CF$_3$, —SO$_2$CF$_2$H, and —O$_{(0-1)}$($C_{1-10}$)haloalkyl.

The invention also encompasses pharmaceutical compositions containing a compound of formula I, and methods for treatment or prevention of JAK3-mediated diseases using compounds of formula I.

The invention is described using the following definitions unless otherwise indicated.

As used herein except where noted, "alkyl" is intended to include both branched- and straight-chain saturated aliphatic hydrocarbon groups, including all isomers, having the specified number of carbon atoms. Commonly used abbreviations for alkyl groups are used throughout the specification, e.g. methyl may be represented by "Me" or $CH_3$, ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. The term "alkylene" refers to both branched- and straight-chain saturated aliphatic hydrocarbon groups, including all isomers, having the specified number of carbons, and having two terminal end chain attachments. For illustration, the term "unsubstituted A-$C_4$alkylene-B" represents A-$CH_2$—$CH_2$—$CH_2$—$CH_2$—B. The term "alkoxy" represents a linear or branched alkyl group of indicated number of carbon atoms attached through an oxygen bridge.

The term "alkyl" refers to an aliphatic hydrocarbon group which may be straight or branched and having the indicated number of carbon atoms. Non-limiting examples of alkyl groups include methyl, ethyl, propyl, isopropyl, butyl, s- and t-butyl, pentyl, hexyl.

"Alkenyl" refers to an aliphatic hydrocarbon group containing at least one carbon-carbon double bond and which may be straight or branched and having the indicated number of carbon atoms. Preferably alkenyl contains one carbon to carbon double bond, and up to four nonaromatic carbon-carbon double bonds may be present. Examples of alkenyl groups include ethenyl, propenyl, n-butenyl, 2-methyl-1-butenyl, 3-methylbut-2-enyl, n-pentenyl, octenyl and decenyl.

"Alkynyl" refers to an aliphatic hydrocarbon group containing at least one carbon-carbon triple bond and which may be straight or branched and having the indicated number of carbon atoms. Non-limiting examples of suitable alkynyl groups include ethynyl, propynyl, 2-butynyl and 3-methylbutynyl.

"Alkoxy" refers to an alkyl-O— group in which the alkyl group is as described above. $C_{1-6}$alkoxy, for example, includes methoxy, ethoxy, propoxy, isopropoxy, and the like.

"Alkoxyalkyl" refers to an alkyl group as described above in which one or more (in particular 1 to 3) hydrogen atoms have been replaced by alkoxy groups. Examples include $CH_2OCH_3$, $CH_2CH_2OCH_3$ and $CH(OCH_3)CH_3$.

"Aminoalkyl" refers to an alkyl group as described above in which one hydrogen atom has been replaced by an amino, monoalkylamino or dialkylamino group. Examples include $CH_2NH_2$, $CH_2CH_2NHCH_3$ and $CH(N(CH_3)_2)CH_3$.

The term "$C_0$" as employed in expressions such as "$C_{0-6}$ alkyl" means a direct covalent bond; or when the term appears at the terminus of a substituent, $C_{0-6}$ alkyl means hydrogen or C1-6alkyl. Similarly, when an integer defining the presence of a certain number of atoms in a group is equal to zero, it means that the atoms adjacent thereto are connected directly by a bond. For example, in the structure

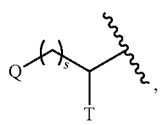

wherein s is an integer equal to zero, 1 or 2, the structure is

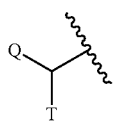

when s is zero.

The term "$C_{3-8}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "$C_{3-7}$ cycloalkyl", "$C_{3-6}$ cycloalkyl", "$C_{5-7}$ cycloalkyl" and the like have analogous meanings.

The term "halogen" (or "halo") refers to fluorine, chlorine, bromine and iodine (alternatively referred to as fluoro (F), chloro (Cl), bromo (Br), and iodo (I)).

The term "aryl" refers to aromatic mono- and poly-carbocyclic ring systems, wherein the individual carbocyclic rings in the polyring systems are fused or attached to each other via a single bond. Suitable aryl groups include phenyl, naphthyl, 2,3-dihydro-1H-indenyl, and biphenyl.

"Halo-aryl" refers to an aryl group as described above in which one or more hydrogen atoms have been replaced by a halogen group.

"Cyano-aryl" refers to an aryl group as described above in which one atom has been replaced by a cyano group.

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. A fused bicyclic carbocycle in which one ring is saturated and the other is saturated is a saturated bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. Unless otherwise noted, carbocycle is unsubstituted or substituted with $C_{1-6}$ alkyl, $C_{1-6}$ alkenyl, $C_{1-6}$ alkynyl, aryl, halogen, $NH_2$ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

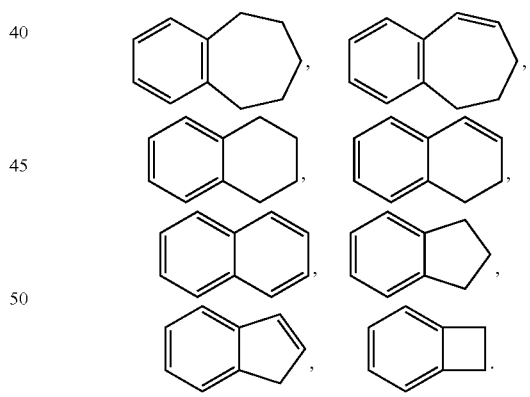

"Cycloalkyl" means a carbocyclic ring system having 3 to 12 ring carbon atoms; said ring system may be (a) a monocyclic saturated carbocycle optionally fused to a benzene or a partially unsaturated carbocycle, or (b) a bicyclic saturated carbocycle. For a bicyclic system, within either (a) or (b), the rings are fused across two adjacent ring carbon atoms (e.g., decalin), at one ring carbon atom (e.g., spiro[2.2]pentane), or are bridged groups (e.g., norbornane). Additional examples within the above meaning include, but are not limited to, cyclopropane, cyclobutane, cyclopentane, cyclohexane, perhydroindan, decalin, spiro[4.5]decane, bicyclo[2.2.2]octane, and the like.

"Cyanoalkyl" refers to an alkyl group as described above in which one hydrogen atom has been replaced by a cyano group. Examples include CH$_2$CN, CH$_2$CH$_2$CN and CH(CN)CH$_3$.

"Haloalkyl" refers to an alkyl group as described above wherein one or more (in particular 1 to 5) hydrogen atoms have been replaced by halogen atoms, with up to complete substitution of all hydrogen atoms with halo groups. C$_{1-6}$haloalkyl, for example, includes —CF$_3$, —CF$_2$CF$_3$, CHFCH$_3$, and the like.

"Heterocycle" or "heterocyclic" represents a monocyclic or bicyclic 4-10 membered ring system in which at least one ring is non-aromatic (saturated or partially unsaturated) and containing at least one heteroatom selected from O, S and N. In a bicyclic ring system, the second ring may be a heteroaryl, heterocycle or a saturated, partially unsaturated or aromatic carbocycle, and the point(s) of attachment to the rest of the molecule may be on either ring. Examples of heterocycle include, but are not limited to, azetidinyl, pyrrolidinyl, piperidinyl, piperazinyl, morpholinyl, thiamorpholinyl, tetrahydrofuranyl, dihydrofuranyl, tetrahydrothienyl, tetrahydropyranyl, dihydropyranyl, dihydroimidazolyl, dihydroindolyl, 1,2,3,4-tetrahydroisoquinolinyl, 5,6,7,8-tetrahydro-imidazo[1,2-a]pyrazine, 2,3-dihydrobenzofuranyl, benzo-1,4-dioxanyl and the like.

Saturated heterocyclics form a subset of the heterocycles; i.e., the terms "saturated heterocyclic and (C$_{3-8}$)heterocycloalkyl" generally refers to a heterocycle as defined above in which the entire ring system (whether mono- or poly-cyclic) is saturated. The term "saturated heterocyclic ring" refers to a 4- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

"Heteroaryl" or "heteroaromatic" as used herein represents a 5-10 membered aromatic ring system containing one ring (monocyclic) or two fused rings (bicyclic), and 1-4 heteroatoms independently selected from O, S and N.

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic which consists of carbon atoms and one or more heteroatoms selected from N, O and S. For a bicyclic heteroaryl only one of the rings need to be heteroaromatic, the second ring may be a heteroaromatic or an aromatic, saturated, or partially unsatuated carbocycle, and the point(s) of attachment to the rest of the molecule may be on either ring. In the case of substituted heteroaryl rings containing at least one nitrogen atom (e.g., pyridine), such substitutions can be those resulting in N-oxide formation. Examples of heteroaryl include, but are not limited to, furanyl, thienyl (or thiophenyl), pyrrolyl, imidazolyl, pyrazolyl, oxazolyl, thiazolyl, isoxazolyl, isothiazolyl, triazolyl, oxadiazolyl, thiadiazolyl, tetrazolyl, pyridyl, pyrimidinyl, pyrazinyl, pyridazinyl, triazinyl, quinolinyl, isoquinolinyl, naphthyridinyl, benzothienyl, benzofuranyl, benzimidazole, benzpyrazolyl, indolyl, isoindolyl, indolizinyl, indazolyl, purinyl, quinolizinyl, phthalazinyl, quinoxalinyl, quinazolinyl, benzoxazolyl, benzisoxazolyl, 5,6,7,8-tetrahydroquinolinyl, imidazo[1,2-a]pyridinyl, imidazo[1,2-a]-pyrimidinyl, 5,6-dihydropyrrolo[1,2-b]pyrazolyl, pyrrolo[3,2-c]pyridinyl, pyrrolo[2,3-b]pyridinyl, thieno[2,3-b]pyrrolyl, furopyridine and thienopyridine.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl

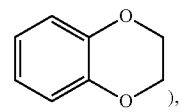), imidazo(2,1-b)(1,3)thiazole,

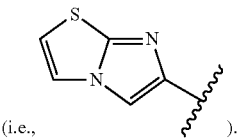 [SMILES: *c1cn2ccsc2n1]

(i.e., ).

and benzo-1,3-dioxolyl

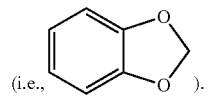

(i.e., ).

In certain contexts herein,

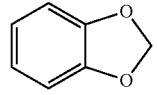

is alternatively referred to as phenyl having as a substituent methylenedioxy attached to two adjacent carbon atoms.

"Cyano-heteroaryl" and "cyano-heterocyclyl" refer to a heteroaryl and a hetrocyclyl group, respectively, as described above in which one atom has been replaced by a cyano group.

"Halo-heteroaryl" and "halo-heterocyclyl" refer to a heteroaryl and a heterocyclyl group, respectively, as described above in which one or more atoms have been replaced by a halogen group.

"Hydroxyalkyl" refers to an alkyl group as described above in which one or more (in particular 1 to 3) hydrogen atoms have been replaced by hydroxy groups. Examples include CH$_2$OH, CH$_2$CHOH and CHOHCH$_3$.

"Alkylene," "alkenylene," "alkynylene," "cycloalkylene," "arylene," "heteroarylene," and "heterocyclylene" refer to a divalent radical obtained by the removal of one hydrogen atom from an alkyl, alkenyl, alkynyl, cycloalkyl, aryl, heteroaryl, and heterocyclyl group, respectively, each of which is as defined above.

Unless expressly stated to the contrary, an "unsaturated" ring is a partially or fully unsaturated ring. For example, an "unsaturated monocyclic C$_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

The term "oxy" means an oxygen (O) atom. The term "thio" means a sulfur (S) atom. The term "oxo" means "=O". The term "carbonyl" means "C=O."

The term "ureylenyl" refers to: —NH—CO—NH—.

Structural representations of compounds having substituents terminating with a methyl group may display the terminal methyl group either using the characters "CH$_3$", e.g. "—CH$_3$" or using a straight line representing the presence of the methyl group, e.g. "—", i.e.,

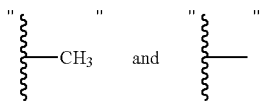

have equivalent meanings.

For variable definitions containing terms having repeated terms, e.g., (CR$^i$R$^j$)$_r$, where r is the integer 2, R$^i$ is a defined variable, and R$^j$ is a defined variable, the value of R$^i$ may differ in each instance in which it occurs, and the value of R$^j$ may differ in each instance in which it occurs. For example, if R$^i$ and R$^j$ are independently selected from the group consisting of methyl, ethyl, propyl and butyl, then (CR$^i$R$^j$)$_2$ can be

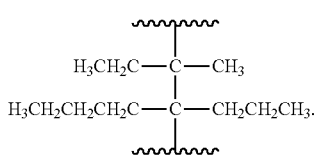

"Patient" includes both human and animals.

"Mammal" means humans and other mammalian animals.

"Therapeutically effective amount" means that amount of a drug or pharmaceutical agent that will elicit the biological or medical response of a tissue, a system, animal or human that is being sought by a researcher, veterinarian, medical doctor or other clinician.

The term "treatment" or "treating" includes alleviating, ameliorating, relieving or otherwise reducing the signs and symptoms associated with a disease or disorder.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of formula I, and pharmaceutically acceptable excipients.

The term "optionally substituted" means "unsubstituted or substituted," and therefore, the generic structural formulas described herein encompasses compounds containing the specified optional substituent as well as compounds that do not contain the optional substituent.

Each variable is independently defined each time it occurs within the generic structural formula definitions. For example, when there is more than one substituent for arylheteroaryl, each substituent is independently selected at each occurrence, and each substituent can be the same or different from the other(s). As another example, for the group —(CR$^8$R$^9$)$_2$—, each occurrence of the two R$^8$ groups may be the same or different. As used herein, unless explicitly stated to the contrary, each reference to a specific compound of the present invention or a generic formula of compounds of the present invention is intended to include the compound(s) as well as pharmaceutically acceptable salts thereof.

Optical Isomers—Diastereomers—Geometric Isomers—Tautomers

Compounds of formula I may contain one or more asymmetric centers and could thus occur as racemates and racemic mixtures, single enantiomers, diastereomeric mixtures and individual diastereomers. Furthermore, compounds of formula I may contain one or more chiral axes, such as about a biaryl bond, and could thus occur as stable isolable atropisomers or as atropisomeric mixtures. The present invention is meant to comprehend all such isomeric forms of the compounds of formula I, either as single species or mixtures thereof.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of formula I.

Compounds of formula I may be separated into their individual diastereoisomers by, e.g., fractional crystallization from suitable solvents, e.g., methylene chloridehexanes or EtOAc/hexanes, or via chiral chromatography using an optically active stationary phase. Absolute stereochemistry may be determined by X-ray crystallography of crystalline products or crystalline intermediates which are derivatized, if necessary, with a reagent containing a stereogenic center of known configuration. Alternatively, any stereoisomer of a compound of this invention may be obtained by stereospecific synthesis using optically pure starting materials or reagents of known absolute configuration.

Compounds of the formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent. Alternatively, any enantiomer of a compound of the general formula I may be obtained by stereospecific synthesis using optically pure starting materials, intermediates or reagents of known configuration. Absolute stereochemistry may be determined by X-ray crystallography of crystalline products or crystalline intermediates which are derivatized, if necessary, with a reagent containing a stereogenic center of known configuration.

Salts

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylene-diamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, unless otherwise specified, references to the compound of formula I subsets thereof, embodiments thereof, as well as specific compounds are meant to also include the pharmaceutically acceptable salts.

Furthermore, some of the crystalline forms for compounds of the present invention may exist as polymorphs and as such all forms are intended to be included in the present invention. In addition, some of the compounds of the instant invention may form solvates with water (hydrates) or common organic solvents. Such solvates are encompassed within the scope of this invention.

Labelled Compounds

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Utilities

Compound of formula I or its pharmaceutically acceptable salts and pharmaceutical compositions can be used to treat or prevent a variety of conditions or diseases mediated by Janus kinases, in particular diseases or conditions that can be ameliorated by the inhibition of a Janus kinase such as JAK1, JAK2 or JAK3, in particular JAK3. Such conditions and diseases include, but are not limited to: (1) arthritis, including rheumatoid arthritis, juvenile arthritis, and psoriatic arthritis; (2) asthma and other obstructive airways diseases, including chronic asthma, late asthma, airway hyper-responsiveness, bronchitis, bronchial asthma, allergic asthma, intrinsic asthma, extrinsic asthma, dust asthma, recurrent airway obstruction, and chronic obstruction pulmonary disease including emphysema; (3) autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, rheumatoid arthritis, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be B-cell (humoral) based or T-cell based, including Cogan's syndrome, ankylosing spondylitis, Wegener's granulomatosis, autoimmune alopecia, Type I or juvenile onset diabetes, and thyroiditis; (4) cancers or tumors, including alimentary gastrointestinal tract cancer, colon cancer, liver cancer, skin cancer including mast cell tumor and squamous cell carcinoma, breast and mammary cancer, ovarian cancer, prostate cancer, lymphoma, leukemia, including acute myelogenous leukemia and chronic myelogenous leukemia, kidney cancer, lung cancer, muscle cancer, bone cancer, bladder cancer, brain cancer, melanoma including oral and metastatic melanoma, Kaposi's sarcoma, myelomas including multiple myeloma, myeloproliferative disorders, proliferative diabetic retinopathy, and angiogenic-associated disorders including solid tumors; (5) diabetes, including Type I diabetes and complications from diabetes; (6) eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization; (7) intestinal inflammations, allergies or conditions including Crohn's disease and/or ulcerative colitis, inflammatory bowel disease, coeliac diseases, proctitis, eosinophilic gastroenteritis, and mastocytosis; (8) neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemicreperfusion injury in stroke, myocardial ischemica, renal ischemia, heart attacks, cardiac hypertrophy, atherosclerosis and arteriosclerosis, organ hypoxia, and platelet aggregation; (9) skin diseases, conditions or disorders including atopic dermatitis, eczema, psoriasis, scleroderma, pruritus and other pruritic conditions; (10) allergic reactions including anaphylaxis, allergic rhinitis, allergic dermatitis, allergic urticaria, angioedema, allergic asthma, or allergic reaction to insect bites, food, drugs, or pollen; (11) transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, and xeno transplantation.

Accordingly, another aspect of the present invention provides a method for the treatment or prevention of a JAK3-mediated disease or disorder comprising administering to a mammal in need thereof a therapeutically effective amount of a compound of formula I. In one embodiment such diseases include asthma and rheumatoid arthritis.

Another aspect of the present invention provides for the use of a compound of formula I in the manufacture of a medicament for the treatment or prevention of a JAK3-mediated diseases or disorder.

Dose Ranges

The magnitude of prophylactic or therapeutic dose of a compound of formula I will, of course, vary with the nature and the severity of the condition to be treated and with the particular compound of formula I and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration of humans may contain from 0.05 mg to 5 g of active agent compounded with an appropriate and convenient amount of carrier material which may vary from about 5 to about 99.95 percent of the total composition. Dosage unit forms will generally contain between from about 0.1 mg to about 0.4 g of an active ingredient, typically 0.5 mg, 1 mg, 2 mg, 5 mg, 10 mg, 25 mg, 50 mg, 100 mg, 200 mg, or 400 mg.

Pharmaceutical Compositions

Another aspect of the present invention provides pharmaceutical compositions comprising a compound of formula I with a pharmaceutically acceptable carrier. For the treatment of any of the prostanoid mediated diseases compounds of formula I may be administered orally, by inhalation spray, topically, parenterally or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these.

Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Dosage forms for inhaled administration may conveniently be formulated as aerosols or dry powders. For compositions suitable and/or adapted for inhaled administration, it is preferred that the active substance is in a particle-size-reduced form, and more preferably the size-reduced form is obtained or obtainable by micronization.

In one embodiment the medicinal preparation is adapted for use with a pressurized metered dose inhaler (pMDI) which releases a metered dose of medicine upon each actuation. The formulation for pMDIs can be in the form of solutions or suspensions in halogenated hydrocarbon propellants. The type of propellant being used in pMDIs is being shifted to hydrofluoroalkanes (HFAs), also known as hydrofluorocarbons (HFCs). In particular, 1,1,1,2-tetrafluoroethane (HFA 134a) and 1,1,1,2,3,3,3-heptafluoropropane (HFA 227) are used in several currently marketed pharmaceutical inhalation products. The composition may include other pharmaceutically acceptable excipients for inhalation use such as ethanol, oleic acid, polyvinylpyrrolidone and the like.

Pressurized MDIs typically have two components. Firstly, there is a canister component in which the drug particles are stored under pressure in a suspension or solution form. Secondly, there is a receptacle component used to hold and actuate the canister. Typically, a canister will contain multiple doses of the formulation, although it is possible to have single dose canisters as well. The canister component typically includes a valve outlet from which the contents of the canister can be discharged. Aerosol medication is dispensed from the pMDI by applying a force on the canister component to push it into the receptacle component thereby opening the valve outlet and causing the medication particles to be conveyed from the valve outlet through the receptacle component and discharged from an outlet of the receptacle. Upon discharge from the canister, the medication particles are "atomized", forming an aerosol. It is intended that the patient coordinate the discharge of aerosolized medication with his or her inhalation, so that the medication particles are entrained in the patient's aspiratory flow and conveyed to the lungs. Typically, pMDIs use propellants to pressurize the contents of the canister and to propel the medication particles out of the outlet of the receptacle component. In pMDIs, the formulation is provided in a liquid or suspension form, and resides within the container along with the propellant. The propellant can take a variety of forms. For example, the propellant can comprise a compressed gas or liquefied gas.

In another embodiment the medicinal preparation is adapted for use with a dry powder inhaler (DPI). The inhalation composition suitable for use in DPIs typically comprises particles of the active ingredient and particles of a pharmaceutically acceptable carrier. The particle size of the active material may vary from about 0.1 µm to about 10 µM; however, for effective delivery to the distal lung, at least 95 percent of the active agent particles are 5 µm or smaller. Each of the active agent can be present in a concentration of 0.01-99%. Typically however, each of the active agents is present in a concentration of about 0.05 to 50%, more typically about 0.2-20% of the total weight of the composition.

As noted above, in addition to the active ingredients, the inhalable powder preferably includes pharmaceutically acceptable carrier, which may be composed of any pharmacologically inert material or combination of materials which is acceptable for inhalation. Advantageously, the carrier particles are composed of one or more crystalline sugars; the carrier particles may be composed of one or more sugar alcohols or polyols. Preferably, the carrier particles are particles of dextrose or lactose, especially lactose. In embodiments of the present invention which utilize conventional dry powder inhalers, such as the Handihaler, Rotohaler, Diskhaler, Twisthaler and Turbohaler, the particle size of the carrier particles may range from about 10 microns to about 1000 microns. In certain of these embodiments, the particle size of the carrier particles may range from about 20 microns to about 120 microns. In certain other embodiments, the size of at least 90% by weight of the carrier particles is less than 1000 microns and preferably lies between 60 microns and 1000 microns. The relatively large size of these carrier particles gives good flow and entrainment characteristics. Where present, the amount of carrier particles will generally be up to 95%, for example, up to 90%, advantageously up to 80% and preferably up to 50% by weight based on the total weight of the powder. The amount of any fine excipient material, if present, may be up to 50% and advantageously up to 30%, especially up to 20%, by weight, based on the total weight of the powder. The powder may optionally contain a performance modifier such as L-leucine or another amino acid, and/or metals salts of stearic acid such as magnesium or calcium stearate.

Compounds of formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the compound of formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Combinations with Other Drugs

For the treatment and prevention of JAK mediated diseases, compound of formula I may be co-administered with other therapeutic agents. Thus in another aspect the present invention provides pharmaceutical compositions for treating JAK mediated diseases comprising a therapeutically effective amount of a compound of formula I and one or more other therapeutic agents. In particular, for the treatment of the inflammatory diseases rheumatoid arthritis, psoriasis, inflammatory bowel disease, COPD, asthma and allergic rhinitis a compound of formula I may be combined with agents such as: (1) TNF-α inhibitors such as Remicade® and Enbrel®); (2) non-selective COX-ICOX-2 inhibitors (such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including low dose methotrexate, lefunomide, ciclesonide, hydroxychloroquine, d-penicillamine, auranofin or parenteral or oral gold; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast; (8) antihistaminic H1 receptor antagonists such as cetirizine, loratadine, desloratadine, fexofenadine, astemizole, azelastine, and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclindinium bromide, glycopyrrolate, pirenzepine, and telenzepine; (11) β-adrenoceptor agonists such as metaproterenol, isoproterenol, isoprenaline, albuterol, salbutamol, formoterol, salmeterol, terbutaline, orciprenaline, bitolterol mesylate, and pirbuterol, or methylxanthanines including theophylline and aminophylline, sodium cromoglycate; (12) insulin-like growth factor type I (IGF-1) mimetic; (13) inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate.

SCHEMES AND EXAMPLES

The abbreviations used herein have the following tabulated meanings. Abbreviations not tabulated below have their meanings as commonly used unless specifically stated otherwise.

| | |
|---|---|
| ACN | acetonitrile |
| MeCN | acetonitrile |
| BAST | bis(2-methoxyethyl)aminosulfur trifluoride |
| Chiral SFC | chiral super critical fluid chromatography |
| $CO_2$ | carbon dioxide |
| $Cs_2CO_3$ | cesium carbonate |
| DBU | 1,8-diazabicyclo[5.4.0]undec-7-ene |
| DCE | 1,2-dichloroethane |
| DCM | dichloromethane |
| DIPEA | N,N-diisopropylethylamine |
| DMF | N,N-dimethylformamide |
| DMSO | dimethyl sulfoxide |
| DSC | N,N-disuccinimidyl carbonate |
| EDC | 3-(ethyliminomethyleneamino)-N,N-dimethyl-propan-1-amine |
| EtOAc | ethyl acetate |
| ESI | electrospray ionization |
| HATU | O-(7-aza-1H-benzotriazol-1-yl)-N,N,N',N'-tetramethyluronium hexafluorophosphate |
| HCl | hydrogen chloride |
| HOBt | 1-hydroxybenzotriazole |
| HPLC | high pressure liquid chromatography |
| IPA | 2-propanol |
| LDA | lithium diisopropylamide |
| mCPBA | meta-chloroperoxybenzoic acid |
| LRMS | low resolution mass spectrometry |
| MeI | iodomethane |
| Me-THF | 2-methyltetrahydrofuran |
| $MgSO_4$ | magnesium sulfate |
| MP-(OAc)$_3$BH | solid supported (macro porous) triacetoxyborohydride |
| MPLC | medium pressure liquid chromatography |
| NaH | sodium hydride |
| $Na_2SO_4$ | sodium sulfate |
| $NaBH_4$ | sodium borohydride |
| $NaHCO_3$ | sodium bicarbonate |
| NaOMe | sodium methoxide |
| $Pd_2(dba)_3$ | tris(dibenzylideneacetone)dipalladium(0) |
| $POCl_3$ | phosphorus (V) oxychloride |
| PyBOP | (7-azabenzotriazol-1-yloxy)tripyrrolidinophosphonium hexafluorophosphate |
| SEM-Cl | 2-(trimethylsilyl)ethoxymethyl chloride |
| SiliaCat ® DPP-Pd | silica bound diphenylphosphine palladium (II) |
| TBAF | tetra-n-butylammonium fluoride |
| TBS-Cl | tert-butyldimethylsilyl chloride |
| t-BuOH | tert-butanol |
| TEA | triethylamine |
| TFA | trifluoroacetic acid |
| THF | tetrahydrofuran |
| X-Phos | 2-dicyclohexylphosphino-2',4',6'-triisopropylbiphenyl |
| $^t$Bu-X-Phos | di-tert-butyl[2',4',6'-tri(propan-2-yl)biphenyl-2-yl]phosphane |
| NMO | 4-methylmorpholine-N-oxide |
| TPAP | tetra-n-propylammonium perruthenate (VII) |
| HCOOH | formic acid |
| K$^t$OBu | potassium tert-butoxide |
| $Na_2S_2O_5$ | sodium metabisulfite |
| NMR | nuclear magnetic reasonance |
| TLC | thin layer chromatography |
| (EtO)$_2$P(O)CH$_2$CN | diethyl (cyanomethyl)phosphonate |
| MsCl | methanesulfonyl chloride |
| TsOH | p-toluenesulfonic acid |
| KCN | potassium cyanide |
| PS | polystryene |
| TMS | trimethylsilane |
| CA | commercially available |
| BINAP | (R)-(+)-2,2'-bis(diphenylphosphino)-1,1'-binapthyl |
| MeOH | methanol |
| $NH_4Cl$ | ammonium chloride |
| MTBE | methyl t-butyl ether |
| KOH | potassium hydroxide |
| $KHSO_4$ | potassium hydrogen sulfate |
| NaOH | sodium hydroxide |
| DME | dimethoxyethane |
| THF | tetrahydrofuran |
| Tetrakis | tetrakis(triphenylphosphine)palladium(0) |
| RP-HPLC | reverse phase high pressure liquid chromatography |

Alkyl Group Abbreviations

| | |
|---|---|
| Me | methyl |
| Et | ethyl |
| n-Pr | normal propyl |
| i-Pr | isopropyl |
| n-Bu | normal butyl |
| i-Bu | isobutyl |
| s-Bu | secondary butyl |
| t-Bu | tertiary butyl |
| c-Pr | cyclopropyl |
| c-Bu | cyclobutyl |

-continued

| c-Pen | cyclopentyl |
| c-Hex | cyclohexyl |

Methods of Synthesis

The compounds of the present invention can be prepared according to the following general schemes using appropriate materials, and are further exemplified by the subsequent specific examples. The compounds illustrated in the examples are not to be construed as forming the only genus that is considered as the invention. The illustrative Examples below, therefore, are not limited by the compounds listed or by any particular substituents employed for illustrative purposes. Substituent numbering as shown in the schemes does not necessarily correlate to that used in the claims and often, for clarity, a single substituent is shown attached to the compound where multiple substituents are allowed under the definitions of the instant invention hereinabove.

Those skilled in the art will readily understand that known variations of the conditions and processes of the following preparative procedures can be used to prepare these compounds. The invention will now be illustrated in the following non-limiting Examples in which, unless otherwise stated: all reactions were stirred (mechanically, stir bar/stir plate, or shaken) and conducted under an inert atmosphere of nitrogen or argon unless specifically stated otherwise. All temperatures are degrees Celsius unless otherwise noted. Ambient temperature is 15-25° C.

Most compounds were purified by reverse-phase preparative HPLC, MPLC on silica gel, recrystallization and/or swish (suspension in a solvent followed by filtration of the solid). The course of the reactions was followed by thin layer chromatography (TLC) and/or LCMS and/or NMR and reaction times are given for illustration only. All end products were analyzed by NMR and LCMS. Intermediates were analyzed by NMR and/or TLC and/or LCMS.

Pyrrolopyrimidine Intermediates

Ethyl
4-chloro-7H-pyrrolo[2,3-d]pyrimidine-5-carboxylate
(I-1)

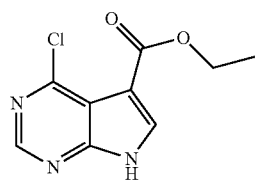

Step 1:
5-Bromo-4-chloro-7H-pyrrolo[2,3-d]pyrimidine

To a magnetically stirred solution of 4-chloropyrrolo(2,3-d)pyrimidine (30.0 g, 195 mmol) in acetonitrile (300 mL) at 85° C. was added N-bromosuccinimide (34.8 g, 195 mmol) portion-wise during a period of 10 minutes and the reaction mixture was stirred at 40° C. for 1 hour, then at room temperature for another 30 minutes. The reaction progress was monitored by TLC using 30% ethyl acetate in petroleum ether with iodine and 254 nm UV light to visualize the spot. The reaction mixture was allowed to stand for 1 hour so that precipitation occurred completely. The resulting solid was filtered and washed with chilled water (250 mL), then dried under high vacuum to give 5-bromo-4-chloro-7H-pyrrolo[2,3-d]pyrimidine as brown solid. LRMS (ESI) calc'd for $C_6H_4BrClN_3$ $[M+H]^+$, 232; found 232. $^1$H NMR (400 MHz, DMSO-$D_6$,) δ: 12.98 (s, 1 H), 8.60 (s, 1H), 7.96 (d, J=2.4 Hz, 1H).

Step 2: Ethyl
4-chloro-7H-pyrrolo[2,3-d]pyrimidine-5-carboxylate

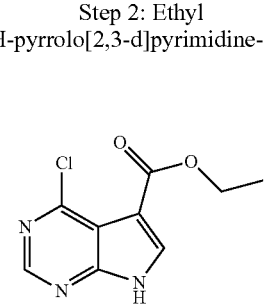

To a solution of 5-bromo-4-chloro-7H-pyrrolo[2,3-d]pyrimidine (40.0 g, 173 mmol) in dry tetrahydrofuran (700 mL) at −78° C. was added n-butyl lithium (195 mL, 2.5 M solution in hexane, 487 mmol) over the period of 2 hours. The reaction mixture was stirred for another 30 minutes at −78° C., after which ethyl chloroformate (17.8 mL, 186 mmol) was added over 30 minutes. The reaction mixture was stirred for 2 hours at −60° C. and then the temperature was slowly increased to 30° C. The reaction mixture was allowed to stir for 12 hours at 30° C. The progress of the reaction was monitored by TLC using 25% ethyl acetate in petroleum ether using iodine and 254 nm UV light to visualize the spot. The reaction mixture was then quenched with saturated solution of ammonium chloride (200 mL) at 0° C. and the reaction mixture was extracted with ethyl acetate (×3). The combined organic layers were washed with water, dried over anhydrous sodium sulfate, filtered and concentrated under reduced pressure to afford a crude reaction mixture. The residue was purified by chromatography on silica eluting with 5-100% ethyl acetate/petroleum ether to afford ethyl 4-chloro-7H-pyrrolo[2,3-d]pyrimidine-5-carboxylate as pale yellow solid. LRMS (ESI) calc'd for $C_9H_7ClN_3O_2$ $[M-H]^+$: 224. found 224. $^1$H NMR (400 MHz, DMSO-$D_6$): δ 13.28 (s, 1H), 8.70 (s, 1H), 8.39 (s, 1H), 4.31 (q, J=7.2, 6.8 Hz, 2H), 1.34 (t, J=7.6, 6.8 Hz, 3H).

Ethyl-4-chloro-7-((2-(trimethylsilyl)ethoxy)methyl)-7H-pyrrolo[2,3-d]pyrimidine-5-carboxylate (I-2)

To a stirred mixture of ethyl 4-chloro-7H-pyrrolo[2,3-d]pyrimidine-5-carboxylate (4.00 g, 17.7 mmol) and SEMCl (4.71 mL, 26.6 mmol) in DMF (90 mL) was added sodium hydride (0.851 g, 21.3 mmol) portion-wise at 0° C. The resulting yellow suspension was stirred at 0° C. for one hour and then allowed to warm to room temperature over one hour. The reaction was quenched with water slowly then extracted with ethyl acetate (×3). The combined organic layers were washed with brine (150 mL), dried over sodium sulfate, filtered and concentrated under reduced pressure. The residue was purified by chromatography on silica eluting with 0-50% ethyl acetatehexane to afford ethyl-4-chloro-7-((2-(trimethylsilyl)ethoxy)methyl)-7H-pyrrolo[2,3-d]pyrimidine-5-carboxylate. LRMS (ESI) calc'd for $C_{15}H_{23}ClN_3O_3Si$ [M+H]$^+$: 356; found 356.

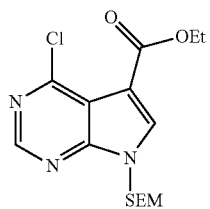 [SMILES: CCOC(=O)c1cn(COCC[Si](C)(C)C)c2ncnc(Cl)c12]

Example 1

General Scheme A:

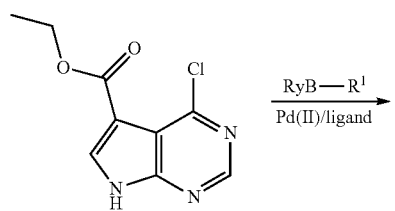

Examples Generated Via General Scheme A

Example 1-1

Ethyl 4-phenyl-7H-pyrrolo[2,3-d]pyrimidine-5-carboxylate

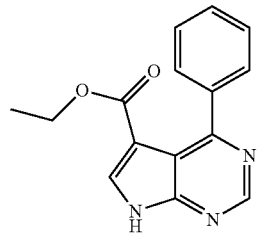 [SMILES: CCOC(=O)c1c[nH]c2ncnc(-c3ccccc3)c12]

Ethyl 4-chloro-7H-pyrrolo[2,3-d]pyrimidine-5-carboxylate (50.0 mg, 0.222 mmol), phenyl boronic acid (32.4 mg, 0.266 mmol) and potassium carbonate (0.332 mL, 0.665 mmol) were added to tetrahydrofuran (1.5 mL) in a microwave vial. The solution was purged with nitrogen for 5 minutes and PdCl$_2$(dppf)-CH$_2$Cl$_2$ (18 mg, 0.022 mmol) was then added. The reaction was sealed and heated at 125° C. by microwave irradiation for 30 minutes. The reaction mixture was diluted with EtOAc and washed with saturated sodium bicarbonate, dried over sodium sulfate, filtered and concentrated under reduced pressure. Purification of desired product was carried out by reverse phase HPLC using an acetonitrile gradient in water with 0.1% TFA modifier. Pure fractions were pooled and concentrated under reduced pressure. Saturated aqueous sodium bicarbonate and EtOAc were added to the residue. The organic layer was separated and the aqueous layer was then extracted with EtOAc (×3). The combined organic layers were then washed with brine, dried over sodium sulfate, filtered and concentrated under reduced pressure to afford the product as a solid. LRMS (ESI) calc'd for $C_{15}H_{14}ClN_3O_2$ [M+H]$^+$: 268, found 268. $^1$H NMR (600 MHz, DMSO-D$_6$) δ 13.01 (s, 1H), 8.91 (s, 1H), 8.30 (s, 1H), 7.63 (m, 2H), 7.49 (m, 3H), 3.82 (q, 2H, J=7.04 Hz), 0.78 (t, 3H, J=7.04 Hz).

Example 1-2

Ethyl 4-(4-chlorophenyl)-7H-pyrrolo[2,3-d]pyrimidine-5-carboxylate (1-2)

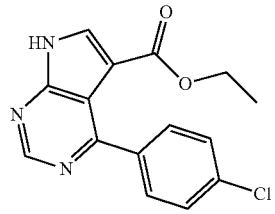 [SMILES: CCOC(=O)c1c[nH]c2ncnc(-c3ccc(Cl)cc3)c12]

A mixture of phenyl boronic acid (17 mg, 0.20 mmol), ethyl 4-chloro-7H-pyrrolo[2,3-d]pyrimidine-5-carboxylate (30 mg, 0.13 mmol), sodium carbonate (70.5 mg, 0.665 mmol) and SiliaCat® Heterogeneous Catalysts DPP-Pd (loading=0.28 mmol/g, 95 mg, 0.27 mmol) in dioxane (1.1 mL) and water (0.2 mL) was heated to 170° C. under micro-

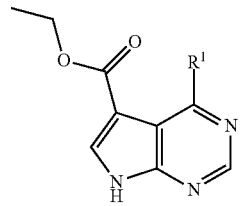

wave irradiation for 15 minutes. The reaction mixture was concentrated, redissolved in DMSO, and filtered through a fritted funnel (washed with DMSO). The solution was further concentrated, redissolved to 1 mL of DMSO and purified by mass-triggered reverse-phase HPLC using an ACN/water gradient (0.1% trifluoroacetic acid as an acid modifier) to afford ethyl 4-(4-chlorophenyl)-7H-pyrrolo[2,3-d]pyrimidine-5-carboxylate. LRMS (ESI) calc'd for $C_{15}H_{13}ClN_3O_2$ [M+H]$^+$: 302, found 302. $^1$H NMR (600 MHz, DMSO-D$_6$, water presat) δ 8.87 (s, 1H); 8.29 (s, 1H); 7.60 (d, 2H, J=7 Hz), 7.50 (d, 2H, J=7 Hz); 3.87 (q, 2H, J=6 Hz); 0.85 (t, 3H, J=6 Hz).

Example 1-3

Ethyl 4-(3-aminophenyl)-7H-pyrrolo[2,3-d]pyrimidine-5-carboxylate (1-3)

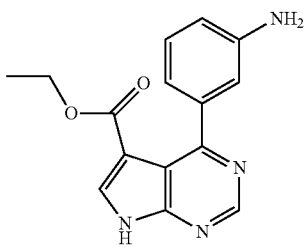 [SMILES: CCOC(=O)c1c[nH]c2ncnc(-c3cccc(N)c3)c12]

Step 1: Ethyl 4-(3-nitrophenyl)-7H-pyrrolo[2,3-d]pyrimidine-5-carboxylate

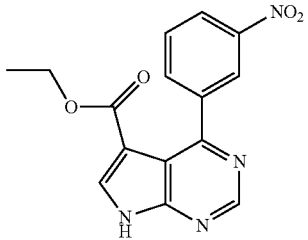 [SMILES: CCOC(=O)c1c[nH]c2ncnc(-c3cccc([N+](=O)[O-])c3)c12]

To ethyl 4-chloro-7H-pyrrolo[2,3-d]pyrimidine-5-carboxylate (10.0 g, 44.3 mmol), (3-nitrophenyl)boronic acid (11.8 g, 70.9 mmol), PdCl$_2$(dppf)-CH$_2$Cl$_2$ (3.62 g, 4.43 mmol) and aqueous sodium carbonate (2 M solution, 55.4 mL, 111 mmol) in a flask was added DMF (148 mL). The mixture was degassed for 10 minutes then heated at 115° C. for 1.5 hours. The reaction was cooled to ambient temperature, then water was added and the mixture was extracted with DCM (×3) and EtOAc (×1). The combined organics were concentrated, diluted with EtOAc (300 mL) and washed with sorbitol/Na$_2$CO$_3$ solution to remove excess boronic acid. The aqueous layer was extracted with EtOAc (×4). The combined organics were concentrated after which EtOAc and hexanes were added with stirring. The resulting precipitate was filtered to give solid product that was further triturated with DCM and hexanes to give ethyl 4-(3-nitrophenyl)-7H-pyrrolo[2,3-d]pyrimidine-5-carboxylate. The combined organic fractions were concentrated under reduced pressure to give a residue containing product and DMF. Addition of MeOH and water led to formation of a precipitate which was filtered to afford additional ethyl 4-(3-nitrophenyl)-7H-pyrrolo[2,3-d]pyrimidine-5-carboxylate. LRMS (ESI) calc'd for $C_{15}H_{13}N_4O_4$ [M+H]$^+$: 313, found 313. $^1$H NMR (600 MHz, DMSO-D6) δ 13.17 (s, 1H), 8.99 (s, 1H), 8.43 (s, 1H), 8.39-8.36 (m, 2H), 8.12 (d, J=7.8 Hz, 1H), 7.79 (t, J=7.8 Hz, 1H), 3.93 (q, J=7.2 Hz, 2H), 0.95 (t, J=7.2 Hz, 3H).

Step 2: Ethyl 4-(3-aminophenyl)-7H-pyrrolo[2,3-d]pyrimidine-5-carboxylate

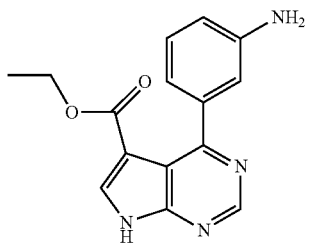 [SMILES: CCOC(=O)c1c[nH]c2ncnc(-c3cccc(N)c3)c12]

To ethyl 4-(3-nitrophenyl)-7H-pyrrolo[2,3-d]pyrimidine-5-carboxylate (7.60 g, 24.3 mmol) in methanol (40.6 mL) and CH$_2$Cl$_2$ (40.6 mL) was added 3% Pt on carbon doped with 0.6% V (4.75 g, 0.730 mmol) and the mixture was stirred under a H$_2$ balloon overnight. The mixture was filtered with celite and washed with DCM and MeOH solution to give ethyl 4-(3-aminophenyl)-7H-pyrrolo[2,3-d]pyrimidine-5-carboxylate after removal of solvent. LRMS (ESI) calc'd for $C_{15}H_{15}N_4O_2$ [M+H]$^+$: 283, found 283. $^1$H NMR (600 MHz, DMSO-D6) δ 12.85 (s, 1H), 8.85 (s, 1H), 8.22 (s, 1H), 7.09 (t, J=7.8 Hz, 1H), 6.90 (s, 1H), 6.71 (d, J=7.2 Hz, 1H), 6.67 (d, J 6.0 Hz, 1H), 5.17 (s, 2H, NH$_2$), 3.86 (q, J=7.2 Hz, 2H), 0.84 (t, J=7.2 Hz, 3H).

Example 1-4

Prop-2-en-1-yl 4-(2-methyl-2H-indazol-6-yl)-7H-pyrrolo[2,3-d]pyrimidine-5-carboxylate (1-4)

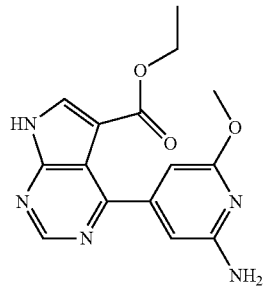 [SMILES: CCOC(=O)c1c[nH]c2ncnc(-c3cc(N)nc(OC)c3)c12]

Step 1: Ethyl 4-(2-amino-6-methoxypyridin-4-yl)-7-{[2-(trimethylsilyl)ethoxy]methyl}-7H-pyrrolo[2,3-d]pyrimidine-5-carboxylate

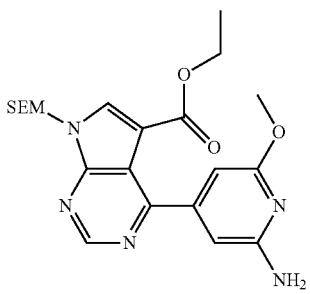 [SMILES: CCOC(=O)c1cn(COCC[Si](C)(C)C)c2ncnc(-c3cc(N)nc(OC)c3)c12]

The title compound was prepared in an analogous manner to Example 1-2, using ethyl 4-chloro-7-{[2-(trimethylsilyl)ethoxy]methyl}-7H-pyrrolo[2,3-d]pyrimidine-5-carboxylate to afford the desired product. LRMS (ESI) calc'd for $C_{21}H_{30}N_5O_4Si$ [M+H]+: 444, found 444.

Step 2: Prop-2-en-1-yl 4-(2-methyl-2H-indazol-6-yl)-7H-pyrrolo[2,3-d]pyrimidine-5-carboxylate Ethyl 4-(2-amino-6-methoxypyridin-4-yl)-7-{[2-(trimethylsilyl)ethoxy]methyl}-7H-pyrrolo[2,3-d]pyrimidine-5-carboxylate (50 mg, 0.11 mmol) was dissolved in DCM (0.5 mL) and then TFA (0.5 mL, 6.5 mmol) was added and the solution was stirred for 2 hours at room temperature before being concentrated in vacuo. Acetonitrile (1.0 mL) and ammonium hydroxide (1.0 mL, 7.2 mmol) were added to the residue and the solution was stirred at room temperature for 1 hour. The reaction was concentrated in vacuo and purified by reverse phase HPLC using an acetonitrile gradient in water with 0.1% TFA modifier. The pure fractions were pooled and lyophilized to give the desired product as the TFA salt. LRMS (ESI) calc'd for $C_{15}H_{16}N_5O_3$ [M+H]+: 314, found 314. $^1$H NMR (600 MHz, DMSO-D6) δ 13.11 (s, 1H), 8.96 (s, 1H), 8.37 (d, 1H, J=2.8 Hz), 6.33 (s, 1H), 6.16 (s, 1H), 4.00 (q, 2H, J=7.2 Hz), 3.86 (s, 3H), 1.02 (t, 3H, J=7.2 Hz).

The following examples, 1-5 through 1-110, as shown in Table 1, were prepared in an analogous manner of that described above using materials that are commercially available or known, or that can be prepared using procedures known in the art or by generally following procedures described herein for various intermediates.

TABLE 1

| Example Number | Structure | IUPAC Name | Exact Mass [M + H]+ |
| --- | --- | --- | --- |
| 1-5 | 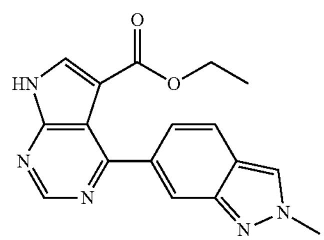 [SMILES: CCOC(=O)c1c[nH]c2ncnc(-c3ccc4cn(C)nc4c3)c12] | ethyl 4-(2-methyl-2H-indazol-6-yl)-7H-pyrrolo[2,3-d]pyrimidine-5-carboxylate | Calc'd 322, found 322 |
| 1-6 | 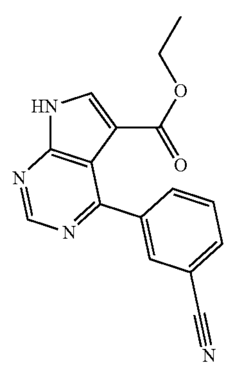 [SMILES: CCOC(=O)c1c[nH]c2ncnc(-c3cccc(C#N)c3)c12] | ethyl 4-(3-cyanophenyl)-7H-pyrrolo[2,3-d]pyrimidine-5-carboxylate | Calc'd 293, found 293 |
| 1-7 | 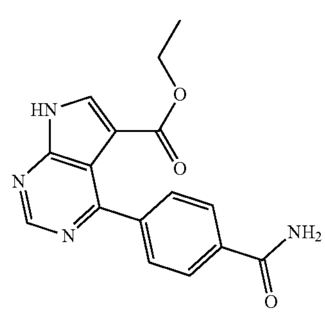 [SMILES: CCOC(=O)c1c[nH]c2ncnc(-c3ccc(C(N)=O)cc3)c12] | ethyl 4-(4-carbamoylphenyl)-7H-pyrrolo[2,3-d]pyrimidine-5-carboxylate | Calc'd 311, found 311 |

TABLE 1-continued

| Example Number | Structure | IUPAC Name | Exact Mass [M + H]+ |
|---|---|---|---|
| 1-8 | 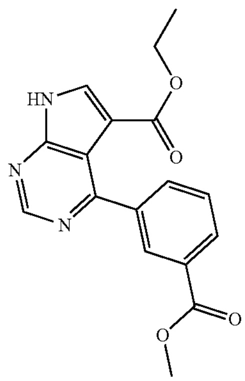 [SMILES: CCOC(=O)c1c[nH]c2ncnc(-c3cccc(C(=O)OC)c3)c12] | ethyl 4-[3-(methoxycarbonyl)phenyl]-7H-pyrrolo[2,3-d]pyrimidine-5-carboxylate | Calc'd 326, found 326 |
| 1-9 | 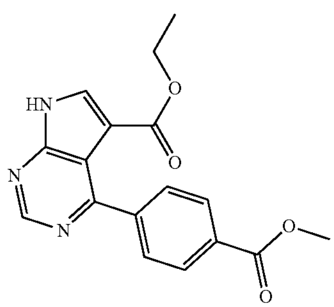 [SMILES: CCOC(=O)c1c[nH]c2ncnc(-c3ccc(C(=O)OC)cc3)c12] | ethyl 4-[4-(methoxycarbonyl)phenyl]-7H-pyrrolo[2,3-d]pyrimidine-5-carboxylate | Calc'd 326, found 326 |
| 1-10 | 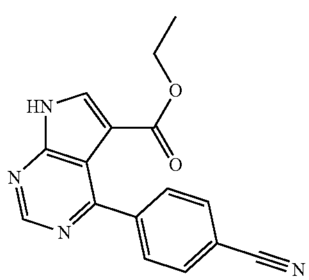 [SMILES: CCOC(=O)c1c[nH]c2ncnc(-c3ccc(C#N)cc3)c12] | ethyl 4-(4-cyanophenyl)-7H-pyrrolo[2,3-d]pyrimidine-5-carboxylate | Calc'd 293, found 293 |
| 1-11 | 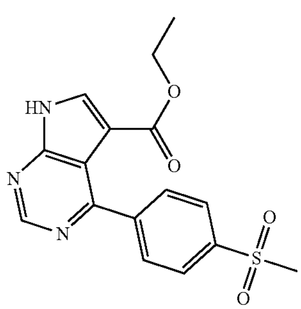 [SMILES: CCOC(=O)c1c[nH]c2ncnc(-c3ccc(S(C)(=O)=O)cc3)c12] | ethyl 4-[4-(methylsulfonyl)phenyl]-7H-pyrrolo[2,3-d]pyrimidine-5-carboxylate | Calc'd 346, found 346 |

TABLE 1-continued

| Example Number | Structure | IUPAC Name | Exact Mass [M + H]+ |
|---|---|---|---|
| 1-12 | 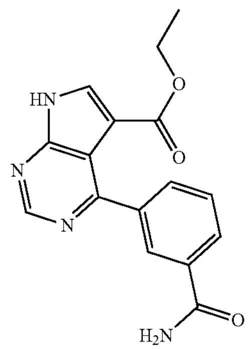 [SMILES: CCOC(=O)c1c[nH]c2ncnc(-c3cccc(C(N)=O)c3)c12] | ethyl 4-(3-carbamoylphenyl)-7H-pyrrolo[2,3-d]pyrimidine-5-carboxylate | Calc'd 311, found 311 |
| 1-13 | 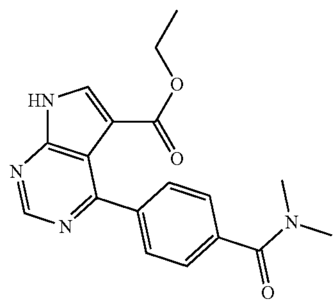 [SMILES: CCOC(=O)c1c[nH]c2ncnc(-c3ccc(C(=O)N(C)C)cc3)c12] | ethyl 4-[4-(dimethylcarbamoyl)phenyl]-7H-pyrrolo[2,3-d]pyrimidine-5-carboxylate | Calc'd 339, found 339 |
| 1-14 | 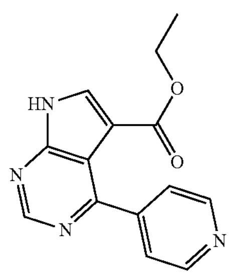 [SMILES: CCOC(=O)c1c[nH]c2ncnc(-c3ccncc3)c12] | ethyl 4-pyridin-4-yl-7H-pyrrolo[2,3-d]pyrimidine-5-carboxylate | Calc'd 269, found 269 |
| 1-15 | 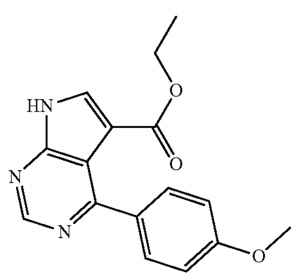 [SMILES: CCOC(=O)c1c[nH]c2ncnc(-c3ccc(OC)cc3)c12] | ethyl 4-(4-methoxyphenyl)-7H-pyrrolo[2,3-d]pyrimidine-5-carboxylate | Calc'd 298, found 298 |
| 1-16 | 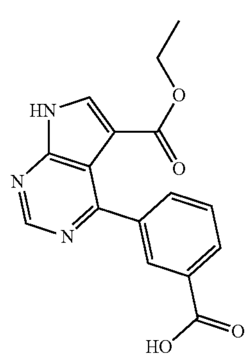 [SMILES: CCOC(=O)c1c[nH]c2ncnc(-c3cccc(C(=O)O)c3)c12] | 3-[5-(ethoxycarbonyl)-7H-pyrrolo[2,3-d]pyrimidin-4-yl]benzoic acid | Calc'd 312, found 312 |

TABLE 1-continued

| Example Number | Structure | IUPAC Name | Exact Mass [M + H]+ |
|---|---|---|---|
| 1-17 | 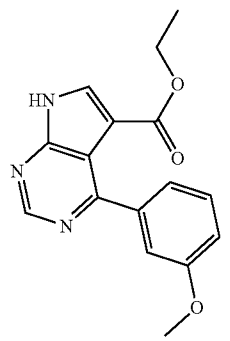 [SMILES: CCOC(=O)c1c[nH]c2ncnc(-c3cccc(OC)c3)c12] | ethyl 4-(3-methoxyphenyl)-7H-pyrrolo[2,3-d]pyrimidine-5-carboxylate | Calc'd 298, found 298 |
| 1-18 | 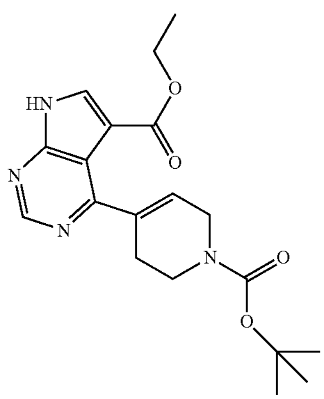 [SMILES: CCOC(=O)c1c[nH]c2ncnc(C3=CCN(C(=O)OC(C)(C)C)CC3)c12] | ethyl 4-[1-(tert-butoxycarbonyl)-1,2,3,6-tetrahydropyridin-4-yl]-7H-pyrrolo[2,3-d]pyrimidine-5-carboxylate | Calc'd 373, found 373 |
| 1-19 | 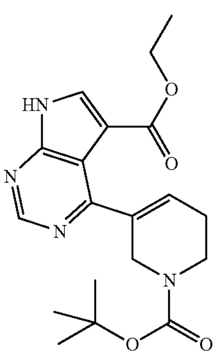 [SMILES: CCOC(=O)c1c[nH]c2ncnc(C3=CCCN(C(=O)OC(C)(C)C)C3)c12] | ethyl 4-[1-(tert-butoxycarbonyl)-1,2,5,6-tetrahydropyridin-3-yl]-7H-pyrrolo[2,3-d]pyrimidine-5-carboxylate | Calc'd 373, found 373 |
| 1-20 | 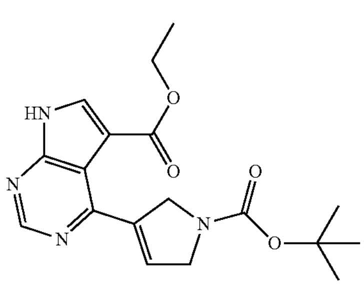 [SMILES: CCOC(=O)c1c[nH]c2ncnc(C3=CCN(C(=O)OC(C)(C)C)C3)c12] | ethyl 4-[1-(tert-butoxycarbonyl)-2,5-dihydro-1H-pyrrol-3-yl]-7H-pyrrolo[2,3-d]pyrimidine-5-carboxylate | Calc'd 359, found 359 |

TABLE 1-continued

| Example Number | Structure | IUPAC Name | Exact Mass [M + H]+ |
|---|---|---|---|
| 1-21 | 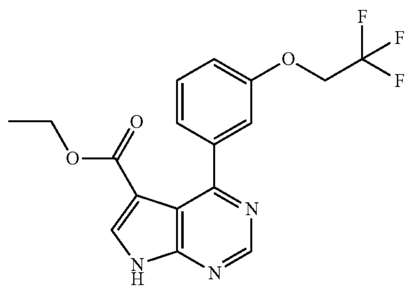 [SMILES: CCOC(=O)c1c[nH]c2ncnc(-c3cccc(OCC(F)(F)F)c3)c12] | ethyl 4-[3-(2,2,2-trifluoroethoxy)phenyl]-7H-pyrrolo[2,3-d]pyrimidine-5-carboxylate | Calc'd 366, found 366 |
| 1-22 | 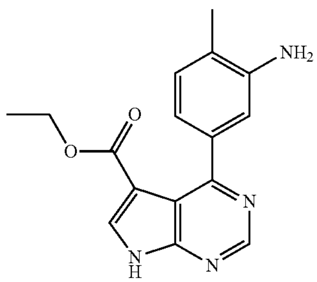 [SMILES: CCOC(=O)c1c[nH]c2ncnc(-c3ccc(C)c(N)c3)c12] | ethyl 4-(3-amino-4-methylphenyl)-7H-pyrrolo[2,3-d]pyrimidine-5-carboxylate | Calc'd 297, found 297 |
| 1-23 | 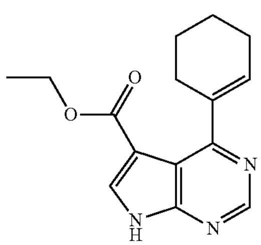 [SMILES: CCOC(=O)c1c[nH]c2ncnc(C3=CCCCC3)c12] | ethyl 4-cyclohex-1-en-1-yl-7H-pyrrolo[2,3-d]pyrimidine-5-carboxylate | Calc'd 272, found 272 |
| 1-24 | 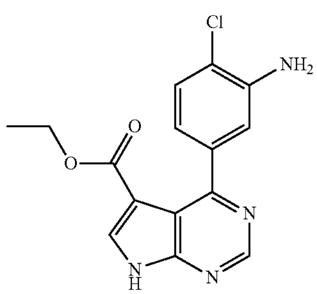 [SMILES: CCOC(=O)c1c[nH]c2ncnc(-c3ccc(Cl)c(N)c3)c12] | ethyl 4-(3-amino-4-chlorophenyl)-7H-pyrrolo[2,3-d]pyrimidine-5-carboxylate | Calc'd 317, found 317 |
| 1-25 | 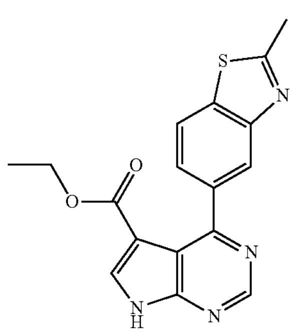 [SMILES: CCOC(=O)c1c[nH]c2ncnc(-c3ccc4sc(C)nc4c3)c12] | ethyl 4-(2-methyl-1,3-benzothiazol-5-yl)-7H-pyrrolo[2,3-d]pyrimidine-5-carboxylate | Calc'd 339, found 339 |

TABLE 1-continued

| Example Number | Structure | IUPAC Name | Exact Mass [M + H]+ |
|---|---|---|---|
| 1-26 | 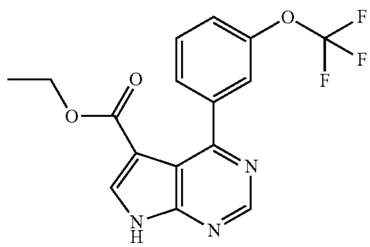 [SMILES: CCOC(=O)c1c[nH]c2ncnc(-c3cccc(OC(F)(F)F)c3)c12] | ethyl 4-[3-(trifluoromethoxy)phenyl]-7H-pyrrolo[2,3-d]pyrimidine-5-carboxylate | Calc'd 352, found 352 |
| 1-27 | 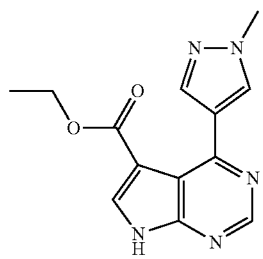 [SMILES: CCOC(=O)c1c[nH]c2ncnc(-c3cnn(C)c3)c12] | ethyl 4-(1-methyl-1H-pyrazol-4-yl)-7H-pyrrolo[2,3-d]pyrimidine-5-carboxylate | Calc'd 272, found 272 |
| 1-28 | 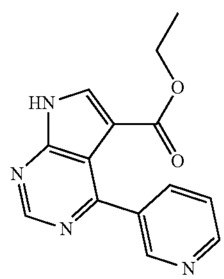 [SMILES: CCOC(=O)c1c[nH]c2ncnc(-c3cccnc3)c12] | ethyl 4-pyridin-3-yl-7H-pyrrolo[2,3-d]pyrimidine-5-carboxylate | Calc'd 269, found 269 |
| 1-29 | 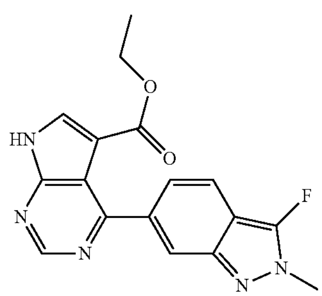 [SMILES: CCOC(=O)c1c[nH]c2ncnc(-c3ccc4c(F)n(C)nc4c3)c12] | ethyl 4-(3-fluoro-2-methyl-2H-indazol-6-yl)-7H-pyrrolo[2,3-d]pyrimidine-5-carboxylate | Calc'd 340, found 340 |
| 1-30 | 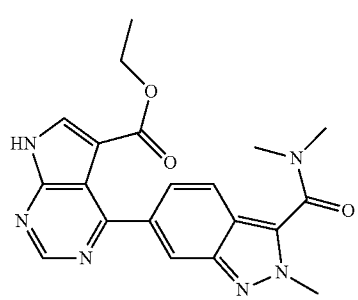 [SMILES: CCOC(=O)c1c[nH]c2ncnc(-c3ccc4c(C(=O)N(C)C)n(C)nc4c3)c12] | ethyl 4-[3-(dimethylcarbamoyl)-2-methyl-2H-indazol-6-yl]-7H-pyrrolo[2,3-d]pyrimidine-5-carboxylate | Calc'd 393, found 393 |

TABLE 1-continued

| Example Number | Structure | IUPAC Name | Exact Mass [M + H]+ |
|---|---|---|---|
| 1-31 | 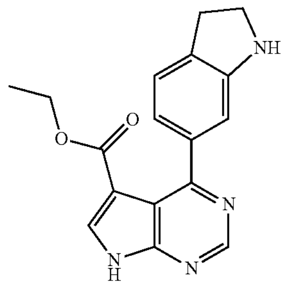 [SMILES: CCOC(=O)c1c[nH]c2ncnc(-c3ccc4c(c3)NCC4)c12] | ethyl 4-(2,3-dihydro-1H-indol-6-yl)-7H-pyrrolo[2,3-d]pyrimidine-5-carboxylate | Calc'd 309, found 309 |
| 1-32 | 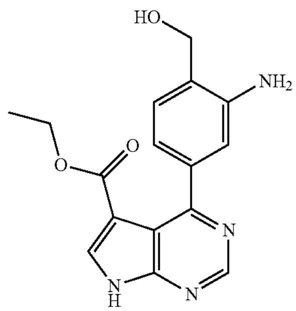 [SMILES: CCOC(=O)c1c[nH]c2ncnc(-c3ccc(CO)c(N)c3)c12] | ethyl 4-[3-amino-4-(hydroxymethyl)phenyl]-7H-pyrrolo[2,3-d]pyrimidine-5-carboxylate | Calc'd 313, found 313 |
| 1-33 | 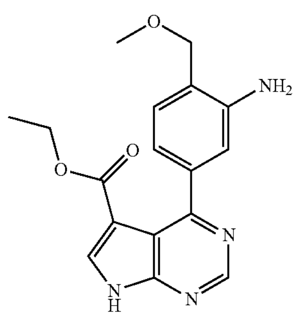 [SMILES: CCOC(=O)c1c[nH]c2ncnc(-c3ccc(COC)c(N)c3)c12] | ethyl 4-[3-amino-4-(methoxymethyl)phenyl]-7H-pyrrolo[2,3-d]pyrimidine-5-carboxylate | Calc'd 327, found 327 |
| 1-34 | 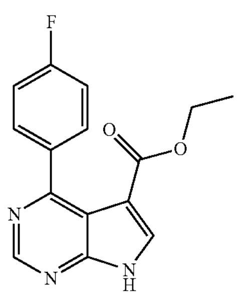 [SMILES: CCOC(=O)c1c[nH]c2ncnc(-c3ccc(F)cc3)c12] | ethyl 4-(4-fluorophenyl)-7H-pyrrolo[2,3-d]pyrimidine-5-carboxylate | Calc'd 286, found 286 |
| 1-35 | 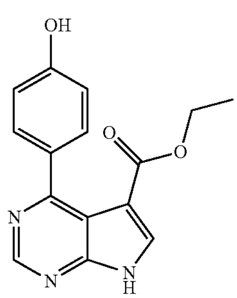 [SMILES: CCOC(=O)c1c[nH]c2ncnc(-c3ccc(O)cc3)c12] | ethyl 4-(4-hydroxyphenyl)-7H-pyrrolo[2,3-d]pyrimidine-5-carboxylate | Calc'd 284, found 284 |

TABLE 1-continued

| Example Number | Structure | IUPAC Name | Exact Mass [M + H]+ |
|---|---|---|---|
| 1-36 | 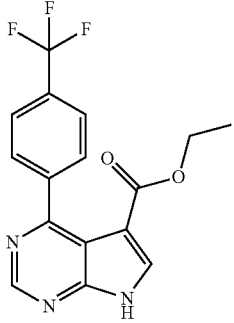 [SMILES: CCOC(=O)c1c[nH]c2ncnc(-c3ccc(C(F)(F)F)cc3)c12] | ethyl 4-[4-(trifluoromethyl)phenyl]-7H-pyrrolo[2,3-d]pyrimidine-5-carboxylate | Calc'd 336, found 336 |
| 1-37 | 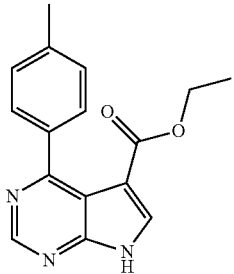 [SMILES: CCOC(=O)c1c[nH]c2ncnc(-c3ccc(C)cc3)c12] | ethyl 4-(4-methylphenyl)-7H-pyrrolo[2,3-d]pyrimidine-5-carboxylate | Calc'd 282, found 282 |
| 1-38 | 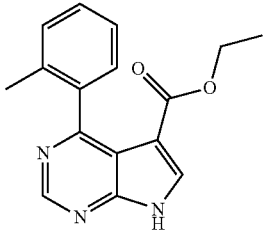 [SMILES: CCOC(=O)c1c[nH]c2ncnc(-c3ccccc3C)c12] | ethyl 4-(2-methylphenyl)-7H-pyrrolo[2,3-d]pyrimidine-5-carboxylate | Calc'd 282, found 282 |
| 1-39 | 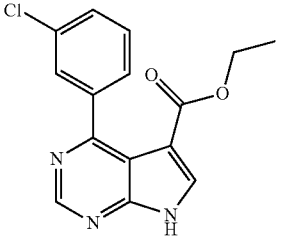 [SMILES: CCOC(=O)c1c[nH]c2ncnc(-c3cccc(Cl)c3)c12] | ethyl 4-(3-chlorophenyl)-7H-pyrrolo[2,3-d]pyrimidine-5-carboxylate | Calc'd 302, found 302 |
| 1-40 | 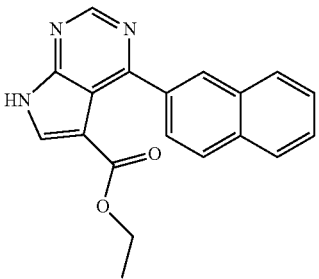 [SMILES: CCOC(=O)c1c[nH]c2ncnc(-c3ccc4ccccc4c3)c12] | ethyl 4-naphthalen-2-yl-7H-pyrrolo[2,3-d]pyrimidine-5-carboxylate | Calc'd 318, found 318 |

TABLE 1-continued

| Example Number | Structure | IUPAC Name | Exact Mass [M + H]+ |
|---|---|---|---|
| 1-41 | 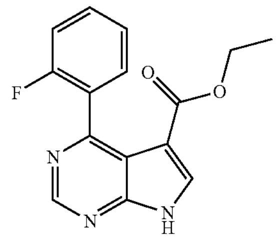 [SMILES: CCOC(=O)c1c[nH]c2ncnc(-c3ccccc3F)c12] | ethyl 4-(2-fluorophenyl)-7H-pyrrolo[2,3-d]pyrimidine-5-carboxylate | Calc'd 286, found 286 |
| 1-42 | 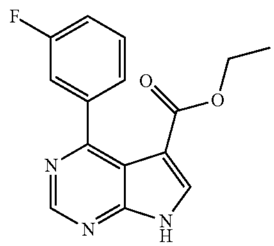 [SMILES: CCOC(=O)c1c[nH]c2ncnc(-c3cccc(F)c3)c12] | ethyl 4-(3-fluorophenyl)-7H-pyrrolo[2,3-d]pyrimidine-5-carboxylate | Calc'd 286, found 286 |
| 1-43 | 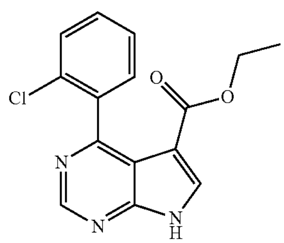 [SMILES: CCOC(=O)c1c[nH]c2ncnc(-c3ccccc3Cl)c12] | ethyl 4-(2-chlorophenyl)-7H-pyrrolo[2,3-d]pyrimidine-5-carboxylate | Calc'd 302, found 302 |
| 1-44 | 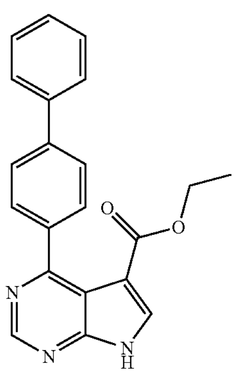 [SMILES: CCOC(=O)c1c[nH]c2ncnc(-c3ccc(-c4ccccc4)cc3)c12] | ethyl 4-biphenyl-4-yl-7H-pyrrolo[2,3-d]pyrimidine-5-carboxylate | Calc'd 344, found 344 |
| 1-45 | 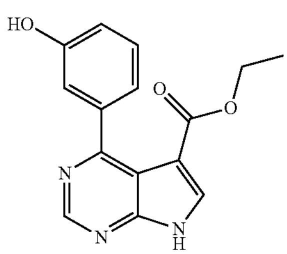 [SMILES: CCOC(=O)c1c[nH]c2ncnc(-c3cccc(O)c3)c12] | ethyl 4-(3-hydroxyphenyl)-7H-pyrrolo[2,3-d]pyrimidine-5-carboxylate | Calc'd 284, found 284 |

TABLE 1-continued

| Example Number | Structure | IUPAC Name | Exact Mass [M + H]+ |
|---|---|---|---|
| 1-46 | 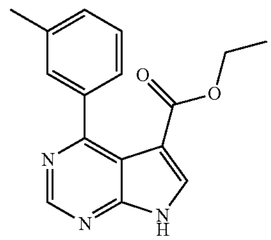 [SMILES: CCOC(=O)c1c[nH]c2ncnc(-c3cccc(C)c3)c12] | ethyl 4-(3-methylphenyl)-7H-pyrrolo[2,3-d]pyrimidine-5-carboxylate | Calc'd 282, found 282 |
| 1-47 | 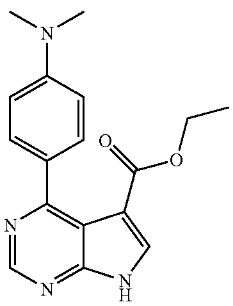 [SMILES: CCOC(=O)c1c[nH]c2ncnc(-c3ccc(N(C)C)cc3)c12] | ethyl 4-[4-(dimethylamino)phenyl]-7H-pyrrolo[2,3-d]pyrimidine-5-carboxylate | Calc'd 311, found 311 |
| 1-48 | 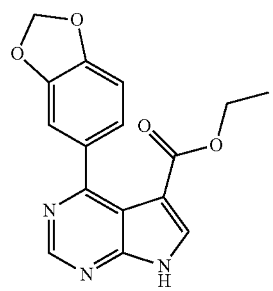 [SMILES: CCOC(=O)c1c[nH]c2ncnc(-c3ccc4c(c3)OCO4)c12] | ethyl 4-(1,3-benzodioxol-5-yl)-7H-pyrrolo[2,3-d]pyrimidine-5-carboxylate | Calc'd 312, found 312 |
| 1-49 | 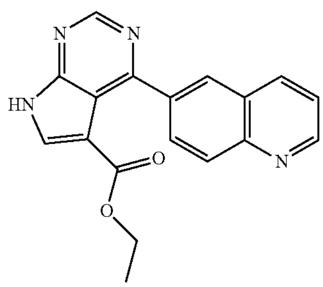 [SMILES: CCOC(=O)c1c[nH]c2ncnc(-c3ccc4ncccc4c3)c12] | ethyl 4-quinolin-6-yl-7H-pyrrolo[2,3-d]pyrimidine-5-carboxylate | Calc'd 319, found 319 |
| 1-50 | 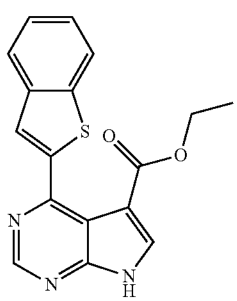 | ethyl 4-(1-benzothiophen-2-yl)-7H-pyrrolo[2,3-d]pyrimidine-5-carboxylate | Calc'd 324, found 324 |

TABLE 1-continued

| Example Number | Structure | IUPAC Name | Exact Mass [M + H]+ |
| --- | --- | --- | --- |
| 1-51 | 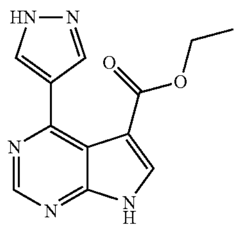 [SMILES: CCOC(=O)c1c[nH]c2ncnc(-c3cn[nH]c3)c12] | ethyl 4-(1H-pyrazol-4-yl)-7H-pyrrolo[2,3-d]pyrimidine-5-carboxylate | Calc'd 258, found 258 |
| 1-52 | 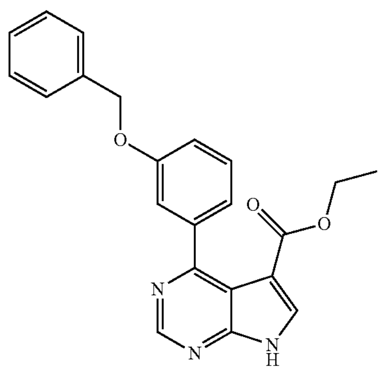 [SMILES: CCOC(=O)c1c[nH]c2ncnc(-c3cccc(OCc4ccccc4)c3)c12] | ethyl 4-[3-(benzyloxy)phenyl]-7H-pyrrolo[2,3-d]pyrimidine-5-carboxylate | Calc'd 374, found 374 |
| 1-53 | 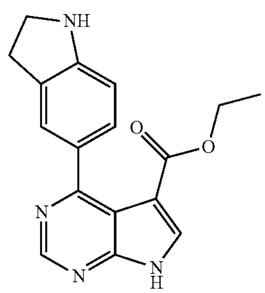 [SMILES: CCOC(=O)c1c[nH]c2ncnc(-c3ccc4c(c3)CCN4)c12] | ethyl 4-(1H-indol-5-yl)-7H-pyrrolo[2,3-d]pyrimidine-5-carboxylate | Calc'd 307, found 307 |
| 1-54 | 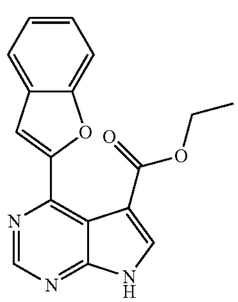 [SMILES: CCOC(=O)c1c[nH]c2ncnc(-c3cc4ccccc4o3)c12] | ethyl 4-(1-benzofuran-2-yl)-7H-pyrrolo[2,3-d]pyrimidine-5-carboxylate | Calc'd 308, found 308 |
| 1-55 | 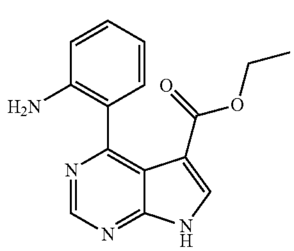 [SMILES: CCOC(=O)c1c[nH]c2ncnc(-c3ccccc3N)c12] | ethyl 4-(2-aminophenyl)-7H-pyrrolo[2,3-d]pyrimidine-5-carboxylate | Calc'd 283, found 283 |

TABLE 1-continued

| Example Number | Structure | IUPAC Name | Exact Mass [M + H]+ |
| --- | --- | --- | --- |
| 1-56 | 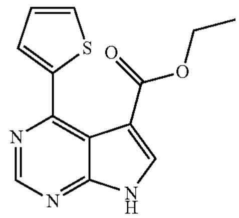 [SMILES: CCOC(=O)c1c[nH]c2ncnc(-c3cccs3)c12] | ethyl 4-thiophen-2-yl-7H-pyrrolo[2,3-d]pyrimidine-5-carboxylate | Calc'd 274, found 274 |
| 1-57 | 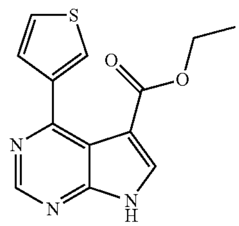 [SMILES: CCOC(=O)c1c[nH]c2ncnc(-c3ccsc3)c12] | ethyl 4-thiophen-3-yl-7H-pyrrolo[2,3-d]pyrimidine-5-carboxylate | Calc'd 274, found 274 |
| 1-58 | 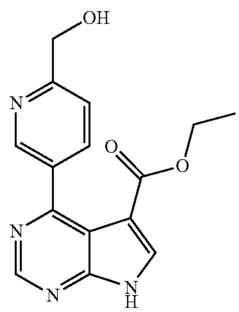 [SMILES: CCOC(=O)c1c[nH]c2ncnc(-c3ccc(CO)nc3)c12] | ethyl 4-[6-(hydroxymethyl)pyridin-3-yl]-7H-pyrrolo[2,3-d]pyrimidine-5-carboxylate | Calc'd 299, found 299 |
| 1-59 | 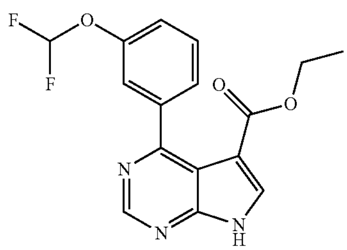 [SMILES: CCOC(=O)c1c[nH]c2ncnc(-c3cccc(OC(F)F)c3)c12] | ethyl 4-[3-(difluoromethoxy)phenyl]-7H-pyrrolo[2,3-d]pyrimidine-5-carboxylate | Calc'd 334, found 334 |
| 1-60 | 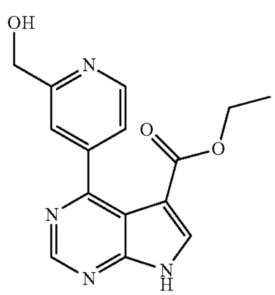 [SMILES: CCOC(=O)c1c[nH]c2ncnc(-c3ccnc(CO)c3)c12] | ethyl 4-[2-(hydroxymethyl)pyridin-4-yl]-7H-pyrrolo[2,3-d]pyrimidine-5-carboxylate | Calc'd 299, found 299 |
| 1-61 | 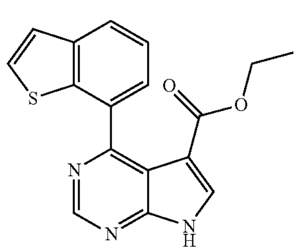 [SMILES: CCOC(=O)c1c[nH]c2ncnc(-c3cccc4ccsc34)c12] | ethyl 4-(1-benzothiophen-7-yl)-7H-pyrrolo[2,3-d]pyrimidine-5-carboxylate | Calc'd 324, found 324 |

TABLE 1-continued

| Example Number | Structure | IUPAC Name | Exact Mass [M + H]+ |
|---|---|---|---|
| 1-62 | 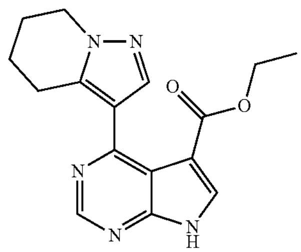 [SMILES: CCOC(=O)c1c[nH]c2ncnc(-c3cnn4c3CCCC4)c12] | ethyl 4-(4,5,6,7-tetrahydropyrazolo[1,5-a]pyridin-3-yl)-7H-pyrrolo[2,3-d]pyrimidine-5-carboxylate | Calc'd 312, found 312 |
| 1-63 | 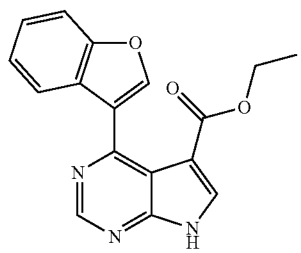 [SMILES: CCOC(=O)c1c[nH]c2ncnc(-c3coc4ccccc34)c12] | ethyl 4-(1-benzofuran-3-yl)-7H-pyrrolo[2,3-d]pyrimidine-5-carboxylate | Calc'd 308, found 308 |
| 1-64 | 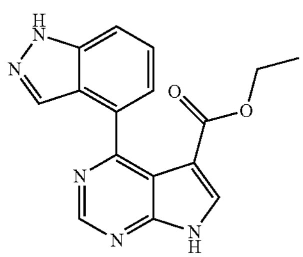 [SMILES: CCOC(=O)c1c[nH]c2ncnc(-c3cccc4[nH]ncc34)c12] | ethyl 4-(1H-indazol-4-yl)-7H-pyrrolo[2,3-d]pyrimidine-5-carboxylate | Calc'd 308, found 308 |
| 1-65 | 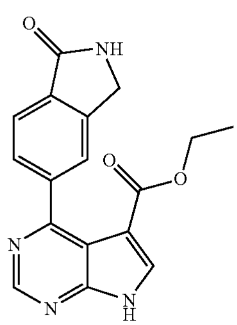 [SMILES: CCOC(=O)c1c[nH]c2ncnc(-c3ccc4c(c3)CNC4=O)c12] | ethyl 4-(1-oxo-2,3-dihydro-1H-isoindol-5-yl)-7H-pyrrolo[2,3-d]pyrimidine-5-carboxylate | Calc'd 323, found 323 |
| 1-66 | 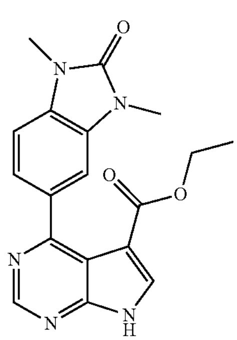 [SMILES: CCOC(=O)c1c[nH]c2ncnc(-c3ccc4c(c3)n(C)c(=O)n4C)c12] | ethyl 4-(1,3-dimethyl-2-oxo-2,3-dihydro-1H-benzimidazol-5-yl)-7H-pyrrolo[2,3-d]pyrimidine-5-carboxylate | Calc'd 352, found 352 |

TABLE 1-continued

| Example Number | Structure | IUPAC Name | Exact Mass [M + H]+ |
|---|---|---|---|
| 1-67 | 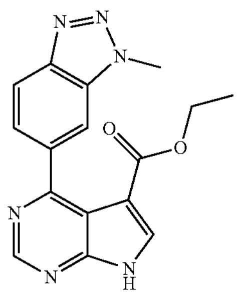 [SMILES: CCOC(=O)c1c[nH]c2ncnc(-c3ccc4nnn(C)c4c3)c12] | ethyl 4-(1-methyl-1H-benzotriazol-6-yl)-7H-pyrrolo[2,3-d]pyrimidine-5-carboxylate | Calc'd 323, found 323 |
| 1-68 | 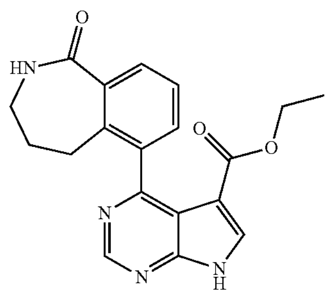 [SMILES: CCOC(=O)c1c[nH]c2ncnc(-c3cccc4c3CCCNC4=O)c12] | ethyl 4-(1-oxo-2,3,4,5-tetrahydro-1H-2-benzazepin-6-yl)-7H-pyrrolo[2,3-d]pyrimidine-5-carboxylate | Calc'd 351, found 351 |
| 1-69 | 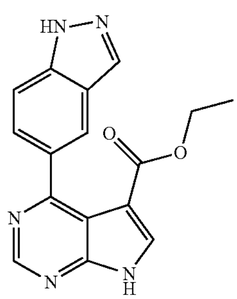 [SMILES: CCOC(=O)c1c[nH]c2ncnc(-c3ccc4[nH]ncc4c3)c12] | ethyl 4-(1H-indazol-5-yl)-7H-pyrrolo[2,3-d]pyrimidine-5-carboxylate | Calc'd 308, found 308 |
| 1-70 | 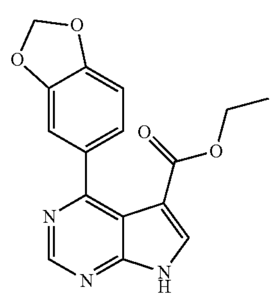 [SMILES: CCOC(=O)c1c[nH]c2ncnc(-c3ccc4c(c3)OCO4)c12] | ethyl 4-(1,3-benzodioxol-5-yl)-7H-pyrrolo[2,3-d]pyrimidine-5-carboxylate | Calc'd 312, found 312 |
| 1-71 | 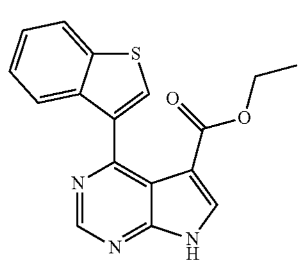 [SMILES: CCOC(=O)c1c[nH]c2ncnc(-c3csc4ccccc34)c12] | ethyl 4-(1-benzothiophen-3-yl)-7H-pyrrolo[2,3-d]pyrimidine-5-carboxylate | Calc'd 324, found 324 |

TABLE 1-continued

| Example Number | Structure | IUPAC Name | Exact Mass [M + H]+ |
|---|---|---|---|
| 1-72 | 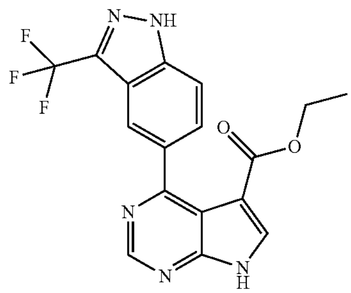 [SMILES: CCOC(=O)c1c[nH]c2ncnc(-c3ccc4[nH]nc(C(F)(F)F)c4c3)c12] | ethyl 4-[3-(trifluoromethyl)-1H-indazol-5-yl]-7H-pyrrolo[2,3-d]pyrimidine-5-carboxylate | Calc'd 376, found 376 |
| 1-73 | 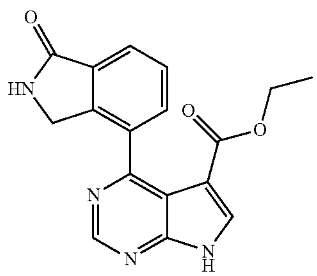 [SMILES: CCOC(=O)c1c[nH]c2ncnc(-c3cccc4c3CNC4=O)c12] | ethyl 4-(1-oxo-2,3-dihydro-1H-isoindol-4-yl)-7H-pyrrolo[2,3-d]pyrimidine-5-carboxylate | Calc'd 323, found 323 |
| 1-74 | 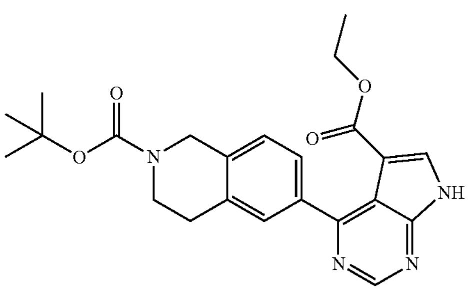 [SMILES: CCOC(=O)c1c[nH]c2ncnc(-c3ccc4c(c3)CCN(C(=O)OC(C)(C)C)C4)c12] | tert-butyl 6-[5-(ethoxycarbonyl)-7H-pyrrolo[2,3-d]pyrimidin-4-yl]-3,4-dihydroisoquinoline-2(1H)-carboxylate | Calc'd 423, found 423 |
| 1-75 | 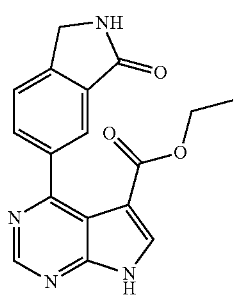 [SMILES: CCOC(=O)c1c[nH]c2ncnc(-c3ccc4c(c3)C(=O)NC4)c12] | ethyl 4-(3-oxo-2,3-dihydro-1H-isoindol-5-yl)-7H-pyrrolo[2,3-d]pyrimidine-5-carboxylate | Calc'd 323, found 323 |
| 1-76 | 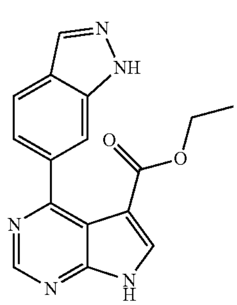 [SMILES: CCOC(=O)c1c[nH]c2ncnc(-c3ccc4cn[nH]c4c3)c12] | ethyl 4-(1H-indazol-6-yl)-7H-pyrrolo[2,3-d]pyrimidine-5-carboxylate | Calc'd 308, found 308 |

TABLE 1-continued

| Example Number | Structure | IUPAC Name | Exact Mass [M + H]+ |
|---|---|---|---|
| 1-77 | 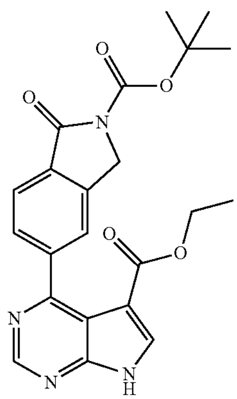 [SMILES: CCOC(=O)c1c[nH]c2ncnc(-c3ccc4c(c3)CN(C(=O)OC(C)(C)C)C4=O)c12] | ethyl 4-[2-(tert-butoxycarbonyl)-1-oxo-2,3-dihydro-1H-isoindol-5-yl]-7H-pyrrolo[2,3-d]pyrimidine-5-carboxylate | Calc'd 423, found 423 |
| 1-78 | 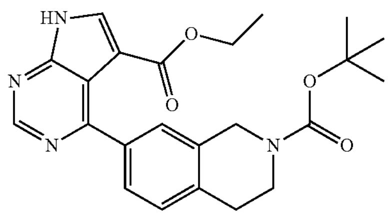 [SMILES: CCOC(=O)c1c[nH]c2ncnc(-c3ccc4c(c3)CN(C(=O)OC(C)(C)C)CC4)c12] | tert-butyl 7-[5-(ethoxycarbonyl)-7H-pyrrolo[2,3-d]pyrimidin-4-yl]-3,4-dihydroisoquinoline-2(1H)-carboxylate | Calc'd 423, found 423 |
| 1-79 | 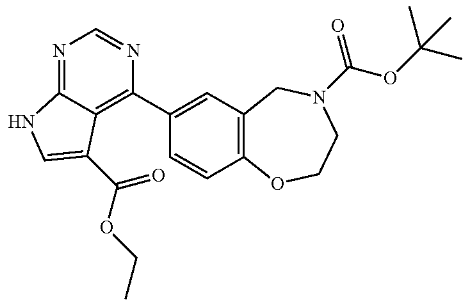 [SMILES: CCOC(=O)c1c[nH]c2ncnc(-c3ccc4c(c3)CN(C(=O)OC(C)(C)C)CCO4)c12] | tert-butyl 7-[5-(ethoxycarbonyl)-7H-pyrrolo[2,3-d]pyrimidin-4-yl]-2,3-dihydro-1,4-benzoxazepine-4(5H)-carboxylate | Calc'd 439, found 439 |
| 1-80 | 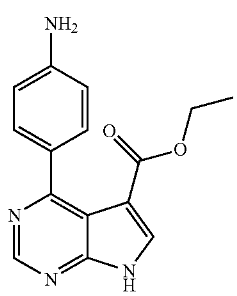 [SMILES: CCOC(=O)c1c[nH]c2ncnc(-c3ccc(N)cc3)c12] | ethyl 4-(4-aminophenyl)-7H-pyrrolo[2,3-d]pyrimidine-5-carboxylate | Calc'd 283, found 283 |
| 1-81 | 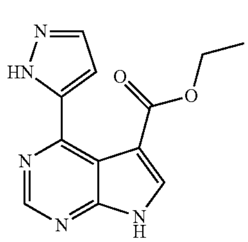 [SMILES: CCOC(=O)c1c[nH]c2ncnc(-c3ccn[nH]3)c12] | ethyl 4-(1H-pyrazol-5-yl)-7H-pyrrolo[2,3-d]pyrimidine-5-carboxylate | Calc'd 258, found 258 |

TABLE 1-continued

| Example Number | Structure | IUPAC Name | Exact Mass [M + H]+ |
| --- | --- | --- | --- |
| 1-82 | 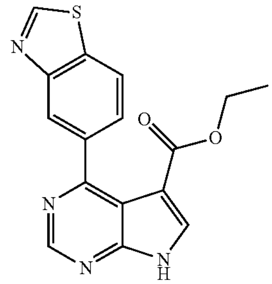 [SMILES: CCOC(=O)c1c[nH]c2ncnc(-c3ccc4scnc4c3)c12] | ethyl 4-(1,3-benzothiazol-5-yl)-7H-pyrrolo[2,3-d]pyrimidine-5-carboxylate | Calc'd 325, found 325 |
| 1-83 | 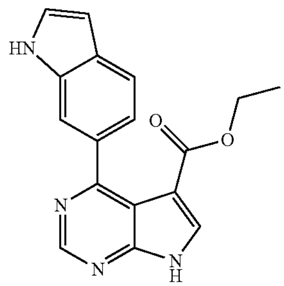 [SMILES: CCOC(=O)c1c[nH]c2ncnc(-c3ccc4cc[nH]c4c3)c12] | ethyl 4-(1H-indol-6-yl)-7H-pyrrolo[2,3-d]pyrimidine-5-carboxylate | Calc'd 307, found 307 |
| 1-84 | 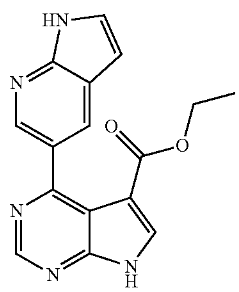 [SMILES: CCOC(=O)c1c[nH]c2ncnc(-c3cnc4[nH]ccc4c3)c12] | ethyl 4-(1H-pyrrolo[2,3-b]pyridin-5-yl)-7H-pyrrolo[2,3-d]pyrimidine-5-carboxylate | Calc'd 308, found 308 |
| 1-85 | 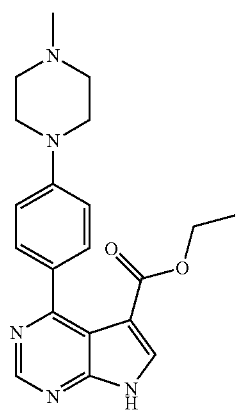 [SMILES: CCOC(=O)c1c[nH]c2ncnc(-c3ccc(N4CCN(C)CC4)cc3)c12] | ethyl 4-[4-(4-methylpiperazin-1-yl)phenyl]-7H-pyrrolo[2,3-d]pyrimidine-5-carboxylate | Calc'd 366, found 366 |
| 1-86 | 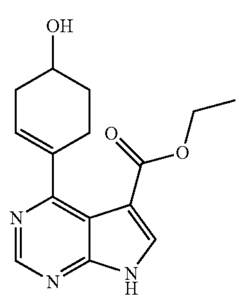 [SMILES: CCOC(=O)c1c[nH]c2ncnc(C3=CCC(O)CC3)c12] | ethyl 4-(4-hydroxycyclohex-1-en-1-yl)-7H-pyrrolo[2,3-d]pyrimidine-5-carboxylate | Calc'd 288, found 288 |

TABLE 1-continued

| Example Number | Structure | IUPAC Name | Exact Mass [M + H]+ |
| --- | --- | --- | --- |
| 1-87 | 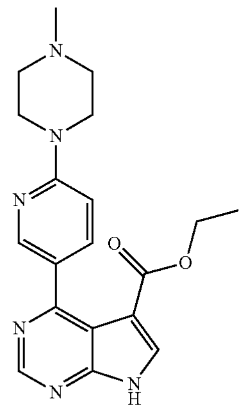 [SMILES: CCOC(=O)c1c[nH]c2ncnc(-c3ccc(N4CCN(C)CC4)nc3)c12] | ethyl 4-[6-(4-methylpiperazin-1-yl)pyridin-3-yl]-7H-pyrrolo[2,3-d]pyrimidine-5-carboxylate | Calc'd 367, found 367 |
| 1-88 | 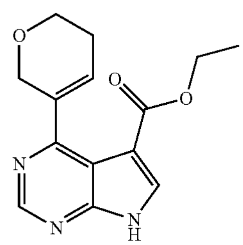 [SMILES: CCOC(=O)c1c[nH]c2ncnc(C3=CCCOC3)c12] | ethyl 4-(5,6-dihydro-2H-pyran-3-yl)-7H-pyrrolo[2,3-d]pyrimidine-5-carboxylate | Calc'd 274, found 274 |
| 1-89 | 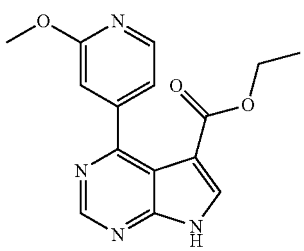 [SMILES: CCOC(=O)c1c[nH]c2ncnc(-c3ccnc(OC)c3)c12] | ethyl 4-(2-methoxypyridin-4-yl)-7H-pyrrolo[2,3-d]pyrimidine-5-carboxylate | Calc'd 299, found 299 |
| 1-90 | 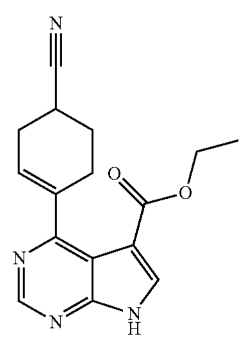 [SMILES: CCOC(=O)c1c[nH]c2ncnc(C3=CCC(C#N)CC3)c12] | ethyl 4-(4-cyanocyclohex-1-en-1-yl)-7H-pyrrolo[2,3-d]pyrimidine-5-carboxylate | Calc'd 297, found 297 |
| 1-91 | 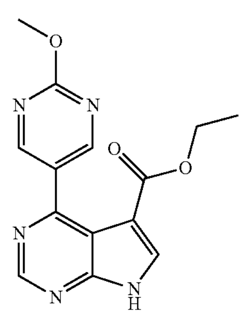 [SMILES: CCOC(=O)c1c[nH]c2ncnc(-c3cnc(OC)nc3)c12] | ethyl 4-(2-methoxypyrimidin-5-yl)-7H-pyrrolo[2,3-d]pyrimidine-5-carboxylate | Calc'd 300, found 300 |

TABLE 1-continued

| Example Number | Structure | IUPAC Name | Exact Mass [M + H]+ |
|---|---|---|---|
| 1-92 | 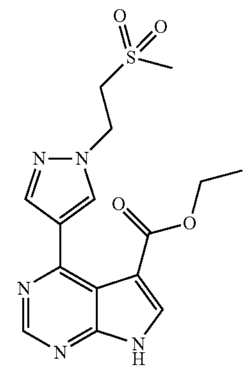 [SMILES: CCOC(=O)c1c[nH]c2ncnc(-c3cnn(CCS(C)(=O)=O)c3)c12] | ethyl 4-{1-[2-(methylsulfonyl)ethyl]-1H-pyrazol-4-yl}-7H-pyrrolo[2,3-d]pyrimidine-5-carboxylate | Calc'd 364, found 364 |
| 1-93 | 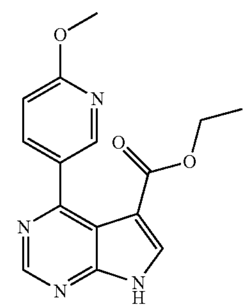 [SMILES: CCOC(=O)c1c[nH]c2ncnc(-c3ccc(OC)nc3)c12] | ethyl 4-(6-methoxypyridin-3-yl)-7H-pyrrolo[2,3-d]pyrimidine-5-carboxylate | Calc'd 299, found 299 |
| 1-94 | 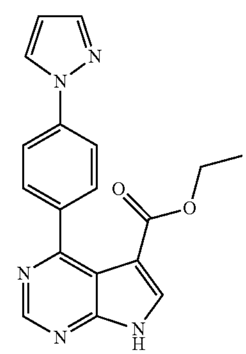 [SMILES: CCOC(=O)c1c[nH]c2ncnc(-c3ccc(-n4cccn4)cc3)c12] | ethyl 4-[4-(1H-pyrazol-1-yl)phenyl]-7H-pyrrolo[2,3-d]pyrimidine-5-carboxylate | Calc'd 334, found 334 |
| 1-95 | 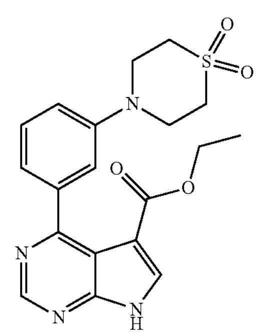 [SMILES: CCOC(=O)c1c[nH]c2ncnc(-c3cccc(N4CCS(=O)(=O)CC4)c3)c12] | ethyl 4-[3-(1,1-dioxidothiomorpholin-4-yl)phenyl]-7H-pyrrolo[2,3-d]pyrimidine-5-carboxylate | Calc'd 401, found 401 |

TABLE 1-continued

| Example Number | Structure | IUPAC Name | Exact Mass [M + H]+ |
|---|---|---|---|
| 1-96 | 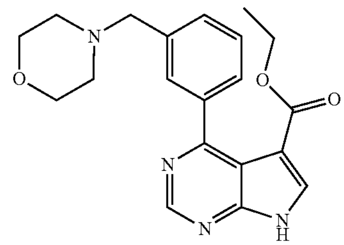 [SMILES: CCOC(=O)c1c[nH]c2ncnc(-c3cccc(CN4CCOCC4)c3)c12] | ethyl 4-[3-(morpholin-4-ylmethyl)phenyl]-7H-pyrrolo[2,3-d]pyrimidine-5-carboxylate | Calc'd 367, found 367 |
| 1-97 | 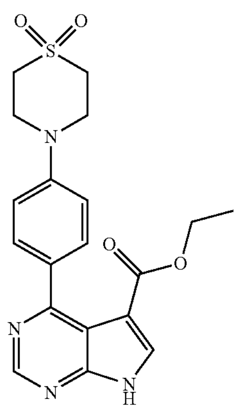 [SMILES: CCOC(=O)c1c[nH]c2ncnc(-c3ccc(N4CCS(=O)(=O)CC4)cc3)c12] | ethyl 4-[4-(1,1-dioxidothiomorpholin-4-yl)phenyl]-7H-pyrrolo[2,3-d]pyrimidine-5-carboxylate | Calc'd 401, found 401 |
| 1-98 | 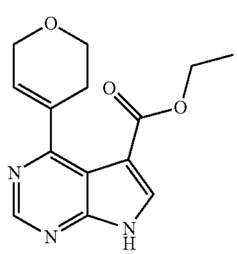 [SMILES: CCOC(=O)c1c[nH]c2ncnc(C3=CCOCC3)c12] | ethyl 4-(3,6-dihydro-2H-pyran-4-yl)-7H-pyrrolo[2,3-d]pyrimidine-5-carboxylate | Calc'd 274, found 274 |
| 1-99 | 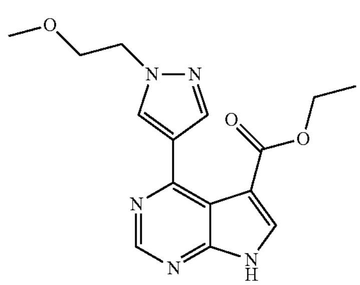 [SMILES: CCOC(=O)c1c[nH]c2ncnc(-c3cnn(CCOC)c3)c12] | ethyl 4-[1-(2-methoxyethyl)-1H-pyrazol-4-yl]-7H-pyrrolo[2,3-d]pyrimidine-5-carboxylate | Calc'd 316, found 316 |

TABLE 1-continued

| Example Number | Structure | IUPAC Name | Exact Mass [M + H]+ |
| --- | --- | --- | --- |
| 1-100 | 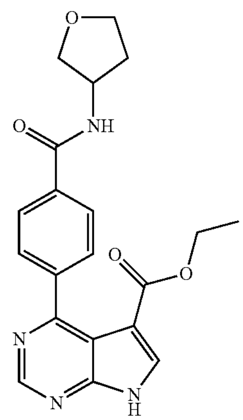 [SMILES: CCOC(=O)c1c[nH]c2ncnc(-c3ccc(C(=O)NC4CCOC4)cc3)c12] | ethyl 4-[4-(tetrahydrofuran-3-ylcarbamoyl)phenyl]-7H-pyrrolo[2,3-d]pyrimidine-5-carboxylate | Calc'd 381, found 381 |
| 1-101 | 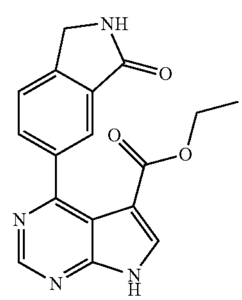 [SMILES: CCOC(=O)c1c[nH]c2ncnc(-c3ccc4c(c3)C(=O)NC4)c12] | ethyl 4-(3-oxo-2,3-dihydro-1H-isoindol-5-yl)-7H-pyrrolo[2,3-d]pyrimidine-5-carboxylate | Calc'd 323, found 323 |
| 1-102 | 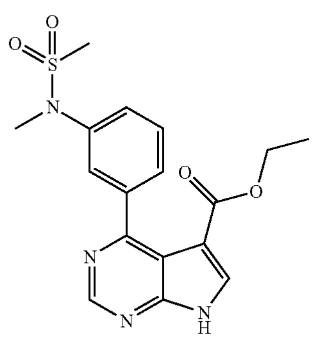 [SMILES: CCOC(=O)c1c[nH]c2ncnc(-c3cccc(N(C)S(C)(=O)=O)c3)c12] | ethyl 4-{3-[methyl(methylsulfonyl)amino]phenyl}-7H-pyrrolo[2,3-d]pyrimidine-5-carboxylate | Calc'd 375, found 375 |
| 1-103 | 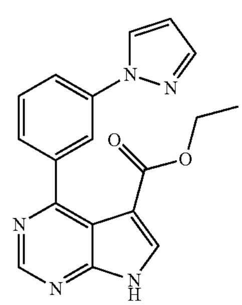 [SMILES: CCOC(=O)c1c[nH]c2ncnc(-c3cccc(-n4cccn4)c3)c12] | ethyl 4-[3-(1H-pyrazol-1-yl)phenyl]-7H-pyrrolo[2,3-d]pyrimidine-5-carboxylate | Calc'd 334, found 334 |

TABLE 1-continued

| Example Number | Structure | IUPAC Name | Exact Mass [M + H]+ |
|---|---|---|---|
| 1-104 | 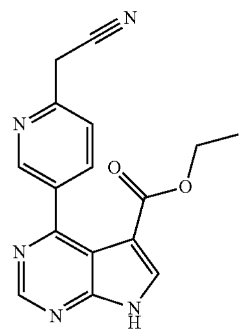 [SMILES: CCOC(=O)c1c[nH]c2ncnc(-c3ccc(CC#N)nc3)c12] | ethyl 4-[6-(cyanomethyl)pyridin-3-yl]-7H-pyrrolo[2,3-d]pyrimidine-5-carboxylate | Calc'd 308, found 308 |
| 1-105 | 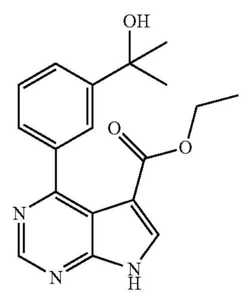 [SMILES: CCOC(=O)c1c[nH]c2ncnc(-c3cccc(C(C)(C)O)c3)c12] | ethyl 4-[3-(1-hydroxy-1-methylethyl)phenyl]-7H-pyrrolo[2,3-d]pyrimidine-5-carboxylate | Calc'd 326, found 326 |
| 1-106 | 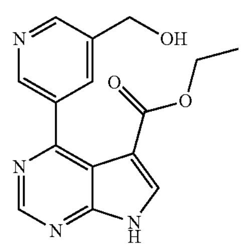 [SMILES: CCOC(=O)c1c[nH]c2ncnc(-c3cncc(CO)c3)c12] | ethyl 4-[5-(hydroxymethyl)pyridin-3-yl]-7H-pyrrolo[2,3-d]pyrimidine-5-carboxylate | Calc'd 299, found 299 |
| 1-107 | 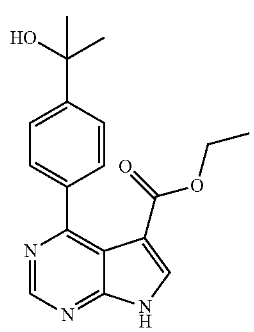 [SMILES: CCOC(=O)c1c[nH]c2ncnc(-c3ccc(C(C)(C)O)cc3)c12] | ethyl 4-[4-(1-hydroxy-1-methylethyl)phenyl]-7H-pyrrolo[2,3-d]pyrimidine-5-carboxylate | Calc'd 326, found 326 |
| 1-108 | 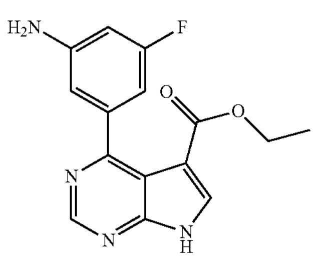 [SMILES: CCOC(=O)c1c[nH]c2ncnc(-c3cc(N)cc(F)c3)c12] | ethyl 4-(3-amino-5-fluorophenyl)-7H-pyrrolo[2,3-d]pyrimidine-5-carboxylate | Calc'd 301, found 301 |

TABLE 1-continued
| Example Number | Structure | IUPAC Name | Exact Mass [M + H]+ |
|---|---|---|---|
| 1-109 | 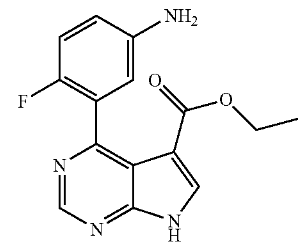 [SMILES: CCOC(=O)c1c[nH]c2ncnc(-c3cc(N)ccc3F)c12] | ethyl 4-(5-amino-2-fluorophenyl)-7H-pyrrolo[2,3-d]pyrimidine-5-carboxylate | Calc'd 301, found 301 |
| 1-110 | 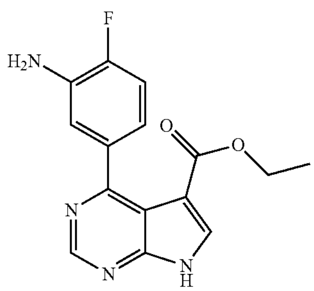 [SMILES: CCOC(=O)c1c[nH]c2ncnc(-c3ccc(F)c(N)c3)c12] | ethyl 4-(3-amino-4-fluorophenyl)-7H-pyrrolo[2,3-d]pyrimidine-5-carboxylate | Calc'd 301, found 301 |
General Scheme B:
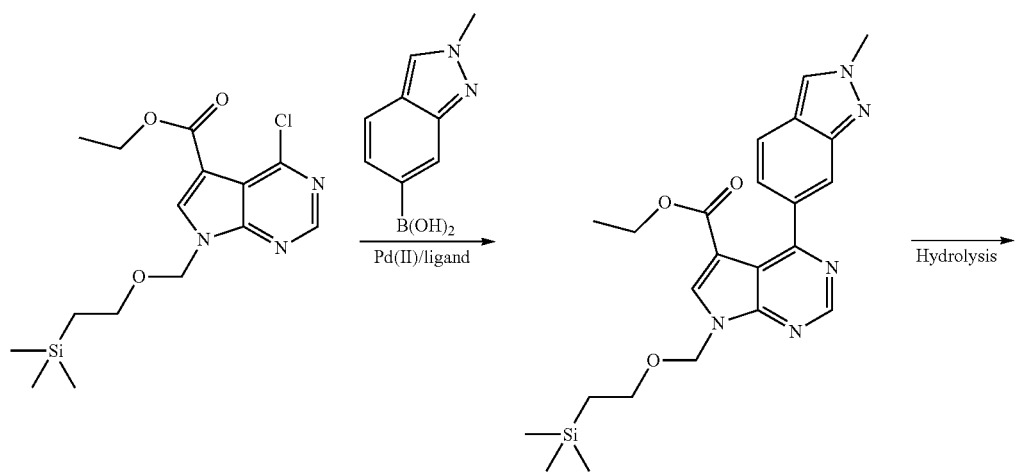

-continued
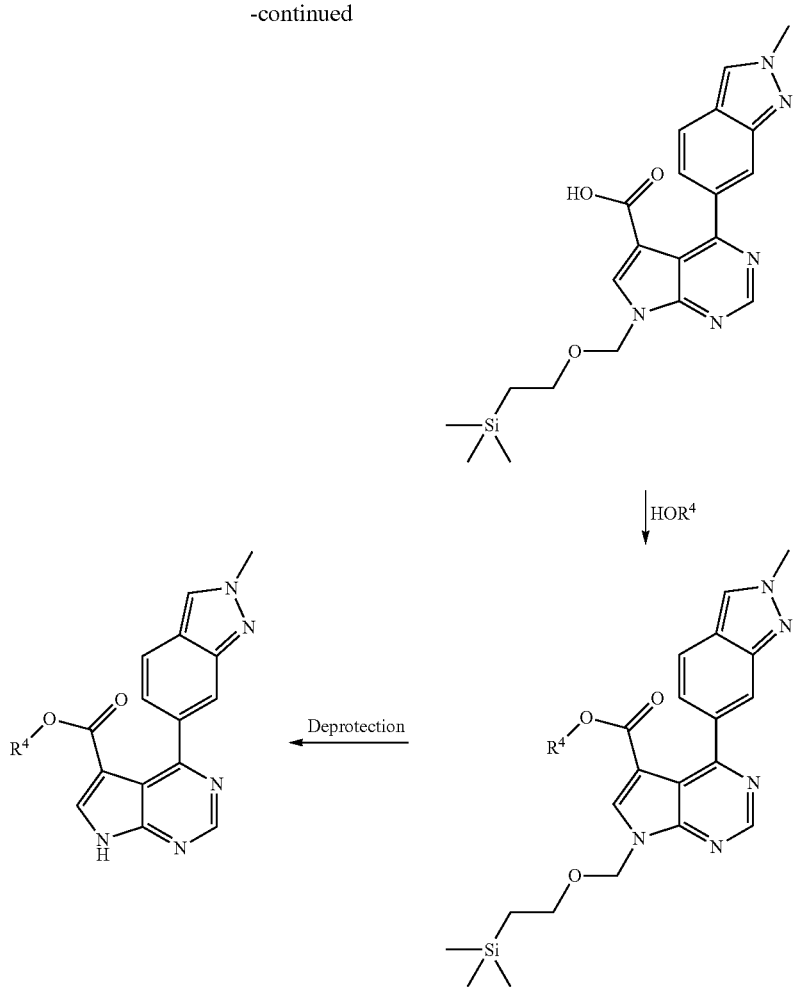
Examples Generated Via General Scheme B
Example 2-1
Propyl 4-(2-methyl-2H-indazol-6-yl)-7H-pyrrolo[2,3-d]pyrimidine-5-carboxylate (2-1)
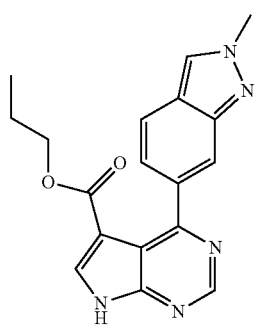 [SMILES: CCCOC(=O)c1c[nH]c2ncnc(-c3ccc4cn(C)nc4c3)c12]
Step 1: Ethyl 4-(2-methyl-2H-indazol-6-yl)-7-{[2-(trimethylsilyl)ethoxy]methyl}-7H-pyrrolo[2,3-d]pyrimidine-5-carboxylate
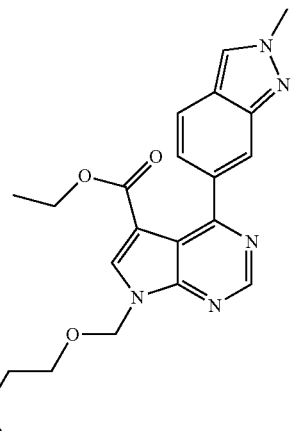
The title compound was prepared in an analogous manner to Example 1-2, using ethyl 4-chloro-7-{[2-(trimethylsilyl)

ethoxy]methyl}-7H-pyrrolo[2,3-d]pyrimidine-5-carboxylate. LRMS (ESI) calc'd for $C_{23}H_{30}SiN_5O_3$ [M+H]$^+$: 452; found 452.

Step 2: 4-(2-Methyl-2H-indazol-6-yl)-7-{[2-(trimethylsilyl)ethoxy]methyl}-7H-pyrrolo[2,3-d]pyrimidine-5-carboxylic acid

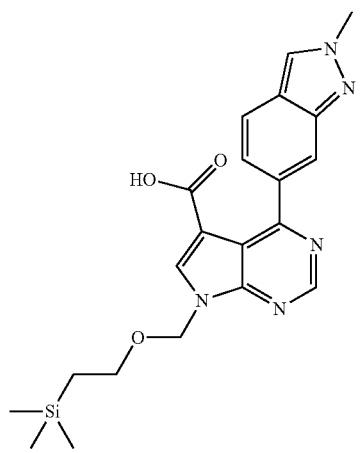

To a solution of ethyl 4-(2-methyl-2H-indazol-6-yl)-7-{[2-(trimethylsilyl)ethoxy]methyl}-7H-pyrrolo[2,3-d]pyrimidine-5-carboxylate in MeOH (2.0 mL) was added 2 M aqueous LiOH (1.1 mL) and the reaction mixture was heated at 60° C. for 17 hours. The reaction mixture was then acidified with AcOH and extracted with EtOAc (×3). The combined organic layers were then washed with brine, dried with sodium sulfate, filtered and concentrated under reduced pressure to give 4-(2-methyl-2H-indazol-6-yl)-7-{[2-(trimethylsilyl)ethoxy]methyl}-7H-pyrrolo[2,3-d]pyrimidine-5-carboxylic acid. No further purification was carried out. LRMS (ESI) calc'd for $C_{21}H_{26}SiN_5O_3$ [M+H]$^+$: 424, found 424.

Step 3: Propyl 4-(2-methyl-2H-indazol-6-yl)-7H-pyrrolo[2,3-d]pyrimidine-5-carboxylate

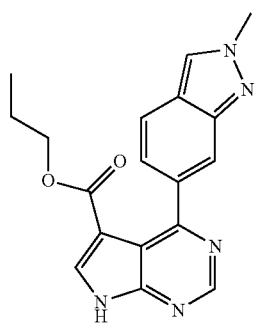 [SMILES: CCCOC(=O)c1c[nH]c2ncnc(-c3ccc4cn(C)nc4c3)c12]

4-(2-Methyl-2H-indazol-6-yl)-7-{[2-(trimethylsilyl)ethoxy]methyl}-7H-pyrrolo[2,3-d]pyrimidine-5-carboxylic acid (50 mg, 0.12 mmol), HATU (90 mg, 0.24 mmol), and propanol (14.2 mg, 0.236 mmol) were added to DMSO (1.0 mL), followed by Hunig's base (0.103 mL, 0.590 mmol). The reaction was then stirred for 17 hours at room temperature at which point additional HATU (90 mg, 0.236 mmol), Hunig's base (0.103 mL, 0.590 mmol) and propanol (14.2 mg, 0.236 mmol) were added and the reaction stirred for an additional 17 hours at room temperature. Saturated aqueous sodium bicarbonate and EtOAc were added to the reaction mixture. The organic layer was separated and the aqueous layer extracted with EtOAc (×3). The combined organic layers were then washed with brine, dried with sodium sulfate, filtered and concentrated under reduced pressure. The residue was dissolved in DMSO (1 mL) and CsF (179 mg, 1.18 mmol) was then added. The reaction mixture was heated at 140° C. for 2 hours open to the air. Upon cooling, the solution was made acidic by addition of TFA. The reaction mixture was then filtered and purified by reverse phase HPLC using an acetonitrile gradient in water with 0.1% TFA modifier. Pure fractions were combined and then saturated aqueous sodium bicarbonate was added. The organic layer was separated and the aqueous layer extracted with 3:1 $CHCl_3$:IPA (×3). The combined organic layers were then washed with brine, dried over sodium sulfate, filtered, and concentrated under reduced pressure to afford propyl 4-(2-methyl-2H-indazol-6-yl)-7H-pyrrolo[2,3-d]pyrimidine-5-carboxylate as a solid. LRMS (ESI) calc'd for $C_{18}H_{18}N_5O_2$ [M+11]$^+$: 336; found 336. $^1$H NMR (600 MHz, DMSO-D$_6$) δ 13.01 (s, 1H), 8.91 (s, 1H), 8.40 (s, 1H), 8.30 (s, 1H), 7.78 (s, 1H), 7.76 (d, 1H, J=8.80 Hz), 7.36 (d, 1H, J=8.80 Hz), 4.22 (s, 3H), 3.68 (t, 2H, J=6.45 Hz), 1.03 (m, 2H), 0.55 (t, 3H, J=7.04 Hz).

Example 2-2

Prop-2-en-1-yl 4-(2-methyl-2H-indazol-6-yl)-7H-pyrrolo[2,3-d]pyrimidine-5-carboxylate (2-2)

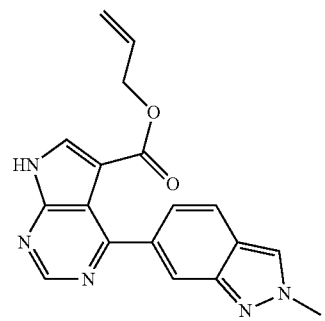 [SMILES: C=CCOC(=O)c1c[nH]c2ncnc(-c3ccc4cn(C)nc4c3)c12]

Step 1: Prop-2-en-1-yl 4-(2-methyl-2H-indazol-6-yl)-7-{[2-(trimethylsilyl)ethoxy]methyl}-7H-pyrrolo[2,3-d]pyrimidine-5-carboxylate

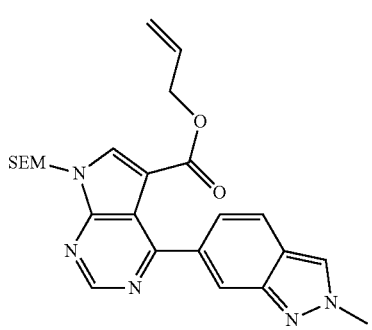 [SMILES: C=CCOC(=O)c1cn(COCC[Si](C)(C)C)c2ncnc(-c3ccc4cn(C)nc4c3)c12]

4-(2-Methyl-2H-indazol-6-yl)-7-{[2-(trimethylsilyl)ethoxy]methyl}-7H-pyrrolo[2,3-d]pyrimidine-5-carboxylic acid (50 mg, 0.12 mmol), HATU (90 mg, 0.24 mmol), and allyl alcohol (0.016 mL, 0.24 mmol) were sequentially added to DMSO (1.0 mL) followed by the addition of Hunig's base (0.10 mL, 0.59 mmol). The reaction was stirred for 17 hours at room temperature at which point an additional amount of HATU (90 mg, 0.24 mmol), Hunig's base (0.10 mL, 0.59 mmol) and allyl alcohol (0.016 mL, 0.24 mmol) were added. The reaction was stirred at room temperature for 17 hours and then extracted with EtOAc (×3) from a saturated sodium bicarbonate solution. The combined organics were washed with brine, dried over sodium sulfate, filtered and concentrated in vacuo to give prop-2-en-1-yl 4-(2-methyl-2H-indazol-6-yl)-7-{[2-(trimethylsilyl)ethoxy]methyl}-7H-pyrrolo[2,3-d]pyrimidine-5-carboxylate. LRMS (ESI) calcd for $C_{24}H_{30}N_5O_3Si$ [M+H]$^+$: 464, found 464.

Step 2: Prop-2-en-1-yl 4-(2-methyl-2H-indazol-6-yl)-7H-pyrrolo[2,3-d]pyrimidine-5-carboxylate

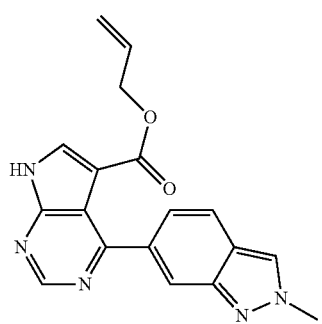 [SMILES: C=CCOC(=O)c1c[nH]c2ncnc(-c3ccc4cn(C)nc4c3)c12]

Prop-2-en-1-yl 4-(2-methyl-2H-indazol-6-yl)-7-{[2-(trimethylsilyl)ethoxy]methyl}-7H-pyrrolo[2,3-d]pyrimidine-5-carboxylate was dissolved in DCM (1.0 mL) and then TFA (0.91 mL, 12 mmol) was added. The resulting solution was stirred for 2 hours at room temperature before being concentrated in vacuo. Acetonitrile (0.50 mL) and ammonium hydroxide (0.50 mL, 3.6 mmol) were added to the residue and the solution was heated to 50° C. for 3 hours. The reaction was concentrated in vacuo and purified by reverse phase chromatography using a 5-35% acetonitrile gradient in water with 0.1% TFA modifier. Pure fractions were free-based by extracting from a saturated sodium bicarbonate solution using 3:1 CHCl$_3$:IPA (×3). The combined organic layers were then washed with brine, dried over sodium sulfate, filtered and concentrated in vacuo to afford prop-2-en-1-yl 4-(2-methyl-2H-indazol-6-yl)-7H-pyrrolo[2,3-d]pyrimidine-5-carboxylate as a white solid. LRMS (ESI) calcd for $C_{18}H_{16}N_5O_2$ [M+H]$^+$: 334, found 334. $^1$H NMR (600 MHz, DMSO-D6) δ 13.04 (s, 1H), 8.96 (s, 1H), 8.43 (s, 1H), 8.39 (s, 1H), 7.81 (m, 1H), 7.79 (dd, 1H, J=8.4, 0.8 Hz), 7.39 (dd, 1H, J=8.4, 1.4 Hz), 5.5 (m, 1H), 4.97-5.04 (m, 2H), 4.30 (dm, 2H, J=5.7 Hz), 4.25 (s, 3H).

General Scheme C:

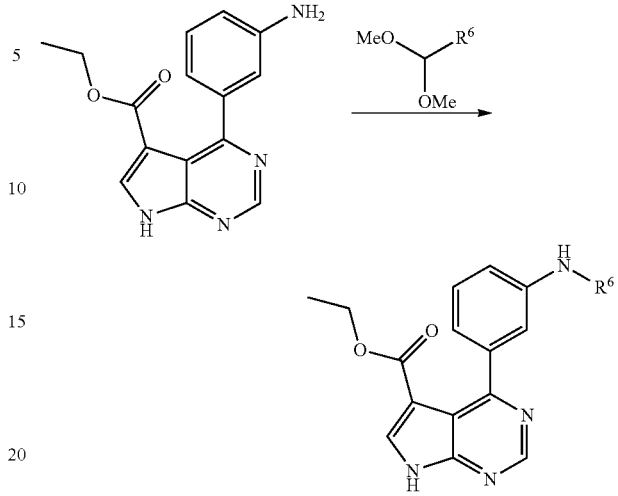

Examples Generated Via General Scheme C

Example 3-1

Ethyl 4-{3-[(2,2,2-trifluoroethyl)amino]phenyl}-7H-pyrrolo[2,3-d]pyrimidine-5-carboxylate (3-1)

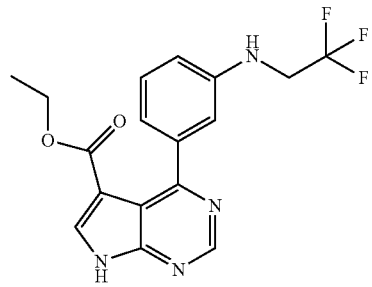 [SMILES: CCOC(=O)c1c[nH]c2ncnc(-c3cccc(NCC(F)(F)F)c3)c12]

To a mixture of ethyl 4-(3-aminophenyl)-7H-pyrrolo[2,3-d]pyrimidine-5-carboxylate and 2,2,2-trifluoroethane-1,1-diol in CH$_2$Cl$_2$ (242 µL) at 0° C. was added sodium cyanoborohydride (32.0 mg, 0.509 mmol). The reaction mixture was allowed to stir for 16 hours and then neutralized with 2M aqueous sodium carbonate and extracted with ethyl acetate (×3). The combined organic fractions were dried with sodium sulfate, filtered and concentrated under reduced pressure. The residue was purified by reverse phase HPLC using an acetonitrile gradient in water with 0.1% TFA modifier. The combined fractions containing the desired product were concentrated until only the water layer remained. The water layer was neutralized with saturated aqueous sodium bicarbonate and the mixture was extracted with ethyl acetate (×3). The combined organic fractions were dried over sodium sulfate, filtered and concentrated under reduced pressure to give ethyl 4-{3-[(2,2,2-trifluoroethyl)amino]phenyl}-7H-pyrrolo[2,3-d]pyrimidine-5-carboxylate. LRMS (ESI) calc'd for $C_{17}H_{16}F_3N_4O_2$ [M+H]$^+$: 365, found 365. $^1$H NMR (600 MHz, DMSO-D$_6$) δ 12.92 (s, 1H), 8.87 (s, 1H), 8.25 (s, 1H), 7.21 (t, 1H, J=7.63 Hz), 7.00 (s, 1H), 6.86 (m, 2H), 6.37 (m, 1H), 3.94 (m, 2H), 3.83 (q, 2H, J=7.04 Hz), 0.81 (t, 3H, J=7.04 Hz).

The following example, 3-2 as shown in Table 2, was prepared in an analogous manner of that described above using materials that are commercially available or known, or that can be prepared using procedures known in the art or by generally following procedures described herein for various intermediates.

TABLE 2

| Example | Structure | IUPAC Name | Exact Mass [M + H]+ |
|---|---|---|---|
| 3-2 | 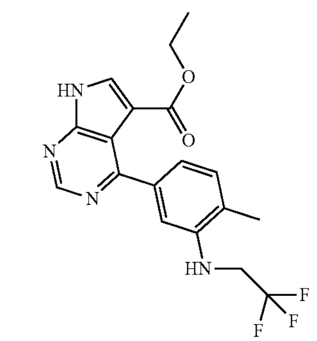 [SMILES: CCOC(=O)c1c[nH]c2ncnc(-c3ccc(C)c(NCC(F)(F)F)c3)c12] | ethyl 4-{4-methyl-3-[(2,2,2-trifluoroethyl)amino]phenyl}-7H-pyrrolo[2,3-d]pyrimidine-5-carboxylate | Calc'd 379, found 379 |

General Scheme D:

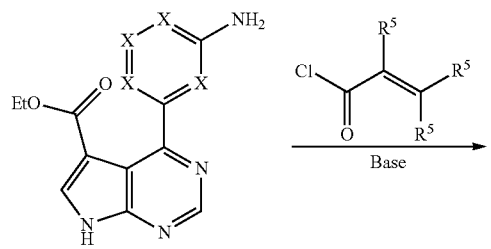

Examples Generated Via General Scheme D

Example 4-1

Ethyl-4-{3-[(2-methylacryloyl)amino]phenyl}-7H-pyrrolo[2,3-d]pyrimidine-5-carboxylate (4-1)

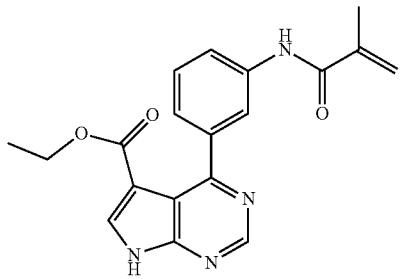 [SMILES: C=C(C)C(=O)Nc1cccc(-c2ncnc3[nH]cc(C(=O)OCC)c23)c1]

To a solution of ethyl 4-(3-aminophenyl)-7H-pyrrolo[2,3-d]pyrimidine-5-carboxylate (50 mg, 0.18 mmol) and DIPEA (93 µL, 0.53 mmol) in THF (1.8 mL) at room temperature was added methacryloyl chloride (27.8 mg, 0.266 mmol) and the solution stirred for 1 hour. The reaction was quenched with ethanol (0.1 mL). The desired product was purified by reverse phase HPLC using an acetonitrile gradient in water with 0.1% TFA modifier. The combined fractions with the desired product were concentrated until only the water layer remained. The water layer was neutralized with 2M aqueous potassium bicarbonate and the mixture was extracted with ethyl acetate (×5). The combined organic fractions were dried over sodium sulfate, filtered and concentrated under reduced pressure to give ethyl 4-{3-[(2-methylacryloyl)amino]phenyl}-7H-pyrrolo[2,3-d]pyrimidine-5-carboxylate. LRMS (ESI) calc'd for $C_{19}H_{19}N_4O_3$ [M+H]$^+$: 351, found 351. $^1$H NMR (600 MHz, DMSO-D$_6$) δ 13.0 (s, 1H), 9.91 (s, 1H), 8.91 (s, 1H), 8.30 (s, 1H), 8.05 (s, 1H), 7.84 (d, 1H, J=7.04 Hz), 7.40 (t, 1H, J=7.63 Hz), 7.32 (d, 1H, J=7.04 Hz), 5.82 (s, 1H), 5.53 (s, 1H), 3.86 (q, 2H, J=7.04 Hz), 1.95 (s, 3H), 0.85 (t, 3H, J=7.04 Hz).

Example 4-2

Ethyl 4-{2-fluoro-3-[(2-methylacryloyl)amino]phenyl}-7H-pyrrolo[2,3-d]pyrimidine-5-carboxylate (4-2)

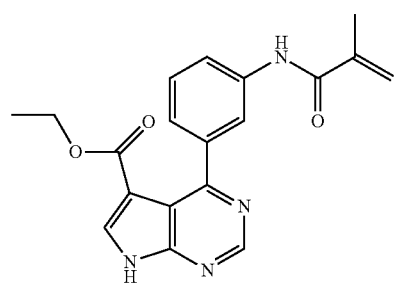 [SMILES: C=C(C)C(=O)Nc1cccc(-c2ncnc3[nH]cc(C(=O)OCC)c23)c1]

To a solution of ethyl 4-(3-amino-2-fluorophenyl)-7H-pyrrolo[2,3-d]pyrimidine-5-carboxylate (6.5 mg, 0.022 mmol) and DIPEA (12 µL, 0.066 mmol) in THF (220 µL) at room temperature was added methacryloyl chloride (3.5 mg, 0.033 mmol) and the solution was stirred for 1 hour. The reaction was concentrated and the residues, dissolved in 2 mL of DMSO, were purified by reverse phase HPLC using an acetonitrile gradient in water with 0.1% TFA modifier. Lyophilization of the desired fractions afforded a colorless solid. LRMS (ESI) calc'd for $C_{19}H_{18}N_4O_3F$ [M+H]$^+$: 369, found 369.

Example 4-3

Ethyl 4-{5-[(2-methylacryloyl)amino]pyridin-3-yl}-7H-pyrrolo[2,3-d]pyrimidine-5-carboxylate

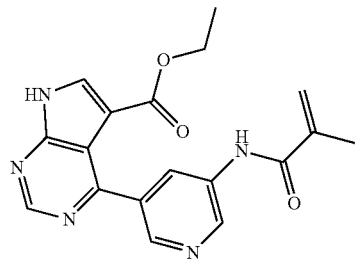 [SMILES: C=C(C)C(=O)Nc1cncc(-c2ncnc3[nH]cc(C(=O)OCC)c23)c1]

To ethyl 4-(5-aminopyridin-3-yl)-7H-pyrrolo[2,3-d]pyrimidine-5-carboxylate (59 mg, 0.14 mmol) in DCM (1.0 mL) was added Hunig's base (0.060 mL, 0.34 mmol) at 0° C. Methacyloyl chloride (0.015 mL, 0.15 mmol) was then added dropwise and the reaction was allowed to warm to room temperature. After being stirred for 17 hours at room temperature, MeOH was added to quench the reaction and the solution was concentrated in vacuo. The crude reaction was purified by reverse phase HPLC using an acetonitrile gradient in water with 0.1% TFA modifier. The products were collected and lyophilized to afford a colorless solid. LRMS (ESI) calc'd for $C_{18}H_{18}N_5O_3$ [M+H]$^+$: 352, found 352. $^1$H NMR (600 MHz, DMSO-D6) δ 13.17 (s, 1H), 10.22 (s, 1H), 9.04 (s, 1H), 9.02 (d, 1H, J=1.7 Hz), 8.55 (s, 1H), 8.50 (m, 1H), 8.45 (m, 1H), 5.93 (s, 1H), 5.65 (s, 1H), 3.99 (q, 2H, J=7.2 Hz), 2.01 (s, 3H), 1.00 (t, 3H, J=7.2 Hz).

Example 4-4

Ethyl 4-{2-methoxy-6-[(2-methylacryloyl)amino]pyridin-4-yl}-7H-pyrrolo[2,3-d]pyrimidine-5-carboxylate

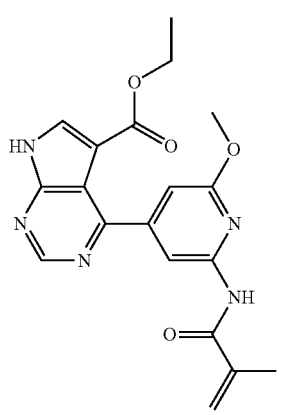 [SMILES: C=C(C)C(=O)Nc1cc(-c2ncnc3[nH]cc(C(=O)OCC)c23)cc(OC)n1]

Step 1: Ethyl 4-{2-methoxy-6-[(2-methylacryloyl)amino]pyridine-4-yl}-7-{[2-(trimethylsilyl)ethoxy]methyl}-7H-pyrrolo[2,3-d]pyrimidine-5-carboxylate

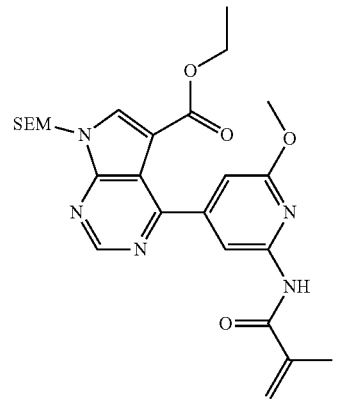 [SMILES: C=C(C)C(=O)Nc1cc(-c2ncnc3c2c(C(=O)OCC)cn3COCC[Si](C)(C)C)cc(OC)n1]

Using ethyl 4-(2-amino-6-methoxypyridin-4-yl)-7-{[2-(trimethylsilyl)ethoxy]methyl}-7H-pyrrolo[2,3-d]pyrimidine-5-carboxylate from Example 1-4, the title compound was prepared in an analogous manner to Example 4-3. LRMS (ESI) calc'd for $C_{25}H_{34}N_5O_5Si$ {M+H]$^+$: 512, found 512.

Step 2: Ethyl 4-{2-methoxy-6-[(2-methylacryloyl)amino]pyridin-4-yl}-7H-pyrrolo[2,3-d]pyrimidine-5-carboxylate

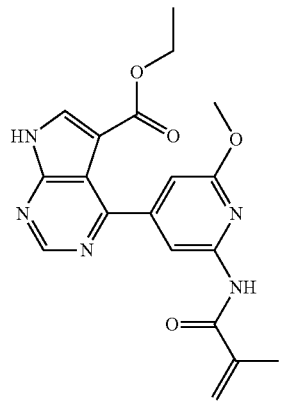 [SMILES: C=C(C)C(=O)Nc1cc(-c2ncnc3[nH]cc(C(=O)OCC)c23)cc(OC)n1]

To ethyl 4-{2-methoxy-6-[(2-methylacryloyl)amino]pyridine-4-yl}-7-{[2 (trimethylsilyl)ethoxy]methyl}-7H-pyrrolo[2,3-d]pyrimidine-5-carboxylate (20 mg, 0.039 mmol) in DCM (0.50 mL) was added TFA (500 µL, 6.49 mmol) and the reaction was stirred for 2 hours at room temperature. The reaction was then concentrated in vacuo, and the residue dissolved in acetonitrile (1.0 mL) and ammonium hydroxide (1.0 mL) was added. The reaction was stirred for an additional 1 hour at room temperature before being concentrated in vacuo and purified by reverse phase HPLC using an acetonitrile gradient in water with 0.1% TFA modifier. The products were collected and lyophilized to afford a colorless solid. LRMS calcd for $C_{19}H_{20}N_5O_4$[M+H]$^+$: 382, found 382. $^1$H NMR (600 MHz, DMSO-D6) δ 13.08 (bs, 1H), 10.05 (s, 1H), 8.92 (s, 1H), 8.33 (d, 1H, J=3.1 Hz), 7.87 (d, 1H, J=0.9 Hz), 6.67 (d, 1H, J=1.1 Hz), 5.87 (s, 1H), 5.52 (s, 1H), 3.90 (q, 2H, J=7.2 Hz), 3.89 (s, 3H), 1.91 (s, 3H), 0.92 (t, 3H, J=7.2 Hz).

The following examples, 4-5 through 4-35, as shown in Table 3, were prepared in an analogous manner of that described above using materials that are commercially available or known, or that can be prepared using procedures known in the art or by generally following procedures described herein for various intermediates.

TABLE 3

| Example Number | Structure | IUPAC Name | Exact Mass [M + H]+ |
|---|---|---|---|
| 4-5 | 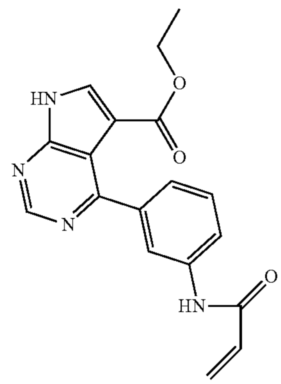 [SMILES: C=CC(=O)Nc1cccc(-c2ncnc3[nH]cc(C(=O)OCC)c23)c1] | ethyl 4-[3-(acryloylamino)phenyl]-7H-pyrrolo[2,3-d]pyrimidine-5-carboxylate | Calc'd 337, found 337 |
| 4-6 | 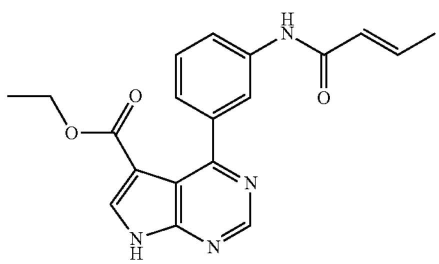 [SMILES: C/C=C/C(=O)Nc1cccc(-c2ncnc3[nH]cc(C(=O)OCC)c23)c1] | ethyl 4-{3-[(2E)-but-2-enoylamino]phenyl}-7H-pyrrolo[2,3-d]pyrimidine-5-carboxylate | Calc'd 351, found 351 |
| 4-7 | 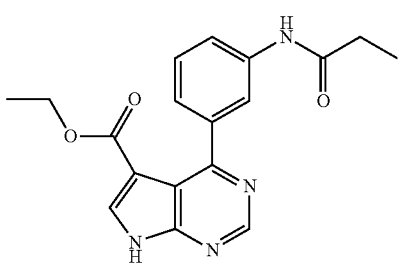 [SMILES: CCOC(=O)c1c[nH]c2ncnc(-c3cccc(NC(=O)CC)c3)c12] | ethyl 4-[3-(propanoylamino)phenyl]-7H-pyrrolo[2,3-d]pyrimidine-5-carboxylate | Calc'd 339, found 339 |
| 4-8 | 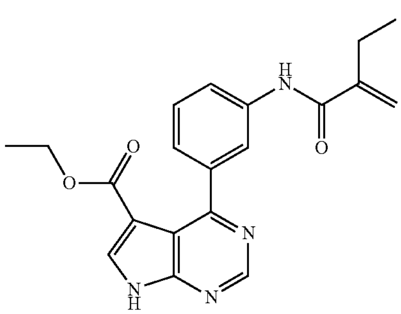 [SMILES: C=C(CC)C(=O)Nc1cccc(-c2ncnc3[nH]cc(C(=O)OCC)c23)c1] | ethyl 4-{3-[(2-methylidenebutanoyl)amino]phenyl}-7H-pyrrolo[2,3-d]pyrimidine-5-carboxylate | Calc'd 365, found 365 |

TABLE 3-continued

| Example Number | Structure | IUPAC Name | Exact Mass [M + H]+ |
|---|---|---|---|
| 4-9 | 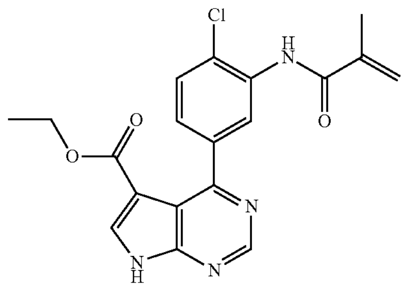 [SMILES: C=C(C)C(=O)Nc1cc(-c2ncnc3[nH]cc(C(=O)OCC)c23)ccc1Cl] | ethyl 4-{4-chloro-3-[(2-methylacryloyl)amino]phenyl}-7H-pyrrolo[2,3-d]pyrimidine-5-carboxylate | Calc'd 385, found 385 |
| 4-10 | 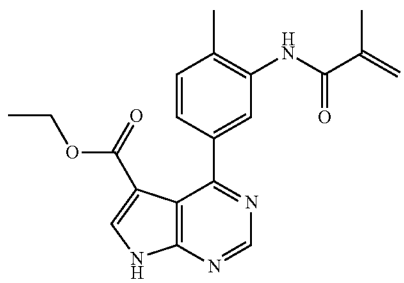 [SMILES: C=C(C)C(=O)Nc1cc(-c2ncnc3[nH]cc(C(=O)OCC)c23)ccc1C] | ethyl 4-{4-methyl-3-(2-methylacryloyl)amino]phenyl}-7H-pyrrolo[2,3-d]pyrimidine-5-carboxylate | Calc'd 365, found 365 |
| 4-11 | 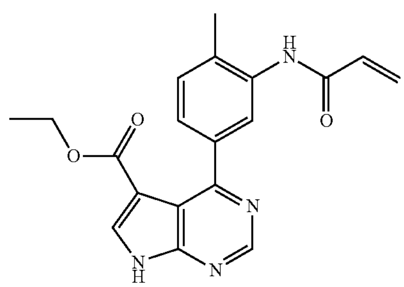 [SMILES: C=CC(=O)Nc1cc(-c2ncnc3[nH]cc(C(=O)OCC)c23)ccc1C] | ethyl 4-[3-(acryloylamino)-4-methylphenyl]-7H-pyrrolo[2,3-d]pyrimidine-5-carboxylate | Calc'd 351, found 351 |
| 4-12 | 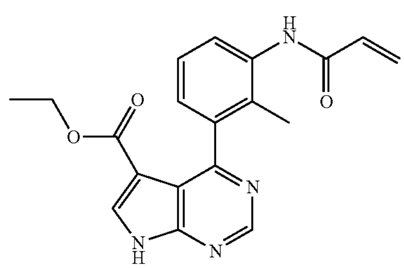 [SMILES: C=CC(=O)Nc1cccc(-c2ncnc3[nH]cc(C(=O)OCC)c23)c1C] | ethyl 4-[3-(acryloylamino)-2-methylphenyl]-7H-pyrrolo[2,3-d]pyrimidine-5-carboxylate | Calc'd 351, found 351 |
| 4-13 | 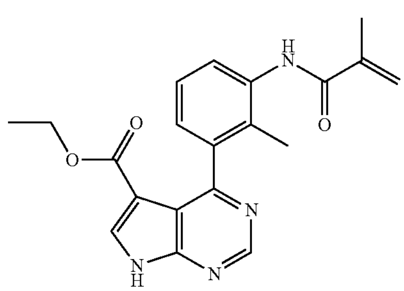 [SMILES: C=C(C)C(=O)Nc1cccc(-c2ncnc3[nH]cc(C(=O)OCC)c23)c1C] | ethyl 4-{2-methyl-3-[(2-methylacryloyl)amino]phenyl}-7H-pyrrolo[2,3-d]pyrimidine-5-carboxylate | Calc'd 365, found 365 |

TABLE 3-continued

| Example Number | Structure | IUPAC Name | Exact Mass [M + H]+ |
|---|---|---|---|
| 4-14 | 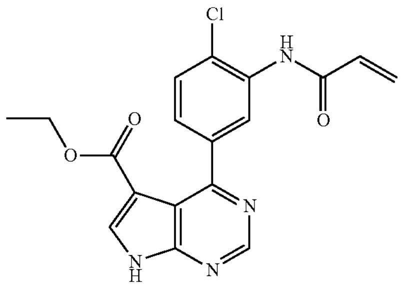 [SMILES: C=CC(=O)Nc1cc(-c2ncnc3[nH]cc(C(=O)OCC)c23)ccc1Cl] | ethyl 4-[3-(acryloylamino)-4-chlorophenyl]-7H-pyrrolo[2,3-d]pyrimidine-5-carboxylate | Calc'd 371, found 371 |
| 4-15 | 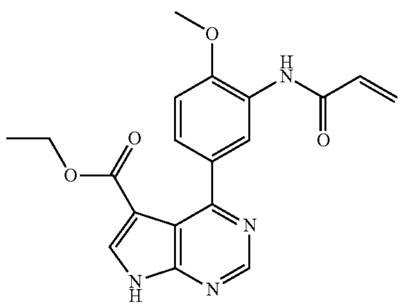 [SMILES: C=CC(=O)Nc1cc(-c2ncnc3[nH]cc(C(=O)OCC)c23)ccc1OC] | ethyl 4-[3-(acryloylamino)-4-methoxyphenyl]-7H-pyrrolo[2,3-d]pyrimidine-5-carboxylate | Calc'd 367, found 367 |
| 4-16 | 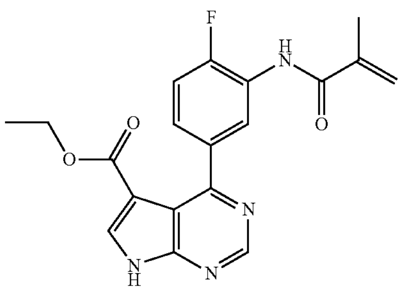 | ethyl 4-{4-fluoro-3-[(2-methylacryloyl)amino]phenyl}-7H-pyrrolo[2,3-d]pyrimidine-5-carboxylate | Calc'd 369, found 369 |
| 4-17 | 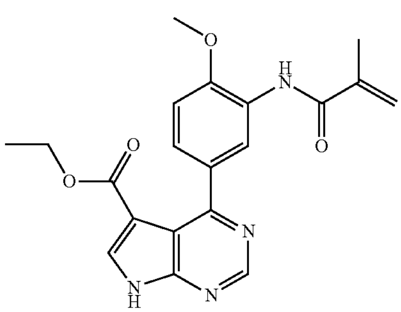 [SMILES: C=C(C)C(=O)Nc1cc(-c2ncnc3[nH]cc(C(=O)OCC)c23)ccc1OC] | ethyl 4-{4-methoxy-3-[(2-methylacryloyl)amino]phenyl}-7H-pyrrolo[2,3-d]pyrimidine-5-carboxylate | Calc'd 381, found 381 |
| 4-18 | 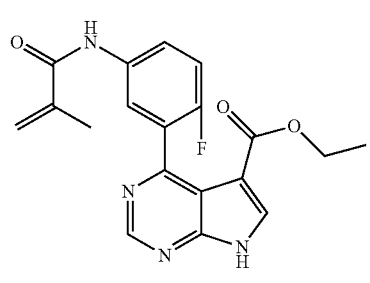 [SMILES: C=C(C)C(=O)Nc1ccc(F)c(-c2ncnc3[nH]cc(C(=O)OCC)c23)c1] | ethyl 4-{2-fluoro-5-[(2-methylacryloyl)amino]phenyl}-7H-pyrrolo[2,3-d]pyrimidine-5-carboxylate | Calc'd 369, found 369 |

TABLE 3-continued

| Example Number | Structure | IUPAC Name | Exact Mass [M + H]+ |
|---|---|---|---|
| 4-19 | 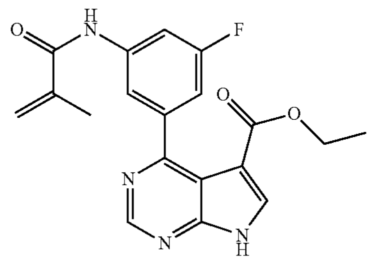 [SMILES: C=C(C)C(=O)Nc1cc(F)cc(-c2ncnc3[nH]cc(C(=O)OCC)c23)c1] | ethyl 4-{3-fluoro-5-[(2-methylacryloyl)amino]phenyl}-7H-pyrrolo[2,3-d]pyrimidine-5-carboxylate | Calc'd 369, found 369 |
| 4-20 | 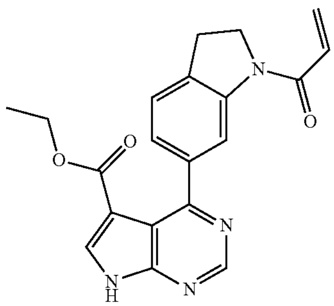 [SMILES: C=CC(=O)N1CCc2ccc(-c3ncnc4[nH]cc(C(=O)OCC)c34)cc21] | ethyl 4-(1-acryloyl-2,3-dihydro-1H-indol-6-yl)-7H-pyrrolo[2,3-d]pyrimidine-5-carboxylate | Calc'd 363, found 363 |
| 4-21 | 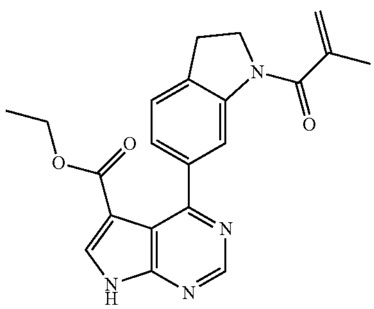 [SMILES: C=C(C)C(=O)N1CCc2ccc(-c3ncnc4[nH]cc(C(=O)OCC)c34)cc21] | ethyl 4-[1-(2-methylacryloyl)-2,3-dihydro-1H-indol-6-yl]-7H-pyrrolo[2,3-d]pyrimidine-5-carboxylate | Calc'd 377, found 377 |
| 4-22 | 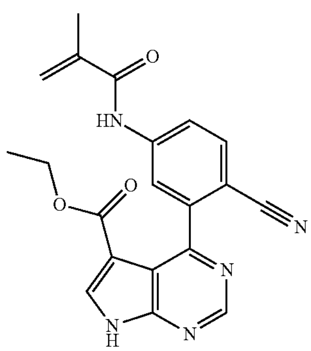 [SMILES: C=C(C)C(=O)Nc1ccc(C#N)c(-c2ncnc3[nH]cc(C(=O)OCC)c23)c1] | ethyl 4-{2-cyano-5-[(2-methylacryloyl)amino]phenyl}-7H-pyrrolo[2,3-d]pyrimidine-5-carboxylate | Calc'd 376, found 376 |
| 4-23 | 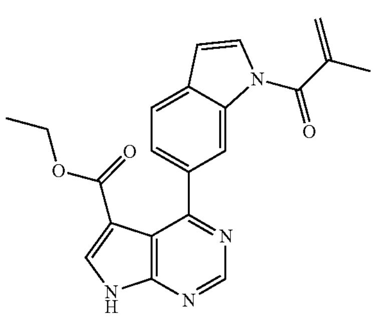 [SMILES: C=C(C)C(=O)n1ccc2ccc(-c3ncnc4[nH]cc(C(=O)OCC)c34)cc21] | ethyl 4-[1-(2-methylacryloyl)-1H-indol-6-yl]-7H-pyrrolo[2,3-d]pyrimidine-5-carboxylate | Calc'd 375, found 375 |

TABLE 3-continued

| Example Number | Structure | IUPAC Name | Exact Mass [M + H]+ |
|---|---|---|---|
| 4-24 | 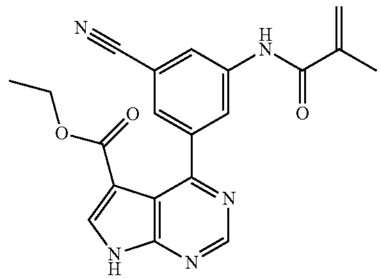 [SMILES: C=C(C)C(=O)Nc1cc(C#N)cc(-c2ncnc3[nH]cc(C(=O)OCC)c23)c1] | ethyl 4-{3-cyano-5-[(2-methylacryloyl)amino]phenyl}-7H-pyrrolo[2,3-d]pyrimidine-5-carboxylate | Calc'd 376, found 376 |
| 4-25 | 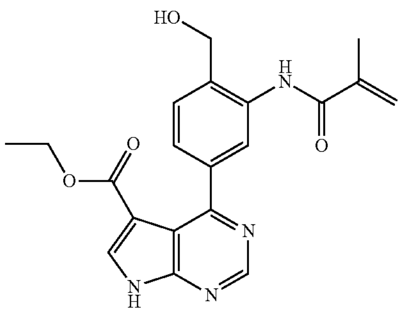 [SMILES: C=C(C)C(=O)Nc1cc(-c2ncnc3[nH]cc(C(=O)OCC)c23)ccc1CO] | ethyl 4-{4-(hydroxymethyl)-3-[(2-methylacryloyl)amino]phenyl}-7H-pyrrolo[2,3-d]pyrimidine-5-carboxylate | Calc'd 381, found 381 |
| 4-26 | 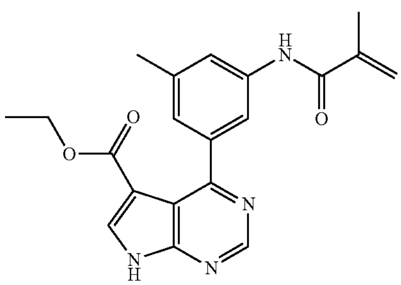 [SMILES: C=C(C)C(=O)Nc1cc(C)cc(-c2ncnc3[nH]cc(C(=O)OCC)c23)c1] | ethyl 4-{3-methyl-5-[(2-methylacryloyl)amino]phenyl}-7H-pyrrolo[2,3-d]pyrimidine-5-carboxylate | Calc'd 365, found 365 |
| 4-27 | 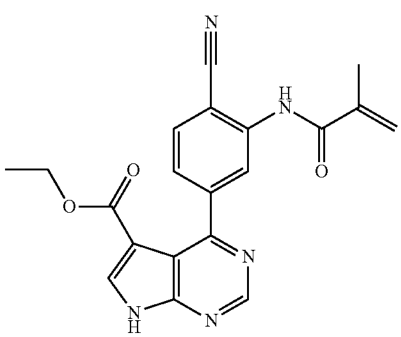 [SMILES: C=C(C)C(=O)Nc1cc(-c2ncnc3[nH]cc(C(=O)OCC)c23)ccc1C#N] | ethyl 4-{4-cyano-3-[(2-methylacryloyl)amino]phenyl}-7H-pyrrolo[2,3-d]pyrimidine-5-carboxylate | Calc'd 376, found 376 |
| 4-28 | 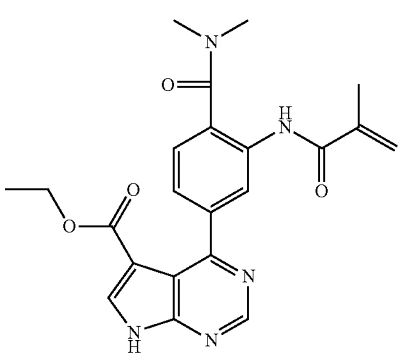 [SMILES: C=C(C)C(=O)Nc1cc(-c2ncnc3[nH]cc(C(=O)OCC)c23)ccc1C(=O)N(C)C] | ethyl 4-{4-(dimethylcarbamoyl)-3-[(2-methylacryloyl)amino]phenyl}-7H-pyrrolo[2,3-d]pyrimidine-5-carboxylate | Calc'd 422, found 422 |

TABLE 3-continued

| Example Number | Structure | IUPAC Name | Exact Mass [M + H]+ |
|---|---|---|---|
| 4-29 | 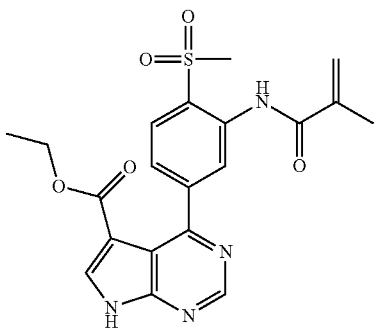 [SMILES: C=C(C)C(=O)Nc1cc(-c2ncnc3[nH]cc(C(=O)OCC)c23)ccc1S(C)(=O)=O] | ethyl 4-{3-[(2-methylacryloyl)amino]-4-(methylsulfonyl)phenyl}-7H-pyrrolo[2,3-d]pyrimidine-5-carboxylate | Calc'd 429, found 429 |
| 4-30 | 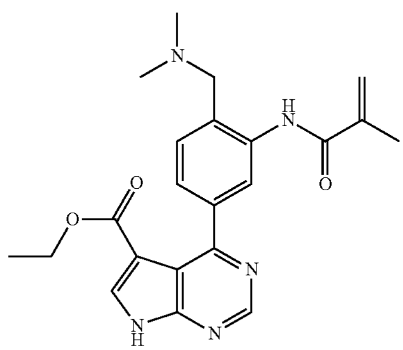 [SMILES: C=C(C)C(=O)Nc1cc(-c2ncnc3[nH]cc(C(=O)OCC)c23)ccc1CN(C)C] | ethyl 4-{4-[(dimethylamino)methyl]-3-[(2-methylacryloyl)amino]phenyl}-7H-pyrrolo[2,3-d]pyrimidine-5-carboxylate | Calc'd 408, found 408 |
| 4-31 | 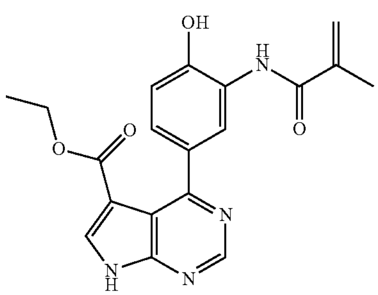 [SMILES: C=C(C)C(=O)Nc1cc(-c2ncnc3[nH]cc(C(=O)OCC)c23)ccc1O] | ethyl 4-{4-hydroxy-3-[(2-methylacryloyl)amino]phenyl}-7H-pyrrolo[2,3-d]pyrimidine-5-carboxylate | Calc'd 367, found 367 |
| 4-32 | 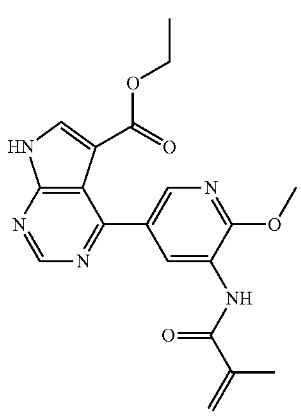 [SMILES: C=C(C)C(=O)Nc1cc(-c2ncnc3[nH]cc(C(=O)OCC)c23)cnc1OC] | ethyl 4-{6-methoxy-5-[(2-methylacryloyl)amino]pyridin-3-yl)-7H-pyrrolo[2,3-d]pyrimidine-5-carboxylate | Calc'd 382, found 382 |

TABLE 3-continued

| Example Number | Structure | IUPAC Name | Exact Mass [M + H]+ |
|---|---|---|---|
| 4-33 | 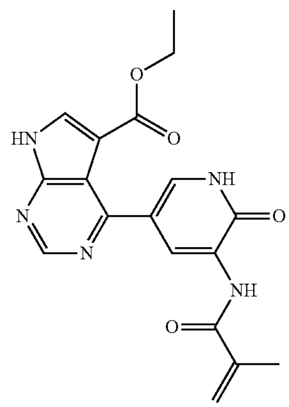 [SMILES: C=C(C)C(=O)Nc1cc(-c2ncnc3[nH]cc(C(=O)OCC)c23)c[nH]c1=O] | ethyl 4-{5-[(2-methylacryloyl)amino]-6-oxo-1,6-dihydropyridin-3-yl}-7H-pyrrolo[2,3-d]pyrimidine-5-carboxylate | Calc'd 368, found 368 |
| 4-34 | 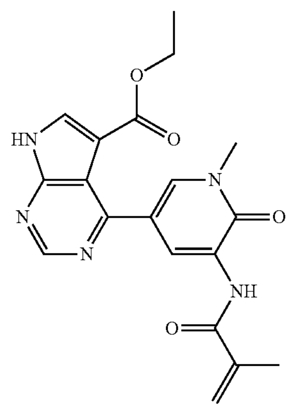 [SMILES: C=C(C)C(=O)Nc1cc(-c2ncnc3[nH]cc(C(=O)OCC)c23)cn(C)c1=O] | ethyl 4-{1-methyl-5-[(2-methylacryloyl)amino]-6-oxo-1,6-dihydropyridin-3-yl}-7H-pyrrolo[2,3-d]pyrimidine-5-carboxylate | Calc'd 382, found 382 |
| 4-35 | 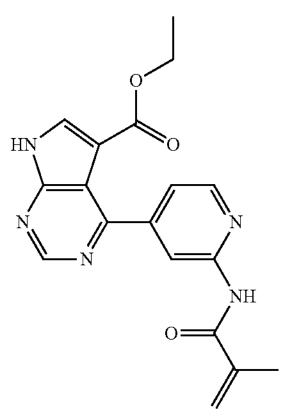 [SMILES: C=C(C)C(=O)Nc1cc(-c2ncnc3[nH]cc(C(=O)OCC)c23)ccn1] | ethyl 4-{2-[(2-methylacryloyl)amino]pyridin-4-yl}-7H-pyrrolo[2,3-d]pyrimidine-5-carboxylate | Calc'd 352, found 352 |

General Scheme E:

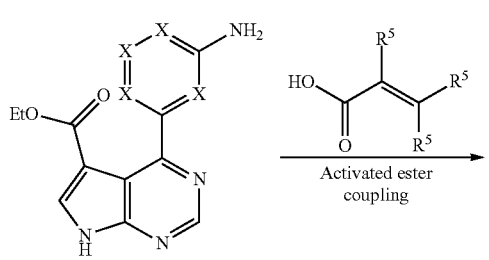
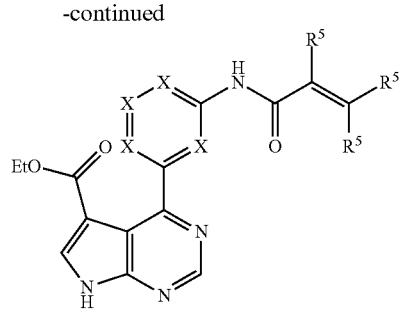

Examples Generated Via General Scheme E

Example 5-1

Ethyl 4-{3-[(2-fluoroacryloyl)amino]phenyl}-7H-pyrrolo[2,3-d]pyrimidine-5-carboxylate

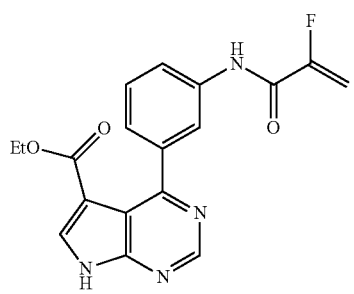 [SMILES: C=C(F)C(=O)Nc1cccc(-c2ncnc3[nH]cc(C(=O)OCC)c23)c1]

Ethyl 4-(3-aminophenyl)-7H-pyrrolo[2,3-d]pyrimidine-5-carboxylate (0.028 g, 0.10 mmol), 2-fluoroacrylic acid (0.013 g, 0.15 mmol), 3-[(diethoxyphosphoryl)oxy]-1,2,3-benzotriazin-4(3H)-one (0.060 g, 0.20 mmol), and DIPEA (0.070 mL, 0.40 mmol) were suspended in DMA (1.0 mL) in a sealed tube. The reaction mixture was purged with argon and the reaction flask was capped and heated to 50° C. for 12 hours. The completed reaction was passed through a syringe filter, and was directly purified by reverse phase HPLC using an acetonitrile gradient in water with 0.1% NH$_4$OH modifier to afford ethyl 4-{3-[(2-fluoroacryloyl)amino]phenyl}-7H-pyrrolo[2,3-d]pyrimidine-5-carboxylate. LRMS (ESI) calc'd for C$_{18}$H$_{16}$FN$_4$O$_3$ [M+H]$^+$: 355, found 355. $^1$H NMR (600 MHz, DMSO-D6) δ 12.99 (s, 1H), 10.44 (s, 1H), 8.91 (s, 1H), 8.32 (s, 1H), 8.09 (t, J=1.8 Hz, 1H), 7.87 (ddd, J=1.1, 2.1, 8.0 Hz, 1H), 7.45 (t, J=7.8 Hz, 1H), 7.40 (dt, J=1.3, 7.7 Hz, 1H), 5.72 (dd, J=3.6, 47.6 Hz, 1H), 5.44 (dd, J=3.7, 15.6 Hz, 1H), 3.85 (q, J=7.1 Hz, 2H), 0.84 (t, J=7.1 Hz, 3H).

Example 5-2

Ethyl 4-{2-fluoro-5-[(2-methylacryloyl)amino]phenyl}-7H-pyrrolo[2,3-d]pyrimidine-5-carboxylate

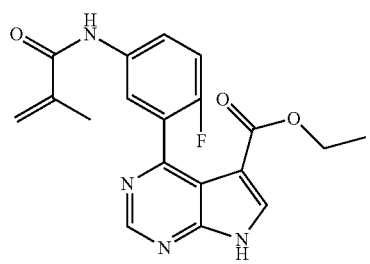 [SMILES: C=C(C)C(=O)Nc1ccc(F)c(-c2ncnc3[nH]cc(C(=O)OCC)c23)c1]

To crude ethyl 4-(5-amino-2-fluorophenyl)-7H-pyrrolo[2,3-d]pyrimidine-5-carboxylate (133 mg, 0.443 mmol) was added THF (4.43 mL), TEA (93 µL, 0.66 mmol), methylacrylic acid (57 mg, 0.66 mmol) and 1-propanephosphonic acid cyclic anhydride (3.26 mL, 0.443 mmol). The reaction was stirred at 25° C. overnight. The reaction was quenched by pouring into a separatory funnel containing aqueous sodium hydrogen carbonate (5%) and was extracted with ethyl acetate (×3). The organic layers were combined and dried with Na$_2$SO$_4$, filtered, and evaporated in vacuo. The crude reaction was purified by reverse phase HPLC using an acetonitrile gradient in water with 0.1% TFA modifier. The products were collected and lyophilized to afford a colorless solid. LRMS (ESI) calc'd for C$_{19}$H$_{18}$N$_4$O$_3$F [M+H]$^+$: 369, found 369.

The following examples, 5-3 through 5-45, as shown in Table 4, were prepared in an analogous manner of that described above using materials that are commercially available or known, or that can be prepared using procedures known in the art or by generally following procedures described herein for various intermediates.

TABLE 4

| Example Number | Structure | IUPAC Name | Exact Mass [M + H]+ |
|---|---|---|---|
| 5-3 | ![structure] | ethyl 4-[3-(but-2-ynoylamino)phenyl]-7H-pyrrolo[2,3-d]pyrimidine-5-carboxylate | Calc'd 349, found 349 |

TABLE 4-continued

| Example Number | Structure | IUPAC Name | Exact Mass [M + H]+ |
|---|---|---|---|
| 5-4 | 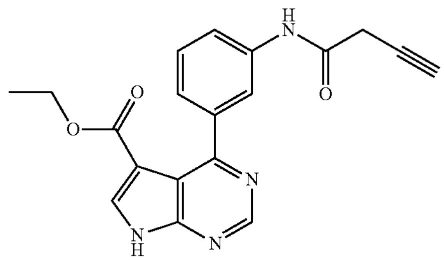 [SMILES: C#CCC(=O)Nc1cccc(-c2ncnc3[nH]cc(C(=O)OCC)c23)c1] | ethyl 4-{3-[(cyanoacetyl)amino]phenyl}-7H-pyrrolo[2,3-d]pyrimidine-5-carboxylate | Calc'd 350, found 350 |
| 5-5 | 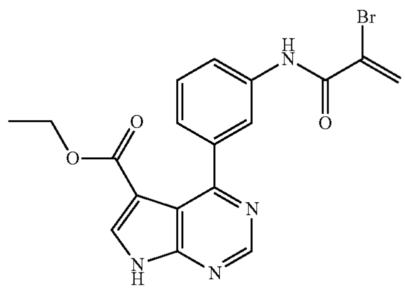 [SMILES: C=C(Br)C(=O)Nc1cccc(-c2ncnc3[nH]cc(C(=O)OCC)c23)c1] | ethyl 4-{3-[(2-bromoacryloyl)amino]phenyl}-7H-pyrrolo[2,3-d]pyrimidine-5-carboxylate | Calc'd 415, found 415 |
| 5-6 | 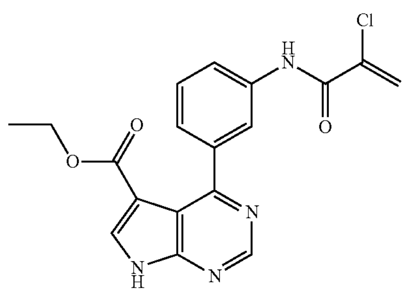 [SMILES: C=C(Cl)C(=O)Nc1cccc(-c2ncnc3[nH]cc(C(=O)OCC)c23)c1] | ethyl 4-{3-[(2-chloroacryloyl)amino]phenyl}-7H-pyrrolo[2,3-d]pyrimidine-5-carboxylate | Calc'd 371, found 371 |
| 5-7 | 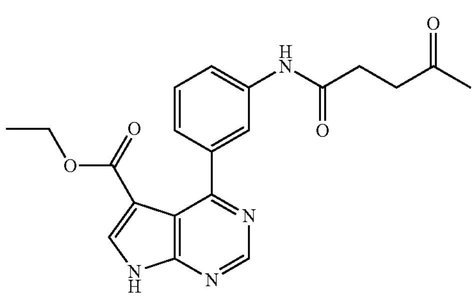 [SMILES: CCOC(=O)c1c[nH]c2ncnc(-c3cccc(NC(=O)CCC(C)=O)c3)c12] | ethyl 4-{3-[(4-oxopentanoyl)amino]phenyl}-7H-pyrrolo[2,3-d]pyrimidine-5-carboxylate | Calc'd 381, found 381 |
| 5-8 | 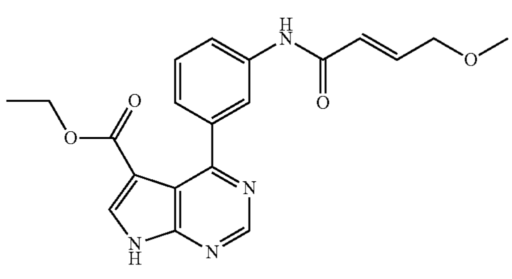 [SMILES: CCOC(=O)c1c[nH]c2ncnc(-c3cccc(NC(=O)/C=C/COC)c3)c12] | ethyl 4-(3-{[(2E)-4-methoxybut-2-enoyl]amino}phenyl)-7H-pyrrolo[2,3-d]pyrimidine-5-carboxylate | Calc'd 381, found 381 |

TABLE 4-continued

| Example Number | Structure | IUPAC Name | Exact Mass [M + H]+ |
|---|---|---|---|
| 5-9 | 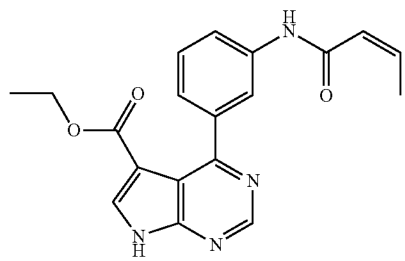 [SMILES: C/C=C\C(=O)Nc1cccc(-c2ncnc3[nH]cc(C(=O)OCC)c23)c1] | ethyl 4-{3-[(2Z)-but-2-enoylamino]phenyl}-7H-pyrrolo[2,3-d]pyrimidine-5-carboxylate | Calc'd 351, found 351 |
| 5-10 | 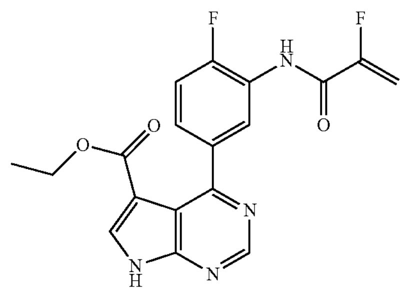 [SMILES: C=C(F)C(=O)Nc1cc(-c2ncnc3[nH]cc(C(=O)OCC)c23)ccc1F] | ethyl 4-{4-fluoro-3-[(2-fluoroacryloyl)amino]phenyl}-7H-pyrrolo[2,3-d]pyrimidine-5-carboxylate | Calc'd 373, found 373 |
| 5-11 | 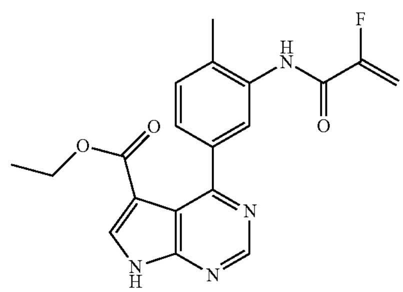 [SMILES: C=C(F)C(=O)Nc1cc(-c2ncnc3[nH]cc(C(=O)OCC)c23)ccc1C] | ethyl 4-{3-[(2-fluoroacryloyl)amino]-4-methylphenyl}-7H-pyrrolo[2,3-d]pyrimidine-5-carboxylate | Calc'd 369, found 369 |
| 5-12 | 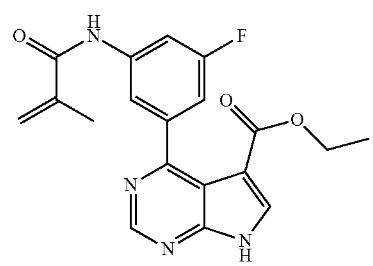 [SMILES: C=C(C)C(=O)Nc1cc(F)cc(-c2ncnc3[nH]cc(C(=O)OCC)c23)c1] | ethyl 4-{3-fluoro-5-[(2-methylacryloyl)amino]phenyl}-7H-pyrrolo[2,3-d]pyrimidine-5-carboxylate | Calc'd 369, found 369 |
| 5-13 | 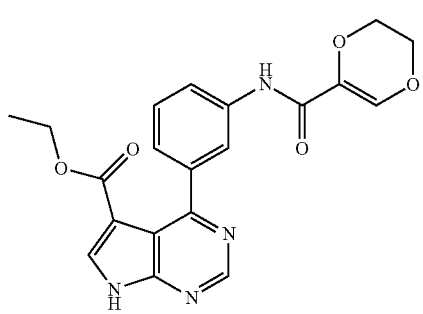 [SMILES: CCOC(=O)c1c[nH]c2ncnc(-c3cccc(NC(=O)C4=COCCO4)c3)c12] | ethyl 4-{3-[(5,6-dihydro-1,4-dioxin-2-ylcarbonyl)amino]phenyl}-7H-pyrrolo[2,3-d]pyrimidine-5-carboxylate | Calc'd 395, found 395 |

TABLE 4-continued

| Example Number | Structure | IUPAC Name | Exact Mass [M + H]+ |
|---|---|---|---|
| 5-14 | 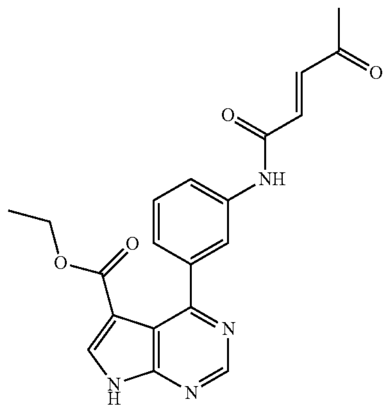 [SMILES: CCOC(=O)c1c[nH]c2ncnc(-c3cccc(NC(=O)/C=C/C(C)=O)c3)c12] | ethyl 4-(3-{[(2E)-4-oxopent-2-enoyl]amino}phenyl)-7H-pyrrolo[2,3-d]pyrimidine-5-carboxylate | Calc'd 379, found 379 |
| 5-15 | 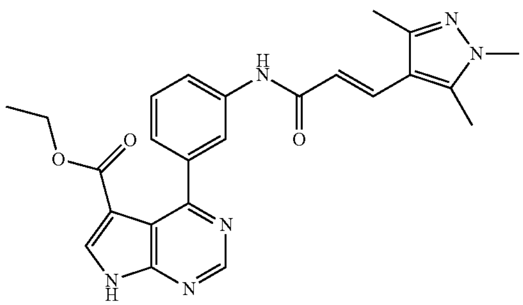 [SMILES: CCOC(=O)c1c[nH]c2ncnc(-c3cccc(NC(=O)/C=C/c4c(C)nn(C)c4C)c3)c12] | ethyl 4-(3-{[(2E)-3-(1,3,5-trimethyl-1H-pyrazol-4-yl)prop-2-enoyl]amino}phenyl)-7H-pyrrolo[2,3-d]pyrimidine-5-carboxylate | Calc'd 445, found 445 |
| 5-16 | 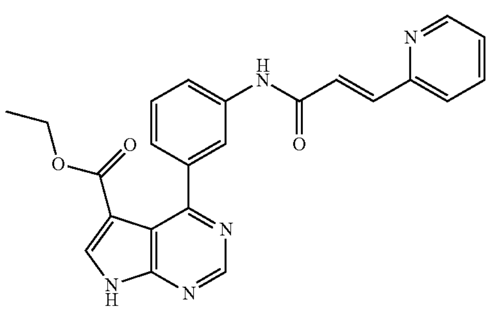 [SMILES: CCOC(=O)c1c[nH]c2ncnc(-c3cccc(NC(=O)/C=C/c4ccccn4)c3)c12] | ethyl 4-(3-{[(2E)-3-pyridin-2-ylprop-2-enoyl]amino}phenyl)-7H-pyrrolo[2,3-d]pyrimidine-5-carboxylate | Calc'd 414, found 414 |
| 5-17 | 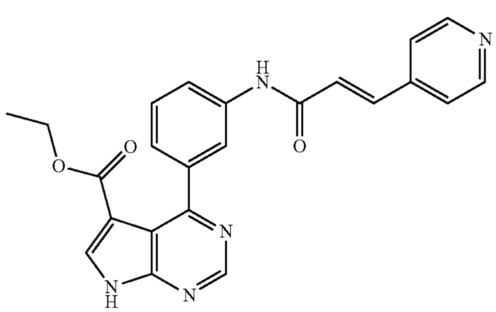 [SMILES: CCOC(=O)c1c[nH]c2ncnc(-c3cccc(NC(=O)/C=C/c4ccncc4)c3)c12] | ethyl 4-(3-{[(2E)-3-pyridin-4-ylprop-2-enoyl]amino}phenyl)-7H-pyrrolo[2,3-d]pyrimidine-5-carboxylate | Calc'd 414, found 414 |

TABLE 4-continued

| Example Number | Structure | IUPAC Name | Exact Mass [M + H]+ |
|---|---|---|---|
| 5-18 | 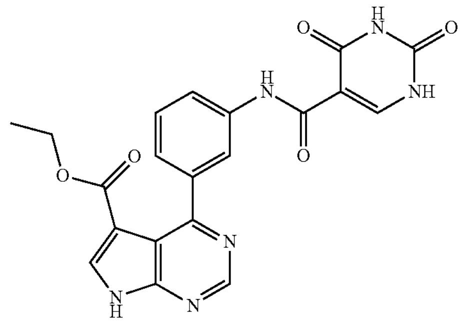 [SMILES: CCOC(=O)c1c[nH]c2ncnc(-c3cccc(NC(=O)c4c[nH]c(=O)[nH]c4=O)c3)c12] | ethyl 4-(3-{[(2,4-dioxo-1,2,3,4-tetrahydropyrimidin-5-yl)carbonyl]amino}phenyl)-7H-pyrrolo[2,3-d]pyrimidine-5-carboxylate | Calc'd 421, found 421 |
| 5-19 | 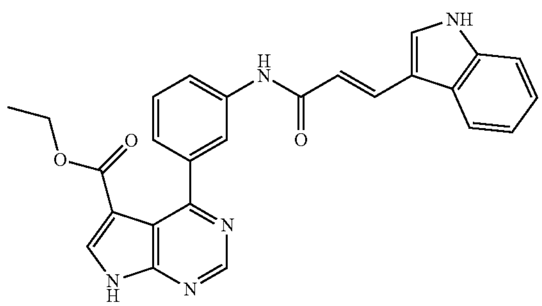 [SMILES: CCOC(=O)c1c[nH]c2ncnc(-c3cccc(NC(=O)/C=C/c4c[nH]c5ccccc45)c3)c12] | ethyl 4-(3-{[(2E)-3-(1H-indol-3-yl)prop-2-enoyl]amino}phenyl)-7H-pyrrolo[2,3-d]pyrimidine-5-carboxylate | Calc'd 452, found 452 |
| 5-20 | 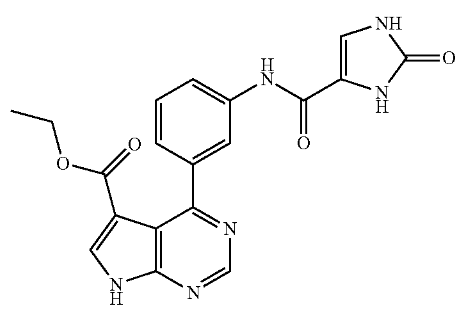 [SMILES: CCOC(=O)c1c[nH]c2ncnc(-c3cccc(NC(=O)c4c[nH]c(=O)[nH]4)c3)c12] | ethyl 4-(3-{[(2-oxo-2,3-dihydro-1H-imidazol-4-yl)carbonyl]amino}phenyl)-7H-pyrrolo[2,3-d]pyrimidine-5-carboxylate | Calc'd 393, found 393 |
| 5-21 | 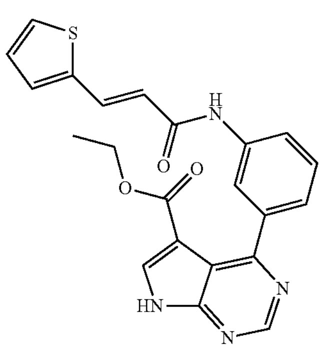 [SMILES: CCOC(=O)c1c[nH]c2ncnc(-c3cccc(NC(=O)/C=C/c4cccs4)c3)c12] | ethyl 4-(3-{[(2E)-3-thiophen-2-ylprop-2-enoyl]amino}phenyl)-7H-pyrrolo[2,3-d]pyrimidine-5-carboxylate | Calc'd 419, found 419 |

TABLE 4-continued

| Example Number | Structure | IUPAC Name | Exact Mass [M + H]+ |
| --- | --- | --- | --- |
| 5-22 | 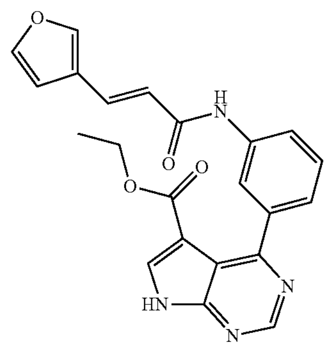 [SMILES: CCOC(=O)c1c[nH]c2ncnc(-c3cccc(NC(=O)/C=C/c4ccoc4)c3)c12] | ethyl 4-(3-{[(2E)-3-furan-3-ylprop-2-enoyl]amino}phenyl)-7H-pyrrolo[2,3-d]pyrimidine-5-carboxylate | Calc'd 403, found 403 |
| 5-23 | 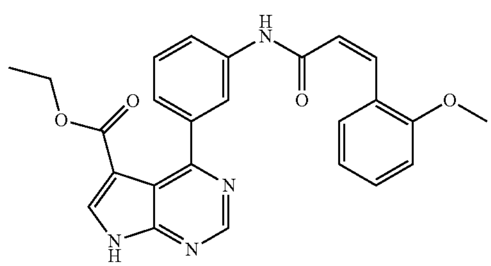 [SMILES: CCOC(=O)c1c[nH]c2ncnc(-c3cccc(NC(=O)/C=C\c4ccccc4OC)c3)c12] | ethyl 4-(3-{[(2Z)-3-(2-methoxyphenyl)prop-2-enoyl]amino}phenyl)-7H-pyrrolo[2,3-d]pyrimidine-5-carboxylate | Calc'd 443, found 443 |
| 5-24 | 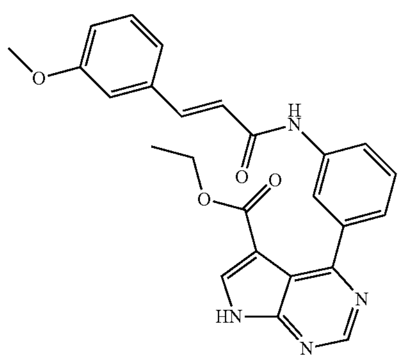 [SMILES: CCOC(=O)c1c[nH]c2ncnc(-c3cccc(NC(=O)/C=C/c4cccc(OC)c4)c3)c12] | ethyl 4-(3-{[(2E)-3-(3-methoxyphenyl)prop-2-enoyl]amino}phenyl)-7H-pyrrolo[2,3-d]pyrimidine-5-carboxylate | Calc'd 443, found 443 |
| 5-25 | 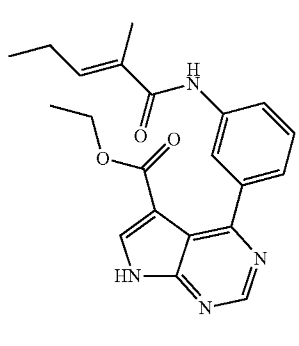 [SMILES: CC/C=C(\C)C(=O)Nc1cccc(-c2ncnc3[nH]cc(C(=O)OCC)c23)c1] | ethyl 4-(3-{[(2E)-2-methylpent-2-enoyl]amino}phenyl)-7H-pyrrolo[2,3-d]pyrimidine-5-carboxylate | Calc'd 379, found 379 |

TABLE 4-continued

| Example Number | IUPAC Name | Exact Mass [M + H]+ |
|---|---|---|
| 5-26 | ethyl 4-(3-{[(2Z)-2-fluoro-3-phenylprop-2-enoyl]amino}phenyl)-7H-pyrrolo[2,3-d]pyrimidine-5-carboxylate | Calc'd 431, found 431 |
| 5-27 | ethyl 4-{3-[(3-methylbut-2-enoyl)amino]phenyl}-7H-pyrrolo[2,3-d]pyrimidine-5-carboxylate | Calc'd 365, found 365 |
| 5-28 | ethyl 4-(3-{[(2E)-2-methyl-3-phenylprop-2-enoyl]amino}phenyl)-7H-pyrrolo[2,3-d]pyrimidine-5-carboxylate | Calc'd 427, found 427 |
| 5-29 | ethyl 4-(3-{[(2E)-3-(4-methoxyphenyl)prop-2-enoyl]amino}phenyl)-7H-pyrrolo[2,3-d]pyrimidine-5-carboxylate | Calc'd 443, found 443 |

TABLE 4-continued

| Example Number | Structure | IUPAC Name | Exact Mass [M + H]+ |
|---|---|---|---|
| 5-30 | 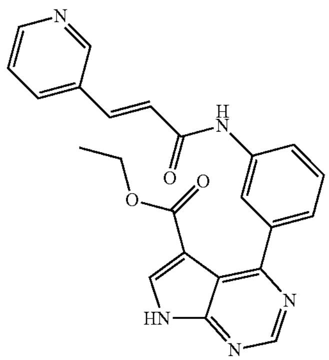 [SMILES: CCOC(=O)c1c[nH]c2ncnc(-c3cccc(NC(=O)/C=C/c4cccnc4)c3)c12] | ethyl 4-(3-{[(2E)-3-pyridin-3-ylprop-2-enoyl]amino}phenyl)-7H-pyrrolo[2,3-d]pyrimidine-5-carboxylate | Calc'd 414, found 414 |
| 5-31 | 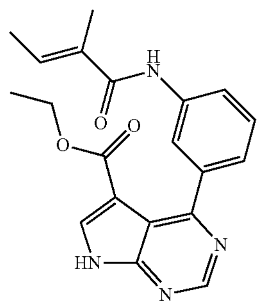 [SMILES: C/C=C(\C)C(=O)Nc1cccc(-c2ncnc3[nH]cc(C(=O)OCC)c23)c1] | ethyl 4-(3-{[(2E)-2-methylbut-2-enoyl]aminol}phenyl)-7H-pyrrolo[2,3-d]pyrimidine-5-carboxylate | Calc'd 365, found 365 |
| 5-32 | 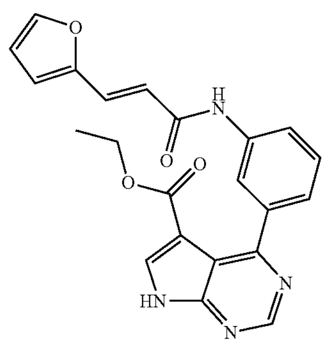 | ethyl 4-(3-{[(2E)-3-furan-2-ylprop-2-enoyl]amino}phenyl)-7H-pyrrolo[2,3-d]pyrimidine-5-carboxylate | Calc'd 403, found 403 |
| 5-33 | 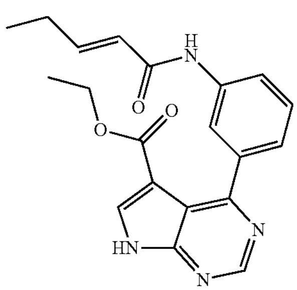 [SMILES: CC/C=C/C(=O)Nc1cccc(-c2ncnc3[nH]cc(C(=O)OCC)c23)c1] | ethyl 4-{3-[(2E)-pent-2-enoylamino]phenyl}-7H-pyrrolo[2,3-d]pyrimidine-5-carboxylate | Calc'd 365, found 365 |
| 5-34 | 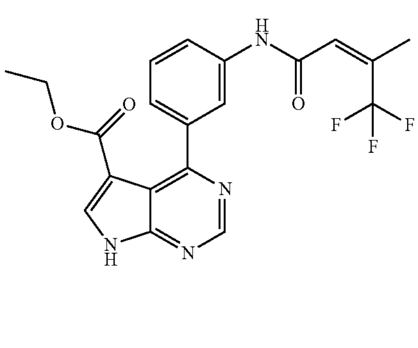 [SMILES: CCOC(=O)c1c[nH]c2ncnc(-c3cccc(NC(=O)/C=C(/C)C(F)(F)F)c3)c12] | ethyl 4-(3-{[(2Z)-4,4,4-trifluoro-3-methylbut-2-enoyl]amino}phenyl)-7H-pyrrolo[2,3-d]pyrimidine-5-carboxylate | Calc'd 419, found 419 |

TABLE 4-continued

| Example Number | Structure | IUPAC Name | Exact Mass [M + H]+ |
| --- | --- | --- | --- |
| 5-35 | 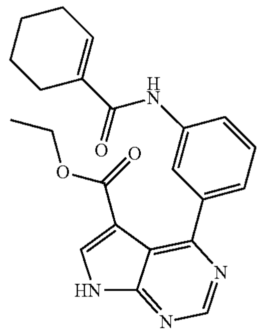 [SMILES: CCOC(=O)c1c[nH]c2ncnc(-c3cccc(NC(=O)C4=CCCCC4)c3)c12] | ethyl 4-{3-[(cyclohex-1-en-1-ylcarbonyl)amino]phenyl}-7H-pyrrolo[2,3-d]pyrimidine-5-carboxylate | Calc'd 391, found 391 |
| 5-36 | 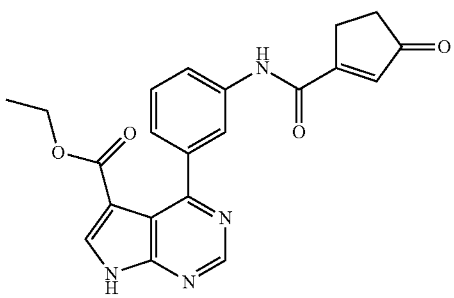 [SMILES: CCOC(=O)c1c[nH]c2ncnc(-c3cccc(NC(=O)C4=CC(=O)CC4)c3)c12] | ethyl 4-(3-{[(3-oxocyclopent-1-en-1-yl)carbonyl]amino}phenyl)-7H-pyrrolo[2,3-d]pyrimidine-5-carboxylate | Calc'd 391, found 391 |
| 5-37 | 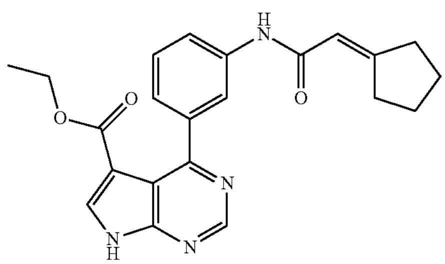 [SMILES: CCOC(=O)c1c[nH]c2ncnc(-c3cccc(NC(=O)C=C4CCCC4)c3)c12] | ethyl 4-{3-[(cyclopentylideneacetyl)amino]phenyl}-7H-pyrrolo[2,3-d]pyrimidine-5-carboxylate | Calc'd 391, found 391 |
| 5-38 | 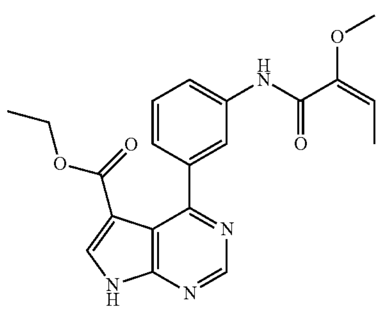 [SMILES: C/C=C(/OC)C(=O)Nc1cccc(-c2ncnc3[nH]cc(C(=O)OCC)c23)c1] | ethyl 4-(3-{[(2E)-2-methoxybut-2-enoyl]amino}phenyl)-7H-pyrrolo[2,3-d]pyrimidine-5-carboxylate | Calc'd 381, found 381 |
| 5-39 | 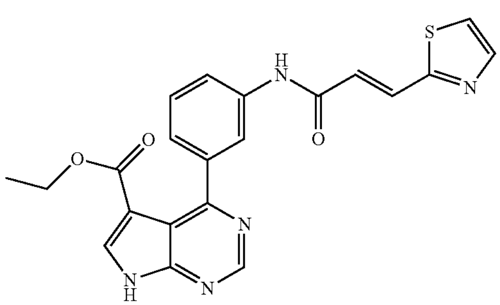 [SMILES: CCOC(=O)c1c[nH]c2ncnc(-c3cccc(NC(=O)/C=C/c4nccs4)c3)c12] | ethyl 4-(3-{[(2E)-3-(1,3-thiazol-2-yl)prop-2-enoyl]amino}phenyl)-7H-pyrrolo[2,3-d]pyrimidine-5-carboxylate | Calc'd 420, found 420 |

TABLE 4-continued

| Example Number | Structure | IUPAC Name | Exact Mass [M + H]+ |
|---|---|---|---|
| 5-40 | 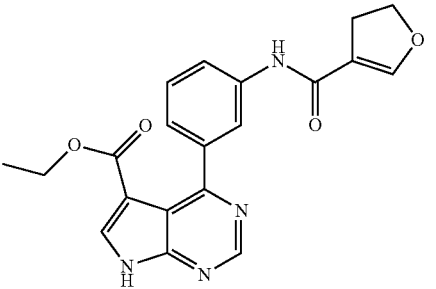 [SMILES: CCOC(=O)c1c[nH]c2ncnc(-c3cccc(NC(=O)C4=COCC4)c3)c12] | ethyl 4-{3-[(4,5-dihydrofuran-3-ylcarbonyl)amino]phenyl}-7H-pyrrolo[2,3-d]pyrimidine-5-carboxylate | Calc'd 379, found 379 |
| 5-41 | 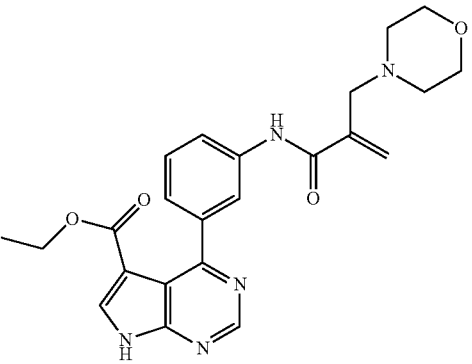 [SMILES: C=C(CN1CCOCC1)C(=O)Nc1cccc(-c2ncnc3[nH]cc(C(=O)OCC)c23)c1] | ethyl 4-(3-{[2-(morpholin-4-ylmethyl)acryloyl]amino}phenyl)-7H-pyrrolo[2,3-d]pyrimidine-5-carboxylate | Calc'd 436, found 436 |
| 5-42 | 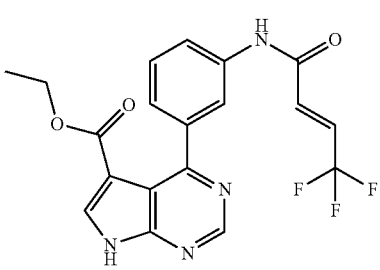 [SMILES: CCOC(=O)c1c[nH]c2ncnc(-c3cccc(NC(=O)/C=C/C(F)(F)F)c3)c12] | ethyl 4-(3-{[(2E)-4,4,4-trifluorobut-2-enoyl]amino}phenyl)-7H-pyrrolo[2,3-d]pyrimidine-5-carboxylate | Calc'd 405, found 405 |
| 5-43 | 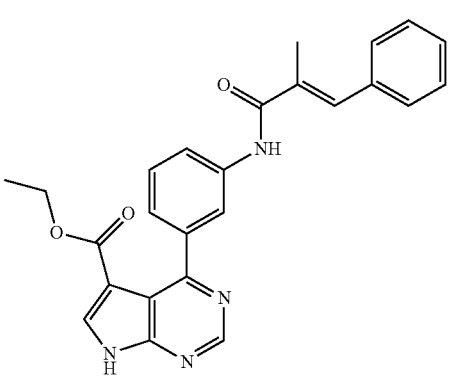 [SMILES: CCOC(=O)c1c[nH]c2ncnc(-c3cccc(NC(=O)/C(C)=C/c4ccccc4)c3)c12] | ethyl 4-(3-{[(2E)-2-methyl-3-phenylprop-2-enoyl]amino}phenyl)-7H-pyrrolo[2,3-d]pyrimidine-5-carboxylate | Calc'd 427, found 427 |

TABLE 4-continued

| Example Number | Structure | IUPAC Name | Exact Mass [M + H]+ |
|---|---|---|---|
| 5-44 | 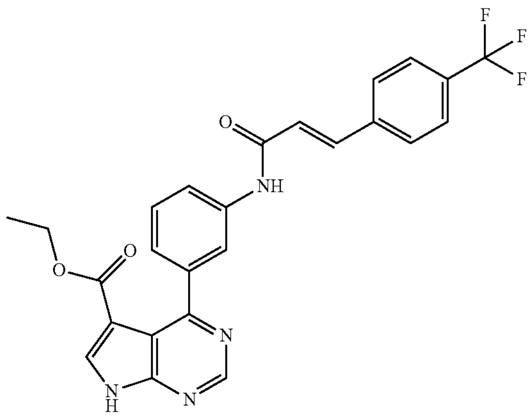 [SMILES: CCOC(=O)c1c[nH]c2ncnc(-c3cccc(NC(=O)/C=C/c4ccc(C(F)(F)F)cc4)c3)c12] | ethyl 4-[3-({(2E)-3-[4-(trifluoromethyl)phenyl]prop-2-enoyl}amino)phenyl]-7H-pyrrolo[2,3-d]pyrimidine-5-carboxylate | Calc'd 481, found 481 |
| 5-45 | 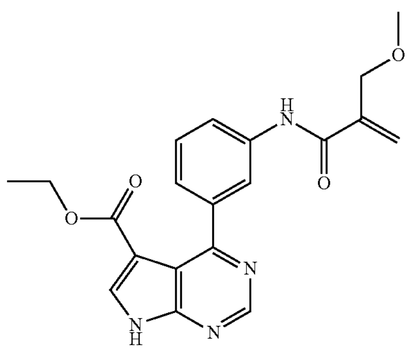 [SMILES: C=C(COC)C(=O)Nc1cccc(-c2ncnc3[nH]cc(C(=O)OCC)c23)c1] | ethyl 4-(3-{[2-(methoxymethyl)acryloyl]amino}phenyl)-7H-pyrrolo[2,3-d]pyrimidine-5-carboxylate | Calc'd 381, found 381 |

General Scheme F:

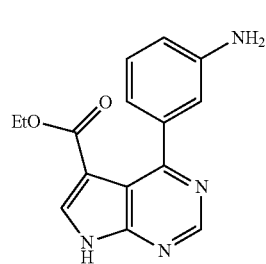 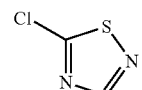

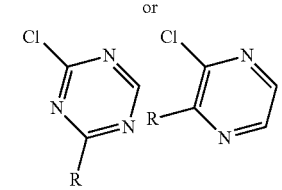

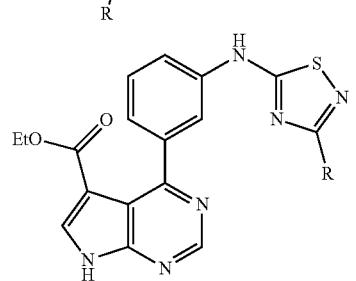

Examples Generated Via General Scheme F

Example 6-1

Ethyl 4-{3-[(3-chloro-1,2,4-thiadiazol-5-yl)amino]phenyl}-7H-pyrrolo[2,3-d]pyrimidine-5-carboxylate

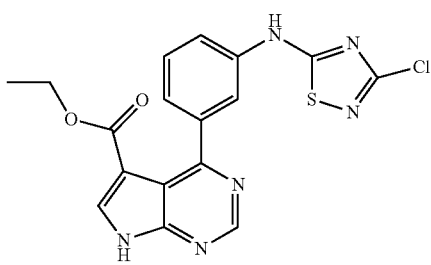 [SMILES: CCOC(=O)c1c[nH]c2ncnc(-c3cccc(Nc4nc(Cl)ns4)c3)c12]

Step 1: Ethyl 4-{3-[(3-chloro-1,2,4-thiadiazol-5-yl)amino]phenyl}-7-{[2-(trimethylsilyl)ethoxy]methyl}-7H-pyrrolo[2,3-d]pyrimidine-5-carboxylate

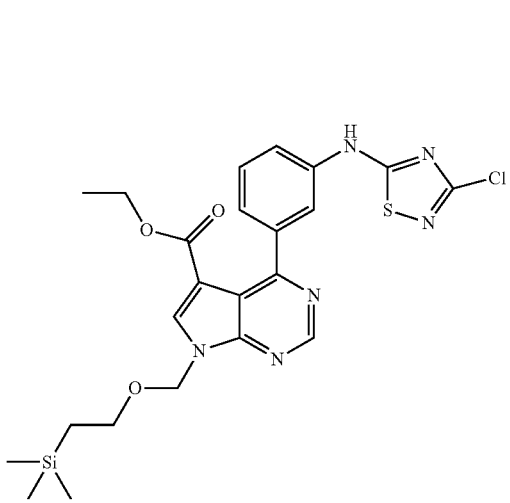 [SMILES: CCOC(=O)c1cn(COCC[Si](C)(C)C)c2ncnc(-c3cccc(Nc4nc(Cl)ns4)c3)c12]

A solution of ethyl 4-(3-aminophenyl)-7H-pyrrolo[2,3-d]pyrimidine-5-carboxylate (37.6 mg, 0.242 mmol), 3,5-dichloro-1,2,4-thiadiazole (100 mg, 0.242 mmol), and DIPEA (127 µL, 0.727 mmol) in THF (2.4 mL) was heated by microwave irradiation at 100° C. in a sealed microwave vessel for 1 hour. Saturated aqueous sodium carbonate (4 mL) was added and the mixture was extracted with ethyl acetate (×3). The combined organic fractions were washed with water, dried with sodium sulfate, and concentrated under reduced pressure. Purification of the residue by MPLC (0-10% methanol-dichloromethane) gave ethyl 4-{3-[(3-chloro-1,2,4-thiadiazol-5-yl)amino]phenyl}-7-{[2-(trimethylsilyl)ethoxy]methyl}-7H-pyrrolo[2,3-d]pyrimidine-5-carboxylate. LRMS (ESI) calc'd for $C_{23}H_{28}ClN_6O_3SSi$ [M+H]$^+$: 531; found 531.

Step 2: Ethyl-4-{3-[(3-chloro-1,2,4-thiadiazol-5-yl)amino]phenyl}-7H-pyrrolo[2,3-d]pyrimidine-5-carboxylate

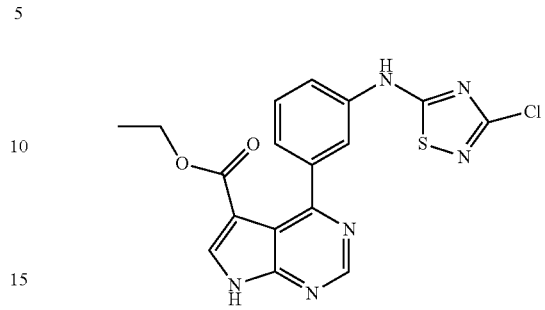

A solution of ethyl 4-{3-[(3-chloro-1,2,4-thiadiazol-5-yl)amino]phenyl}-7-{[2-(trimethylsilyl)ethoxy]methyl}-7H-pyrrolo[2,3-d]pyrimidine-5-carboxylate (75 mg, 0.14 mmol) in TFA (1.0 mL) was stirred for 1 hour. The reaction mixture was then concentrated under reduced pressure and the residue dissolved in ethyl acetate (2.0 mL). Potassium carbonate (2.0 mL, 4.0 mmol) was added and the reaction mixture was allowed to stir for 1 hour. The organic layer was separated and the aqueous layer was extracted with ethyl acetate (×3). The combined organic fractions were washed with water, dried with sodium sulfate, filtered and concentrated under reduced pressure. Purification of the residue by MPLC (0-10% methanol-dichloromethane) gave ethyl 4-{3-[(3-chloro-1,2,4-thiadiazol-5-yl)amino]phenyl}-7H-pyrrolo[2,3-d]pyrimidine-5-carboxylate. LRMS (ESI) calc'd for $C_7H_{14}ClN_6O_2S$ [M+H]$^+$: 401, found 401. $^1$H NMR (600 MHz, DMSO-D$_6$) δ 13.0 (s, 1H), 11.4 (s, 1H), 8.94 (s, 1H), 8.35 (s, 1H), 7.81 (s, 1H), 7.63 (d, 1H, J 7.63 Hz), 7.53 (t, 1H, J=7.62 Hz), 7.39 (d, 1H, J=7.63 Hz), 3.85 (q, 2H, J=7.04 Hz), 0.85 (t, 3H, J=7.04 Hz).

The following examples, 6-2 through 6-4, as shown in Table 5, were prepared in an analogous manner of that described above using materials that are commercially available or known, or that can be prepared using procedures known in the art or by generally following procedures described herein for various intermediates.

TABLE 5

| Example Number | Structure | IUPAC Name | Exact Mass [M + H]+ |
|---|---|---|---|
| 6-2 | 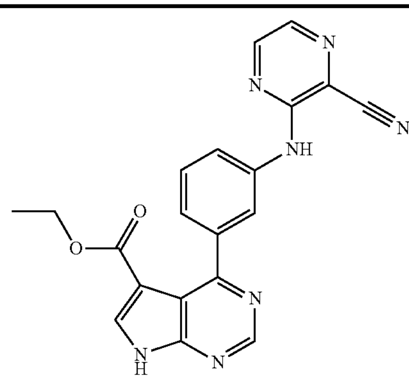 | Ethyl-4-{3-[(3-cyanopyrazin-2-yl)amino]phenyl}-7H-pyrrolo[2,3-d]pyrimidine-5-carboxylate | Calc'd 386, found 386 |

TABLE 5-continued
| Example Number | Structure | IUPAC Name | Exact Mass [M + H]+ |
|---|---|---|---|
| 6-3 | 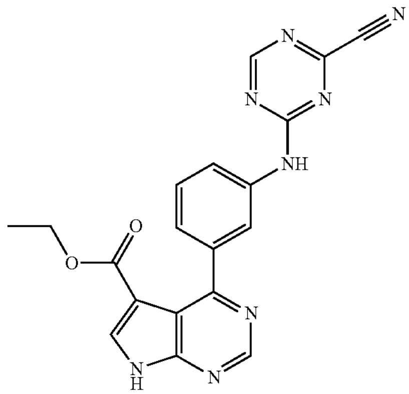 [SMILES: CCOC(=O)c1c[nH]c2ncnc(-c3cccc(Nc4ncnc(C#N)n4)c3)c12] | ethyl 4-{3-[(4-cyano-1,3,5-triazin-2-yl)amino]phenyl}-7H-pyrrolo[2,3-d]pyrimidine-5-carboxylate | Calc'd 387, found 387 |
| 6-4 | 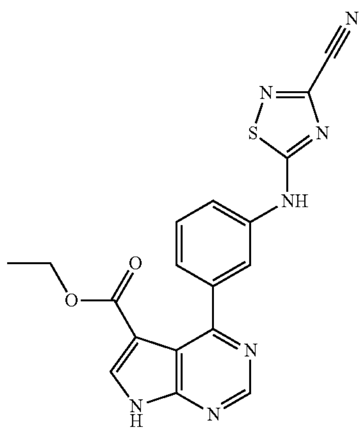 [SMILES: CCOC(=O)c1c[nH]c2ncnc(-c3cccc(Nc4nc(C#N)ns4)c3)c12] | ethyl 4-{3-[(3-cyano-1,2,4-thiadiazol-5-yl)amino]phenyl}-7H-pyrrolo[2,3-d]pyrimidine-5-carboxylate | Calc'd 392, found 392 |
General Scheme G:
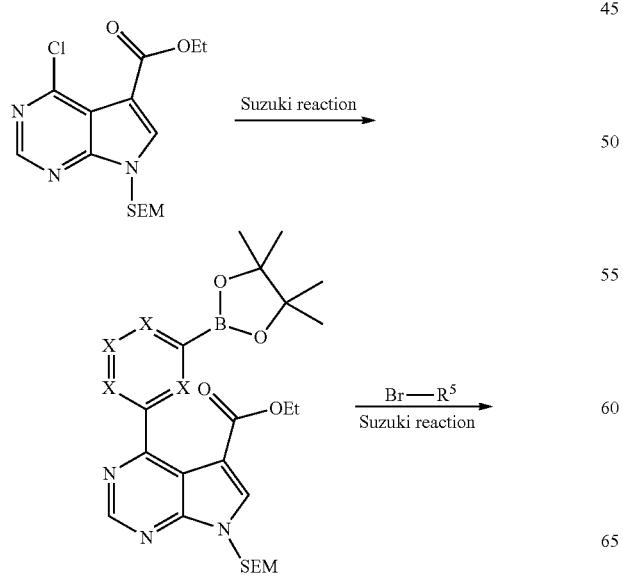
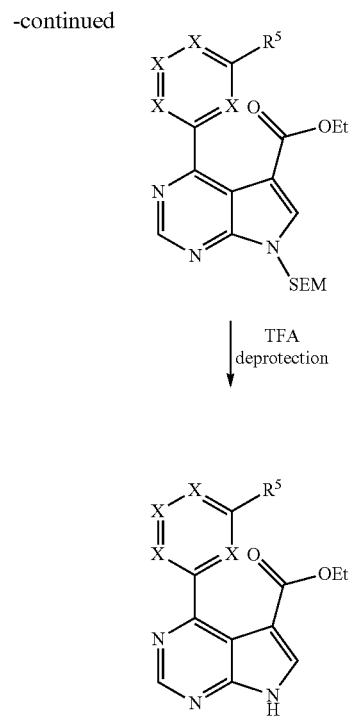

Examples Generated Via General Scheme G

Example 7-1

Ethyl 4-(3-(2-cyanopyrimidin-4-yl)phenyl)-7H-pyrrolo[2,3-d]pyrimidine-5-carboxylate

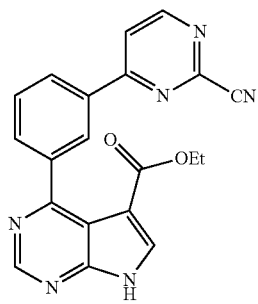 [SMILES: CCOC(=O)c1c[nH]c2ncnc(-c3cccc(-c4ccnc(C#N)n4)c3)c12]

Step 1: Ethyl 4-(3-(4,4,5,5-tetramethyl-1,3,2-dioxaborolan-2-yl)phenyl)-7-((2-(trimethylsilyl)ethoxy)methyl)-7H-pyrrolo[2,3-d]pyrimidine-5-carboxylate

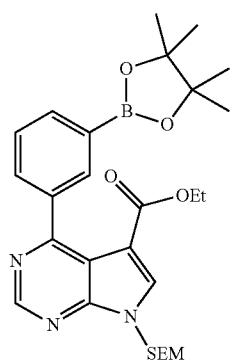 [SMILES: CCOC(=O)c1cn(COCC[Si](C)(C)C)c2ncnc(-c3cccc(B4OC(C)(C)C(C)(C)O4)c3)c12]

A mixture of ethyl 4-chloro-7-((2-(trimethylsilyl)ethoxy)methyl)-7H-pyrrolo[2,3-d]pyrimidine-5-carboxylate (200 mg, 0.562 mmol), 1,3-phenyldiboronic acid (502 mg, 1.52 mmol), sodium carbonate (119 mg, 1.12 mmol), PdCl$_2$(dppf)-CH$_2$Cl$_2$ (92 mg, 0.11 mmol) in dioxane (2.0 mL) and water (0.4 mL) was purged with argon for 10 minutes and then heated at 95° C. for 3 hours. The reaction mixture was filtered through Celite and rinsed with ethyl acetate. The reaction solution was then concentrated under reduced pressure and the residue purified by chromatography on silica eluting with 0-30% ethyl acetatehexane to afford ethyl 4-(3-(4,4,5,5-tetramethyl-1,3,2-dioxaborolan-2-yl)phenyl)-7-((2-(trimethylsilyl)ethoxy)methyl)-7H-pyrrolo[2,3-d]pyrimidine-5-carboxylate. LRMS (ESI) calc'd for C$_{27}$H$_{38}$BN$_3$O$_5$Si [M+]$^+$: 523, found 523.

Step 2: Ethyl 4-(3-(2-cyanopyrimidin-4-yl)phenyl)-7-((2-(trimethylsilyl)ethoxy)methyl)-7H-pyrrolo[2,3-d]pyrimidine-5-carboxylate

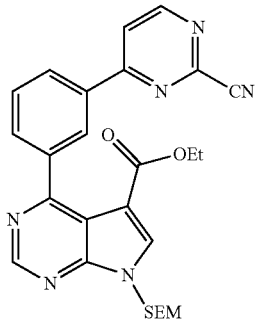 [SMILES: CCOC(=O)c1cn(COCC[Si](C)(C)C)c2ncnc(-c3cccc(-c4ccnc(C#N)n4)c3)c12]

A mixture of ethyl 4-(3-(4,4,5,5-tetramethyl-1,3,2-dioxaborolan-2-yl)phenyl)-7-((2-(trimethylsilyl)ethoxy)methyl)-7H-pyrrolo[2,3-d]pyrimidine-5-carboxylate (54.4 mg, 0.104 mmol), 4-bromopyrimidine-2-carbonitrile (38.2 mg, 0.208 mmol), and tetrakis(triphenylphosphine)palladium(0) (24 mg, 0.021 mmol) in 2 M aqueous sodium carbonate (150 uL) and DME (500 µL) was purged with argon. The reaction vessel was then sealed and heated at 95° C. overnight. The reaction mixture was filtered through Celite and rinsed with ethyl acetate. The reaction solution was concentrated under reduced pressure and the residue purified by chromatography on silica eluting with 40-60% ethyl acetatehexane to give the desired product. LRMS calc'd for C$_{26}$H$_{29}$N$_6$O$_3$Si [M+H]$^+$: 501, found 501.

Step 3: Ethyl 4-(3-(2-cyanopyrimidin-4-yl)phenyl)-7H-pyrrolo[2,3-d]pyrimidine-5-carboxylate

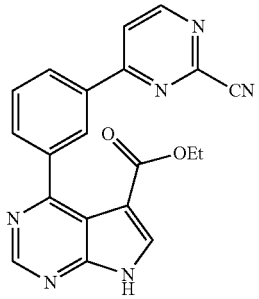 [SMILES: CCOC(=O)c1c[nH]c2ncnc(-c3cccc(-c4ccnc(C#N)n4)c3)c12]

Ethyl 4-(3-(2-cyanopyrimidin-4-yl)phenyl)-7-((2-(trimethylsilyl)ethoxy)methyl)-7H-pyrrolo[2,3-d]pyrimidine-5-carboxylate (17 mg, 0.035 mmol) was treated with TFA (500 µL) and stirred at room temperature for 1 hour. To the resulting mixture was added 1 N sodium hydroxide solution (1 mL) and ethyl acetate (3 mL), then allowed to keep stirring for 30 minutes. The organic layer was separated, and the aqueous layer was extracted with ethyl acetate (×3). The combined organic layers were concentrated under reduced pressure and then purified by chromatography on silica eluting with 60-80% ethyl acetatehexane to give ethyl 4-(3-(2-cyanopyrimidin-4-yl)phenyl)-7H-pyrrolo[2,3-d]pyrimidine-5-carboxylate. LRMS (ESI) calc'd for $C_{20}H_{15}N_6O_2[M+H]^+$: 371, found 371. $^1$H NMR (600 MHz, DMSO-$D_6$) δ 13.04 (bs, 1H), 9.07 (d, J=5.28 Hz, 1H), 8.97 (s, 1H), 8.49 (m, 2H), 8.38 (m, 2H), 7.91 (d, J=7.63 Hz, 1H), 7.72 (t, J 7.63 Hz, 1H), 3.84 (q, J=7.04 Hz, 2H), 0.84 (t, J=7.04 Hz, 3H).

The following examples, 7-2 through 7-3, as shown in Table 6, were prepared in an analogous manner of that described above using materials that are commercially available or known, or that can be prepared using procedures known in the art or by generally following procedures described herein for various intermediates.

TABLE 6

| Example Number | Structure | IUPAC Name | LRMS (ESI) m/z $(M + H)^+$ |
|---|---|---|---|
| 7-2 | 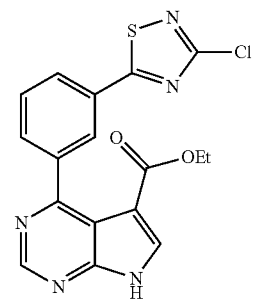 [SMILES: CCOC(=O)c1c[nH]c2ncnc(-c3cccc(-c4nc(Cl)ns4)c3)c12] | ethyl 4-(3-(3-chloro-1,2,4-thiadiazol-5-yl)phenyl)-7H-pyrrolo[2,3-d]pyrimidine-5-carboxylate | Calc'd 386, found 386 |
| 7-3 | 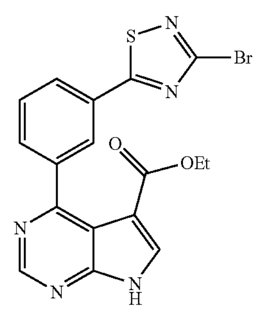 [SMILES: CCOC(=O)c1c[nH]c2ncnc(-c3cccc(-c4nc(Br)ns4)c3)c12] | ethyl 4-(3-(3-bromo-1,2,4-thiadiazol-5-yl)phenyl)-7H-pyrrolo[2,3-d]pyrimidine-5-carboxylate | Calc'd 430, found 430 |

Example 7-4

Ethyl 4-(3-(cyano-1,2,4-thiadiazol-5-yl)phenyl)-7H-pyrrolo[2,3-d]pyrimidine-5-carboxylate

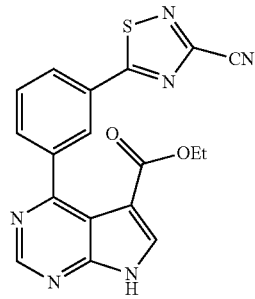 [SMILES: CCOC(=O)c1c[nH]c2ncnc(-c3cccc(-c4nc(C#N)ns4)c3)c12]

Step 1: Ethyl-4-(3-(3-cyano-1,2,4-thiadiazol-5-yl)phenyl)-7-((2-(trimethylsilyl)ethoxy)methyl)-7H-pyrrolo[2,3-d]pyrimidine-5-carboxylate

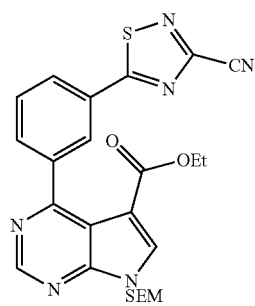 [SMILES: CCOC(=O)c1cn(COCC[Si](C)(C)C)c2ncnc(-c3cccc(-c4nc(C#N)ns4)c3)c12]

A mixture of ethyl 4-(3-(3-bromo-1,2,4-thiadiazol-5-yl)phenyl)-7-((2-(trimethylsilyl)ethoxy)methyl)-7H-pyrrolo[2,3-d]pyrimidine-5-carboxylate (51 mg, 0.092 mmol), tetrakis(triphenylphosphine)palladium(0) (53 mg, 0.046 mmol), and zinc cyanide (107 mg, 0.915 mmol) in DMF (1.0 mL) was heated to 95° C. overnight. The resulting mixture was filtered and concentrated under reduced pressure. Purification by chromatography on silica eluting with 0-50% ethyl acetate-hexane gave ethyl 4-(3-(3-cyano-1,2,4-thiadiazol-5-yl)phenyl)-7-((2-(trimethylsilyl)ethoxy)methyl)-7H-pyrrolo[2,3-d]pyrimidine-5-carboxylate. LRMS (ESI) calc'd for $C_{24}H_{27}N_6O_3SSi$ [M+H]$^+$: 507, found 507.

Step 2: Ethyl 4-(3-(3-cyano-1,2,4-thiadiazol-5-yl)phenyl)-7H-pyrrolo[2,3-d]pyrimidine-5-carboxylate

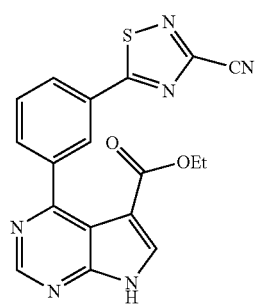 [SMILES: CCOC(=O)c1c[nH]c2ncnc(-c3cccc(-c4nc(C#N)ns4)c3)c12]

The title compound was prepared in an analogous manner to Example 7-1, using ethyl 4-(3-(3-cyano-1,2,4-thiadiazol-5-yl)phenyl)-7-((2-(trimethylsilyl)ethoxy)methyl)-7H-pyrrolo[2,3-d]pyrimidine-5-carboxylate. LRMS (ESI) calc'd for $C_{18}H_{13}N_6O_2S$ [M+H]$^+$: 377, found 377. $^1$H NMR (600 MHz, DMSO-D$_6$) δ 13.12 (bs, 1H), 8.98 (s, 1H), 8.41 (s, 1H), 8.30 (s, 1H), 8.25 (d, J=7.63 Hz, 1H), 7.98 (d, J=7.63 Hz, 1H), 7.75 (t, J=7.63 Hz, 1H), 3.90 (q, J=7.04 Hz, 2H), 0.91 (t, J=7.04 Hz, 3H).

Example 8

Ethyl 4-(3-cyanomethylcarboamoyl)phenyl)-7H-pyrrolo[2,3-d]pyrimidine-5-carboxylate

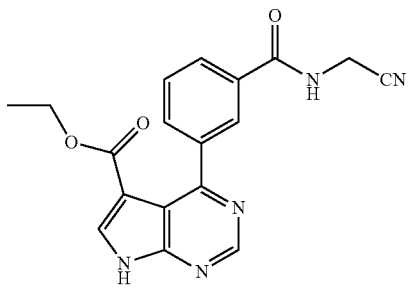 [SMILES: CCOC(=O)c1c[nH]c2ncnc(-c3cccc(C(=O)NCC#N)c3)c12]

Step 1: 3-(5-(Ethoxycarbonyl)-7H-pyrrolo[2,3-d]pyrimidin-4-yl)benzoic acid

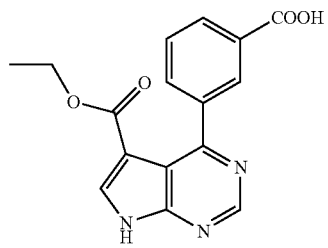 [SMILES: CCOC(=O)c1c[nH]c2ncnc(-c3cccc(C(=O)O)c3)c12]

To a mixture of 3-carboxyphenyboronic acid (215 mg, 1.30 mmol) and ethyl 4-chloro-7H-pyrrolo[2,3-d]pyrimidine-5-carboxylate (195 mg, 0.864 mmol) in 2 M aqueous sodium carbonate (2.0 mL, 2.1 mmol) and dioxane (8.0 mL) was added SiliaCat® heterogeneous catalysts DPP-Pd (loading=0.28 mmol/g, 617 mg, 0.173 mmol). The reaction mixture was purged with argon and heated to 100° C. overnight. The reaction mixture was filtered and rinsed with ethyl acetate and methanol. The reaction solution was concentrated under reduced pressure to give 3-(5-(ethoxycarbonyl)-7H-pyrrolo[2,3-d]pyrimidin-4-yl)benzoic acid which was used for next step without further purification. LRMS (ESI) calc'd for $C_{16}H_{14}N_3O_4$ [M+H]$^+$: 312, found 312.

Step 2: Ethyl 4-(3-(cyanomethylcarbamoyl)phenyl)-7H-pyrrolo[2,3-d]pyrimidine-5-carboxylate

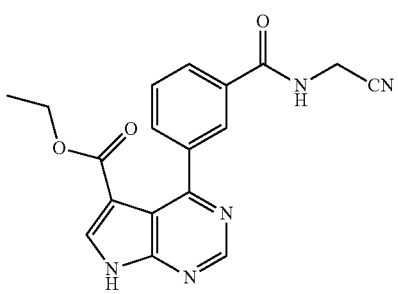 [SMILES: CCOC(=O)c1c[nH]c2ncnc(-c3cccc(C(=O)NCC#N)c3)c12]

To a mixture of crude 3-(5-(ethoxycarbonyl)-7H-pyrrolo[2,3-d]pyrimidin-4-yl)benzoic acid 113 mg (theoretical mass 55 mg, 0.18 mmol), 2-aminoacetonitrile (49.5 mg, 0.883 mmol), HATU (101 mg, 0.265 mmol) in DMF (1.0 mL) was added DIPEA (62 μL, 0.35 mmol). The reaction mixture was heated to 45° C. for 2 hours and then diluted with ethyl acetate (5 mL). The reaction mixture was washed with 2 M aqueous sodium bicarbonate (5 mL) and brine (5 mL), dried over sodium sulfate, filtered and concentrated under reduced pressure. The residue was purified by reverse phase HPLC using an acetonitrile gradient in water with 0.1% TFA modifier to give ethyl 4-(3-(cyanomethylcarbamoyl)phenyl)-7H-pyrrolo[2,3-d]pyrimidine-5-carboxylate. LRMS (ESI) calc'd for $C_{18}H_{16}N_5O_3[M+H]^+$: 350, found 350. $^1H$ NMR (600 MHz, DMSO-$D_6$) δ 9.19 (t, J=5.28 Hz 1H), 8.55 (s, 1H), 8.20 (s, 1H), 8.12 (s, 1H), 7.86 (d, J=8.21 Hz, 1H), 7.75 (d, J=7.63 Hz, 1H), 7.48 (t, J=7.63 Hz, 1H), 6.86 (bs, 1H), 4.30 (q, J=5.28 Hz, 2H), 3.76 (q, J=7.04 Hz, 2H), 0.83 (t, J=7.04 Hz, 3H).

General Scheme H:

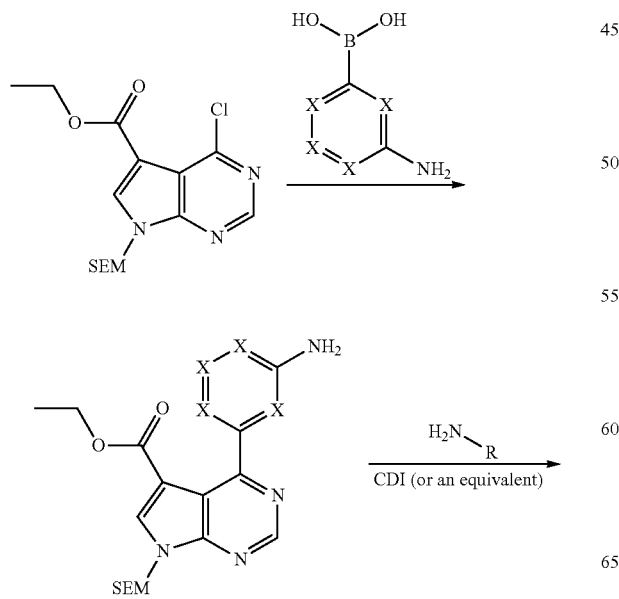

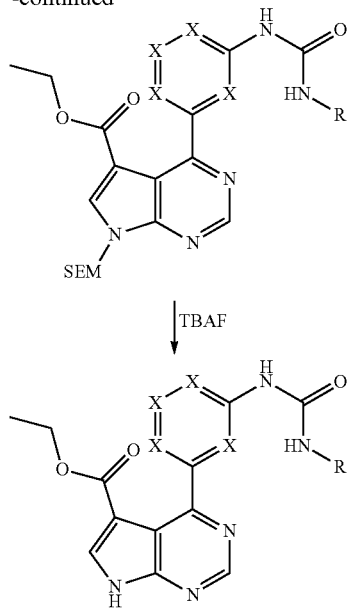

Examples Generated Via General Scheme H

Example 9-1

Ethyl 4-(3-(3-(cyanomethyl)ureido)phenyl)-7H-pyrrolo[2,3-d]pyrimidine-5-carboxylate

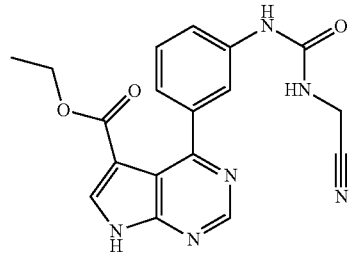 [SMILES: CCOC(=O)c1c[nH]c2ncnc(-c3cccc(NC(=O)NCC#N)c3)c12]

Step 1: Ethyl 4-(3-aminophenyl)-7-((2-(trimethylsilyl)ethoxy)methyl)-7H-pyrrolo[2,3-d]pyrimidine-5-carboxylate

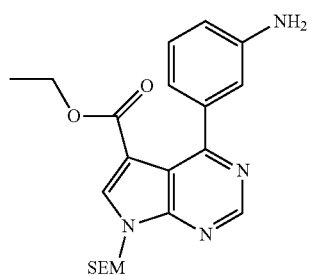 [SMILES: CCOC(=O)c1cn(COCC[Si](C)(C)C)c2ncnc(-c3cccc(N)c3)c12]

A mixture of ethyl 4-chloro-7-((2-(trimethylsilyl)ethoxy)methyl)-7H-pyrrolo[2,3-d]pyrimidine-5-carboxylate (1.00 g, 2.81 mmol), 3-aminophenylboronic acid monohydrate (577 mg, 4.21 mmol), 2 M aqueous sodium carbonate (893 mg, 8.43 mmol), and tetrakis(triphenylphosphine)palladium (0) (649 mg, 0.562 mmol) in dioxane (10 mL) and water (2 mL) was purged with argon. The reaction vessel was sealed in a microwave vial and the reaction mixture heated at 95° C. for 2 hours. The resulting mixture was filtered through Celite. Water (10 mL) was added and the organic layer was separated. The aqueous layer was extracted with ethyl acetate (×3). The combined organic layers were washed with brine (15 mL), dried over sodium sulfate, filtered and concentrated under reduced pressure. The residue was purified by chromatography on silica eluting with 0-100% ethyl acetate hexane to afford ethyl 4-(3-aminophenyl)-7-((2-(trimethylsilyl)ethoxy)methyl)-7H-pyrrolo[2,3-d]pyrimidine-5-carboxylate. LRMS (ESI) calc'd for $C_{21}H_{29}N_4O_3Si$ [M+H]$^+$: 413, found 413.

Step 2: Ethyl 4-(3-(3-(cyanomethyl)ureido)phenyl)-7-((2-(trimethylsilyl)ethoxy)methyl)-7H-pyrrolo[2,3-d]pyrimidine-5-carboxylate

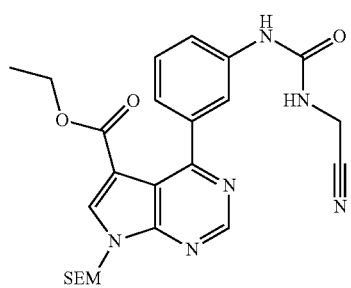 [SMILES: CCOC(=O)c1cn(COCC[Si](C)(C)C)c2ncnc(-c3cccc(NC(=O)NCC#N)c3)c12]

To a mixture of ethyl 4-(3-aminophenyl)-7-((2-(trimethylsilyl)ethoxy)methyl)-7H-pyrrolo[2,3-d]pyrimidine-5-carboxylate (103 mg, 0.250 mmol), DIPEA (0.131 mL, 0.749 mmol) in DCM (1 mL) was added CDI (81 mg, 0.50 mmol). The reaction mixture was stirred at room temperature overnight. At that point aminoacetonitrile (70.0 mg, 1.25 mmol) was added and the reaction mixture was stirred at room temperature for 5 hours. The resulting mixture was concentrated and purified by chromatography on silica eluting with 0-100% ethyl acetate/hexanes to give ethyl 4-(3-(3-(cyanomethyl)ureido)phenyl)-7-((2-(trimethylsilyl)ethoxy)methyl)-7H-pyrrolo[2,3-d]pyrimidine-5-carboxylate as a pale yellow solid. LRMS (ESI) calc'd for $C_{24}H_{31}N_6O_4Si$ [M+H]$^+$: 495, found 495.

Step 3: Ethyl 4-(3-(3-(cyanomethyl)ureido)phenyl)-7H-pyrrolo[2,3-d]pyrimidine-5-carboxylate

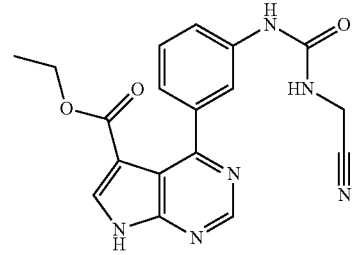 [SMILES: CCOC(=O)c1c[nH]c2ncnc(-c3cccc(NC(=O)NCC#N)c3)c12]

Ethyl 4-(3-(3-(cyanomethyl)ureido)phenyl)-7-((2-(trimethylsilyl)ethoxy)methyl)-7H-pyrrolo[2,3-d]pyrimidine-5-carboxylate (65.4 mg, 0.132 mmol) was mixed with 1 M TBAF in THF (2.64 mL, 2.64 mmol) and heated at 45° C. for 1 hour. The reaction mixture was diluted with ethyl acetate (5 mL) and washed with water (5 mL), dried over sodium sulfate, filtered and concentrated under reduced pressure. The residue was purified by chromatography on silica eluting with 0-20% MeOH/DCM to give ethyl 4-(3-(3-(cyanomethyl)ureido)phenyl)-7H-pyrrolo[2,3-d]pyrimidine-5-carboxylate. LRMS (EST) calc'd for $C_{18}H_{17}N_6O_3$ [M+H]$^+$: 365, found 365. $^1$H NMR (600 MHz, DMSO-D$_6$) δ 12.96 (bs, 1H), 9.08 (s, 1H), 8.89 (s, 1H), 8.29 (s, 1H), 7.76 (s, 1H), 7.54 (d, J=8.21 Hz, 1H), 7.35 (t, J=7.63 Hz, 1H), 7.20 (d, J=7.63 Hz, 1H), 6.71 (d, J=5.28 Hz, 1H), 4.13 (d, J=5.87 Hz, 2H), 3.86 (q, J=6.8 Hz, 2H), 0.84 (t, J=7.04 Hz, 3H).

The following example, 9-2, as shown in Table 7, was prepared in an analogous manner of that described above using materials that are commercially available or known, or that can be prepared using procedures known in the art or by generally following procedures described herein for various intermediates.

TABLE 7

| Example Number | Structure | IUPAC Name | LRMS (ESI) m/z (M + H)$^+$ |
|---|---|---|---|
| 9-2 | 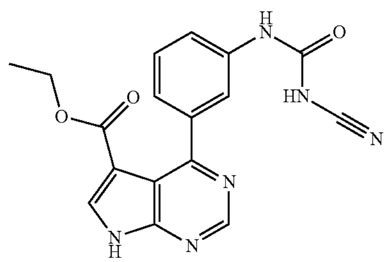 [SMILES: CCOC(=O)c1c[nH]c2ncnc(-c3cccc(NC(=O)NC#N)c3)c12] | ethyl 4-(3-(3-cyanoureido)phenyl)-7H-pyrrolo[2,3-d]pyrimidine-5-carboxylate | Calc'd 351, found 351 |

General Scheme I:

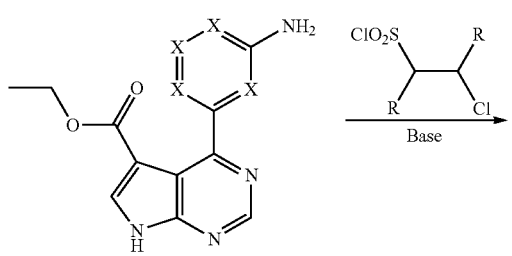

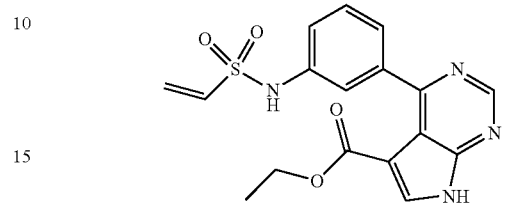

Examples Generated Via General Scheme I

Example 10-1

Ethyl 4-{3-[(ethenylsulfonyl)amino]phenyl}-7H-pyrrolo[2,3-d]pyrimidine-5-carboxylate To ethyl 4-(3-aminophenyl)-7H-pyrrolo[2,3-d]pyrimidine-5-carboxylate (60 mg, 0.21 mmol) was added DCM (1.1 mL) and DIPEA (45 µL, 0.26 mmol) at 0° C. Then 2-chloroethanesulfonyl chloride (68 mg, 0.42 mmol) was added and the reaction was stirred vigorously for 15 hours before being quenched by pouring into a separatory funnel containing aqueous sodium hydrogen carbonate (20%). The aqueous layer was then extracted with ethyl acetate (×3) and the organic layers were combined, dried with $Na_2SO_4$, filtered, and concentrated in vacuo. The crude product was then purified using a silica column, eluting with DCM with a 10-80% of a 2% methanol/EtOAc modifying co-solvents. The product was collected and concentrated in vacuo to afford the desired product as a yellow solid. LRMS (ESI) calc'd for $C_{17}H_{17}N_4O_4S$ [M+H]$^+$: 373, found 373. $^1$H NMR (600 MHz, CDCl$_3$) δ 10.74 (bs, 1H), 9.04 (s, 1H), 8.12 (s, 1H), 7.38-7.54 (m, 5H), 6.61 (dd, 1H, J=17.4, 10.8 Hz), 6.33 (d, 1H, J=16.2 Hz), 5.96 (d, 1H, J=10.2 Hz), 4.04 (q, 2H, J=7.2 Hz), 1.01 (t, 3H, J=7.2 Hz).

The following examples, 10-2 through 10-3, as shown in Table 8, were prepared in an analogous manner of that described above using materials that are commercially available or known, or that can be prepared using procedures known in the art or by generally following procedures described herein for various intermediates.

TABLE 8

| Example | Structure | IUPAC Name | Exact Mass [M + H]+ |
|---------|-----------|------------|---------------------|
| 10-2 | 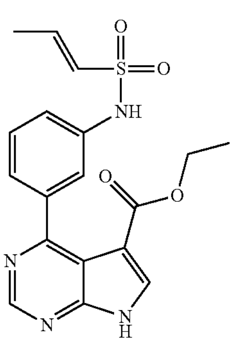 [SMILES: C/C=C/S(=O)(=O)Nc1cccc(-c2ncnc3[nH]cc(C(=O)OCC)c23)c1] | ethyl 4-(3-{[(1E)-prop-1-en-1-ylsulfonyl]amino}phenyl)-7H-pyrrolo[2,3-d]pyrimidine-5-carboxylate | Calc'd 387, found 387 |

TABLE 8-continued

| Example | Structure | IUPAC Name | Exact Mass [M + H]+ |
|---|---|---|---|
| 10-3 | 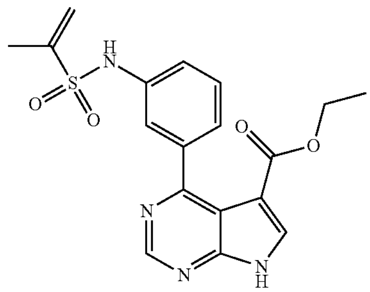 [SMILES: C=C(C)S(=O)(=O)Nc1cccc(-c2ncnc3[nH]cc(C(=O)OCC)c23)c1] | ethyl 4-(3-{[(1-methylethenyl)sulfonyl]amino}phenyl)-7H-pyrrolo[2,3-d]pyrimidine-5-carboxylate | Calc'd 387, found 387 |

Example 11-1

Methyl 4-{4-fluoro-3-[(2-methylacryloyl)amino]phenyl}-7H-pyrrolo[2,3-d]pyrimidine-5-carboxylate

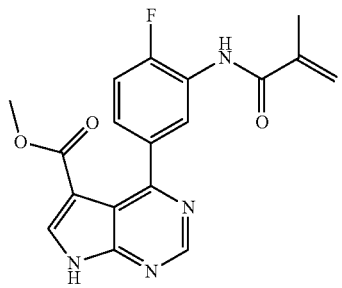 [SMILES: C=C(C)C(=O)Nc1cc(-c2ncnc3[nH]cc(C(=O)OC)c23)ccc1F]

Step 1: Methyl 4-(3-amino-4-fluorophenyl)-7H-pyrrolo[2,3-d]pyrimidine-5-carboxylate

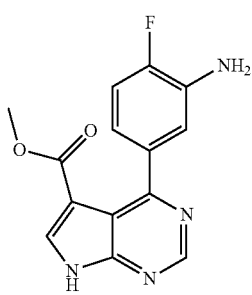 [SMILES: COC(=O)c1c[nH]c2ncnc(-c3ccc(F)c(N)c3)c12]

To a sodium methoxide solution (5.71 mL, 25.0 mmol, 25 wt. % in methanol) was added ethyl 4-(3-amino-4-fluorophenyl)-7H-pyrrolo[2,3-d]pyrimidine-5-carboxylate (150 mg, 0.500 mmol) and the reaction mixture heated at 60° C. for 1 hour. The reaction mixture was neutralized with 1 M HCl and then extracted with ethyl acetate (×3). The combined organic fractions were dried with sodium sulfate, filtered and concentrated under reduced pressure. Purification of the residue by MPLC (0-10% methanol-dichloromethane) gave methyl 4-(3-amino-4-fluorophenyl)-7H-pyrrolo[2,3-d]pyrimidine-5-carboxylate. LRMS (ESI) calc'd for $C_{14}H_{13}FN_4O_2$ [M+H]+, 287, found 287.

Step 2: Methyl 4-{4-fluoro-3-[(2-methylacryloyl)amino]phenyl}-7H-pyrrolo[2,3-d]pyrimidine-5-carboxylate

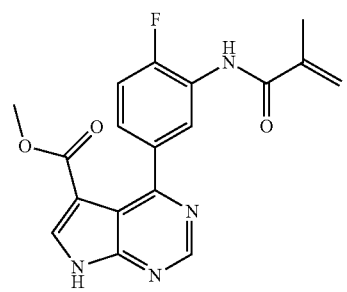 [SMILES: C=C(C)C(=O)Nc1cc(-c2ncnc3[nH]cc(C(=O)OC)c23)ccc1F]

To a solution of methyl 4-(3-amino-4-fluorophenyl)-7H-pyrrolo[2,3-d]pyrimidine-5-carboxylate (100 mg, 0.349 mmol) and DIPEA (183 µL, 1.05 mmol) in THF (1.7 mL) at room temperature was added methacyloyl chloride (36.5 mg, 0.349 mmol) and the solution was stirred for 1 hour. The desired product was purified by reverse phase HPLC using an acetonitrile gradient in water with 0.1% TFA modifier. The combined fractions with the desired product were concentrated until only the water layer remained. The water layer was neutralized with 2 M aqueous potassium carbonate and the mixture was extracted with ethyl acetate (×5). The combined organic fractions were dried with sodium sulfate, filtered and concentrated under reduced pressure to give methyl 4-{4-fluoro-3-[(2-methylacryloyl)amino]phenyl}-7H-pyrrolo[2,3-d]pyrimidine-5-carboxylate. LRMS (ESI) calc'd for $C_{18}H_{16}FN_4O_3$ [M+H]+, 355; found 355. $^1$H NMR (600 MHz, DMSO-$D_6$) δ 13.0 (s, 1H), 9.69 (s, 1H), 8.91 (s, 1H), 8.35 (s, 1H), 7.88 (d, 1H, J=7.04 Hz), 7.42 (m, 1H), 7.35 (t, 1H, J=9.39 Hz), 5.89 (s, 1H), 5.54 (s, 1H), 3.44 (s, 3H), 1.96 (s, 3H).

The following example, 11-2, as shown in Table 9, was prepared in an analogous manner of that described above using materials that are commercially available or known, or that can be prepared using procedures known in the art or by generally following procedures described herein for various intermediates.

TABLE 9

| Example Number | Structure | IUPAC Name | LRMS (ESI) m/z (M + H)+ |
|---|---|---|---|
| 11-2 | 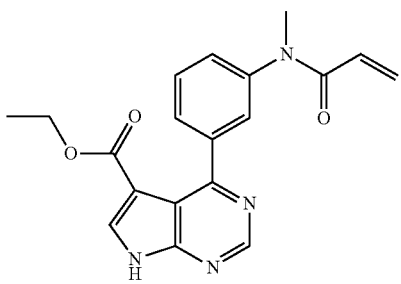 [SMILES: C=CC(=O)N(C)c1cccc(-c2ncnc3[nH]cc(C(=O)OCC)c23)c1] | methyl 4-{3-[(2-methylacryloyl)amino]phenyl}-7H-pyrrolo[2,3-d]pyrimidine-5-carboxylate | Calc'd 337, found 337 |

Example 12

Ethyl 4-(3-(N-methylacrylamido)phenyl)-7H-pyrrolo[2,3-d]pyrimidine-5-carboxylate

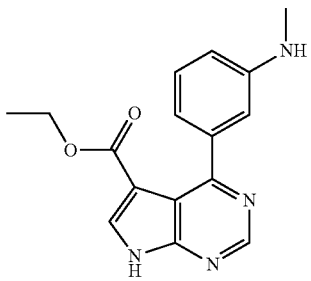

Step 1: N-Methyl-3-(4,4,5,5-tetramethyl-1,3,2-dioxaborolan-2-yl)aniline

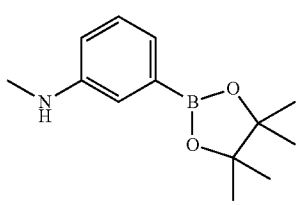

A mixture of 3-bromo-N-methylaniline (500 mg, 2.69 mmol), PdCl$_2$(dppf)-CH$_2$Cl$_2$ (219 mg, 0.269 mmol), potassium acetate (791 mg, 8.06 mmol) and 4,4,4',4',5,5,5',5'-octamethyl-2,2'-bi(1,3,2-dioxaborolane) (955 mg, 3.76 mmol) in dioxane (8.0 mL) was purged with argon for 5 minutes. The reaction vessel was sealed and then heated at 100° C. overnight. The reaction mixture was filtered through Celite and rinsed with ethyl acetate. The reaction solution was concentrated under reduced pressure and the residue was purified by chromatography on silica eluting with 0-50% ethyl acetate/hexane to give N-methyl-3-(4,4,5,5-tetramethyl-1,3,2-dioxaborolan-2-yl)aniline. LRMS (ESI) calc'd for C$_{13}$H$_{21}$BNO$_2$ [M+H]$^+$: 234, found 234.

Step 2: Ethyl 4-(3-(methylamino)phenyl)-7H-pyrrolo[2,3-d]pyrimidine-5-carboxylate To a nitrogen purged mixture of ethyl 4-chloro-7H-pyrrolo[2,3-d]pyrimidine-5-carboxylate (300 mg, 1.33 mmol) and N-methyl-3-(4,4,5,5-tetramethyl-1,3,2-dioxaborolan-2-yl)aniline (465 mg, 1.99 mmol) in 2 M aqueous sodium carbonate solution (3.32 mL, 6.65 mmol) and dioxane (10 mL) was added SiliaCat® heterogeneous catalysts DPP-Pd (loading=0.28 mmol/g, 950 mg, 0.266 mmol). The reaction mixture was heated by microwave irradiation at 150° C. in a sealed microwave vessel for 30 minutes. Water (5 mL) was added to the reaction mixture and then the biphasic mixture was filtered. The organic layer was separated and the aqueous layer was extracted with ethyl acetate (×3). The combined organic layers were dried over sodium sulfate, filtered and concentrated under reduced pressure. The residue was purified by chromatography on silica eluting with 0-100% ethyl acetatehexane to give ethyl 4-(3-(methylamino)phenyl)-7H- pyrrolo[2,3-d]pyrimidine-5-carboxylate. LRMS (ESI) calc'd for $C_{16}H_{17}N_4O_2[M+H]^+$: 297, found 297.

Step 3: Ethyl 4-(3-(N-methylacrylamido)phenyl)-7H-pyrrolo[2,3-d]pyrimidine-5-carboxylate

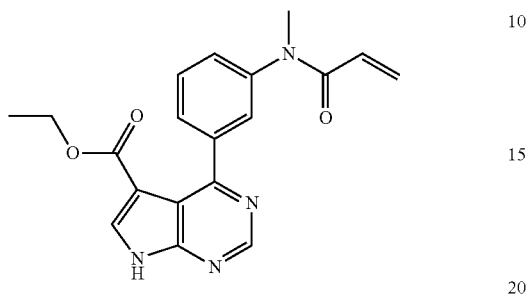

To a solution of ethyl 4-(3-(methylamino)phenyl)-7H-pyrrolo[2,3-d]pyrimidine-5-carboxylate (96 mg, 0.32 mmol) in THF (3.0 mL) at room temperature was added acryloyl chloride (40 µL, 0.49 mmol), and the solution was allowed to stir at room temperature for 30 minutes. Saturated aqueous sodium carbonate (5 mL) was added and the mixture was extracted with ethyl acetate (×3). The combined organic layers were washed with water (10 mL), dried over sodium sulfate, filtered and concentrated under reduced pressure. The residue was purified by reverse phase HPLC using an acetonitrile gradient in water with 0.1% TFA modifier to give ethyl 4-(3-(N-methylacrylamido)phenyl)-7H-pyrrolo[2,3-d]pyrimidine-5-carboxylate. LRMS (ESI) calc'd for $C_{19}H_{19}N_4O_3$ $[M+H]^+$: 351, found 351. $^1$H NMR (600 MHz, DMSO-D$_6$) δ 13.03 (bs, 1H), 8.92 (s, 1H), 8.33 (s, 1H), 7.61 (d, J=7.63 Hz, 1H), 7.55 (t, J=8.21 Hz, 1H), 7.47 (s, 1H), 7.75 (d, J=7.63 Hz, 1H), 7.39 (d, J=8.8 Hz, 1H), 6.17 (s, 1H), 5.57 (t, J=7.04 Hz, 1H), 3.94 (q, J=7.04 Hz, 2H), 3.27 (s, 3H), 0.96 (t, J=7.04 Hz, 3H).

General Scheme J:

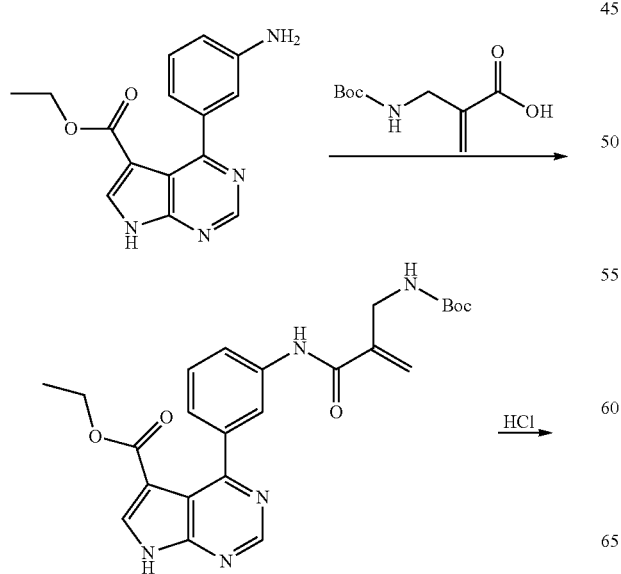

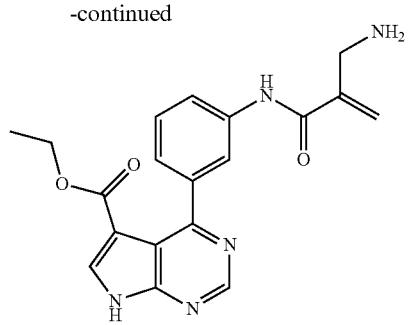

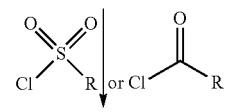

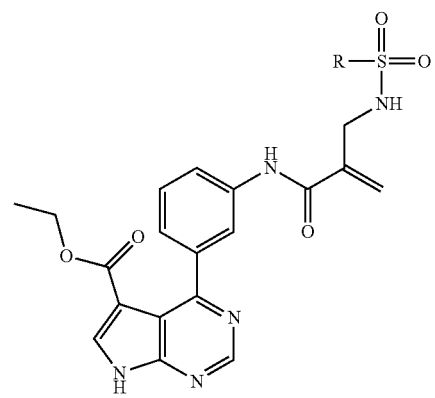

Examples Generated Via General Scheme J

Example 13-1

Ethyl 4-(3-(2-(methylsulfonamidomethyl)acrylamido)phenyl)-7H-pyrrolo[2,3-d]pyrimidine-5-carboxylate

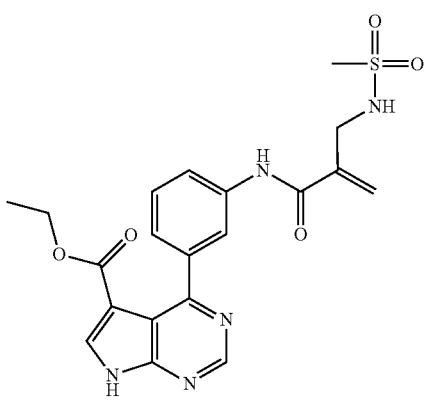 [SMILES: C=C(CNS(C)(=O)=O)C(=O)Nc1cccc(-c2ncnc3[nH]cc(C(=O)OCC)c23)c1]

Step 1: Ethyl 4-(3-(2-((tert-butoxycarbonylamino)methyl)acrylamido)phenyl)-7H-pyrrolo[2,3-d]pyrimidine-5-carboxylate

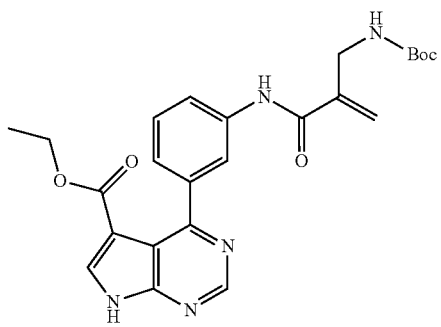 [SMILES: C=C(CNC(=O)OC(C)(C)C)C(=O)Nc1cccc(-c2ncnc3[nH]cc(C(=O)OCC)c23)c1]

A mixture of ethyl 4-(3-aminophenyl)-7H-pyrrolo[2,3-d]pyrimidine-5-carboxylate (300 mg, 1.06 mmol), 2-((tert-butoxycarbonylamino)methyl)acrylic acid (321 mg, 1.60 mmol), HATU (606 mg, 1.59 mmol) and DIPEA (371 μL, 2.13 mmol) in DMF (5.0 mL) was stirred at room temperature for 3 hours. The resulting mixture was diluted with ethyl acetate (15 mL) and washed with saturated aqueous bicarbonate, brine, dried over sodium sulfate, filtered and concentrated under reduced pressure. The residue was purified by reverse phase HPLC using an acetonitrile gradient in water with 0.1% TFA modifier to give ethyl 4-(3-(2-((tert-butoxycarbonylamino)methyl)acrylamido)phenyl)-7H-pyrrolo[2,3-d]pyrimidine-5-carboxylate. LRMS (ESI) calc'd for $C_{24}H_{28}N_5O_5$ [M+H]$^+$: 466, found 466.

Step 2: Ethyl 4-(3-(2-(aminomethyl)acrylamido)phenyl)-7H-pyrrolo[2,3-d]pyrimidine-5-carboxylate (Example 13-2)

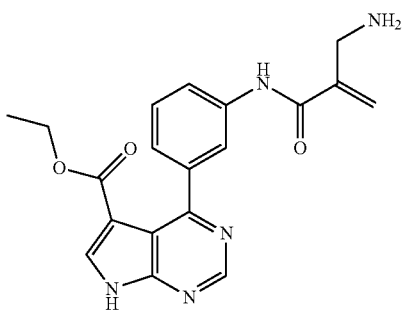 [SMILES: C=C(CN)C(=O)Nc1cccc(-c2ncnc3[nH]cc(C(=O)OCC)c23)c1]

A solution of ethyl 4-(3-(2-((tert-butoxycarbonylamino)methyl) acrylamido)phenyl)-7H-pyrrolo[2,3-d]pyrimidine-5-carboxylate (50 mg, 0.11 mmol) in 4 M HCl in dioxane solution (537 μL, 2.15 mmol) was stirred for 1 hour. The reaction mixture was quenched with aqueous saturated sodium bicarbonate (500 μL) and extracted with ethyl acetate (×3). The combined organic layers were dried over sodium sulfate and concentrated under reduced pressure. The residue was purified by chromatography on silica eluting with 0-20% MeOH/DCM to give ethyl 4-(3-(2-(aminomethyl)acrylamido)phenyl)-7H-pyrrolo[2,3-d]pyrimidine-5-carboxylate. LRMS (ESI) calc'd for $C_{19}H_{20}N_5O_3$ [M+H]$^+$: 366, found 366.

Step 3: Ethyl 4-(3-(2-(methylsulfonamidomethyl)acrylamido)phenyl)-7H-pyrrolo[2,3-d]pyrimidine-5-carboxylate

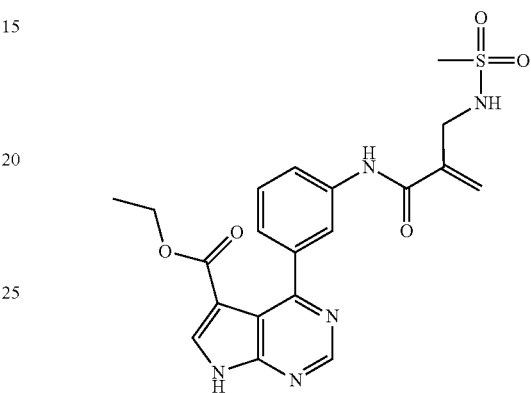

To a solution of ethyl 4-(3-(2-(aminomethyl)acrylamido)phenyl)-7H-pyrrolo[2,3-d]pyrimidine-5-carboxylate (32 mg, 0.088 mmol) in DCM (438 μL) was added triethylamine (12 μL, 0.088 mmol) and methanesulfonyl chloride (7.5 μL, 0.096 mmol) at 0° C. The reaction mixture was allowed to stir at 0° C. for 1 hour and then gradually warmed up to room temperature over 1 hour. The resulting mixture was diluted with DCM (2 mL) and washed with saturated aqueous sodium bicarbonate solution (2 mL). The aqueous layer was extracted with DCM (×3) and the combined organic layers were dried over sodium sulfate, filtered and concentrated under reduced pressure. The residue was purified by reverse phase HPLC using an acetonitrile gradient in water with 0.1% TFA modifier to give ethyl 4-(3-(2-(methylsulfonamidomethyl)acrylamido)phenyl)-7H-pyrrolo[2,3-d]pyrimidine-5-carboxylate. LRMS (ESI) calc'd for $C_{20}H_{22}N_5O_5S$ [M+H]$^+$: 444, found 444. $^1$H NMR (600 MHz, DMSO-D$_6$) δ 12.99 (bs, 1H), 10.11 (s, 1H), 8.90 (s, 1H), 8.30 (s, 1H), 8.05 (s, 1H), 7.84 (d, J=8.21 Hz, 1H), 7.42 (t, J=8.21 Hz, 1H), 7.38 (t, J=6.45 Hz, 1H), 7.33 (d, J=7.63 Hz, 1H), 6.01 (s, 1H), 5.75 (s, 1H), 3.89 (d, J=6.45 Hz, 2H), 3.86 (q, J=7.04 Hz, 2H), 2.94 (s, 3H), 0.86 (t, J=7.04 Hz, 3H).

The following example, 13-3, as shown in Table 10, was prepared in an analogous manner of that described above using materials that are commercially available or known, or that can be prepared using procedures known in the art or by generally following procedures described herein for various intermediates.

TABLE 10

| Example Number | Structure | IUPAC Name | LRMS (ESI) m/z (M + H)+ |
|---|---|---|---|
| 13-3 | 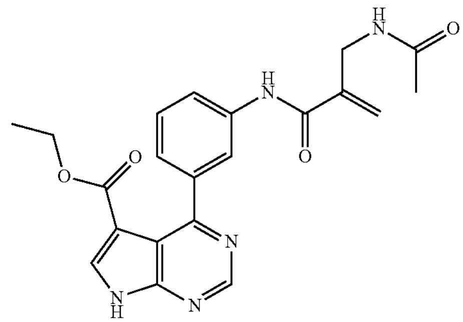 [SMILES: C=C(CNC(C)=O)C(=O)Nc1cccc(-c2ncnc3[nH]cc(C(=O)OCC)c23)c1] | ethyl 4-(3-(2-(acetamidomethyl)acrylamido)phenyl)-7H-pyrrolo[2,3-d]pyrimidine-5-carboxylate | Calc'd 408, found 408 |

Example 14

Ethyl-4-[3-({2-[(dimethylamino)methyl]acryloyl}amino)phenyl]-7H-pyrrolo[2,3-d]pyrimidine-5-carboxylate (14-1)

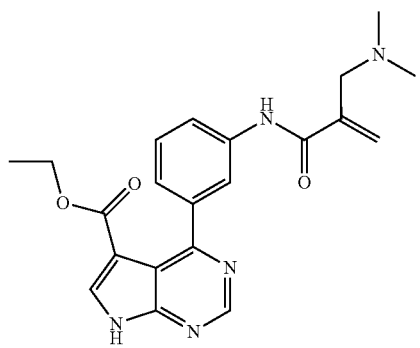 [SMILES: C=C(CN(C)C)C(=O)Nc1cccc(-c2ncnc3[nH]cc(C(=O)OCC)c23)c1]

To methyl 2-[(dimethylamino)methyl]prop-2-enoate (314 mg, 2.19 mmol) in tetrahydrofuran (1.4 mL) and water (1.4 mL) was added LiOH (52.5 mg, 2.19 mmol). The solution was stirred at 40° C. for 4 hours, before being frozen and lyophilized to afford sodium 2-[(dimethylamino)methyl]prop-2-enoate which was used as is in the next step as is. To a solution of ethyl 4-(3-aminophenyl)-7H-pyrrolo[2,3-d]pyrimidine-5-carboxylate (100 mg, 0.354 mmol) in DMF (886 µL) was added sequentially sodium 2-[(dimethylamino)methyl]prop-2-enoate (96 mg, 0.71 mmol), 4 M solution of HCl in dioxane (177 µL, 0.708 mmol), TEA (197 µL, 1.42 mmol), and 1-propanephosphonic acid cyclic anhydride (422 µL, 0.708 mmol) at room temperature. The reaction was stirred overnight before being purified by reverse phase HPLC using an acetonitrile gradient in water with 0.1% TFA modifier. The combined fractions with the desired product were concentrated until only the water layer remained and the water layer was neutralized with saturated aqueous sodium bicarbonate and the mixture was extracted with ethyl acetate (×5). The combined organic fractions were dried with sodium sulfate, filtered and concentrated under reduced pressure to give ethyl 4-[3-({2-[(dimethylamino)methyl]acryloyl}amino)phenyl]-7H-pyrrolo[2,3-d]pyrimidine-5-carboxylate. LRMS (ESI) calc'd for $C_{21}H_{24}N_5O_3$ [M+H]+: 394, found 394. $^1$H NMR (600 MHz, DMSO-D$_6$) δ 12.9 (s, 1H), 11.1 (s, 1H), 8.90 (s, 1H), 8.30 (s, 1H), 7.89 (s, 1H), 7.77 (d, 1H, J=8.21 Hz), 7.42 (t, 1H, J=8.21 Hz), 7.35 (d, 1H, J=7.63 Hz), 6.01 (s, 1H), 5.58 (s, 1H), 3.87 (q, 2H, J=7.04 Hz), 3.23 (s, 2H), 2.24 (s, 6H), 0.86 (t, 3H, J=7.04 Hz).

Example 15-1

Ethyl-4-(3-{[2-(fluoromethyl)acryloyl]amino}phenyl)-7H-pyrrolo[2,3-d]pyrimidine-5-carboxylate

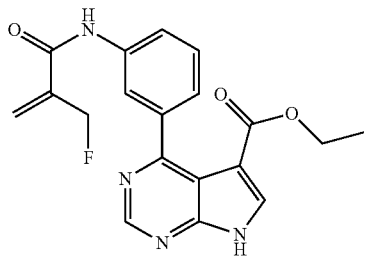 [SMILES: C=C(CF)C(=O)Nc1cccc(-c2ncnc3[nH]cc(C(=O)OCC)c23)c1]

Step 1: Lithium 2-(hydroxymethyl)prop-2-enoate

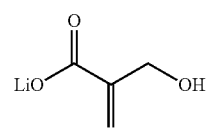

To ethyl 2-hydroxymethyl acrylic acid ester (1.00 g, 7.68 mmol) in tetrahydrofuran (4.8 mL) and water (4.8 mL) was added LiOH (202 mg, 8.45 mmol). The solution was stirred at 40° C. for 4 hours. The reaction was frozen and lyophilized to afford a white semi-solid/oil that was used directly in the next step as is.

Step 2: 2-({[tert-Butyl(dimethyl)silyl]oxy}methyl)prop-2-enoic acid

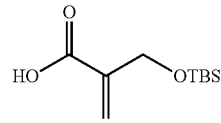

To lithium 2-(hydroxymethyl)prop-2-enoate (926 mg, 8.57 mmol) was added DMF (17.0 mL), HCl (1.07 mL, 4 M in dioxanes, 4.28 mmol) and imidazole (700 mg, 10.3 mmol), followed by TBS-Cl (2.84 g, 18.9 mmol) at 25° C. The reaction was stirred overnight, then quenched by pouring into a separatory funnel containing water. The aqueous layer was brought to pH~3 with 1 N HCl and was extracted with ethyl acetate (×3). The organic layers were combined and dried with Na$_2$SO$_4$, filtered, and concentrated in vacuo. The crude product was purified by chromatography using MPLC using 5-80% EtOAc/hexanes. The monoprotected product was collected and concentrated in vacuo to afford a clear oil. $^1$H NMR (600 MHz, DMSO-D$_6$) δ 12.67 (s, 1H), 6.13 (s, 1H), 5.80 (s, 1H), 4.31 (s, 2H), 0.92 (s, 9H), 0.09 (s, 6H).

Step 3: Ethyl 4-(3-{[2-({[tert-butyl(dimethyl)silyl]oxy}methyl)acryloyl]amino}phenyl)-7H-pyrrolo[2,3-d]pyrimidine-5-carboxylate

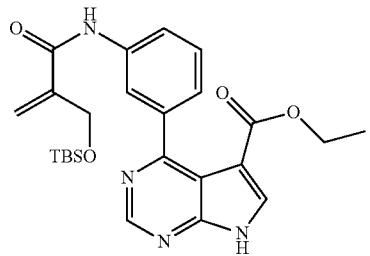 [SMILES: C=C(CO[Si](C)(C)C(C)(C)C)C(=O)Nc1cccc(-c2ncnc3[nH]cc(C(=O)OCC)c23)c1]

To ethyl 4-(3-aminophenyl)-7H-pyrrolo[2,3-d]pyrimidine-5-carboxylate (80 mg, 0.28 mmol) was added tetrahydrofuran (2.8 mL), TEA (59.2 µL, 0.425 mmol), 2-({[tert-butyl(dimethyl)silyl]oxy}methyl)prop-2-enoic acid (80 mg, 0.37 mmol) and 1-propanephosphonic acid cyclic anhydride (169 µL, 0.283 mmol). The reaction was stirred at 25° C. overnight before being quenched by pouring into a separatory funnel containing aqueous sodium bicarbonate (5%). The solution was extracted with ethyl acetate (×3) and the organic layers were combined and dried with Na$_2$SO$_4$, filtered, and concentrated in vacuo. The crude product was then purified by silica chromatography by MPLC using 1-8% CH$_2$Cl$_2$MeOH. Concentration of the desired fractions afforded the title compound as a colorless solid. LRMS (ESI) calc'd for C$_{25}$H$_{33}$N$_4$O$_4$Si [M+H]$^+$, 481; found 481.

Step 4: Ethyl-4-(3-{[2-(hydroxymethyl)acryloyl]amino}phenyl)-7H-pyrrolo[2,3-d]pyrimidine-5-carboxylate Example 15-2

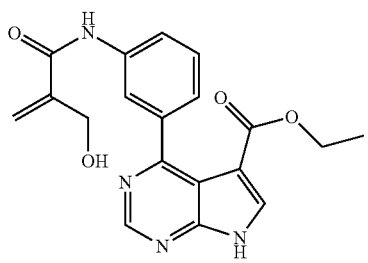 [SMILES: C=C(CO)C(=O)Nc1cccc(-c2ncnc3[nH]cc(C(=O)OCC)c23)c1]

To ethyl 4-(3-{[2-({[tert-butyl(dimethyl)silyl]oxy}methyl)acryloyl]amino}phenyl)-7H-pyrrolo[2,3-d]pyrimidine-5-carboxylate (52.9 mg, 0.110 mmol) in tetrahydrofuran (220 µL) at 25° C., was added TBAF (132 µL, 1.0 M in THF, 0.132 mmol). The reaction was stirred for 3 hours, then concentrated and loaded directly onto a silica column and eluted with 1-8% DCM/methanol to afford the desired product as a white solid. LRMS (ESI) calc'd for C$_{19}$H$_{19}$N$_4$O$_4$ [M+H]$^+$, 367; found 367. $^1$H NMR (600 MHz, DMSO-D$_6$) δ 13.01 (bs, 1H), 10.04 (s, 1H), 8.95 (s, 1H), 8.35 (s, 1H), 8.09 (s, 1H), 7.86 (d, 1H, J=8.4 Hz), 7.45 (t, 1H, J=7.8 Hz), 7.36 (d, 1H, J=7.8 Hz), 5.95 (s, 1H), 5.72 (s, 1H), 5.18 (t, 1H, J=6.0 Hz), 4.26 (d, 2H, J=4.9 Hz), 3.90 (q, 2H, J=7.2 Hz), 0.90 (t, 3H, J=7.2 Hz).

Step 5: Ethyl-4-(3-{[2-(fluoromethyl)acryloyl]amino}phenyl)-7H-pyrrolo[2,3-d]pyrimidine-5-carboxylate

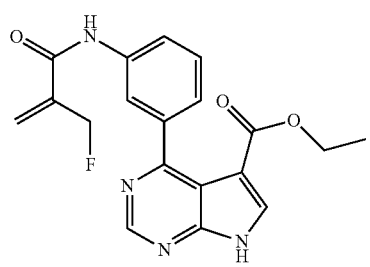 [SMILES: C=C(CF)C(=O)Nc1cccc(-c2ncnc3[nH]cc(C(=O)OCC)c23)c1]

To ethyl-4-(3-{[2-(hydroxymethyl)acryloyl]amino}phenyl)-7H-pyrrolo[2,3-d]pyrimidine-5-carboxylate (17 mg, 0.045 mmol) was added CH$_2$Cl$_2$ (0.90 mL) and the reaction was cooled to −78° C. before DAST (12 µL, 0.090 mmol) was added. The reaction was allowed to warm to room temperature over 2 hours. The reaction was quenched by pouring into a separatory funnel containing aqueous sodium bicarbonate (saturated) and was extracted with ethyl acetate (×3). The combined organic layers were dried over Na$_2$SO$_4$, filtered, and concentrated in vacuo to afford a residue that was dissolved in 2 mL of DMSO, and was purified by reverse phase HPLC using an acetonitrile gradient in water with 0.1% TFA modifier. Lyophilization of the desired fractions affords a colorless solid. LRMS (ESI) calc'd for $C_{19}H_{18}N_4O_3F$ [M+H]$^+$: 369, found 369. $^1$H NMR (600 MHz, DMSO-D$_6$) δ 13.02 (bs, 1H), 10.25 (s, 114), 8.97 (s, 1H), 8.36 (m, 1H), 8.09 (s, 1H), 7.88 (d, 1H, J=7.8 Hz), 7.47 (t, 1H, J=7.8 Hz), 7.38 (d, 1H, J=7.8 Hz), 6.19 (s, 1H), 5.94 (s, 1H), 5.26 (s, 1H), 5.18 (s, 1H), 3.90 (q, 2H, J=7.2 Hz), 0.90 (t, 3H, J=7.2 Hz).

Example 16

Ethyl-4-(3-{[(2E)-4-(dimethylamino)but-2-enoyl]amino}phenyl)-7H-pyrrolo[2,3-d]-pyrimidine-5-carboxylate

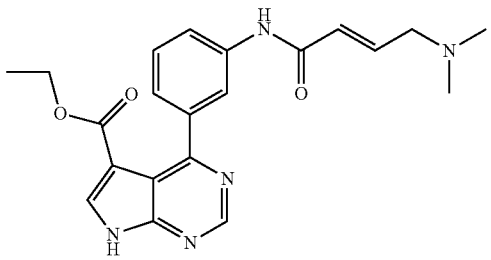 [SMILES: CCOC(=O)c1c[nH]c2ncnc(-c3cccc(NC(=O)/C=C/CN(C)C)c3)c12]

To a solution of ethyl 4-(3-aminophenyl)-7H-pyrrolo[2,3-d]pyrimidine-5-carboxylate (100 mg, 0.354 mmol) in THF (2 mL) was added (E)-4-bromobut-2-enoyl bromide (0.400 mmol) and the resulting reaction mixture was stirred for 1 hour at 0° C. Dimethylamine (0.886 mL, 1.77 mmol, 2 M in THF) was then added and the reaction mixture was sealed and stirred overnight. Water (10 mL) was added and the mixture was extracted with ethyl acetate (×3). The combined organic fractions were dried over sodium sulfate, filtered and concentrated under reduced pressure. The reaction was purified by reverse phase HPLC using an acetonitrile gradient in water with 0.1% TFA modifier. The combined fractions with the desired product were concentrated until only the water layer remained. The water layer was neutralized with saturated aqueous sodium bicarbonate and the mixture was extracted with ethyl acetate (×5). The combined organic fractions were dried over sodium sulfate, filtered and concentrated under reduced pressure to give ethyl-4-(3-{[(2E)-4-(dimethylamino)but-2-enoyl]amino}phenyl)-7H-pyrrolo[2,3-d]pyrimidine-5-carboxylate. LRMS (ESI) calc'd for $C_{21}H_{24}N_5O_3$ [M+H]$^+$: 394, found 394. $^1$H NMR (600 MHz, DMSO-D$_6$) δ 13.0 (s, 1H), 10.2 (s, 1H), 8.91 (s, 1H), 8.31 (s, 1H), 8.00 (s, 1H), 7.78 (d, 1H, J=8.21 Hz), 7.41 (t, 1H, J=8.21 Hz), 7.31 (d, 1H, J=7.63 Hz), 6.73 (dt, 1H, J=15.3, 5.87 Hz), 6.27 (d, 1H, J=15.3 Hz), 3.84 (q, 2H, J=7.04 Hz), 3.06 (d, 2H, J=5.87 Hz), 2.18 (s, 6H), 0.83 (t, 3H, J=7.04 Hz).

Example 17

Ethyl-4-(3-{[(2E)-4-(dimethylamino)-2-methylbut-2-enoyl]amino}phenyl)-7H-pyrrolo[2,3-d]pyrimidine-5-carboxylate

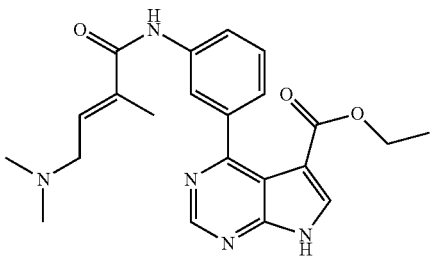 [SMILES: CCOC(=O)c1c[nH]c2ncnc(-c3cccc(NC(=O)/C(C)=C/CN(C)C)c3)c12]

Step 1: Methyl(2E)-4-bromo-2-methylbut-2-enoate

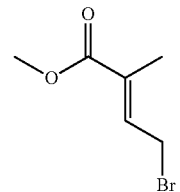

To a solution of methyl tiglate (2.00 g, 17.5 mmol) in CCl$_4$ (8.76 mL) was added NBS (3.43 g, 19.3 mmol) and benzoyl peroxide (212 mg, 0.876 mmol). The reaction was heated to reflux for 3 hours, cooled and filtered through Celite using DCM to wash the filtrate. The reaction was concentrated in vacuo and then purified by silica chromatography using 1-15% EtOAc/hexane. The product was collected and concentrated in vacuo to afford the desired product as a colorless oil that was taken on to the next step without further purification.

Step 2:
Methyl(2E)-4-(dimethylamino)-2-methylbut-2-enoate

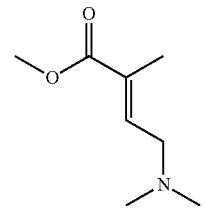

To methyl(2E)-4-bromo-2-methylbut-2-enoate (643 mg, 3.33 mmol) in tetrahydrofuran (6.66 mL) was added dimethylamine (5.00 mL, 9.99 mmol, 2M in THF). The reaction was stirred at 25° C. overnight, then concentrated in vacuo and purified by silica chromatography using 1-8% DCM/MeOH (visualized with potassium permanganate stain). The product was collected and concentrated to afford the desired product as a colorless oil. LRMS (ESI) calc'd for $C_8H_{16}NO_2$ [M+H]$^+$: 158, found 158.

Step 3: Lithium
(2E)-4-(dimethylamino)-2-methylbut-2-enoate

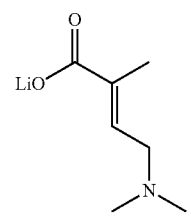

To methyl(2E)-4-(dimethylamino)-2-methylbut-2-enoate (238 mg, 1.51 mmol) in tetrahydrofuran (0.95 mL) and water (0.95 mL) was added LiOH (36 mg, 1.5 mmol). The solution was stirred at 40° C. for 4 hours before being frozen and lyophilized to afford a white semi-solid that was taken on to the next step as is. LRMS (ESI) calc'd for $C_7H_{13}NO_2$ [M+]$^+$: 144, found 144.

Step 4: Ethyl 4-(3-{[(2E)-4-(dimethylamino)-2-methylbut-2-enoyl]amino}phenyl)-7H-pyrrolo[2,3-d]pyrimidine-5-carboxylate

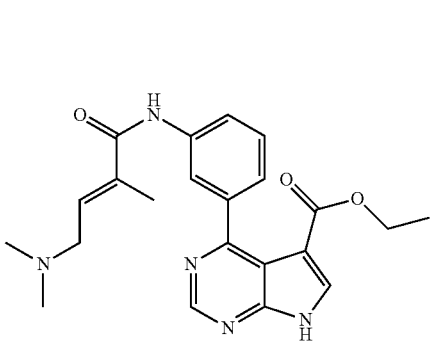 [SMILES: CCOC(=O)c1c[nH]c2ncnc(-c3cccc(NC(=O)/C(C)=C/CN(C)C)c3)c12]

To ethyl 4-(3-aminophenyl)-7H-pyrrolo[2,3-d]pyrimidine-5-carboxylate (100 mg, 0.354 mmol) was added tetrahydrofuran (3.54 mL), TEA (74 μl, 0.53 mmol), lithium (2E)-4-(dimethylamino)-2-methylbut-2-enoate (137 mg, 0.920 mmol) and 1-propanephosphonic acid cyclic anhydride (211 μL, 0.354 mmol). The reaction was stirred at 25° C. overnight and then extracted from aqueous sodium hydrogen carbonate (5%) using ethyl acetate (×3). The organic layers were combined and dried with $Na_2SO_4$, filtered, and evaporated in vacuo. The crude product was then taken up in 2 mL of methanol and purified by reverse phase HPLC using an acetonitrile gradient in water with 0.1% TFA modifier. Lyophilization of the desired fractions afforded the title compound as a colorless solid. LRMS (ESI) calc'd for $C_{22}H_{26}N_5O_3$ [M+H]$^+$: 408, found 408. $^1$H NMR (600 MHz, DMSO-$D_6$) 13.06 (bs, 1H), 10.04 (s, 1H), 9.76 (bs, 1H), 8.96 (s, 1H), 8.36 (d, 1H, J=2.8 Hz), 8.08 (s, 1H), 7.85 (dm, 1H, J=9.0 Hz), 7.47 (t, 1H, J=7.8 Hz), 7.36 (dm, 1H, J=7.8 Hz), 6.33 (t, 1H, J=7.2 Hz), 3.98 (apparent t, 1H, J=7.2 Hz), 3.91 (q, 2H, J=7.2 Hz), 2.89 (s, 3H), 2.88 (s, 3H), 2.02 (s, 3H), 0.90 (t, 3H, J=7.2 Hz).

Example 18-1 and Example 18-2

Ethyl-4-(3-(2-methyloxirane-2-carboxamido)phenyl)-7H-pyrrolo[2,3-d]pyrimidine-5-carboxylate (18-1)

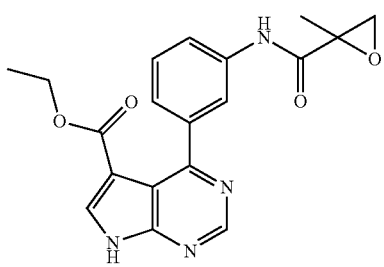 [SMILES: CCOC(=O)c1c[nH]c2ncnc(-c3cccc(NC(=O)C4(C)CO4)c3)c12]

Ethyl-4-(3-(2,3-dihydroxy-2-methylpropanamido)phenyl)-7H-pyrrolo[2,3-d]pyrimidine-5-carboxylate (18-2)

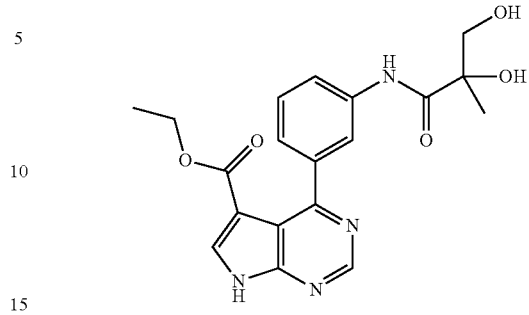

To a solution of ethyl 4-{3-[(2-methylacryloyl)amino]phenyl}-7H-pyrrolo[2,3-d]pyrimidine-5-carboxylate (50 mg, 0.14 mmol) in formic acid (1.08 mL, 26.9 mmol) was slowly added hydrogen peroxide (575 μL, 6.57 mmol, 35% wt.). The reaction mixture was then heated at 40° C. for 2 hours before being quenched with 1 M NaOH solution. The pH was adjusted to 11 with 1 M NaOH and the organic layer was separated and the aqueous layer extracted with ethyl acetate (×3). The combined organic layers were washed with brine (5 mL), dried over sodium sulfate, and concentrated under reduced pressure. The residue was purified by reverse phase HPLC using an acetonitrile gradient in water with 0.1% TFA modifier to give ethyl 4-(3-(2-methyloxirane-2-carboxamido)phenyl)-7H-pyrrolo[2,3-d]pyrimidine-5-carboxylate and ethyl 4-(3-(2,3-dihydroxy-2-methylpropanamido)phenyl)-7H-pyrrolo[2,3-d]pyrimidine-5-carboxylate.

Ethyl-4-(3-(2-methyloxirane-2-carboxamido)phenyl)-7H-pyrrolo[2,3-d]pyrimidine-5-carboxylate LRMS (ESI) calc'd for $C_{19}H_{19}N_4O_4$[M+11]$^+$: 367, found 367. $^1$H NMR (600 MHz, DMSO-$D_6$) δ 12.96 (bs, 1H), 9.60 (s, 1H), 8.90 (s, 1H), 8.30 (s, 1H), 8.11 (s, 1H), 7.79 (d, J=8.04 Hz, 1H), 7.39 (t, J=7.63 Hz, 1H), 7.34 (d, J=7.63 Hz, 1H), 3.85 (q, J=7.04 Hz, 2H), 3.00 (d, J=5.28 Hz, 1H), 2.97 (d, J=4.69 Hz, 1H), 1.53 (s, 3H), 0.86 (t, J=7.04 Hz, 3H).

Ethyl-4-(3-(2,3-dihydroxy-2-methylpropanamido)phenyl)-7H-pyrrolo[2,3-d]pyrimidine-5-carboxylate LRMS (ESI) calc'd for $C_{19}H_{21}N_4O_5$[M+H]$^+$: 385, found 384. $^1$H NMR (600 MHz, DMSO-$D_6$) δ 12.96 (bs, 1H), 9.59 (s, 1H), 8.89 (s, 1H), 8.29 (s, 1H), 8.14 (s, 1H), 7.79 (d, J=8.80 Hz, 1H), 7.39 (t, J=8.21 Hz, 1H), 7.31 (d, J=7.63 Hz, 1H), 5.52 (s, 1H), 4.83 (t, J=6.45 Hz, 1H), 3.86 (q, J=7.04 Hz, 2H), 3.62 (m, 1H), 3.39 (m, 1H), 1.26 (s, 3H), 0.87 (t, J=7.04 Hz, 3H).

Example 19
N-(3-{5-[4-(Aminomethyl)phenyl]-7H-pyrrolo[2,3-d]pyrimidin-4-yl}phenyl)-2-methylprop-2-enamide

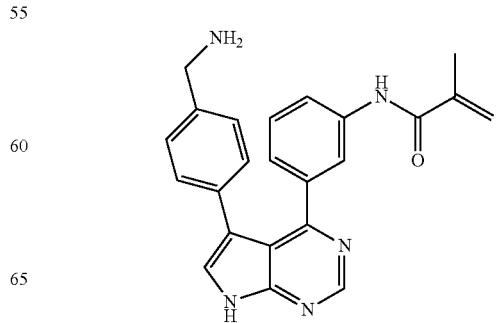

163

Step 1:
4-(3-Nitrophenyl)-7H-pyrrolo[2,3-d]pyrimidine

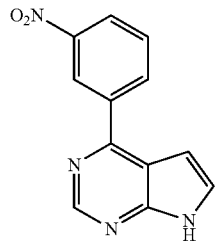 [SMILES: O=[N+]([O-])c1cccc(-c2ncnc3[nH]ccc23)c1]

A mixture of 4-chloro-7H-pyrrolo[2,3-d]pyrimidine (10 g, 65 mmol), 3-nitrophenylboronic acid (17.4 g, 104 mmol), Pd(dppf)Cl$_2$—CH$_2$Cl$_2$ (2.13 g, 2.60 mmol), and 2 M sodium carbonate (81.5 mL, 163 mmol) in DMF (217 mL) was degassed for 10 minutes and then heated at 115° C. for 1 hour. After the reaction mixture was cooled to room temperature, water (700 mL) and sorbitol (20 g) were added which led to the precipitation of the desired product. After 30 minutes of stirring, the precipitate was filtered to give the crude product which was then slurried from EtOAc (100 mL) and hexanes (150 mL) for 30 minutes. Filtration of the precipitate gave 4-(3-nitrophenyl)-7H-pyrrolo[2,3-d]pyrimidine. LRMS (ESI) calc'd for C$_{12}$H$_9$N$_4$O$_2$ [M+H]$^+$: 241, found 241.

Step 2: 5-Bromo-4-(3-nitrophenyl)-7H-pyrrolo[2,3-d]pyrimidine

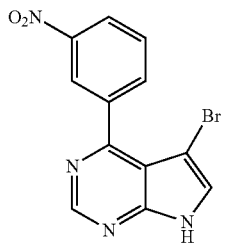 [SMILES: O=[N+]([O-])c1cccc(-c2ncnc3[nH]cc(Br)c23)c1]

To 4-(3-nitrophenyl)-7H-pyrrolo[2,3-d]pyrimidine (12 g, 50 mmol) in DMF (167 mL) was added NBS (10.2 g, 57.4 mmol) and the mixture stirred for 30 minutes. Water (833 mL) was added which led to the precipitation of the desired product. The reaction mixture was allowed to stir for 15 minutes before being filtered and washed with 500 mL of water to give 5-bromo-4-(3-nitrophenyl)-7H-pyrrolo[2,3-d]pyrimidine. LRMS (ESI) calc'd for C$_{12}$H$_8$BrN$_4$O$_2$[M+H]$^+$: 319, found 319.

Step 3:
3-(5-Bromo-7H-pyrrolo[2,3-d]pyrimidin-4-yl)aniline

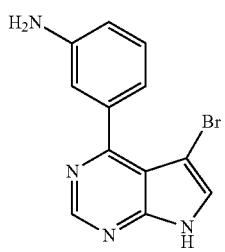

164

To 5-bromo-4-(3-nitrophenyl)-7H-pyrrolo[2,3-d]pyrimidine (9.5 g, 30 mmol) in methanol (99 mL) was added 3% Pt on carbon doped with 0.6% V (4.84 g, 0.744 mmol) and the mixture was stirred under H$_2$ balloon overnight. The mixture was filtered over Celite and the filtrate washed with DCM/MeOH. The reaction solution was then concentrated under reduced pressure to afford 3-(5-bromo-7H-pyrrolo[2,3-d]pyrimidin-4-yl)aniline. LRMS (ESI) calc'd for C$_{12}$H$_{10}$BrN$_4$ [M+H]$^+$: 289, found 289.

Step 4: N-(3-{5-[4-(Aminomethyl)phenyl]-7H-pyrrolo[2,3-d]pyrimidin-4-yl}phenyl)-2-methylprop-2-enamide

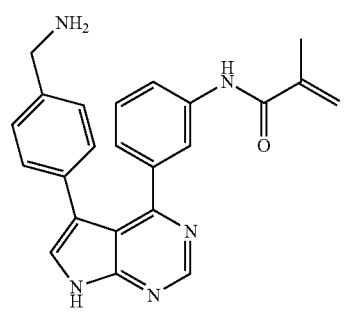 [SMILES: C=C(C)C(=O)Nc1cccc(-c2ncnc3[nH]cc(-c4ccc(CN)cc4)c23)c1]

A mixture of 3-(5-bromo-7H-pyrrolo[2,3-d]pyrimidin-4-yl)aniline (50 mg, 0.17 mmol), (4-{[(tert-butoxycarbonyl)amino]methyl}phenyl)boronic acid (87 mg, 0.35 mmol), PdCl$_2$(dppf)-CH$_2$Cl$_2$ (28 mg, 0.035 mmol), potassium phosphate tribasic (49.3 mg, 0.519 mmol) in dioxane (576 µL) was heated to 110° C. for 17 hours. Upon cooling, dioxane (1.0 mL) and SiliaMetS® DMT (loading=0.58 mmol/g, 298 mg, 0.173 mmol) were added to the reaction mixture and shaken at room temperature for 20 hours. The reaction mixture was filtered through Celite, washed with MeOH, and concentrated under reduced pressure. To this crude intermediate was added DMF (1.73 mL), TEA (36.2 µL, 0.260 mmol), 2-methylprop-2-enoic acid (17.9 mg, 0.208 mmol) and 1-propanephosphonic acid cyclic anhydride (83 µl, 0.14 mmol). The reaction was stirred at room temperature for 70 hours, concentrated under reduced pressure, and purified by reverse phase HPLC using an acetonitrile gradient in water with 0.1% TFA modifier. The purified intermediate was concentrated and redissolved in 4 N HCl in dioxane (0.50 mL, 2.0 mmol). The mixture was stirred at room temperature for 20 hours and concentrated to afford product as a TFA salt that was redissolved in MeOH, passed through an ISOLUTE Si-Carbonate, and then concentrated under reduced pressure to afford N-(3-{5-[4-(aminomethyl)phenyl]-7H-pyrrolo[2,3-d]pyrimidin-4-yl}phenyl)-2-methylprop-2-enamide. LRMS (ESI) calc'd for C$_{23}$H$_{22}$N$_5$O [M+H]$^+$: 384, found 384. $^1$H NMR (600 MHz, DMSO-D$_6$, water presat) δ 12.66 (br s, 1H); 9.69 (s, 1H); 8.88 (s, 1H); 7.83 (s, 1H); 7.79 (s, 1H); 7.75 (d, 1H, J=6.0 Hz), 7.68 (d, 1H, J=6.5 Hz); 7.13 (d, 214, J=6.5 Hz); 7.01-6.97 (m, 3H); 5.72 (s, 1H); 5.49 (s, 1H); 2.50 (s, 2H); 1.90 (s, 3H).

General Scheme K:

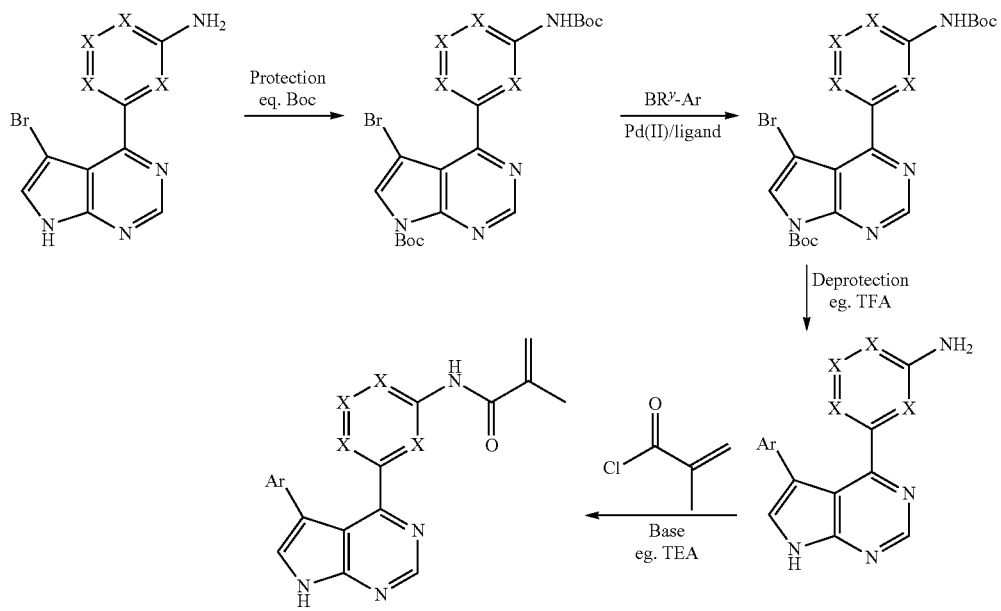

Examples Generated Via General Scheme K

Example 20-1

2-Methyl-N-{3-[5-(3-methylphenyl)-7H-pyrrolo[2,3-d]pyrimidin-4-yl]phenyl}prop-2-enamide

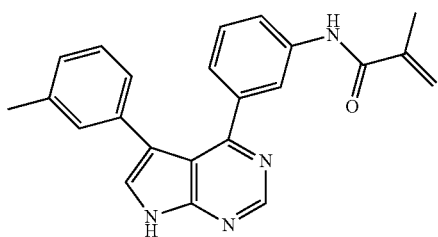 [SMILES: C=C(C)C(=O)Nc1cccc(-c2ncnc3[nH]cc(-c4cccc(C)c4)c23)c1]

Step 1: tert-Butyl 5-bromo-4-{3-[(tert-butoxycarbonyl)amino]phenyl}-7H-pyrrolo[2,3-d]pyrimidine-7-carboxylate

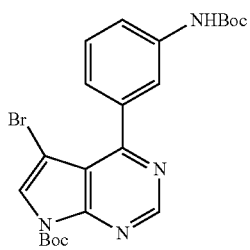

To a solution of 3-(5-bromo-7H-pyrrolo[2,3-d]pyrimidin-4-yl)aniline (400 mg, 1.38 mmol) and sodium hydroxide (166 mg, 4.15 mmol) in water (1.54 mL) and dioxane (3.07 mL) was added di-tert-butyl dicarbonate (964 μL, 4.15 mmol) at room temperature. The reaction mixture was stirred for 20 hours and the solvents were removed in vacuo. The reaction mixture was diluted with water and extracted with ethyl acetate (×3). The combined organic layers were washed with brine, dried with $MgSO_4$, filtered, and concentrated under reduced pressure. The crude reaction mixture was purified on silica, eluting with 5-30% EtOAc in hexanes to afford tert-butyl 5-bromo-4-{3-[(tert-butoxycarbonyl)amino]phenyl}-7H-pyrrolo[2,3-d]pyrimidine-7-carboxylate as a pale yellow solid. LRMS (ESI) calc'd for $C_{22}H_{26}BrN_4O_4$ $[M+H]^+$: 489, found 489. $^1H$ NMR (600 MHz, DMSO-$D_6$) δ 9.53 (br s, 1H); 9.02 (s, 114); 8.09 (s, 1H), 7.81 (br s, 1H), 7.56 (d, 1H, J=6.5 Hz), 7.36 (dd, 1H, J=6.5, 6.5 Hz); 7.49 (dt, 1H, J=1.0, 6.5 Hz); 1.6 (s, 9H), 1.44 (s, 9H).

Step 2: 2-Methyl-N-{3-[5-(3-methylphenyl)-7H-pyrrolo[2,3-d]pyrimidin-4-yl]phenyl}prop-2-enamide

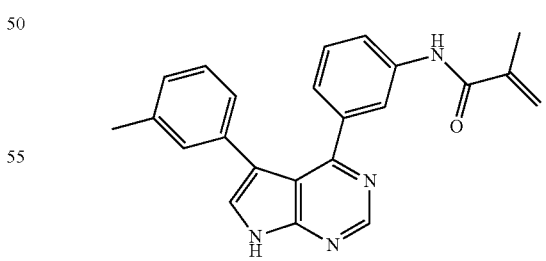

A mixture of (3-methylphenyl)boronic acid (26.4 mg, 0.194 mmol), tert-butyl 5-bromo-4-{3-[(tert-butoxycarbonyl)amino]phenyl}-7H-pyrrolo[2,3-d]pyrimidine-7-carboxylate (50 mg, 0.10 mmol), potassium phosphate (1 M aqueous solution, 511 μL, 0.511 mmol), and 1,1'-bis(di-tert-butylphosphino)ferrocene palladium dichloride (6.66 mg, 10.2 μmol) in degassed toluene (1.02 mL) was heated to 60°

C. for 18 hours. The reaction mixture was filtered through Celite and concentrated under reduced pressure. The crude residue was dissolved in 0.5 mL of DCM:TFA:Water (50:48:2) and stirred at room temperature for 2 hours before being concentrated under reduced pressure. To this deprotected intermediate was added DMF (0.50 mL), TEA (57 μl, 0.41 mmol), 3-(diethoxyphosphoryloxy)-1,2,3-benzotriazin-4-(3H)-one (61.1 mg, 0.204 mmol) and 2-methylprop-2-enoyl chloride (17.6 mg, 0.204 mmol). The reaction mixture was stirred at room temperature for 20 hours, filtered, and purified by reverse phase HPLC using an acetonitrile gradient in water with 0.1% TFA modifier to afford 2-methyl-N-{3-[5-(3-methylphenyl)-7H-pyrrolo[2,3-d]pyrimidin-4-yl]phenyl}prop-2-enamide. LRMS (ESI) calc'd for $C_{23}H_{21}N_4O$ [M+H]$^+$: 369, found 369. $^1$H NMR (600 MHz, DMSO-D$_6$) δ 12.71 (br s, 1H); 9.60 (s, 1H); 8.91 (s, 1H); 7.81 (br s, 1H); 7.74 (s, 1H); 7.65 (d, 1H, J=6.0 Hz), 7.07 (dd, 1H, J=6.5, 6.5 Hz); 6.94 (d, 2H, J=6.0 Hz); 6.88 (d, 1H, J=6.5 Hz); 6.80 (d, 1H, J=5.5 Hz); 6.62 (s, 1H); 5.67 (s, 1H); 5.46 (s, 1H); 1.99 (s, 3H); 1.88 (s, 3H).

The following examples, 20-2 through 20-9, as shown in Table 11, were prepared in an analogous manner of that described above using materials that are commercially available or known, or that can be prepared using procedures known in the art or by generally following procedures described herein for various intermediates.

TABLE 11

| Example Number | Chemical Structure | IUPAC Name | Exact mass [M + H]+ |
| --- | --- | --- | --- |
| 20-2 | 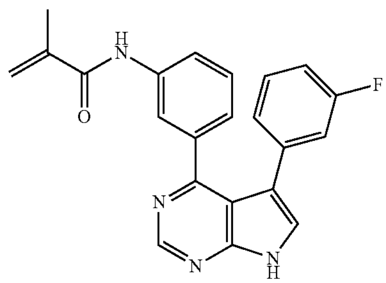 [SMILES: C=C(C)C(=O)Nc1cccc(-c2ncnc3[nH]cc(-c4cccc(F)c4)c23)c1] | N-{3-[5-(3-fluorophenyl)-7H-pyrrolo[2,3-d]pyrimidin-4-yl]phenyl}-2-methylprop-2-enamide | Calc'd 373, found 373 |
| 20-3 | 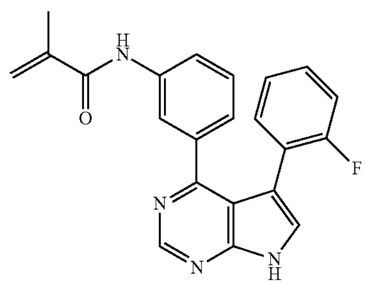 [SMILES: C=C(C)C(=O)Nc1cccc(-c2ncnc3[nH]cc(-c4ccccc4F)c23)c1] | N-{3-[5-(2-fluorophenyl)-7H-pyrrolo[2,3-d]pyrimidin-4-yl]phenyl}-2-methylprop-2-enamide | Calc'd 373, found 373 |
| 20-4 | 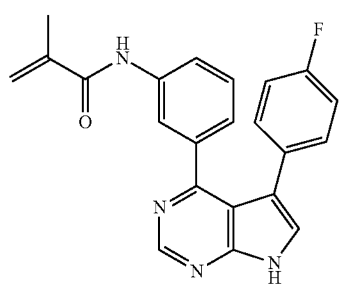 | N-{3-[5-(4-fluorophenyl)-7H-pyrrolo[2,3-d]pyrimidin-4-yl]phenyl}-2-methylprop-2-enamide | Calc'd 373, found 373 |
| 20-5 | 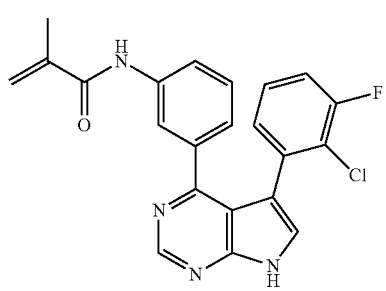 [SMILES: C=C(C)C(=O)Nc1cccc(-c2ncnc3[nH]cc(-c4cccc(F)c4Cl)c23)c1] | N-{3-[5-(2-chloro-3-fluorophenyl)-7H-pyrrolo[2,3-d]pyrimidin-4-yl]phenyl}-2-methylprop-2-enamide | Calc'd 407, found 407 |

TABLE 11-continued

| Example Number | Chemical Structure | IUPAC Name | Exact mass [M + H]+ |
|---|---|---|---|
| 20-6 | 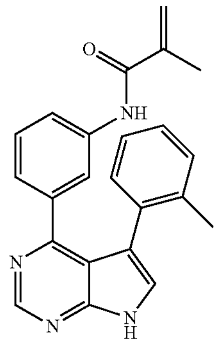 [SMILES: C=C(C)C(=O)Nc1cccc(-c2ncnc3[nH]cc(-c4ccccc4C)c23)c1] | 2-methyl-N-{3-[5-(2-methylphenyl)-7H-pyrrolo[2,3-d]pyrimidin-4-yl]phenyl}prop-2-enamide | Calc'd 369, found 369 |
| 20-7 | 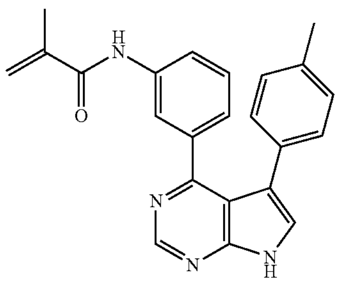 [SMILES: C=C(C)C(=O)Nc1cccc(-c2ncnc3[nH]cc(-c4ccc(C)cc4)c23)c1] | 2-methyl-N-{3-[5-(4-methylphenyl)-7H-pyrrolo[2,3-d]pyrimidin-4-yl]phenyl}prop-2-enamide | Calc'd 369, found 369 |
| 20-8 | 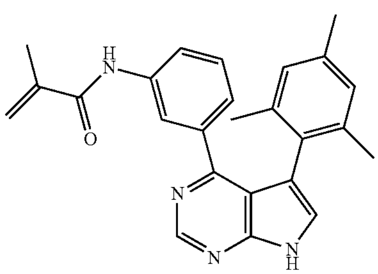 [SMILES: C=C(C)C(=O)Nc1cccc(-c2ncnc3[nH]cc(-c4c(C)cc(C)cc4C)c23)c1] | 2-methyl-N-{3-[5-(2,4,6-trimethylphenyl)-7H-pyrrolo[2,3-d]pyrimidin-4-yl]phenyl}prop-2-enamide | Calc'd 397, found 397 |
| 20-9 | 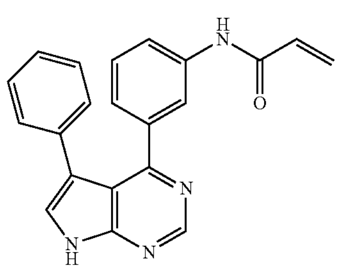 [SMILES: C=CC(=O)Nc1cccc(-c2ncnc3[nH]cc(-c4ccccc4)c23)c1] | N-[3-(5-phenyl-7H-pyrrolo[2,3-d]pyrimidin-4-yl)phenyl]prop-2-enamide | Calc'd 341, found 341 |

General Scheme L:

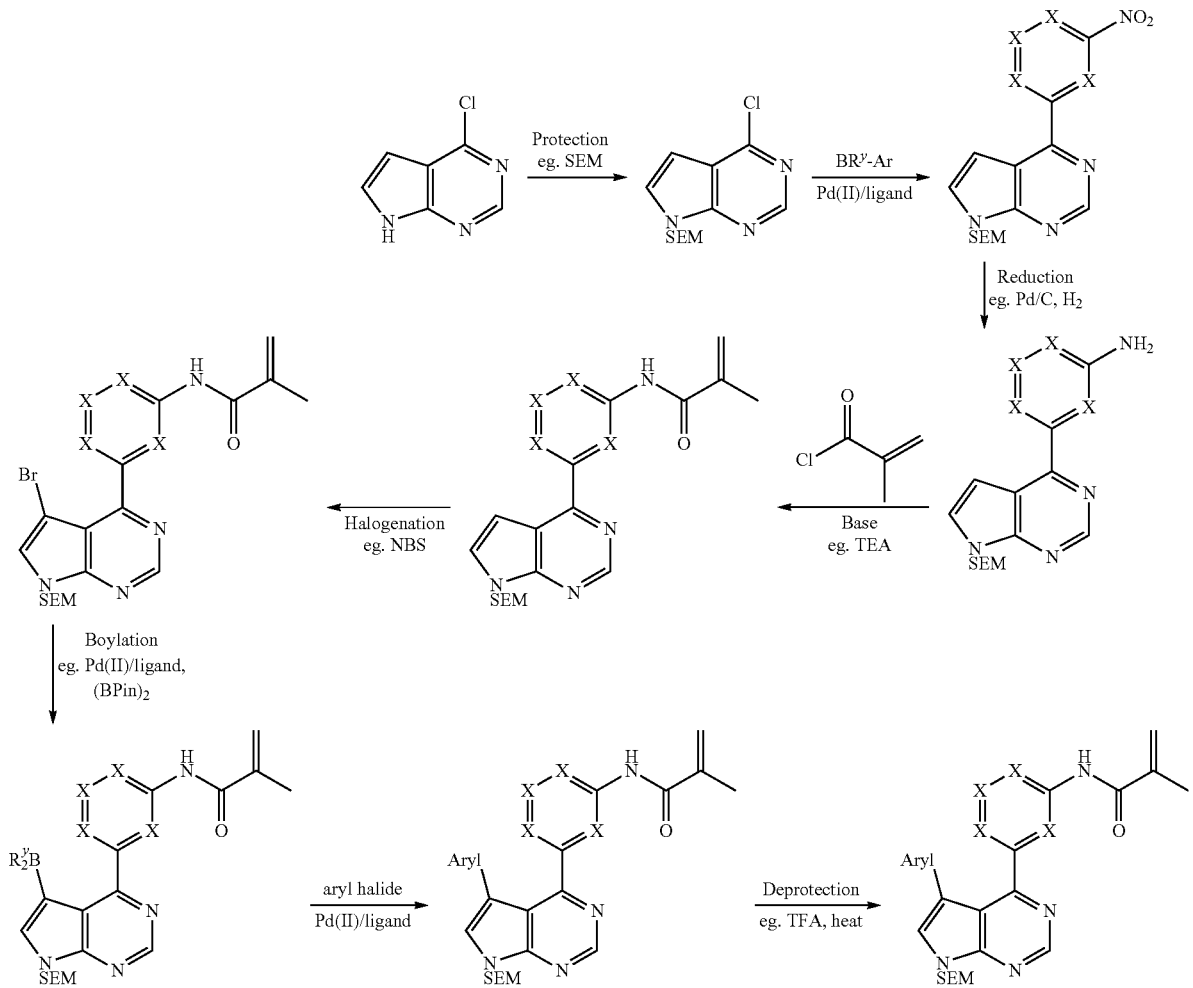

Examples Generated Via General Scheme L

Example 21-1

N-(3-(5-(Pyridin-2-yl)-7H-pyrrolo[2,3-d]pyrimidin-4-yl)phenyl)methacrylamide

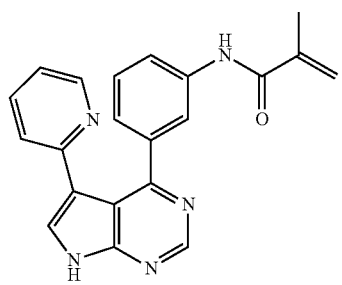 [SMILES: C=C(C)C(=O)Nc1cccc(-c2ncnc3[nH]cc(-c4ccccn4)c23)c1]

Step 1: 4-Chloro-7-((2-(trimethylsilyl)ethoxy)methyl)-7H-pyrrolo[2,3-d]pyrimidine

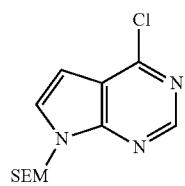 [SMILES: C[Si](C)(C)CCOCn1ccc2c(Cl)ncnc21]

To a solution of 4-chloro-7H-pyrrolo[2,3-d]pyrimidine (15.3 g, 99.6 mmol) in tetrahydrofuran (200 mL) was added NaH (60% dispersion in mineral oil, 4.20 g, 105 mmol) at 0° C. The resulting solution was stirred for 1 hour at 0° C. and then SEMCl (16.6 g, 100 mmol) was added dropwise. After stirring for an additional 5 hours at 25° C., the reaction was quenched by addition of 250 mL of water/ice, and extracted with ethyl acetate (×2). The organic layers were combined and dried over anhydrous sodium sulfate and concentrated in vacuo. The reaction was purified by chromatography using silica gel, eluting with 50% EtOAc/petroleum ether. The product was collected and concentrated in vacuo to afford 4-chloro-7-((2-(trimethylsilyl)ethoxy)methyl)-7H-pyrrolo[2,3-d]pyrimidine as a light yellow oil. LRMS (PSI) calc'd for $C_{12}H_{19}N_3ClOSi$ [M+H]$^+$: 284. found 284.

Step 2: 4-(3-Nitrophenyl)-((7-(trimethylsilyl)ethoxy)methyl)-7H-pyrrolo[2,3-d]pyrimidine

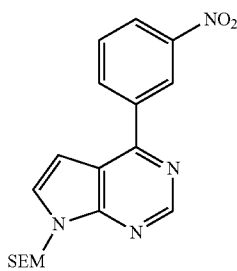 [SMILES: C[Si](C)(C)CCOCn1ccc2c(-c3cccc([N+](=O)[O-])c3)ncnc21]

A solution of 4-chloro-7-((2-(trimethylsilyl)methyl)-7H-pyrrolo[2,3-d]pyrimidine (15.0 g, 52.9 mmol) in N,N-dimethylformamide (200 mL) was added to Pd(dppf)Cl$_2$ (2.2 g, 2.7 mmol), (3-nitrophenyl)boronic acid (13.3 g, 79.7 mmol) under nitrogen. A solution of sodium carbonate (6.00 g, 56.6 mmol) in water (60.0 mL) was then added and the reaction was stirred for 3 hours at 100° C. The resulting mixture was concentrated in vacuo, and the solids were filtered and extracted with dichloromethane (×3). The combined organic layers were washed with H$_2$O, brine, dried over anhydrous sodium sulfate, filtered and concentrated in vacuo. The reaction was then purified by chromatography using silica gel, eluting with 0-33% EtOAc/petroleum ether. The product was collected and concentrated in vacuo to afford 4-(3-nitrophenyl)-7-((2-(trimethylsilyl)ethoxy)methyl)-7H-pyrrolo[2,3-d]pyrimidine as a yellow solid. LRMS (ESI) calc'd for $C_{18}H_{23}N_4O_3Si$ [M+H]$^+$: 371, found 371.

Step 3: 3-(7-((2-(Trimethylsilyl)ethoxy)methyl)-7H-pyrrolo[2,3-d]pyrimidin-4-yl)aniline

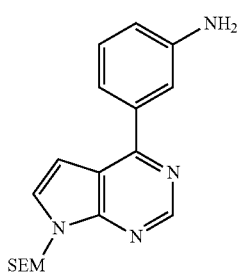

To a solution of 4-(3-nitrophenyl)-7-((2-(trimethylsilyl)ethoxy)methyl)-7H-pyrrolo[2,3-d]pyrimidine (12.0 g, 32.4 mmol) in methanol (200 mL), was added Pd/C (2.00 g, 10 wt. %). The reaction was then purged with hydrogen gas and stirred overnight at room temperature under hydrogen atmosphere (1 atm) before being filtered and concentrated in vacuo. The reaction was then purified by chromatography using silica gel, eluting with 50% EtOAc/petroleum ether. The product was collected and concentrated in vacuo to afford 3-(7-((2-(trimethylsilyl)ethoxy)methyl)-7H-pyrrolo[2,3-d]pyrimidin-4-yl)aniline as a yellow oil. LRMS (ESI) calc'd for $C_{18}H_{25}N_4OSi$ [M+H]$^+$: 341, found 341.

Step 4: N-(3-(7-((2-(Trimethylsilyl)ethoxy)methyl)-7H-pyrrolo[2,3-d]pyrimidin-4-yl)phenyl)methacrylamide

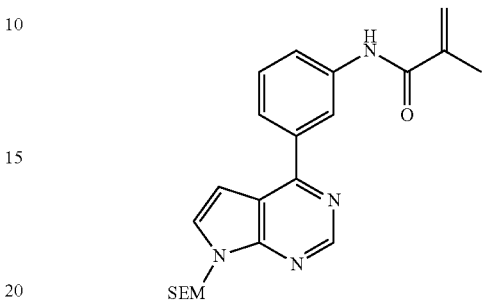

To solution of 3-(7-((2-(trimethylsilyl)ethoxy)methyl)-7H-pyrrolo[2,3-d]pyrimidin-4-yl)aniline (10.0 g, 29.4 mmol) in dichloromethane (200 mL), was added DIPEA (12.0 g, 92.9 mmol) followed by dropwise addition of a solution of 2-methylprop-2-enoyl chloride (4.60 g, 44.0 mmol) in dichloromethane (50 mL) at −5 to 0° C. The reaction was stirred overnight at room temperature, quenched by addition of water (150 mL), and extracted with dichloromethane (×3). The organic layers were combined, washed with water and HCl solution (0.5 M in water), dried over anhydrous sodium sulfate, filtered and concentrated in vacuo. The reaction was then purified by chromatography using silica gel, eluting with 0-33% EtOAc/petroleum ether. The product was collected and concentrated in vacuo to afford N-(3-(7-((2-(trimethylsilyl)ethoxy)methyl)-7H-pyrrolo[2,3-d]pyrimidin-4-yl)phenyl)methacrylamide as a yellow oil. LRMS (ESI) calc'd for $C_{22}H_{29}N_4O_2Si$ [M+H]$^+$: 409, found 409.

Step 5: N-(3-(5-Bromo-7-((2-(trimethylsilyl)ethoxy)methyl)-7H-pyrrolo[2,3-d]pyrimidin-4-yl)phenyl)methacrylamide

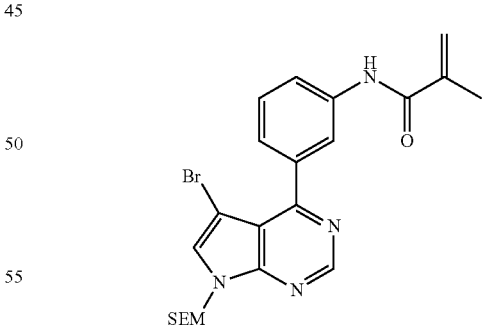

To a solution of N-(3-(7-((2-(trimethylsilyl)ethoxy)methyl)-7H-pyrrolo[2,3-d]pyrimidin-4-yl)phenyl)methacrylamide (5.20 g, 12.7 mmol) in CH$_3$CN (80 mL), was added NBS (2.40 g, 13.5 mmol) in several portions at 80° C. The resulting solution was stirred for 2 hours at 80° C. before being concentrated in vacuo. The reaction was then purified by chromatography using silica gel, eluting with 0-33% EtOAc/petroleum ether. The product was collected and concentrated in vacuo to afford N-(3-(5-bromo-7-((2-(trimethylsilyl)ethoxy)methyl)-7H-pyrrolo[2,3-d]pyrimidin-4-yl)phenyl)methacrylamide as a yellow solid. LRMS (ESI) calc'd for $C_{22}H_{28}N_4O_2SiBr$ [M+H]$^+$: 487, found 487.

Step 6: N-(3-(5-(4,4,5,5-Tetramethyl-1,3,2-dioxaborolan-2-yl)-7-((2-(trimethylsilyl)ethoxy)methyl)-7H-pyrrolo[2,3-d]pyrimidin-4-yl)phenyl)methacrylamide

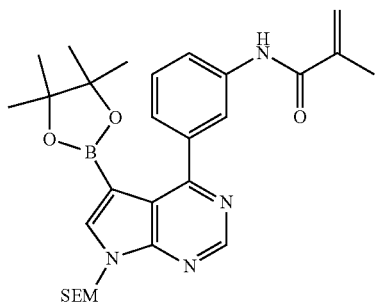 [SMILES: C=C(C)C(=O)Nc1cccc(-c2ncnc3c2c(B2OC(C)(C)C(C)(C)O2)cn3COCC[Si](C)(C)C)c1]

To a solution of N-[3-(5-bromo-7-[[2-(trimethylsilyl)ethoxy]methyl]-7H-pyrrolo[2,3-d]pyrimidin-4-yl)phenyl]-2-methylprop-2-enamide (3.9 g, 8.0 mmol) in DMA (100 mL) under nitrogen, was added 4,4,5,5-tetramethyl-2-(tetramethyl-1,3,2-dioxaborolan-2-yl)-1,3,2-dioxaborolane (6.10 g, 24.0 mmol), Pd(PPh$_3$)$_2$Cl$_2$ (281 mg, 0.400 mmol) and K$_3$PO$_4$ (5.10 g, 24.0 mmol). The reaction was stirred for 3 hours at 80° C. before being concentrated in vacuo. The resulting solution was extracted with dichloromethane (×3) and the combined organic layers were washed with H$_2$O, brine, dried over anhydrous sodium sulfate, filtered and concentrated in vacuo. The reaction was then purified by chromatography using silica gel, eluting with 0-33% EtOAc/petroleum ether. The product was collected and concentrated in vacuo to afford N-(3-(5-(4,4,5,5-tetramethyl-1,3,2-dioxaborolan-2-yl)-7-((2-(trimethylsilyl)ethoxy)methyl)-7H-pyrrolo[2,3-d]pyrimidin-4-yl)phenyl)methacrylamide as a yellow oil. LRMS (ESI) calc'd for $C_{28}H_{40}N_4O_4SiB$ [M+H]$^+$: 535, found 535.

Step 7: N-(3-(5-(Pyridin-2-yl)-7-((2-(trimethylsilyl)ethoxy)methyl)-7H-pyrrolo[2,3-d]pyrimidin-4-yl)phenyl)methacrylamide

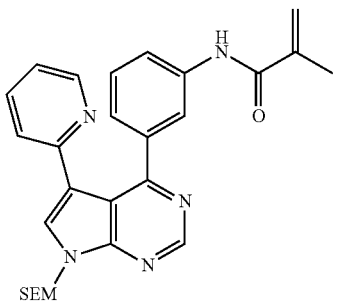 [SMILES: C=C(C)C(=O)Nc1cccc(-c2ncnc3c2c(-c2ccccn2)cn3COCC[Si](C)(C)C)c1]

To a solution of 2-methyl-N-[3-[5-(tetramethyl-1,3,2-dioxaborolan-2-yl)-7-[[2-(trimethylsilyl)ethoxy]methyl]-7H-pyrrolo[2,3-d]pyrimidin-4-yl]phenyl]prop-2-enamide (200 mg, 0.370 mmol) in N,N-dimethylformamide (3.0 mL) under nitrogen, was added Pd(dppf)Cl$_2$CH$_2$Cl$_2$ (16 mg, 0.020 mmol), 2-bromopyridine (60 mg, 0.38 mmol), and a solution of sodium carbonate (120 mg, 1.13 mmol in water, 1 mL). The resulting solution was stirred for 2 hours at 80° C. before being cooled and extracted with ethyl acetate (×3). The organic layers were combined, washed with brine, dried with anhydrous sodium sulfate, filtered and concentrated in vacuo. The reaction was then purified by chromatography using silica gel, eluting with 0-100% EtOAc/petroleum ether. The product was collected and concentrated in vacuo to afford N-(3-(5-(pyridin-2-yl)-7-((2-(trimethylsilyl)ethoxy)methyl)-7H-pyrrolo[2,3-d]pyrimidin-4-yl)phenyl)methacrylamide as a yellow oil. LRMS (ESI) calc'd for $C_{27}H_{32}N_5O_2Si$ [M+H]$^+$: 486, found 486.

Step 8: N-(3-(5-(Pyridin-2-yl)-7H-pyrrolo[2,3-d]pyrimidin-4-yl)phenyl)methacrylamide

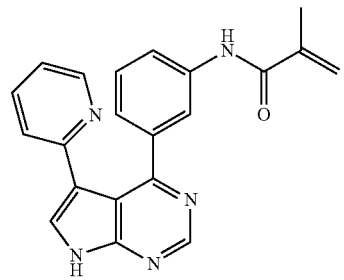 [SMILES: C=C(C)C(=O)Nc1cccc(-c2ncnc3[nH]cc(-c4ccccn4)c23)c1]

To a solution of N-(3-(5-(pyridin-2-yl)-7-((2-(trimethylsilyl)ethoxy)methyl)-7H-pyrrolo[2,3-d]pyrimidin-4-yl)phenyl)methacrylamide (170 mg, 0.350 mmol) in dichloromethane (2.0 mL), was added CF$_3$CO$_2$H (2.0 mL). The resulting solution was stirred for 2 hours at 50° C. and then concentrated in vacuo. The residue was dissolved in methanol (2 mL), and ethane-1,2-diamine (42 mg, 0.70 mmol) and sodium hydroxide (98 mg, 1.6 mmol) were added. The resulting solution was stirred for 30 minutes at room temperature before being concentrated in vacuo. The resulting solution was extracted with ethyl acetate (×3) and the combined organic layers were washed with brine, dried with anhydrous sodium sulfate, filtered and concentrated in vacuo. Purification of the crude product by reverse phase HPLC using an acetonitrile gradient in water with 0.5% TFA modifier afforded N-(3-(5-(pyridin-2-yl)-7H-pyrrolo[2,3-d]pyrimidin-4-yl)phenyl)methacrylamide as a white solid. LRMS (ESI) calc'd for $C_{21}H_{18}N_5O$ [M+H]$^+$: 356, found 356. $^1$H NMR (400 MHz, CD$_3$OD) δ 9.06 (s, 1H), 8.42 (d, J=5.6 Hz, 1H), 8.27 (s, 1H), 8.12-8.16 (m, 1H), 7.90 (s, 1H), 7.64-7.68 (m, 1H), 7.58 (d, J=8.0 Hz, 1H), 7.50 (d, J=6.8 Hz, 1H), 7.37-7.40 (m, 2H), 5.72 (s, 1H), 5.52 (s, 1H), 1.91 (s, 3H).

The following examples, 21-2 through 21-7, as shown in Table 12, were prepared in an analogous manner of that described above using materials that are commercially available or known, or that can be prepared using procedures known in the art or by generally following procedures described herein for various intermediates.

TABLE 12

| Example Number | Chemical Structure | IUPAC Name | Exact mass [M + H]+ |
|---|---|---|---|
| 21-2 | 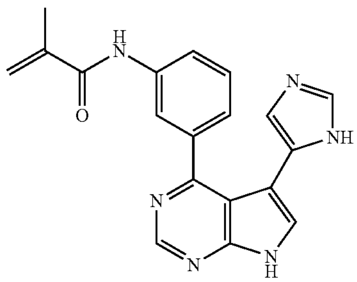 [SMILES: C=C(C)C(=O)Nc1cccc(-c2ncnc3[nH]cc(-c4cnc[nH]4)c23)c1] | N-(3-(5-(1H-imidazol-5-yl)-7H-pyrrolo[2,3-d]pyrimidin-4-yl)phenyl)methacrylamide | Calc'd 345, found 345 |
| 21-3 | 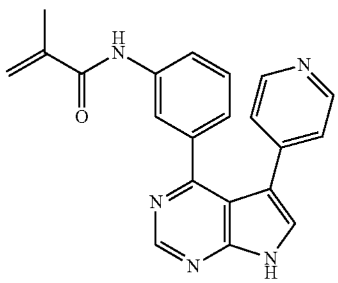 [SMILES: C=C(C)C(=O)Nc1cccc(-c2ncnc3[nH]cc(-c4ccncc4)c23)c1] | N-(3-(5-(pyridin-4-yl)-7H-pyrrolo[2,3-d]pyrimidin-4-yl)phenyl)methacrylamide | Calc'd 356, found 356 |
| 21-4 | 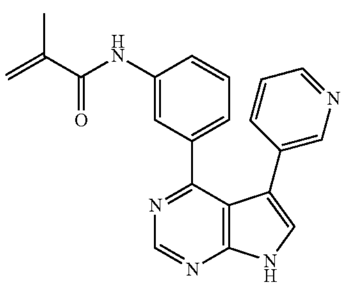 [SMILES: C=C(C)C(=O)Nc1cccc(-c2ncnc3[nH]cc(-c4cccnc4)c23)c1] | N-(3-(5-(pyridin-3-yl)-7H-pyrrolo[2,3-d]pyrimidin-4-yl)phenyl)methacrylamide | Calc'd 356, found 356 |
| 21-5 | 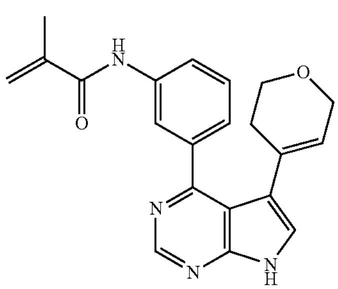 [SMILES: C=C(C)C(=O)Nc1cccc(-c2ncnc3[nH]cc(C4=CCOCC4)c23)c1] | N-(3-(5-(3,6-dihydro-2H-pyran-4-yl)-7H-pyrrolo[2,3-d]pyrimidin-4-yl)phenyl)methacrylamide | Calc'd 361, found 361 |
| 21-6 | 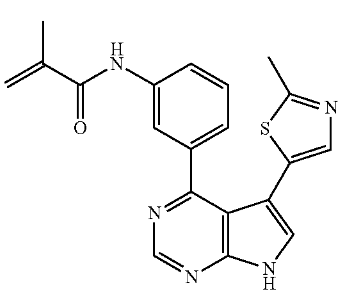 [SMILES: C=C(C)C(=O)Nc1cccc(-c2ncnc3[nH]cc(-c4cnc(C)s4)c23)c1] | N-(3-(5-(2-methylthiazol-5-yl)-7H-pyrrolo[2,3-d]pyrimidin-4-yl)phenyl)methacrylamide | Calc'd 376, found 376 |

TABLE 12-continued

| Example Number | Chemical Structure | IUPAC Name | Exact mass [M + H]+ |
|---|---|---|---|
| 21-7 | 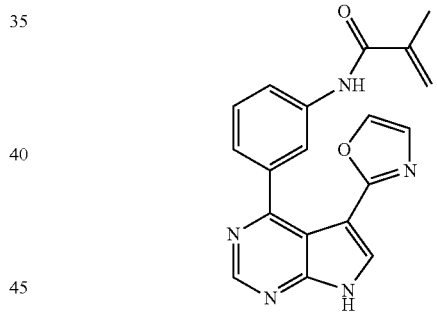 | N-(3-(5-(thiazol-5-yl)-7H-pyrrolo[2,3-d]pyrimidin-4-yl)phenyl)methacrylamide | Calc'd 362, found 362 |

Example 22

N-(3-(5-(Oxazol-2-yl)-7H-pyrrolo[2,3-d]pyrimidin-4-yl)phenyl)methacrylamide

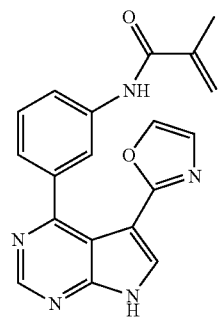 [SMILES: C=C(C)C(=O)Nc1cccc(-c2ncnc3[nH]cc(-c4ncco4)c23)c1]

Step 1: N-(3-(5-(Oxazol-2-yl)-7-((2-(trimethylsilyl)ethoxy)methyl)-7H-pyrrolo[2,3-d]pyrimidin-4-yl)phenyl)methacrylamide

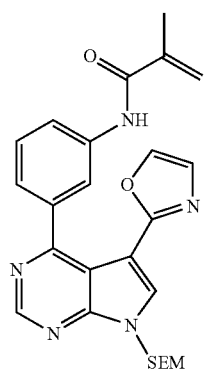 [SMILES: C=C(C)C(=O)Nc1cccc(-c2ncnc3c2c(-c2ncco2)cn3COCC[Si](C)(C)C)c1]

To a solution of N-(3-(5-bromo-7-((2-(trimethylsilyl)ethoxy)methyl)-7H-pyrrolo[2,3-d]pyrimidin-4-yl)phenyl)methacrylamide (249 mg, 0.51 mmol) in toluene (10 mL) under nitrogen, was added 2-(tributylstannyl)-1,3-oxazole (548 mg, 1.53 mmol), Pd$_2$(dba)$_3$ (93 mg, 0.10 mmol), and X-Phos (95 mg, 0.20 mmol). The resulting solution was stirred overnight at 60° C. and then concentrated in vacuo, and the resulting crude reaction was extracted with ethyl acetate (×3). The combined organic layers were washed with brine, dried with anhydrous sodium sulfate, filtered and concentrated in vacuo. The reaction was then purified by chromatography using silica gel, eluting with 0-100% EtOAc/petroleum ether. The product was collected and concentrated in vacuo to afford N-(3-(5-(oxazol-2-yl)-7-((2-(trimethylsilyl)ethoxy)methyl)-7H-pyrrolo[2,3-d]pyrimidin-4-yl)phenyl)methacrylamide as a yellow oil. LRMS (ESI) calc'd for C$_{25}$H$_{30}$N$_5$O$_3$Si [M+H]$^+$: 476, found 476.

Step 2: N-(3-(5-(Oxazol-2-yl)-7H-pyrrolo[2,3-d]pyrimidin-4-yl)phenyl)methacrylamide To N-(3-(5-(oxazol-2-yl)-7-((2-(trimethylsilyl)ethoxy)methyl)-7H-pyrrolo[2,3-d]pyrimidin-4-yl)phenyl)methacrylamide (140 mg, 0.295 mmol) was added portionwise, a solution of trifluoroacetic acid (3.4 g, 30 mmol) in dichloromethane (10 mL). The reaction was stirred for 1 hour at 50° C., then concentrated in vacuo. To this crude reaction mixture was added ethane-1,2-diamine (35 mg, 0.59 mmol), followed by portionwise addition of a solution of sodium hydroxide (82 mg, 2.1 mmol) in methanol (10 mL). After stirring at room temperature for 30 minutes, the reaction mixture was concentrated in vacuo and extracted with ethyl acetate (×3). The combined organic layers were washed with brine, dried with anhydrous sodium sulfate, filtered and concentrated in vacuo. Purification of the crude product by reverse phase HPLC using an acetonitrile gradient in water with 0.5% TFA modifier afforded N-(3-(5-(oxazol-2-yl)-7H-pyrrolo[2,3-d]pyrimidin-4-yl)phenyl)methacrylamide as a green solid. LRMS (ESI) calc'd for C$_{19}$H$_{16}$N$_5$O$_2$ [M+H]$^+$: 346, found 346. $^1$H NMR (400 MHz, CD$_3$OD) δ 9.05 (s, 1H), 8.25 (s, 1H), 7.93 (s, 1H), 7.80 (d, 1H, J=8.0 Hz), 7.59 (s, 1H), 7.38-7.42 (m, 1H), 7.26 (d, J=8.0 Hz, 1H), 7.13 (s, 1H), 5.80 (s, 1H), 5.55 (s, 1H), 1.99 (s, 3H).

Examples 23 and 24

N-(3-(5-(Tetrahydro-2H-pyran-4-yl)-7H-pyrrolo[2,3-d]pyrimidin-4-yl)phenyl)methacrylamide (A Example 23) and N-Methyl-N-(3-(5-(tetrahydro-2H-pyran-4-yl)-7H-pyrrolo[2,3-d]pyrimidin-4-yl)phenyl)methacrylamide (B Example 24)

A

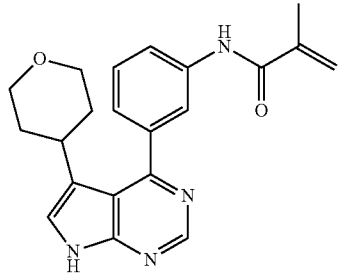

B

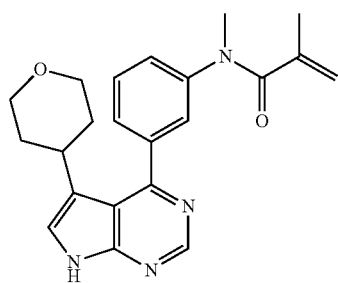

Step 1: 5-Bromo-4-(3-nitrophenyl)-7-((2-(trimethylsilyl)ethoxy)methyl)-7H-pyrrolo[2,3-d]pyrimidine

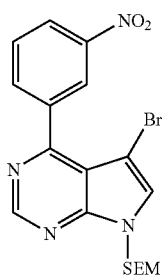 [SMILES: C[Si](C)(C)CCOCn1cc(Br)c2c(-c3cccc([N+](=O)[O-])c3)ncnc21]

To a solution of 4-(3-nitrophenyl)-7-((2-(trimethylsilyl)ethoxy)methyl)-7H-pyrrolo[2,3-d]pyrimidine (4.40 g, 11.9 mmol) in CH$_3$CN (25 mL), was added NBS (3.60 g, 20.2 mmol). The resulting solution was stirred for 30 minutes at 80° C. before being concentrated in vacuo. The reaction was diluted with ethyl acetate (200 mL), washed with water (×3), and the organic layer was dried over anhydrous sodium sulfate, filtered and concentrated in vacuo. The reaction was then purified by chromatography using silica gel, eluting with 2-6% EtOAc/petroleum ether. The product was collected and concentrated in vacuo to afford 5-bromo-4-(3-nitrophenyl)-7-((2-(trimethylsilyl)ethoxy)methyl)-7H-pyrrolo[2,3-d]pyrimidine as a yellow oil. LRMS (ESI) calc'd for C$_{18}$H$_{22}$N$_4$O$_3$SiBr [M+H]$^+$: 449, found 449.

Step 2: 5-(3,6-Dihydro-2H-pyran-4-yl)-4-(3-nitrophenyl)-7-((2-(trimethylsilyl)ethoxy)methyl)-7H-pyrrolo[2,3-d]pyrimidine

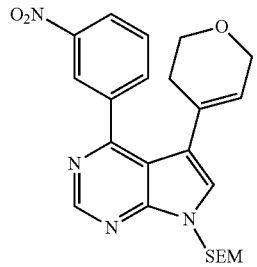 [SMILES: C[Si](C)(C)CCOCn1cc(C2=CCOCC2)c2c(-c3cccc([N+](=O)[O-])c3)ncnc21]

To a solution of 5-bromo-4-(3-nitrophenyl)-7-((2-(trimethylsilyl)ethoxy)methyl)-7H-pyrrolo[2,3-d]pyrimidine (1.00 g, 2.23 mmol) in toluene/EtOH/H$_2$O (4:2:1, 14 mL), was added 2-(3,6-dihydro-2H-pyran-4-yl)-4,4,5,5-tetramethyl-1,3,2-dioxaborolane (0.70 g, 3.3 mmol), sodium carbonate (0.70 g, 6.7 mmol) and Pd(PPh$_3$)$_4$ (0.13 g, 0.11 mmol). The resulting solution was stirred for 12 hours at 80° C., cooled, and quenched by the addition of water (50 mL). The resulting solution was extracted with ethyl acetate (×3) and the organic layers were combined, washed with brine, dried over anhydrous sodium sulfate, filtered and concentrated in vacuo. The reaction was then purified by chromatography using silica gel, eluting with 1-50% EtOAc/petroleum ether. The product was collected and concentrated in vacuo to afford 5-(3,6-dihydro-2H-pyran-4-yl)-4-(3-nitrophenyl)-7-((2-(trimethylsilyl)ethoxy)methyl)-7H-pyrrolo[2,3-d]pyrimidine as a yellow solid. LRMS (ESI) calc'd for C$_{23}$H$_{29}$N$_4$O$_4$Si [M+H]$^+$: 453, found 453.

Step 3: 3-(5-(Tetrahydro-2H-pyran-4-yl)-7-((2-(trimethylsilyl)ethoxy)methyl)-7H-pyrrolo[2,3-d]pyrimidin-4-yl)aniline (A) and N-Methyl-3-(5-(tetrahydro-2H-pyran-4-yl)-7-((2-(trimethylsilyl)ethoxy)methyl)-7H-pyrrolo[2,3-d]pyrimidin-4-yl)aniline (B)

(A)

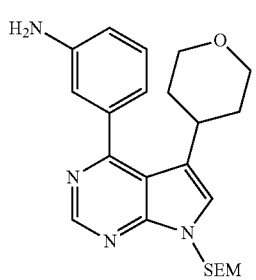

183

-continued

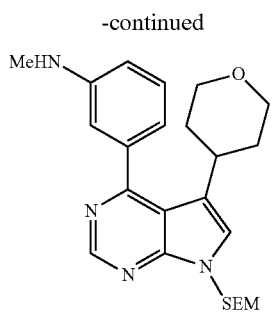

To a solution of 5-(3,6-dihydro-2H-pyran-4-yl)-4-(3-nitrophenyl)-7-((2-(trimethylsilyl)ethoxy)methyl)-7H-pyrrolo[2,3-d]pyrimidine (500 mg, 1.10 mmol) in methanol (10 mL) was added Pd(OH)$_2$/C (500 mg, 10 wt. %). The atmosphere was purged with hydrogen and the reaction was stirred for 3 hours at room temperature under hydrogen (1 atm). The solids were removed by filtration and the resulting mixture was concentrated in vacuo to afford a mixture of 3-(5-(tetrahydro-2H-pyran-4-yl)-7-((2-(trimethylsilyl)ethoxy)methyl)-7H-pyrrolo[2,3-d]pyrimidin-4-yl)aniline (A) and N-methyl-3-(5-(tetrahydro-2H-pyran-4-yl)-7-((2-(trimethylsilyl)ethoxy)methyl)-7H-pyrrolo[2,3-d]pyrimidin-4-yl)aniline (B) as a black solid. LRMS (ESI) calc'd for C$_{23}$H$_{33}$N$_4$O$_2$Si (A) [M+H]$^+$: 425, found 425. LRMS (ESI) calc'd for C$_{24}$H$_{35}$N$_4$O$_2$Si (B) [M+H]$^+$: 439, found 439.

Step 4: N-(3-(5-(Tetrahydro-2H-pyran-4-yl)-7-((2-(trimethylsilyl)ethoxy)methyl)-7H-pyrrolo[2,3-d]pyrimidin-4-yl)phenyl)methacrylamide (A), and N-Methyl-N-(3-(5-(tetrahydro-2H-pyran-4-yl)-7-((2-(trimethylsilyl)ethoxy)methyl)-7H-pyrrolo[2,3-d]pyrimidin-4-yl)phenyl)methacrylamide (B)

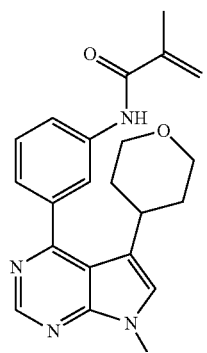

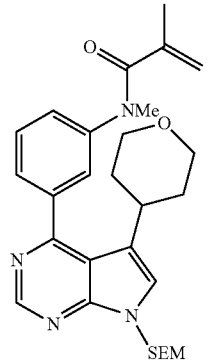

To a mixture of 3-(5-(tetrahydro-2H-pyran-4-yl)-7-((2-(trimethylsilyl)ethoxy)methyl)-7H-pyrrolo[2,3-d]pyrimidin-4-yl)aniline (A) and N-methyl-3-(5-(tetrahydro-2H-pyran-4-yl)-7-((2-(trimethylsilyl)ethoxy)methyl)-7H-pyrrolo

184

[2,3-d]pyrimidin-4-yl)aniline (B) (367 mg) in THF (10 mL) at 0° C., was added DIPEA (335 mg, 2.59 mmol) followed by dropwise addition of 2-methylprop-2-enoyl chloride (0.125 mL, 1.29 mmol). The resulting solution was stirred for 2 hours at room temperature before being quenched by the addition of Na$_2$CO$_3$ (aqueous, 1 M). The resulting solution was extracted with ethyl acetate (×3) and the combined organic layers were washed with brine, dried over anhydrous sodium sulfate, filtered and concentrated in vacuo. The reaction was then purified by chromatography using silica gel, eluting with 1-100% EtOAc/petroleum ether. The product was collected and concentrated in vacuo to afford a mixture of N-(3-(5-(tetrahydro-2H-pyran-4-yl)-7-((2-(trimethylsilyl)ethoxy)methyl)-7H-pyrrolo[2,3-d]pyrimidin-4-yl)phenyl)methacrylamide (A), and N-methyl-N-(3-(5-(tetrahydro-2H-pyran-4-yl)-7-((2-(trimethylsilyl)ethoxy)methyl)-7H-pyrrolo[2,3-d]pyrimidin-4-yl)phenyl)methacrylamide (B), as a yellow oil. LRMS (ESI) calc'd for A: C$_{27}$H$_{37}$N$_4$O$_3$Si [M+H]$^+$: 493, found 493; B: C$_{28}$H$_{39}$N$_4$O$_3$Si [M+H]$^+$: 507, found 507.

Step 5: N-(3-(5-(Tetrahydro-2H-pyran-4-yl)-7H-pyrrolo[2,3-d]pyrimidin-4-yl)phenyl)methacrylamide (A) and N-Methyl-N-(3-(5-(tetrahydro-2H-pyran-4-yl)-7H-pyrrolo[2,3-d]pyrimidin-4-yl)phenyl)methacrylamide (B)

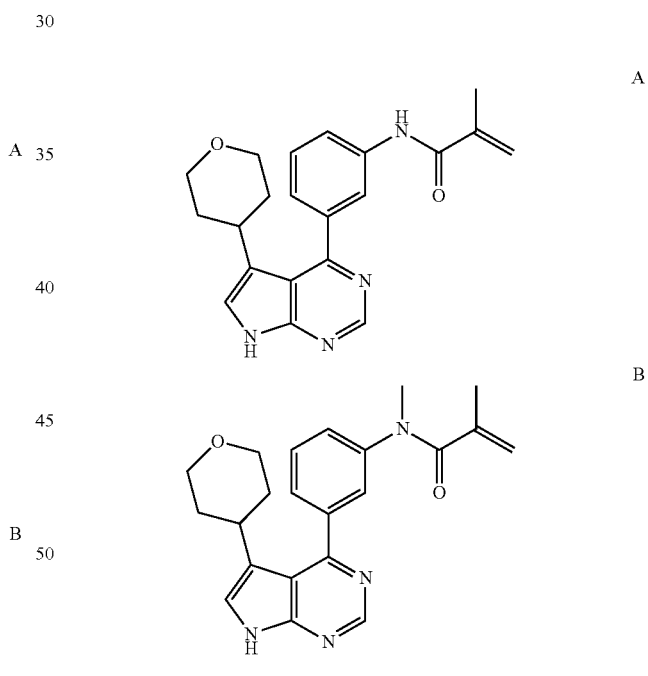

To a mixture of N-(3-(5-(tetrahydro-2H-pyran-4-yl)-7-((2-(trimethylsilyl)ethoxy)methyl)-7H-pyrrolo[2,3-d]pyrimidin-4-yl)phenyl)methacrylamide (A), and N-methyl-N-(3-(5-(tetrahydro-2H-pyran-4-yl)-7-((2-(trimethylsilyl)ethoxy)methyl)-7H-pyrrolo[2,3-d]pyrimidin-4-yl)phenyl)methacrylamide (B) (160 mg, 0.316 mmol) was added a solution of trifluoroacetic acid (3.70 g, 32.7 mmol) in dichloromethane (10 mL). The resulting solution was stirred for 1 hour at 50° C., then concentrated in vacuo. To this crude reaction was added a solution of sodium hydroxide (91 mg, 2.3 mmol) in methanol (10 mL) followed by ethane-1,2-diamine (39 mg, 0.65 mmol). The resulting solution was stirred for 30 minutes at room temperature and then concentrated in vacuo. The crude product was extracted with ethyl acetate (×3) and the combined organic layers were washed with brine and concentrated in vacuo. Purification of the crude product by reverse phase HPLC using an acetonitrile gradient in water with 0.5% TFA modifier afforded N-(3-(5-(tetrahydro-2H-pyran-4-yl)-7H-pyrrolo[2,3-d]pyrimidin-4-yl)phenyl)methacrylamide (A) and N-methyl-N-(3-(5-(tetrahydro-2H-pyran-4-yl)-7H-pyrrolo[2,3-d]pyrimidin-4-yl)phenyl)methacrylamide (B), both as light yellow solids.

For N-(3-(5-(tetrahydro-2H-pyran-4-yl)-7H-pyrrolo[2,3-d]pyrimidin-4-yl)phenyl)methacrylamide (A): LRMS (ESI) calc'd for $C_{21}H_{23}N_4O_2$ [M+H]$^+$: 363, found 363. $^1$H NMR (300 MHz, CD$_3$OD) δ 9.02 (s, 1H), 8.38 (s, 1H), 7.80-7.66 (m, 3H), 7.54-7.51 (d, J 7.8 Hz, 1H), 5.86 (s, 1H), 5.59 (s, 1H), 3.82-3.78 (m, 2H), 3.19-3.03 (m, 3H), 2.05 (s, 3H), 1.66-1.28 (m, 4H).

For N-methyl-N-(3-(5-(tetrahydro-2H-pyran-4-yl)-7H-pyrrolo[2,3-d]pyrimidin-4-yl)phenyl)methacrylamide (B): LRMS (ESI) calc'd for $C_{22}H_{25}N_4O_2$ [M+H]$^+$: 377, found 377. NMR (400 MHz, CD$_3$OD) δ 9.00-8.95 (s, 1H), 7.84-7.57 (m, 5H), 5.08-5.03 (s, 1H), 3.86-3.57 (m, 2H), 3.47 (s, 3l4), 3.20-3.14 (m, 2H), 2.86-2.78 (m, 1H), 2.07 (s, 3H), 1.65-1.51 (m, 4H).

Example 25

N-(3-(5-(Tetrahydrofuran-2-yl)-7H-pyrrolo[2,3-d]pyrimidin-4-yl)phenyl)methacrylamide

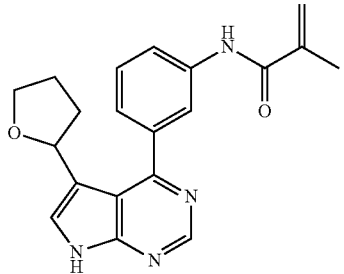 [SMILES: C=C(C)C(=O)Nc1cccc(-c2ncnc3[nH]cc(C4CCCO4)c23)c1]

Step 1: 5-(2,5-Dihydrofuran-2-yl)-4-(3-nitrophenyl)-7-((2-(trimethylsilyl)ethoxy)methyl)-7H-pyrrolo[2,3-d]pyrimidine

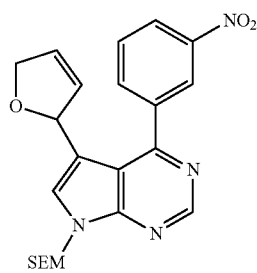 [SMILES: C[Si](C)(C)CCOCn1cc(C2C=CCO2)c2c(-c3cccc([N+](=O)[O-])c3)ncnc21]

To a degassed solution of 5-bromo-4-(3-nitrophenyl)-7-[[2-(trimethylsilyl)ethoxy]methyl]-7H-pyrrolo[2,3-d]pyrimidine (1.30 g, 2.89 mmol) in N,N-dimethylformamide (40 mL), was added Pd(OAc)$_2$ (650 mg, 2.90 mmol), Bu$_4$NCl (1.00 g, 3.60 mmol), NaOAc (714 g, 8.71 mol) and 2,3-dihydrofuran (2.00 g, 28.5 mmol). The reaction was stirred for 2 hours at 50° C. and then quenched by the addition of water. The resulting solution was extracted with ethyl acetate (×3), and the organic layers were combined, washed with water, brine, then dried over anhydrous sodium sulfate, filtered and concentrated in vacuo. The reaction was purified by chromatography using silica gel, eluting with 1-50% EtOAc/petroleum ether. The product was collected and concentrated in vacuo to afford 5-(2,5-dihydrofuran-2-yl)-4-(3-nitrophenyl)-7-((2-(trimethylsilyl)ethoxy)methyl)-7H-pyrrolo[2,3-d]pyrimidine as a yellow oil. LRMS (ESI) calc'd for $C_{22}H_{27}N_4O_4Si$ [M+H]$^+$: 439, found 439.

Step 2: 3-(5-(Tetrahydrofuran-2-yl)-7-((2-(trimethylsilyl)ethoxy)methyl)-7H-pyrrolo[2,3-d]pyrimidin-4-yl)aniline

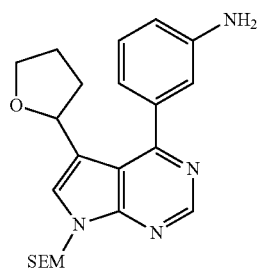 [SMILES: C[Si](C)(C)CCOCn1cc(C2CCCO2)c2c(-c3cccc(N)c3)ncnc21]

To a solution of 5-(2,5-dihydrofuran-2-yl)-4-(3-nitrophenyl)-7-((2-(trimethylsilyl)ethoxy)methyl)-7H-pyrrolo[2,3-d]pyrimidine (500 mg, 1.14 mmol) in methanol (6.0 mL), was added Pd/C (250 mg, 10 wt. % loading Pd). The atmosphere was purged with hydrogen gas and the resulting solution was stirred for 12 hours at room temperature under hydrogen atmosphere (1 atm). The reaction was then filtered and concentrated in vacuo to afford crude 3-(5-(tetrahydrofuran-2-yl)-7-((2-(trimethylsilyl)ethoxy)methyl)-7H-pyrrolo[2,3-d]pyrimidin-4-yl)aniline as a yellow oil. LRMS (ESI) calc'd for $C_{22}H_{31}N_4O_2Si$ [M+H]$^+$: 411, found 411. $^1$H NMR (400 MHz, CD$_3$OD) δ 8.79 (d, J 3.2 Hz, 1H), 7.59 (s, 1H), 7.35-7.26 (m, 1H), 6.88-6.98 (m, 3H), 5.71 (s, 2H), 5.07-5.01 (m, 1H), 3.99-3.97 (m, 1H), 3.75-3.72 (m, 1H), 3.63-3.59 (m, 2H), 1.80-1.73 (m, 2H), 1.58-1.53 (m, 1H), 1.41-1.30 (m, 1H), 0.92-0.88 (m, 2H), 0.02 (s, 9H).

Step 3: N-(3-(5-(Tetrahydrofuran-2-yl)-7-((2-(trimethylsilyl)ethoxy)methyl)-7H-pyrrolo[2,3-d]pyrimidin-4-yl)phenyl)methacrylamide

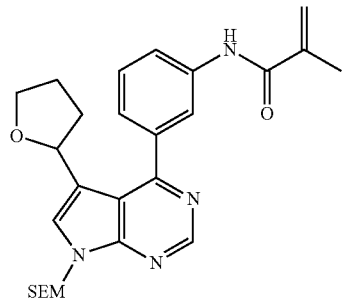 [SMILES: C=C(C)C(=O)Nc1cccc(-c2ncnc3c2c(C2CCCO2)cn3COCC[Si](C)(C)C)c1]

To a 0° C. solution of crude 3-(5-(tetrahydrofuran-2-yl)-7-((2-(trimethylsilyl)ethoxy)methyl)-7H-pyrrolo[2,3-d]pyrimidin-4-yl)aniline (410 mg, 1.00 mmol) in THF (10 mL), was added DIPEA (258 mg, 2.00 mmol) followed by dropwise addition of 2-methylprop-2-enoyl chloride (125 mg, 1.20 mmol). The resulting solution was stirred for 4 hours at room temperature prior to being quenched by addition of water. The resulting solution was extracted with ethyl acetate (×3) and the combined organic layers were washed with brine, dried over anhydrous sodium sulfate, filtered and concentrated in vacuo. The reaction was purified by chromatography using silica gel, eluting with 0-100% EtOAc/petroleum ether. The product was collected and concentrated in vacuo to afford N-(3-(5-(tetrahydrofuran-2-yl)-7-((2-(trimethylsilyl)ethoxy)methyl)-7H-pyrrolo[2,3-d]pyrimidin-4-yl)phenyl)methacrylamide as a off-white solid. LRMS (ESI) calc'd for $C_{26}H_{35}N_4O_3Si$ [M+H]$^+$: 479, found 479.

Step 4: N-(3-(5-(Tetrahydrofuran-2-yl)-7H-pyrrolo[2,3-d]pyrimidin-4-yl)phenyl)methacrylamide

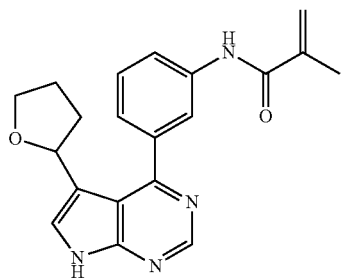 [SMILES: C=C(C)C(=O)Nc1cccc(-c2ncnc3[nH]cc(C4CCCO4)c23)c1]

Following a similar procedure used in Step 2 for Example 22, SEM deprotection followed by reverse phase purification afforded N-(3-(5-(tetrahydrofuran-2-yl)-7H-pyrrolo[2,3-d]pyrimidin-4-yl)phenyl)methacrylamide as a off-white solid. LRMS (ESI) calc'd for $C_{20}H_{21}N_4O_2$ [M+H]$^+$: 349, found 349. $^1$H NMR (400 MHz, CD$_3$OD) δ 9.00 (s, 1H), 8.23 (s, 1H), 7.88-7.83 (m, 2H), 7.68-7.64 (m, 1H), 7.56-7.52 (m, 1H), 5.86 (s, 1H), 5.59 (s, 1H), 5.08-5.05 (m, 1H), 3.97-3.91 (m, 1H), 3.72-3.66 (m, 1H), 2.06 (s, 3H), 1.82-1.70 (m, 2H), 1.69-1.58 (m, 1H), 1.56-1.40 (m, 1H).

Example 26

N-(3-(5-(5-Methyl-1,3,4-oxadiazol-2-yl)-7H-pyrrolo[2,3-d]pyrimidin-4-yl)phenyl)methacrylamide

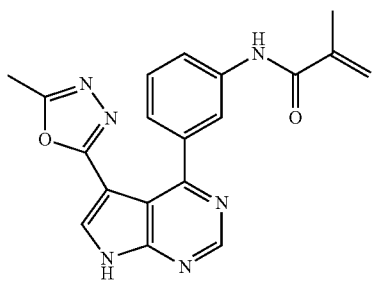 [SMILES: C=C(C)C(=O)Nc1cccc(-c2ncnc3[nH]cc(-c4nnc(C)o4)c23)c1]

Step 1: Ethyl 4-(3-nitrophenyl-7-((2-trimethylsilyl)ethoxy)methyl)-7H-pyrrolo[2,3-d]pyrimidine-5-carboxylate

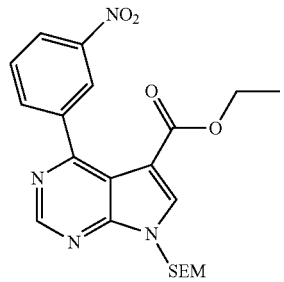 [SMILES: CCOC(=O)c1cn(COCC[Si](C)(C)C)c2ncnc(-c3cccc([N+](=O)[O-])c3)c12]

To a solution of ethyl 4-(3-nitrophenyl)-7H-pyrrolo[2,3-d]pyrimidine-5-carboxylate (2.0 g, 6.4 mmol) in THF (30 mL), was added sodium hydride (180 mg, 7.50 mmol) at 0° C. The reaction was stirred for 1 hour at room temperature, then cooled back to 0° C., followed by the dropwise addition of SEMCl (1.28 g, 7.68 mmol). The solution was stirred for 4 hours at room temperature before being quenched by addition of 50 mL of a water/ice mixture. The resulting mixture was concentrated in vacuo, and the resulting solution was extracted with ethyl acetate (×3). The combined organic layers were dried over anhydrous sodium sulfate, filtered, and concentrated in vacuo. The reaction was then purified by chromatography using silica gel, eluting with 1-50% EtOAc/petroleum ether. The product was collected and concentrated in vacuo to afford ethyl 4-(3-nitrophenyl)-7-((2-(trimethylsilyl)ethoxy)methyl)-7H-pyrrolo[2,3-d]pyrimidine-5-carboxylate as a yellow oil. LRMS (ESI) calc'd for $C_{21}H_{27}N_4O_5Si$ [M+H]$^+$: 443, found 443.

Step 2: 4-(3-Nitrophenyl)-7-((2-(trimethylsilyl)ethoxy)methyl)-7H-pyrrolo[2,3-d]pyrimidine-5-carboxylic acid

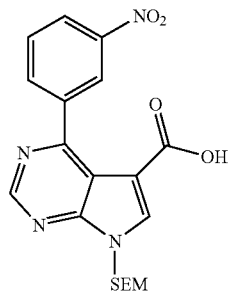 [SMILES: C[Si](C)(C)CCOCn1cc(C(=O)O)c2c(-c3cccc([N+](=O)[O-])c3)ncnc21]

To a solution of ethyl 4-(3-nitrophenyl)-7-((2-(trimethylsilyl)ethoxy)methyl)-7H-pyrrolo[2,3-d]pyrimidine-5-carboxylate (2.00 g, 4.52 mmol) in methanol (5 mL) was added LiOH (500 mg, 20.9 mmol). The resulting solution was stirred for 17 hours at 60° C., concentrated in vacuo, and extracted with ethyl acetate (×3). The combined organic layers were washed with brine, dried over sodium sulfate, filtered, and concentrated in vacuo to afford 4-(3-nitrophenyl)-7-((2-(trimethylsilyl)ethoxy)methyl)-7H-pyrrolo[2,3-d]

pyrimidine-5-carboxylic acid as a yellow solid. LRMS (ESI) calc'd for $C_{19}H_{23}N_4O_5Si$ [M+H]$^+$: 415, found 415.

Step 3: N'-Acetyl-4-(3-nitrophenyl)-7-((2-(trimethylsilyl)ethoxy)methyl)-7H-pyrrolo[2,3-d]pyrimidine-5-carbohydrazide

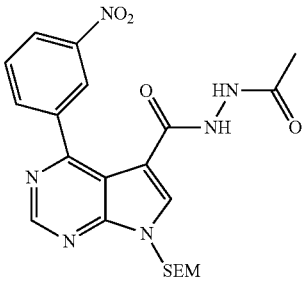 [SMILES: CC(=O)NNC(=O)c1cn(COCC[Si](C)(C)C)c2ncnc(-c3cccc([N+](=O)[O-])c3)c12]

To a solution of 4-(3-nitrophenyl)-7-((2-(trimethylsilyl)ethoxy)methyl)-7H-pyrrolo[2,3-d]pyrimidine-5-carboxylic acid (1.50 g, 2.41 mmol) in pyridine (15 mL) was added EDCI (700 mg, 3.65 mmol) and $CH_3CON_2H_3$ (0.54 g, 4.8 mmol). The reaction was stirred for 12 hours at room temperature and then concentrated in vacuo. The reaction was purified by chromatography using silica gel, eluting with 1-50% $CH_3CN$/water (with 0.5% TFA). The product was collected and concentrated in vacuo to afford N'-acetyl-4-(3-nitrophenyl)-7-((2-(trimethylsilyl)ethoxy)methyl)-7H-pyrrolo[2,3-d]pyrimidine-5-carbohydrazide as a yellow solid. LRMS (ESI) calc'd for $C_{21}H_{27}N_6O_5Si$ [M+H]$^+$: 471, found 471. $^1$H NMR (300 MHz, CDCl$_3$) δ 9.03 (s, 1H), 8.62 (s, 1H), 8.38-8.35 (m, 1H), 8.39-8.27 (m, 1H), 8.09-8.07 (m, 1H), 7.75-7.70 (m, 1H), 5.82 (s, 2H), 3.71-3.66 (m, 2H), 2.29 (s, 3H), 0.98-0.93 (m, 2H), 0.02 (s, 9H).

Step 4: 2-Methyl-5-(4-(3-nitrophenyl)-7-((2-(trimethylsilyl)ethoxy)methyl)-7H-pyrrolo[2,3-d]pyrimidin-5-yl)-1,3,4-oxadiazole

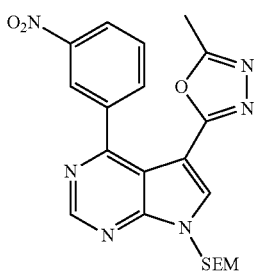 [SMILES: Cc1nnc(-c2cn(COCC[Si](C)(C)C)c3ncnc(-c4cccc([N+](=O)[O-])c4)c23)o1]

To a solution of N'-acetyl-4-(3-nitrophenyl)-7-((2-(trimethylsilyl)ethoxy)methyl)-7H-pyrrolo[2,3-d]pyrimidine-5-carbohydrazide (470 mg, 1.00 mmol) in dichloromethane (10 mL) was added imidazole (0.15 g, 2.2 mmol), CBr$_4$ (0.72 g, 2.2 mmol) and PPh$_3$ (0.58 g, 2.2 mmol). The reaction was stirred for 1 hour at room temperature and then concentrated in vacuo. The reaction was purified by chromatography using silica gel, eluting with 1-20% ethyl acetate/petroleum ether. The product was collected and concentrated in vacuo to afford 2-methyl-5-(4-(3-nitrophenyl)-7-((2-(trimethylsilyl)ethoxy)methyl)-7H-pyrrolo[2,3-d]pyrimidin-5-yl)-1,3,4-oxadiazole as a white solid. $^1$NMR (300 MHz, CD$_3$OD) δ 9.08 (s, 1H), 8.45-8.34 (m, 3H), 8.01-7.98 (m, 1H), 7.74-7.53 (m, 1H), 5.87 (s, 2H), 3.74-3.69 (m, 2H), 2.29 (s, 3H), 0.98-0.93 (m, 2H), 0.02 (s, 9H).

Step 5: 3-(5-(5-Methyl-1,3,4-oxadiazol-2-yl)-7-((2-(trimethylsilyl)ethoxy)methyl)-7H-pyrrolo[2,3-d]pyrimidin-4-yl)aniline

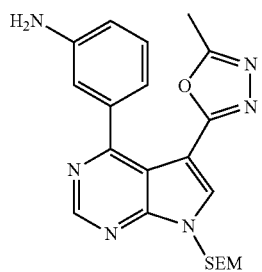 [SMILES: Cc1nnc(-c2cn(COCC[Si](C)(C)C)c3ncnc(-c4cccc(N)c4)c23)o1]

To a solution of 2-methyl-5-[4-(3-nitrophenyl)-7-[[2-(trimethylsilyl)ethoxy]methyl]-7H-pyrrolo[2,3-d]pyrimidin-5-yl]-1,3,4-oxadiazole (0.40 g, 0.88 mmol) in methanol (10 mL), was added Pd on carbon (200 mg, 10 wt. %). The atmosphere was purged with hydrogen and the reaction was stirred for 12 hours at room temperature under a hydrogen atmosphere (1 atm). The solution was filtered and the filtrate was concentrated in vacuo to afford crude 3-(5-(5-methyl-1,3,4-oxadiazol-2-yl)-7-((2-(trimethylsilyl)ethoxy)methyl)-7H-pyrrolo[2,3-d]pyrimidin-4-yl)aniline as a black solid. LRMS (ESI) calc'd for $C_{21}H_{27}N_6O_2Si$ [M+H]$^+$: 423, found 423.

Step 6: N-(3-(5-(5-Methyl-1,3,4-oxadiazol-2-yl)-7-((2-(trimethylsilyl)ethoxy)methyl)-7H-pyrrolo[2,3-d]pyrimidin-4-yl)phenyl)methacrylamide

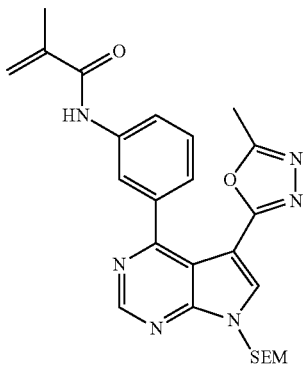 [SMILES: C=C(C)C(=O)Nc1cccc(-c2ncnc3c2c(-c2nnc(C)o2)cn3COCC[Si](C)(C)C)c1]

Following a similar procedure used in Step 3 for Example 25, amidation followed by silica gel chromatography, eluting with 1-50% ethyl acetate/petroleum ether afforded N-(3-(5-(5-methyl-1,3,4-oxadiazol-2-yl)-7-((2-(trimethylsilyl)ethoxy)methyl)-7H-pyrrolo[2,3-d]pyrimidin-4-yl)phenyl)

methacrylamide as a yellow oil. LRMS (ESI) calc'd for $C_{25}H_{30}N_6O_3SiNa$ [M+Na]$^+$: 513, found 513.

Step 7: N-(3-(5-(5-Methyl-1,3,4-oxadiazol-2-yl)-7H-pyrrolo[2,3-d]pyrimidin-4-yl)phenyl)methacrylamide

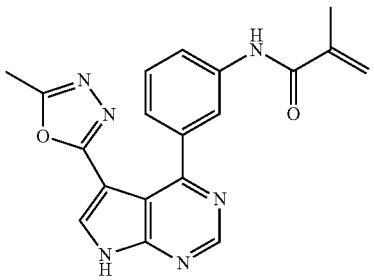 [SMILES: C=C(C)C(=O)Nc1cccc(-c2ncnc3[nH]cc(-c4nnc(C)o4)c23)c1]

Following a similar procedure used in Step 2 for Example 22, SEM deprotection followed by reverse phase purification afforded N-(3-(5-(5-methyl-1,3,4-oxadiazol-2-yl)-7H-pyrrolo[2,3-d]pyrimidin-4-yl)phenyl)methacrylamide as a white solid. LRMS (ESI) calc'd for $C_{19}H_{17}N_6O_2$ [M+H]$^+$: 361, found 361. $^1$H NMR (400 MHz, CDCl$_3$) δ 9.05 (s, 1H), 8.32 (s, 1H), 7.88 (s, 1H), 7.82-7.80 (d, J=8.0 Hz, 1H), 7.49-7.45 (m, 1H), 7.35-7.34 (d, J=7.2 Hz, 1H), 5.81 (s, 1H), 5.55 (s, 1H), 2.22-7.13 (s, 3H), 2.08-2.04 (s, 3H).

Example 27

N-(3-(5-(5-Methyl-1,3,4-thiadiazol-2-yl)-7H-pyrrolo[2,3-d]pyrimidin-4-yl)phenyl)methacrylamide

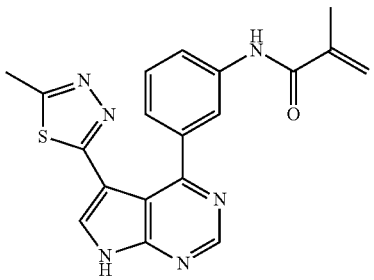 [SMILES: C=C(C)C(=O)Nc1cccc(-c2ncnc3[nH]cc(-c4nnc(C)s4)c23)c1]

Step 1: 2-Methyl-5-(4-(3-nitrophenyl)-7-((2-(trimethylsilyl)ethoxy)methyl)-7H-pyrrolo[2,3-d]pyrimidin-5-yl)-1,3,4-thiadiazole

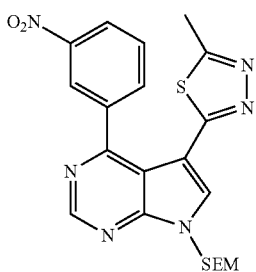 [SMILES: Cc1nnc(-c2cn(COCC[Si](C)(C)C)c3ncnc(-c4cccc([N+](=O)[O-])c4)c23)s1]

To a solution of N-acetyl-4-(3-nitrophenyl)-7-((2-(trimethylsilyl)ethoxy)methyl)-7H-pyrrolo[2,3-d]pyrimidine-5-carbohydrazide (0.40 g, 0.85 mmol) in ethylene glycol dimethyl ether (10 mL), was added P$_2$S$_5$ (378 mg, 1.70 mmol). The resulting solution was stirred for 1 hour at 50° C., then concentrated in vacuo and extracted with ethyl acetate (×3). The combined organic layers were washed with brine, dried over anhydrous sodium sulfate, filtered and concentrated in vacuo. The reaction was purified by chromatography using silica gel, eluting with 1-100% ethyl acetate/petroleum ether. The product was collected and concentrated in vacuo to afford 2-methyl-5-(4-(3-nitrophenyl)-7-((2-(trimethylsilyl)ethoxy)methyl)-7H-pyrrolo[2,3-d]pyrimidin-5-yl)-1,3,4-thiadiazole as a yellow oil. LRMS (ESI) calc'd for $C_{21}H_{25}N_6O_3SSi$ [M+H]$^+$: 469, found 469.

Step 2: 3-(5-(5-Methyl-1,3,4-thiadiazol-2-yl)-7-((2-(trimethylsilyl)ethoxy)methyl)-7H-pyrrolo[2,3-d]pyrimidin-4-yl)aniline

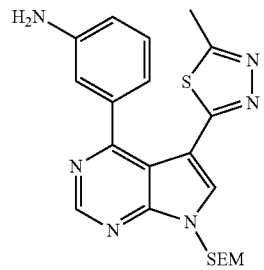

To a solution of 2-methyl-5-(4-(3-nitrophenyl)-7-((2-(trimethylsilyl)ethoxy)methyl)-7H-pyrrolo[2,3-d]pyrimidin-5-yl)-1,3,4-thiadiazole (0.38 g, 0.81 mmol) in methanol (10 mL) was added Pt (1% on C, V doped) (343 mg). The atmosphere was purged with hydrogen and the solution was stirred for 4 hours at room temperature under hydrogen atmosphere (1 atm). The reaction was then filtered and concentrated in vacuo to afford crude 3-(5-(5-methyl-1,3,4-thiadiazol-2-yl)-7-((2-(trimethylsilyl)ethoxy)methyl)-7H-pyrrolo[2,3-d]pyrimidin-4-yl)aniline as a dark green solid. LRMS (ESI) calc'd for $C_{21}H_{27}N_6O_3SSi$ [M+H]$^+$: 439, found 439.

Step 3: N-(3-(5-(5-Methyl-1,3,4-thiadiazol-2-yl)-7-((2-(trimethylsilyl)ethoxy)methyl)-7H-pyrrolo[2,3-d]pyrimidin-4-yl)phenyl)methacrylamide

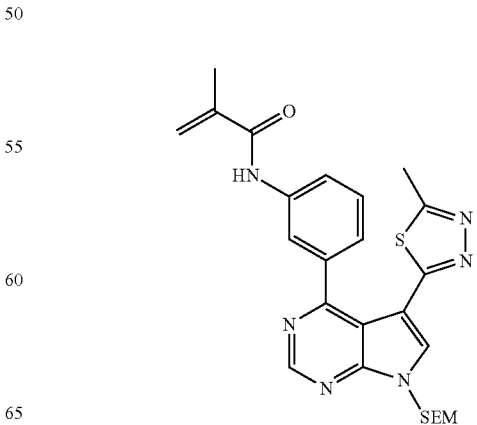

Following a similar procedure used in Step 3 for Example 25, amidation followed by silica gel chromatography, eluting with 1-100% ethyl acetate/petroleum ether afforded N-(3-(5-(5-methyl-1,3,4-thiadiazol-2-yl)-7-((2-(trimethylsilyl)ethoxy)methyl)-7H-pyrrolo[2,3-d]pyrimidin-4-yl)phenyl)methacrylamide as a yellow solid. LRMS (ESI) calc'd for $C_{25}H_{31}N_6O_2SiS$ [M+H]$^+$: 507, found 507.

Step 4: N-(3-(5-(5-Methyl-1,3,4-thiadiazol-2-yl)-7H-pyrrolo[2,3-d]pyrimidin-4-yl)phenyl)methacrylamide

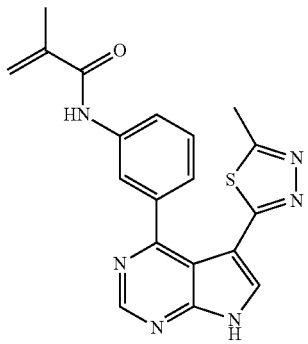 [SMILES: C=C(C)C(=O)Nc1cccc(-c2ncnc3[nH]cc(-c4nnc(C)s4)c23)c1]

Following a similar procedure used in Step 2 for Example 22, SEM deprotection followed by reverse phase purification afforded N-(3-(5-(5-methyl-1,3,4-thiadiazol-2-yl)-7H-pyrrolo[2,3-d]pyrimidin-4-yl)phenyl)methacrylamide as an off-white solid. LRMS (ESI) calc'd for $C_{19}H_{17}N_6OS$ [M+H]$^+$: 377, found 377. $^1$H NMR (400 MHz, CD$_3$OD) δ 9.00 (s, 1H), 8.14 (s, 1H), 7.78-7.75 (m, 2H), 7.40-7.36 (m, 1H), 7.30-7.28 (d, J=8.0 Hz, 1H), 5.80 (s, 1H), 5.55 (s, 1H), 2.64 (s, 3H), 2.04 (s, 3H).

Example 28

N-(3-(5-(5-Methyl-4,5-dihydrooxazol-2-yl)-7H-pyrrolo[2,3-d]pyrimidin-4-yl)phenyl)methacrylamide

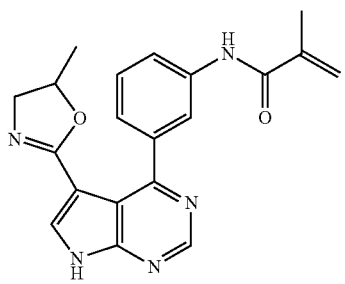 [SMILES: C=C(C)C(=O)Nc1cccc(-c2ncnc3[nH]cc(C4=NCC(C)O4)c23)c1]

Step 1: N-(2-Hydroxypropyl)-4-(3-nitrophenyl)-7-((2-(trimethylsilyl)ethoxy)methyl)-7H-pyrrolo[2,3-d]pyrimidine-5-carboxamide

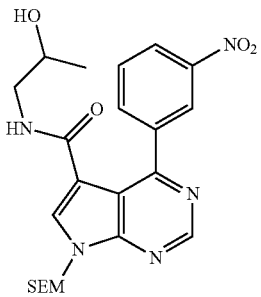 [SMILES: CC(O)CNC(=O)c1cn(COCC[Si](C)(C)C)c2ncnc(-c3cccc([N+](=O)[O-])c3)c12]

To 4-(3-nitrophenyl)-7-((2-(trimethylsilyl)ethoxy)methyl)-7H-pyrrolo[2,3-d]pyrimidine-5-carboxylic acid (2.00 g, 4.83 mmol) in THF (50 mL), was added 1-aminopropan-2-ol (543 mg, 7.23 mmol), EDCI (1.12 g, 5.84 mmol), HOBt (800 mg, 5.92 mmol) and DIPEA (2.48 g, 19.2 mmol). The reaction was stirred for 12 hours at 25° C. and then concentrated in vacuo and quenched by addition of water. The reaction was extracted with DCM (×3) and the combined organic layers were dried over anhydrous sodium sulfate, filtered and concentrated in vacuo. The reaction was purified by chromatography using silica gel, eluting with 33% ethyl acetate/petroleum ether. The product was collected and concentrated in vacuo to afford N-(2-hydroxypropyl)-4-(3-nitrophenyl)-7-((2-(trimethylsilyl)ethoxy)methyl)-7H-pyrrolo[2,3-d]pyrimidine-5-carboxamide as a yellow solid. LRMS (ESI) calc'd for $C_{22}H_{30}N_5O_5Si$ [M+H]$^+$: 472, found 472.

Step 2: 5-Methyl-2-(4-(3-nitrophenyl)-7-((2-(trimethylsilyl)ethoxy)methyl)-7H-pyrrolo[2,3-d]pyrimidin-5-yl)-4,5-dihydrooxazole

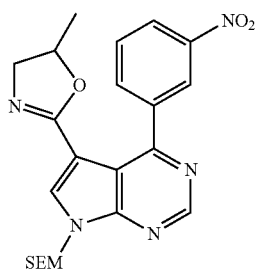

Following a similar procedure used in Step 4 for Example 26, cyclization followed by silica gel chromatography, eluting with 50% ethyl acetate/petroleum ether afforded 5-methyl-2-(4-(3-nitrophenyl)-7-((2-(trimethylsilyl)ethoxy)methyl)-7H-pyrrolo[2,3-d]pyrimidin-5-yl)-4,5-dihydrooxazole as an yellow solid. LRMS (ESI) calc'd for $C_{22}H_{28}N_5O_4Si$ [M+H]$^+$: 454, found 454. $^1$H NMR (400 MHz, CDCl$_3$) δ 9.06 (s, 1H), 8.57 (s, 1H), 8.36 (d, J=8.0 Hz, 1H), 8.19 (d, J=7.6 Hz, 1H), 8.04 (s, 1H), 7.28 (s, 1H), 5.77 (s, 2H), 4.56-4.51 (m, 1H), 3.91-3.85 (m, 1H), 3.65-3.61 (m, 2H), 3.34-3.28 (m, 1H), 1.26-1.24 (m, 3H), 1.00-0.96 (m, 2H), 0.02 (s, 9H).

Step 3: 3-(5-(5-Methyl-4,5-dihydrooxazol-2-yl)-7-((2-(trimethylsilyl)ethoxy)methyl)-7H-pyrrolo[2,3-d]pyrimidin-4-yl)aniline

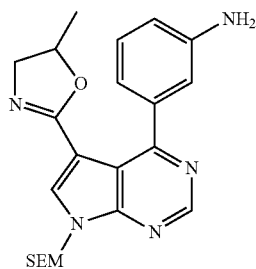 [SMILES: CC1CN=C(c2cn(COCC[Si](C)(C)C)c3ncnc(-c4cccc(N)c4)c23)O1]

Following a similar procedure used in Step 2 for Example 27, nitro group reduction followed by silica gel chromatography, eluting with 20% ethyl acetate/petroleum ether afforded 3-(5-(5-methyl-4,5-dihydrooxazol-2-yl)-7-((2-(trimethylsilyl)ethoxy)methyl)-7H-pyrrolo[2,3-d]pyrimidin-4-yl)aniline as an yellow solid. LRMS (ESI) calc'd for $C_{22}H_{30}N_5O_2Si$ [M+H]$^+$: 424, found 424.

Step 4: N-(3-(5-(5-Methyl-4,5-dihydrooxazol-2-yl)-7-((2-(trimethylsilyl)ethoxy)methyl)-7H-pyrrolo[2,3-d]pyrimidin-4-yl)phenyl)methacrylamide

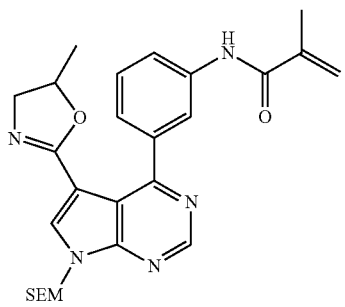 [SMILES: C=C(C)C(=O)Nc1cccc(-c2ncnc3c2c(C2=NCC(C)O2)cn3COCC[Si](C)(C)C)c1]

Following a similar procedure used in Step 3 for Example 25, amidation followed by silica gel chromatography, eluting with 1-50% ethyl acetate/petroleum ether afforded N-(3-(5-(5-methyl-4,5-dihydrooxazol-2-yl)-7-((2-(trimethylsilyl)ethoxy)methyl)-7H-pyrrolo[2,3-d]pyrimidin-4-yl)phenyl)methacrylamide as a yellow oil. LRMS (ESI) calc'd for $C_{26}H_{34}N_5O_3Si$ [M+H]$^+$: 492, found 492.

Step 5: N-(3-(5-(5-Methyl-4,5-dihydrooxazol-2-yl)-7H-pyrrolo[2,3-d]pyrimidin-4-yl)phenyl)methacrylamide

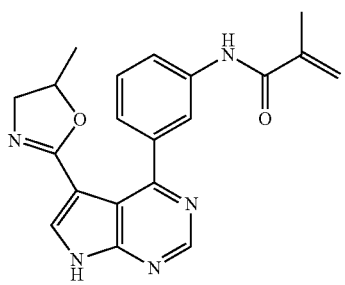 [SMILES: C=C(C)C(=O)Nc1cccc(-c2ncnc3[nH]cc(C4=NCC(C)O4)c23)c1]

Following a similar procedure used in Step 2 for Example 22, SEM deprotection followed by reverse phase purification afforded N-(3-(5-(5-methyl-4,5-dihydrooxazol-2-yl)-7H-pyrrolo[2,3-d]pyrimidin-4-yl)phenyl)methacrylamide as an off-white solid. LRMS (ESI) calc'd for $C_{20}H_{20}N_5O_2$ [M+H]$^+$: 362, found 362. $^1$H NMR (400 MHz, CDCl$_3$) δ 9.04 (s, 1H), 8.63 (s, 1H), 8.12-8.06 (s, 1H), 7.60-7.51 (s, 3H), 5.86-5.84 (s, 1H), 5.57 (s, 1H), 5.16-5.08 (m, 1H), 4.20-4.15 (m, 1H), 3.66-3.60 (m, 1H), 2.06 (s, 3H), 1.37-1.22 (m, 3H).

Example 29

N-(3-(5-(4-Methyloxazol-2-yl)-7H-pyrrolo[2,3-d]pyrimidin-4-yl)phenyl)methacrylamide

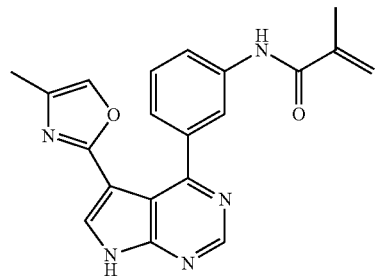 [SMILES: C=C(C)C(=O)Nc1cccc(-c2ncnc3[nH]cc(-c4nc(C)co4)c23)c1]

Step 1: N-(1-Hydroxypropan-2-yl)-4-(3-nitrophenyl)-7-((2-(trimethylsilyl)ethoxy)methyl)-7H-pyrrolo[2,3-d]pyrimidine-5-carboxamide

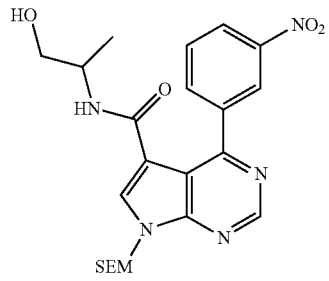 [SMILES: CC(CO)NC(=O)c1cn(COCC[Si](C)(C)C)c2ncnc(-c3cccc([N+](=O)[O-])c3)c12]

Following a similar procedure used in Step 1 for Example 28, amidation followed by silica gel chromatography, eluting with 33% ethyl acetate/petroleum ether afforded N-(1-hydroxypropan-2-yl)-4-(3-nitrophenyl)-7-((2-(trimethylsilyl)ethoxy)methyl)-7H-pyrrolo[2,3-d]pyrimidine-5-carboxamide as a yellow solid. LRMS (ESI) calc'd for $C_{22}H_{30}N_5O_5Si$ [M+H]$^+$: 472, found 472.

Step 2: 4-(3-Nitrophenyl)-N-(1-oxopropan-2-yl)-7-((2-(trimethylsilyl)ethoxy)methyl)-7H-pyrrolo[2,3-d]pyrimidine-5-carboxamide

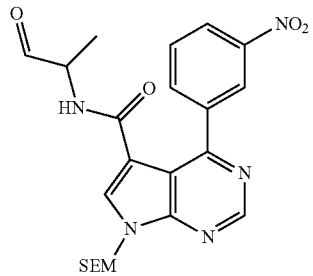 [SMILES: CC(C=O)NC(=O)c1cn(COCC[Si](C)(C)C)c2ncnc(-c3cccc([N+](=O)[O-])c3)c12]

To a solution of N-(1-hydroxypropan-2-yl)-4-(3-nitrophenyl)-7-((2-(trimethylsilyl)ethoxy)methyl)-7H-pyrrolo[2,3-d]pyrimidine-5-carboxamide (800 mg, 1.70 mmol) in dichloromethane (10 mL), was added DMP (1.20 g, 2.83 mmol). The resulting solution was stirred for 2 hours at room temperature and quenched by addition of saturated aqueous NaHCO$_3$. The resulting solution was extracted with ethyl acetate (×3) and the combined organic layers were washed with brine, dried over anhydrous sodium sulfate, filtered and concentrated in vacuo. The reaction was purified by chromatography using silica gel, eluting with 1-50% ethyl acetate/petroleum ether. The product was collected and concentrated in vacuo to afford 4-(3-nitrophenyl)-N-(1-oxopropan-2-yl)-7-((2-(trimethylsilyl)ethoxy)methyl)-7H-pyrrolo[2,3-d]pyrimidine-5-carboxamide as a yellow oil. LRMS (ESI) calc'd for C$_{22}$H$_{28}$N$_5$O$_5$Si [M+H]$^+$: 470, found 470. $^1$H NMR (400 MHz, CDCl$_3$) δ 9.53 (s, 1H), 9.12 (s, 1H), 9.09 (s, 1H), 8.57-7.68 (m, 5H), 5.80-5.78 (s, 2H), 4.54-4.51 (m, 1H), 3.66-3.62 (m, 2H), 1.36-1.27 (m, 3H), 1.02-0.98 (m, 2H), 0.02 (s, 9H).

Step 3: 4-Methyl-2-(4-(3-nitrophenyl)-7-((2-(trimethylsilyl)ethoxy)methyl)-7H-pyrrolo[2,3-d]pyrimidin-5-yl)oxazole

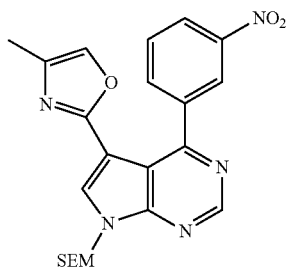 [SMILES: Cc1coc(-c2cn(COCC[Si](C)(C)C)c3ncnc(-c4cccc([N+](=O)[O-])c4)c23)n1]

To a solution of 4-(3-nitrophenyl)-N-(1-oxopropan-2-yl)-7-((2-(trimethylsilyl)ethoxy)methyl)-71-pyrrolo[2,3-d]pyrimidine-5-carboxamide (800 mg, 1.70 mmol) in CH$_3$CN (10 mL) was added TEA (1.42 mL, 10.2 mmol), PPh$_3$ (1.34 g, 5.11 mmol), and hexachloroethane (1.20 g, 5.07 mmol). The resulting solution was stirred for 2 hours at room temperature, concentrated in vacuo, and extracted with ethyl acetate (×3). The combined organic layers were washed with brine, dried over anhydrous sodium sulfate, filtered and concentrated in vacuo to afford 4-methyl-2-(4-(3-nitrophenyl)-7-((2-(trimethylsilyl)ethoxy)methyl)-7H-pyrrolo[2,3-d]pyrimidin-5-yl)oxazole as a white solid. LRMS (ESI) calc'd for C$_{22}$H$_{26}$N$_5$O$_4$Si [M+H]$^+$: 452, found 452.

Step 4: 3-(5-(4-Methyloxazol-2-yl)-7-((2-(trimethylsilyl)ethoxy)methyl)-7H-pyrrolo[2,3-d]pyrimidin-4-yl)aniline

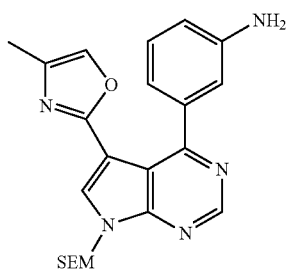

To a solution of 4-methyl-2-(4-(3-nitrophenyl)-7-((2-(trimethylsilyl)ethoxy)methyl)-7H-pyrrolo[2,3-d]pyrimidin-5-yl)oxazole (0.30 g, 0.66 mmol) in methanol (20 mL), was added Pd(OH)$_2$ on carbon (300 mg, 10 wt. %). The flask was purged with hydrogen and was stirred for 4 hours at room temperature under hydrogen atmosphere (1 atm). The reaction was filtered, and concentrated in vacuo to afford crude 3-(5-(4-methyloxazol-2-yl)-7-((2-(trimethylsilyl)ethoxy)methyl)-7H-pyrrolo[2,3-d]pyrimidin-4-yl)aniline as a colorless oil. LRMS (ESI) calc'd for C$_{22}$H$_{28}$N$_5$O$_2$Si [M+H]$^+$: 422, found 422.

Step 5: N-(3-(5-(4-Methyloxazol-2-yl)-7-((2-(trimethylsilyl)ethoxy)methyl)-7H-pyrrolo[2,3-d]pyrimidin-4-yl)phenyl)methacrylamide

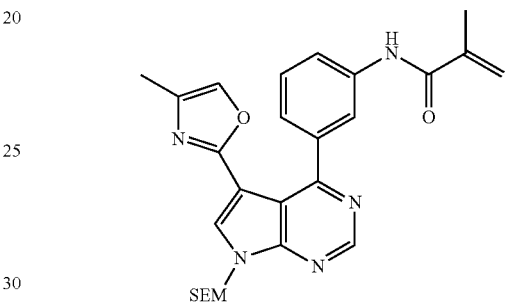

Following a similar procedure used in Step 3 for Example 25, amidation followed by silica gel chromatography, eluting with 1-83% ethyl acetate/petroleum ether afforded N-(3-(5-(4-methyloxazol-2-yl)-7-((2-(trimethylsilyl)ethoxy)methyl)-7H-pyrrolo[2,3-d]pyrimidin-4-yl)phenyl)methacrylamide as a colorless oil. LRMS (ESI) calc'd for C$_{26}$H$_{32}$N$_5$O$_3$Si [M+H]$^+$: 490, found 490.

Step 6: N-(3-(5-(4-Methyloxazol-2-yl)-7H-pyrrolo[2,3-d]pyrimidin-4-yl)phenyl)methacrylamide

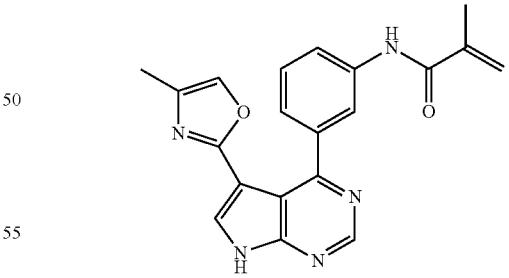

Following a similar procedure used in Step 2 for Example 22, SEM deprotection followed by reverse phase purification afforded N-(3-(5-(4-methyloxazol-2-yl)-7H-pyrrolo[2,3-d]pyrimidin-4-yl)phenyl)methacrylamide as a yellow solid. LRMS (ESI) calc'd for C$_{20}$H$_{18}$N$_5$O$_2$ [M+H]$^+$: 360, found 360. $^1$H NMR (400 MHz, CD$_3$OD) δ 9.08 (s, 1H), 8.27 (s, 1H), 7.93 (s, 1H), 7.81-7.79 (d, J=8.0 Hz, 1H), 7.47-7.43 (m, 1H), 7.32-7.30 (d, J=8.4 Hz, 2H), 5.81 (s, 1H), 5.56 (s, 1H), 2.08-2.04 (d, J=16.4 Hz, 6H).

Example 30

N-(3-(5-(Oxazol-5-yl)-7H-pyrrolo[2,3-d]pyrimidin-4-yl)phenyl)methacrylamide

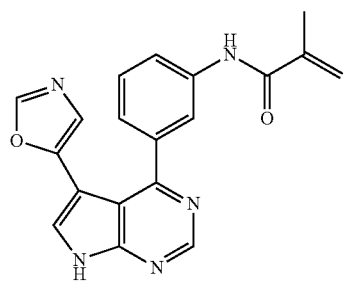 [SMILES: C=C(C)C(=O)Nc1cccc(-c2ncnc3[nH]cc(-c4cnco4)c23)c1]

Step 1: N-Methoxy-N-methyl-4-(3-nitrophenyl)-7-((2-(trimethylsilyl)ethoxy)methyl)-7H-pyrrolo[2,3-d]pyrimidine-5-carboxamide

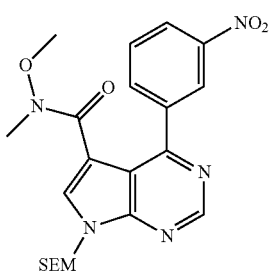 [SMILES: CON(C)C(=O)c1cn(COCC[Si](C)(C)C)c2ncnc(-c3cccc([N+](=O)[O-])c3)c12]

To 4-(3-nitrophenyl)-7-[[2-(trimethylsilyl)ethoxy]methyl]-7H-pyrrolo[2,3-d]pyrimidine-5-carboxylic acid (637 mg, 1.54 mmol), methoxy(methyl)amine hydrochloride (298 mg, 3.06 mmol), was added N,N-dimethylformamide (20 mL), HATU (701 mg, 1.84 mmol) and DIPEA (793 mg, 6.14 mmol). The resulting solution was stirred for 2 hours at 25° C. and then quenched by the addition of water (50 mL). The reaction solution was extracted using ethyl acetate (×3), and the combined organic layers were washed with brine, dried over anhydrous sodium sulfate, filtered and concentrated in vacuo. The product was purified by chromatography using silica gel, eluting with 50% ethyl acetate/petroleum ether. The product was collected and concentrated in vacuo to afford N-methoxy-N-methyl-4-(3-nitrophenyl)-7-((2-(trimethylsilyl)ethoxy)methyl)-7H-pyrrolo[2,3-d]pyrimidine-5-carboxamide as a white solid. LRMS (ESI) calc'd for $C_{21}H_{28}N_5O_5Si$ [M+H]$^+$: 458, found 458. $^1$H NMR (400 MHz, CDCl$_3$) δ 9.07 (s, 1H), 8.59 (s, 1H), 8.36 (d, J=8.4 Hz, 1H), 8.18 (d, 8.4 Hz, 1H), 7.95 (s, 1H), 7.70 (t, J=7.8 Hz, 1H), 5.78 (s, 2H), 3.64 (t, J=8.2 Hz, 2H), 3.49 (s, 3H), 3.09 (s, 3H), 0.98 (t, J=8.2 Hz, 2H), 0.04 (s, 9H).

Step 2: 4-(3-Nitrophenyl)-7-((2-(trimethylsilyl)ethoxy)methyl)-71-pyrrolo[2,3-d]pyrimidine-5-carbaldehyde

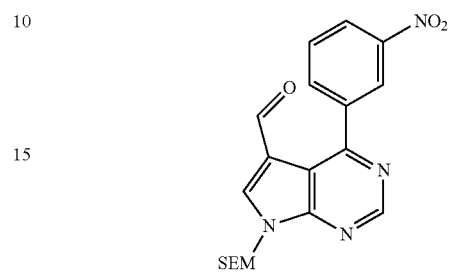

To N-methoxy-N-methyl-4-(3-nitrophenyl)-7-((2-(trimethylsilyl)ethoxy)methyl)-7H-pyrrolo[2,3-d]pyrimidine-5-carboxamide (1.02 g, 2.23 mmol) in THF (10 mL) under nitrogen, was added LAH (124 mg, 3.27 mmol) at 0° C. The resulting solution was stirred for 1 hour at 0° C. and then quenched by addition of water (0.50 mL). The mixture was dried over anhydrous sodium sulfate, filtered, and concentrated in vacuo.

The reaction was purified by chromatography using silica gel, eluting with 25% ethyl acetate/petroleum ether. The product was collected and concentrated in vacuo to afford 4-(3-nitrophenyl)-7-((2-(trimethylsilyl)ethoxy)methyl)-7H-pyrrolo[2,3-d]pyrimidine-5-carbaldehyde as a red solid. LRMS (ESI) calc'd for $C_{19}H_{23}N_4O_4Si$ [M+H]$^+$: 399, found 399.

Step 3: 5-(4-(3-Nitrophenyl)-7-((2-(trimethylsilyl)ethoxy)methyl)-7H-pyrrolo[2,3-d]pyrimidin-5-yl)oxazole

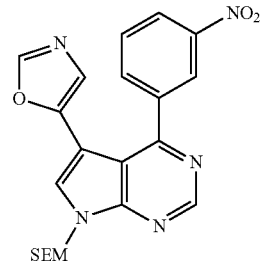 [SMILES: C[Si](C)(C)CCOCn1cc(-c2cnco2)c2c(-c3cccc([N+](=O)[O-])c3)ncnc21]

To 4-(3-nitrophenyl)-7-((2-(trimethylsilyl)ethoxy)methyl)-7H-pyrrolo[2,3-d]pyrimidine-5-carbaldehyde (135 mg, 0.339 mmol), tosmic (73 mg, 0.37 mmol) and potassium hydroxide (38 mg, 0.68 mmol), was added methanol (10 mL). The resulting solution was stirred for 12 hours at 25° C. and then the pH was adjusted to pH=6 with hydrogen chloride (1M aqueous solution). The reaction was extracted with ethyl acetate (×3) and the combined organic layers were washed with brine, dried over anhydrous sodium sulfate, filtered and concentrated in vacuo. The product was purified by chromatography using silica gel, eluting with 25% ethyl acetate/petroleum ether. The product was collected and concentrated in vacuo to afford 5-(4-(3-nitrophenyl)-7-((2-(trimethylsilyl)

ethoxy)methyl)-7H-pyrrolo[2,3-d]pyrimidin-5-yl)oxazole as a yellow oil. LRMS (ESI) calc'd for $C_{21}H_{24}N_5O_4Si$ [M+H]$^+$: 438, found 438.

Step 4: 3-(5-(Oxazol-5-yl)-7-((2-(trimethylsilyl) ethoxy)methyl)-7H-pyrrolo[2,3-d]pyrimidin-4-yl) aniline

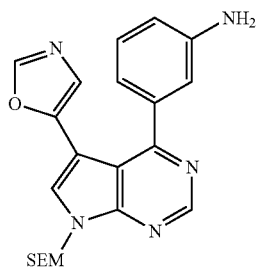 [SMILES: C[Si](C)(C)CCOCn1cc(-c2cnco2)c2c(-c3cccc(N)c3)ncnc21]

To 5-(4-(3-nitrophenyl)-7-((2-(trimethylsilyl)ethoxy)methyl)-7H-pyrrolo[2,3-d]pyrimidin-5-yl)oxazole (175 mg, 0.400 mmol) in methanol (5 mL), was added Pt/C (200 mg, 1 wt. % on carbon, Vanadium doped). The atmosphere was then purged with hydrogen gas, and the resulting solution was stirred under hydrogen atmosphere (1 atm) for 3 hours at 25° C. The reaction was filtered and the filtrate concentrated in vacuo to afford crude 3-(5-(oxazol-5-yl)-7-((2-(trimethylsilyl)ethoxy)methyl)-7H-pyrrolo[2,3-d]pyrimidin-4-yl) aniline as a solid. LRMS (ESI) calc'd for $C_{21}H_{26}N_5O_2Si$ [M+H]$^+$: 408, found 408.

Step 5: N-(3-(5-(Oxazol-5-yl)-7-((2-(trimethylsilyl) ethoxy)methyl)-7H-pyrrolo[2,3-d]pyrimidin-4-yl) phenyl)methacrylamide

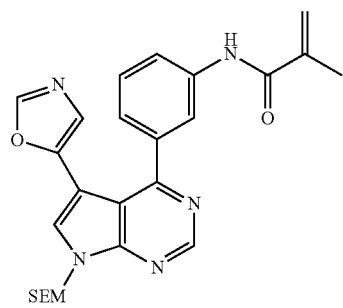 [SMILES: C=C(C)C(=O)Nc1cccc(-c2ncnc3c2c(-c2cnco2)cn3COCC[Si](C)(C)C)c1]

Following a similar procedure used in Step 3 for Example 25, amidation followed by silica gel chromatography, eluting with 50% ethyl acetate/petroleum ether afforded N-(3-(5-(oxazol-5-yl)-7-((2-(trimethylsilyl)ethoxy)methyl)-7H-pyrrolo[2,3-d]pyrimidin-4-yl)phenyl)methacrylamide as a yellow oil. LRMS (ESI) calc'd for $C_{25}H_{30}N_5O_3Si$ [M+H]$^+$: 476, found 476.

Step 6: N-(3-(5-(Oxazol-5-yl)-7H-pyrrolo[2,3-d] pyrimidin-4-yl)phenyl)methacrylamide

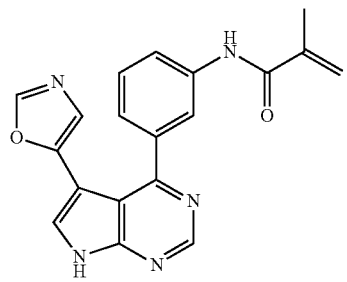 [SMILES: C=C(C)C(=O)Nc1cccc(-c2ncnc3[nH]cc(-c4cnco4)c23)c1]

Following a similar procedure used in Step 2 for Example 22, SEM deprotection followed by reverse phase purification afforded N-(3-(5-(oxazol-5-yl)-7H-pyrrolo[2,3-d]pyrimidin-4-yl)phenyl)methacrylamide as a light yellow solid. LRMS (ESI) calc'd for $C_{19}H_{16}N_5O_2$ [M+H]$^+$: 346, found 346. $^1$H NMR (400 MHz, CD$_3$OD) δ 9.01 (s, 1H), 8.05 (s, 1H), 7.96 (s, 1H), 7.91 (s, 1H), 7.78 (d, J=8 Hz, 1H), 7.44 (t, J=8 Hz, 1H), 7.31 (d, J=7.6 Hz, 1H), 6.62 (s, 1H), 5.81 (s, 1H), 5.54 (s, 1H), 2.04 (s, 3H).

Example 31

N-(3-(5-(Thiazol-2-yl)-7H-pyrrolo[2,3-d]pyrimidin-4-yl)phenyl)methacrylamide

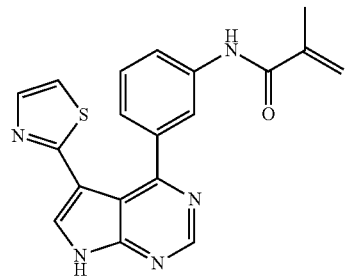 [SMILES: C=C(C)C(=O)Nc1cccc(-c2ncnc3[nH]cc(-c4nccs4)c23)c1]

Step 1: 2-(4-Chloro-7-((2-(trimethylsilyl)ethoxy) methyl)-7H-pyrrolo[2,3-d]pyrimidin-5-yl)thiazole

4-Chloro-5-iodo-7-((2-(trimethylsilyl)ethoxy)methyl)-7H-pyrrolo[2,3-d]pyrimidine (0.10 g, 0.24 mmol) and Pd(Ph$_3$P)$_4$ (28 mg, 0.024 mmol) were added to an oven-dried vial, and placed under nitrogen. To this mixture was added a THF solution of 2-thiazolyzinc bromide (1.9 mL, 0.98 mmol). The resulting solution was sparged with argon for 10 minutes and the reaction was sealed and heated at 70° C. for 16 hours. The reaction mixture was quenched and diluted with MeOH, then QuadraPure™ (1.3 g, 0.24 mmol) was added to scavenge the palladium. After stirring for approximately 2 hours, the resin was removed by filtration through a Celite cartridge, rinsing the cartridge with DCM. Silica gel was added to the filtrate and the solvent was concentrated in vacuo to a crude solid mixture. The reaction was then purified by chromatography using silica gel, eluting with 7-60% ethyl acetate/hexanes. The product was collected and concentrated in vacuo to afford 2-(4-chloro-7-((2-(trimethylsilyl)ethoxy) methyl)-7H-pyrrolo[2,3-d]pyrimidin-5-yl)thiazole. LRMS (ESI) calcd for $C_{15}H_{19}ClN_4OSSi$ [M+11]$^+$: 367, found 367.

Step 2: N-(3-(4,4,5,5-Tetramethyl-1,3,2-dioxaborolan-2-yl)phenyl)methacrylamide

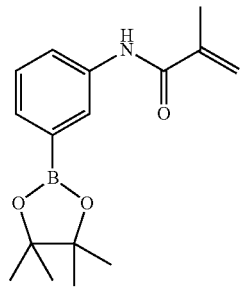 [SMILES: C=C(C)C(=O)Nc1cccc(B2OC(C)(C)C(C)(C)O2)c1]

To a stirred solution of 3-aminophenylboronic acid pinacol ester (5.04 g, 23.0 mmol) in dichloromethane (100 mL) was added TEA (6.41 mL, 46.0 mmol). The resulting solution was cooled to 0° C., then methacrolyl chloride (2.70 mL, 27.6 mmol) was added. The cooling bath was removed, and the reaction was allowed to warm to room temperature and stir for approximately 2 hours. The reaction mixture was washed with 7.5% aqueous ammonium chloride (100 mL) and the layers were separated and the organic layer was dried over anhydrous sodium sulfate, filtered, and concentrated in vacuo to afford a solid. The solid was triturated with hexanes (50 mL) and isolated by filtration to afford N-(3-(4,4,5,5-tetramethyl-1,3,2-dioxaborolan-2-yl)phenyl)methacrylamide. LRMS (ESI) calcd for $C_{16}H_{22}BNO_3$ [M+H]$^+$: 288, found 288.

Step 3: N-(3-(5-(Thiazol-2-yl)-7-((2-(trimethylsilyl)ethoxy)methyl)-7H-pyrrolo[2,3-d]pyrimidin-4-yl)phenyl)methacrylamide

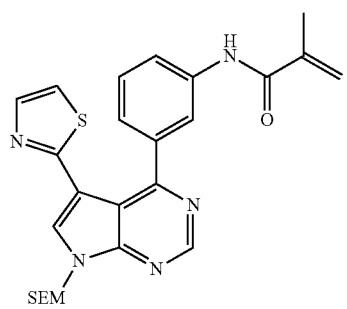 [SMILES: C=C(C)C(=O)Nc1cccc(-c2ncnc3c2c(-c2nccs2)cn3COCC[Si](C)(C)C)c1]

N-(3-(4,4,5,5-Tetramethyl-1,3,2-dioxaborolan-2-yl)phenyl)methacrylamide (29 mg, 0.099 mmol), 4-chloro-5-iodo-7-((2-(trimethylsilyl)ethoxy)methyl)-7H-pyrrolo[2,3-d]pyrimidine (28 mg, 0.076 mmol), PdCl$_2$(dppf)-CH$_2$Cl$_2$ adduct (6.2 mg, 7.6 mop, and potassium carbonate (26 mg, 0.19 mmol) were combined in a vial and degassed with nitrogen. Dioxane (0.75 mL) and water (0.19 mL) were added, and the reaction was sparged with argon, then heated to 100° C. for approximately 1.5 hours. The reaction was cooled to ambient temperature, diluted with EtOAc, and QuadraPure™ (402 mg, 0.076 mmol) was added to scavenge the palladium. The resulting suspension was stirred overnight at room temperature, filtered through Celite and concentrated in vacuo to afford a crude residue that was taken on without further purification. LRMS (ESI) calcd for $C_{25}H_{29}N_5O_2SSi$ [M+11]$^+$: 492, found 492.

Step 4: N-(3-(5-(Thiazol-2-yl)-7H-pyrrolo[2,3-d]pyrimidin-4-yl)phenyl)methacrylamide

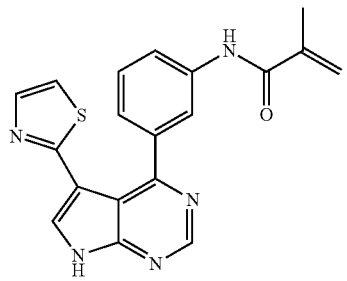 [SMILES: C=C(C)C(=O)Nc1cccc(-c2ncnc3[nH]cc(-c4nccs4)c23)c1]

To a solution of crude N-(3-(5-(thiazol-2-yl)-7-((2-(trimethylsilyl)ethoxy)methyl)-7H-pyrrolo[2,3-d]pyrimidin-4-yl)phenyl)methacrylamide (38 mg, 0.076 mmol) in DCM (1.0 mL), was added TFA (1.0 mL). The resulting solution was stirred at room temperature for approximately 3 hours before being concentrated in vacuo. The crude residue was then taken up into MeOH (1.0 mL) and ammonium hydroxide (1.0 mL) was added, and the resulting mixture was stirred at room temperature for approximately 30 minutes. The reaction was concentrated to afford a crude solid that was dissolved in a mixture of MeOH and EtOAc, filtered through 2 Stratospheres™ PL-HCO$_3$ MP SPE cartridges, concentrated in vacuo and purified by reverse phase HPLC using an acetonitrile gradient in water with 0.1% TFA modifier. Lyophyllization of the desired fractions afforded N-(3-(5-(thiazol-2-yl)-7H-pyrrolo[2,3-d]pyrimidin-4-yl)phenyl)methacrylamide as an off-white solid. LRMS (ESI) calcd for $C_{19}H_{15}N_5O_S$ [M+H]$^+$: 362, found 362. $^1$H NMR (600 MHz, DMSO-d$_6$) δ 12.93 (s, 1H), 9.75 (s, 1H), 8.92 (s, 1H), 8.10 (d, J=2.4 Hz, 1H), 7.91 (s, 1H), 7.69 (d, J=7.8 Hz, 1H), 7.55 (m, 2H), 7.07 (t, J=7.8 Hz, 1H), 6.91 (d, J=7.8 Hz, 1H), 5.74 (s, 1H), 5.47 (s, 1H), 1.90 (s, 3H).

General Scheme L:

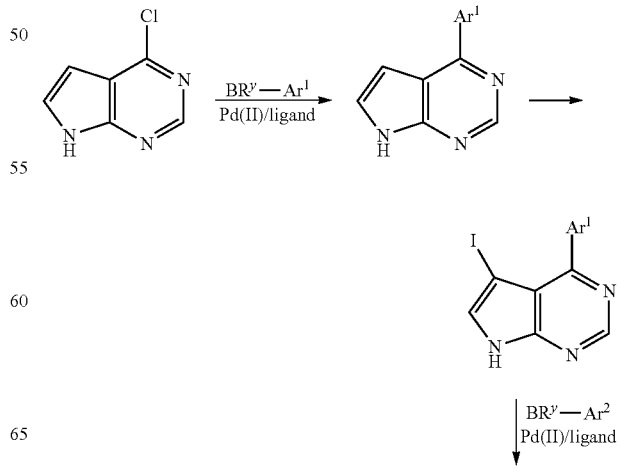

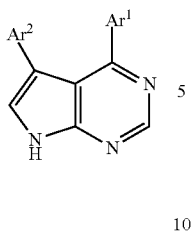

Examples Generated Via General Scheme L

Example 32-1

5-(2-Methoxypyridin-3-yl)-4-phenyl-7H-pyrrolo[2,3-d]pyrimidine

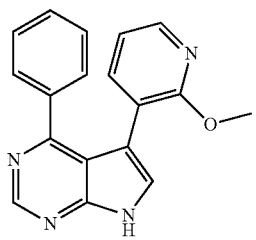 [SMILES: COc1ncccc1-c1c[nH]c2ncnc(-c3ccccc3)c12]

Step 1: 4-Phenyl-7H-pyrrolo[2,3-d]pyrimidine

A mixture of phenylboronic acid (1.59 g, 13.0 mmol), 4-chloro-7H-pyrrolo[2,3-d]pyrimidine (1.00 g, 6.51 mmol), sodium carbonate (1.38 g, 13.0 mmol), PdCl$_2$(dppf) (113 mg, 0.138 mmol) in dioxane (20 mL) and water (5 mL) was purged with argon gas for 10 minutes and then heated by microwave irradiation at 150° C. for 1 hour. Brine was added to the reaction mixture and the organic layer was separated. The aqueous layer was then extracted with ethyl acetate (×3) and the organic layers were combined and dried with sodium sulfate, filtered, and concentrated under reduced pressure. The crude product was then purified by silica chromatography eluting with 10-80% ethyl acetate hexane to afford 4-phenyl-7H-pyrrolo[2,3-d]pyrimidine as a light brown solid. LRMS (ESI) calc'd for C$_{12}$H$_9$N$_3$ [M]$^+$: 195, found 195.

Step 2: 5-Iodo-4-phenyl-7H-pyrrolo[2,3-d]pyrimidine

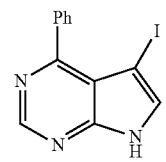

To a solution of 4-phenyl-7H-pyrrolo[2,3-d]pyrimidine (5.28 g, 27.0 mmol) in DMF (100 mL) was added NIS (6.57 g, 29.2 mmol). The reaction was stirred at room temperature for 1.5 hours. The reaction mixture was quenched with water (150 mL) and the resulting precipitated product was filtered and washed with water. The filtrate cake was dried under vacuum to afford 5-iodo-4-phenyl-7H-pyrrolo[2,3-d]pyrimidine as a yellow solid. LRMS (ESI) calcd for C$_{12}$H$_8$IN$_3$ [M]$^+$: 321, found 321. $^1$H NMR (600 MHz, DMSO-D$_6$) δ 12.71 (s, 1H), 8.83 (s, 1H), 7.87 (d, J=2.45 Hz, 1H), 7.68 (t, J 1.45 Hz, 1H), 7.67 (d, J=3.42 Hz, 1H), 7.54 (d, J=1.96 Hz, 2H), 7.53 (t, J=1.46 Hz, 1H).

Step 3: 5-(2-Methoxypyridin-3-yl)-4-phenyl-7H-pyrrolo[2,3-d]pyrimidine

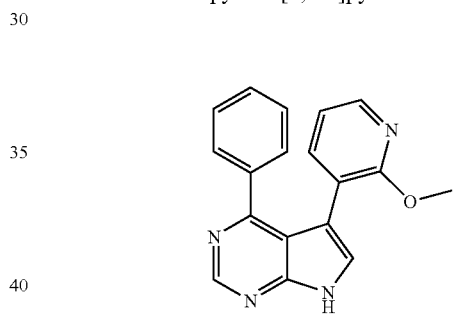

A mixture of (2-methoxypyridin-3-yl)boronic acid (36 mg, 0.23 mmol), 5-iodo-4-phenyl-7H-pyrrolo[2,3-d]pyrimidine (50 mg, 0.16 mmol), sodium carbonate (83 mg, 0.78 mmol) and SiliaCat® heterogeneous catalysts DPP-Pd (loading=0.28 mmol/g, 111 mg, 0.031 mmol) in dioxane (1.30 mL) and water (0.26 mL) was heated to 170° C. under the microwave irradiation for 15 minutes. The reaction mixture was concentrated, redissolved in DMSO, filtered and the resulting solution was reconcentrated. Purification by reverse phase HPLC using an acetonitrile gradient in water with 0.1% formic acid modifier afforded 5-(2-methoxypyridin-3-yl)-4-phenyl-7H-pyrrolo[2,3-d]pyrimidine. LRMS (ESI) calc'd for C$_{18}$H$_{15}$N$_4$O [M+H]$^+$: 303, found 303. $^1$H NMR (600 MHz, DMSO-D$_6$) δ 12.40 (s, 1H), 8.82 (s, 1H); 7.97 (dd, 1H, J=1.1, 4.3 Hz); 7.65 (s, 1H); 7.64 (dd, 1H, J=1.1, 5.6 Hz); 7.28 (d, 2H, J=6.6 Hz), 7.24 (t, 1H, J=6.1 Hz); 7.08 (dd, 2H, J=6.1, 6.6 Hz); 6.94 (dd, 1H, J=4.3, 5.6 Hz); 3.05 (s, 3H).

The following examples, 32-2 through 32-6, as shown in Table 13, were prepared in an analogous manner of that described above using materials that are commercially available or known, or that can be prepared using procedures known in the art or by generally following procedures described herein for various intermediates.

TABLE 13

| Example Number | Chemical Structure | IUPAC Name | Exact mass [M + H]+ |
|---|---|---|---|
| 32-2 | | 4,5-diphenyl-7H-pyrrolo[2,3-d]pyrimidine | Calc'd 272, found 272 |
| 32-2 | | methyl [4-methoxy-3-(4-phenyl-7H-pyrrolo[2,3-d]pyrimidin-5-yl)phenyl]acetate | Calc'd 374, found 374 |
| 32-3 | 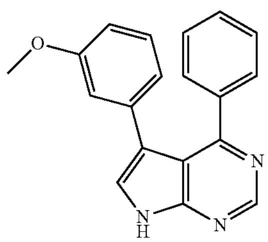 [SMILES: COc1cccc(-c2c[nH]c3ncnc(-c4ccccc4)c23)c1] | 5-(3-methoxyphenyl)-4-phenyl-7H-pyrrolo[2,3-d]pyrimidine | Calc'd 302, found 302 |
| 32-4 | 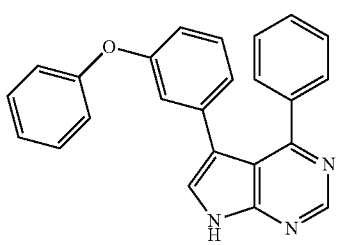 [SMILES: c1ccc(Oc2cccc(-c3c[nH]c4ncnc(-c5ccccc5)c34)c2)cc1] | 5-(3-phenoxyphenyl)-4-phenyl-7H-pyrrolo[2,3-d]pyrimidine | Calc'd 364, found 364 |
| 32-5 | 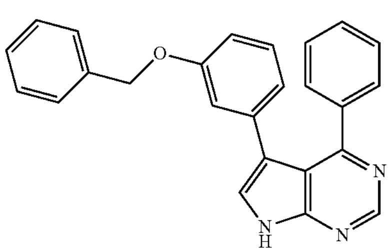 [SMILES: c1ccc(COc2cccc(-c3c[nH]c4ncnc(-c5ccccc5)c34)c2)cc1] | 5-[3-(benzyloxy)phenyl]-4-phenyl-7H-pyrrolo[2,3-d]pyrimidine | Calc'd 378, found 378 |

TABLE 13-continued

| Example Number | Chemical Structure | IUPAC Name | Exact mass [M + H]+ |
|---|---|---|---|
| 32-6 | 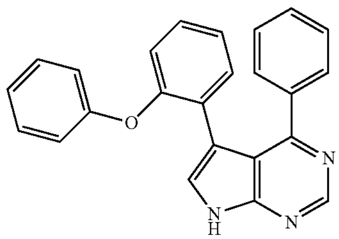 [SMILES: c1ccc(Oc2ccccc2-c2c[nH]c3ncnc(-c4ccccc4)c23)cc1] | 5-(2-phenoxyphenyl)-4-phenyl-7H-pyrrolo[2,3-d]pyrimidine | Calc'd 364, found 364 |

General Scheme M:

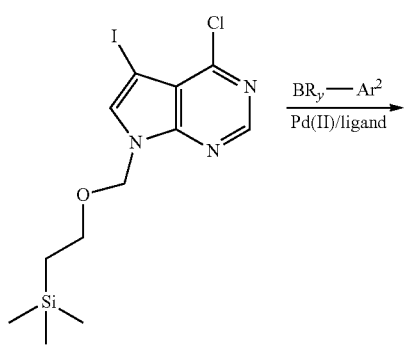

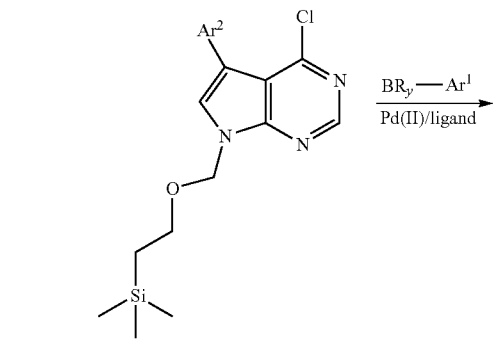

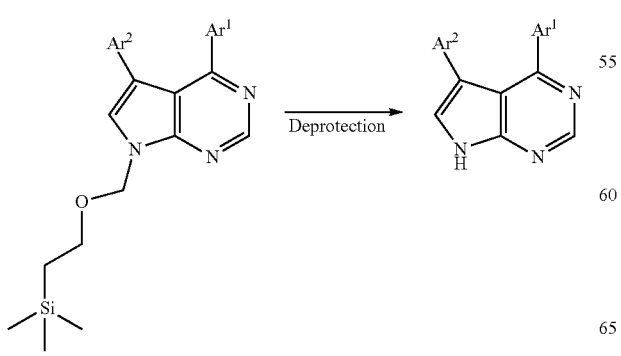

Examples Generated Via General Scheme M

Example 33-1

5-(2-Methoxyphenyl)-4-phenyl-7H-pyrrolo[2,3-d]pyrimidine

Step 1: 4-Chloro-5-(2-methoxyphenyl)-7-((2-(trimethylsilyl)ethoxy)methyl)-7H-pyrrolo[2,3-d]pyrimidine To a nitrogen gas purged mixture of 4-chloro-5-iodo-7-((2-(trimethylsilyl)ethoxy)methyl)-7H-pyrrolo[2,3-d]pyrimidine (200 mg, 0.488 mmol), and (2-methoxyphenyl)boronic acid (96 mg, 0.64 mmol) in 2 M aqueous sodium carbonate (0.610 mL, 1.22 mmol) and DME (3.0 mL) was added tetrakis (triphenylphosphine)palladium(0) (56 mg, 0.049 mmol). The reaction was sealed and heated at 130° C. for 30 minutes. The reaction was then diluted with EtOAc and passed through a column of Celite and sodium sulfate to remove water and solids. The reaction solution was concentrated under reduced pressure and the crude product purified by silica chromatography eluting with 1-20% ethyl acetatehexane to afford 4-chloro-5-(2-methoxyphenyl)-7-((2-(trimethylsilyl) ethoxy)methyl)-7H-pyrrolo[2,3-d]pyrimidine as a solid. LRMS (ESI) calcd for $C_{19}H_{25}ClN_3O_2Si$ [M+H]$^+$: 390, found 390.

Step 2: 5-(2-Methoxyphenyl)-4-phenyl-7-((2-(trimethylsilyl)ethoxy)methyl)-7H-pyrrolo[2,3-d]pyrimidine

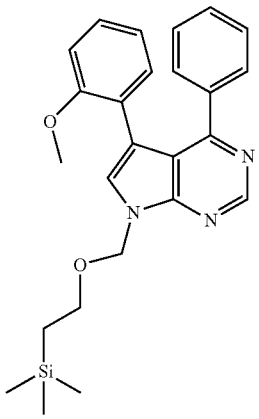 [SMILES: COc1ccccc1-c1cn(COCC[Si](C)(C)C)c2ncnc(-c3ccccc3)c12]

To a nitrogen gas purged mixture of 4-chloro-5-(2-methoxyphenyl)-7-((2-(trimethylsilyl)ethoxy)methyl)-7H-pyrrolo[2,3-d]pyrimidine (50 mg, 0.13 mmol) and phenyl boronic acid (23.5 mg, 0.192 mmol) in 2 M potassium carbonate (0.192 mL, 0.385 mmol) and tetrahydrofuran (1.0 mL) was added PdCl$_2$(dppf)-CH$_2$Cl$_2$ (10 mg, 0.013 mmol). The reaction was sealed and heated to 120° C. for 20 minutes. Upon cooling, the reaction mixture was diluted with EtOAc and washed with saturated sodium bicarbonate and brine. The organic layer was then dried with sodium sulfate, filtered, and concentrated under reduced pressure. The crude product was purified by silica chromatography eluting with 1-20% ethyl acetate/hexanes to afford 5-(2-methoxyphenyl)-4-phenyl-7-((2-(trimethylsilyl)ethoxy)methyl)-7H-pyrrolo[2,3-d]pyrimidine. LRMS (ESI) calcd for $C_{25}H_{30}N_3O_2Si$ [M+H]$^+$: 432, found 432.

Step 3: 5-(2-Methoxyphenyl)-4-phenyl-7H-pyrrolo[2,3-d]pyrimidine

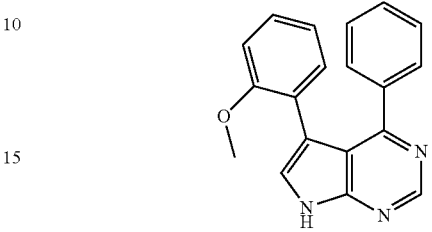

To a solution of 5-(2-methoxyphenyl)-4-phenyl-7-((2-(trimethylsilyl)ethoxy)methyl)-7H-pyrrolo[2,3-d]pyrimidine (60 mg, 0.13 mmol) in DCM (1.0 mL) was added TFA (0.964 mL, 12.5 mmol) and the reaction mixture stirred at room temperature for 1 hour. The reaction mixture was concentrated under reduced pressure and the residue was redissolved in MeOH (1.0 mL). 10 M aqueous NaOH (0.088 mL, 0.88 mmol) and ethylenediamine (17 μL, 0.25 mmol) were then added and the reaction was stirred for 30 minutes at room temperature. The reaction mixture was then acidified with TFA and purified by reverse phase HPLC using an acetonitrile gradient in water with 0.1% TFA modifier. The combined fractions with the desired product were concentrated until only the water layer remained. The water layer was neutralized with 2 M aqueous potassium bicarbonate and the mixture was extracted with ethyl acetate (×5). The combined organic fractions were dried with sodium sulfate, filtered and concentrated under reduced pressure to give 5-(2-methoxyphenyl)-4-phenyl-7H-pyrrolo[2,3-d]pyrimidine. LRMS (ESI) calc'd for $C_{19}H_{16}N_3O$ [M+H]$^+$: 302, found 302. $^1$H NMR (600 MHz, DMSO-D$_6$) δ 12.34 (s, 1H); 8.83 (s, 1H); 7.57 (d, 1H, J=2.3 Hz); 7.31 (m, 3H); 7.22 (m, 2H); 7.07 (t, 2H, J=7.6 Hz); 6.93 (t, 1H, J=7.6 Hz); 6.52 (d, 1H, J=8.2 Hz); 3.33 (s, 3H).

The following examples, 33-2 through 33-6, as shown in Table 14, were prepared in an analogous manner of that described above using materials that are commercially available or known, or that can be prepared using procedures known in the art or by generally following procedures described herein for various intermediates.

TABLE 14

| Example Number | Chemical Structure | IUPAC Name | Exact mass [M + H]$^+$ |
|---|---|---|---|
| 33-2 | 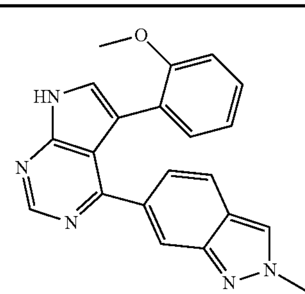 | 5-(2-methoxyphenyl)-4-(2-methyl-2H-indazol-6-yl)-7H-pyrrolo[2,3-d]pyrimidine | Calc'd 356.2, found 356.0 |

TABLE 14-continued

| Example Number | Chemical Structure | IUPAC Name | Exact mass [M + H]+ |
|---|---|---|---|
| 33-3 | 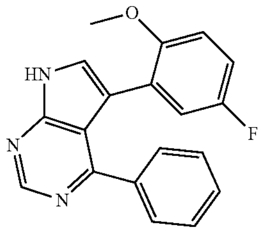 [SMILES: COc1ccc(F)cc1-c1c[nH]c2ncnc(-c3ccccc3)c12] | 5-(5-fluoro-2-methoxyphenyl)-4-phenyl-7H-pyrrolo[2,3-d]pyrimidine | Calc'd 320.1, found 320.1 |
| 33-4 | 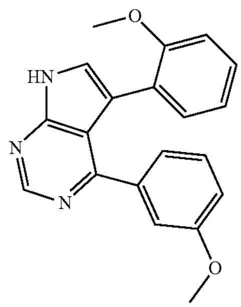 [SMILES: COc1cccc(-c2ncnc3[nH]cc(-c4ccccc4OC)c23)c1] | 5-(2-methoxphenyl)-4-(3-methoxyphenyl)-7H-pyrrolo[2,3-d]pyrimidine | Calc'd 332.1, found 332.0 |
| 33-5 | 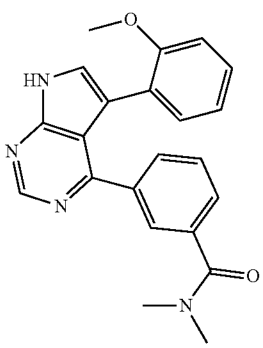 [SMILES: COc1ccccc1-c1c[nH]c2ncnc(-c3cccc(C(=O)N(C)C)c3)c12] | 3-[5-(2-methoxyphenyl)-7H-pyrrolo[2,3-d]pyrimidin-4-yl]-N,N-dimethylbenzamide | Calc'd 373.2, found 373.1 |
| 33-6 | 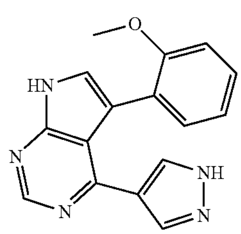 [SMILES: COc1ccccc1-c1c[nH]c2ncnc(-c3cn[nH]c3)c12] | 5-(2-methoxyphenyl)-4-(1H-pyrazol-4-yl)-7H-pyrrolo[2,3-d]pyrimidine | Calc'd 292.1, found 292.0 |

Biological Assays
Jak Biochemical HTRF Assay Protocol

The ability of compounds to inhibit the activity of JAK1, JAK2, JAK3, and Tyk2 was measured using a recombinant purified GST-tagged catalytic domain for each enzyme (Invitrogen JAK1 #M4290, JAK2 #M4290, JAK3 #M4290, Tyk2 #M4290) in an HTRF format biochemical assay. The reactions employed a common peptide substrate, LCB-EQEDE-PEGDYFEWLW-NH2 (in-house). The basic assay protocol is as follows: First, 250 nL of diluted compounds in DMSO were dispensed into the wells of a dry 384-well Black plate (Greiner #781076) using a Labcyte Echo 555 acoustic dispenser. Subsequent reagent additions employed an Agilent Bravo. Next, 18 μL of 1.11× enzyme and 1.11× substrate in 1× assay buffer (Invitrogen kinase buffer # PV3189, 2 mM DTT, 0.05% BSA) were added to the wells and shaken and then preincubated for 30 minutes at room temperature to allow compound binding to equilibrate. After equilibration, 2 μL of 10×ATP in 1× assay buffer was added to initiate the kinase reaction and the plates were shaken and then incubated at room temperature for 120 minutes. At the end of the incubation, 20 μL of 2× stop buffer (streptavidin-Dylight 650 (Thermo #84547B100 mL), Eu-tagged pY20 antibody (Perkin Elmer #AD0067), EDTA, HEPES, and Triton) was added to quench the reaction. Plates were shaken and centrifuged and then incubated 60 minutes at room temperature and then read on a Perkin Elmer Envision ($\lambda_{ex}$=337 nm, $\lambda_{em}$=665 and 615 nm, TRF delay time=20 μs). HTRF signal=10,000*665 nm reading 615 nm reading. After normalization to untreated controls, the percent inhibition of the HTRF signal at each compound concentration was calculated. The plot of percent inhibition versus the log of compound concentration was fit with a 4-parameter dose response equation to calculate $IC_{50}$ values.

Final Reaction Conditions were:

| Enzyme | [E] (nM) | [S] (µM) | [ATP] (µM) | [Eu-pY20] (nM) | [SA-Dylight] (nM) |
|---|---|---|---|---|---|
| JAK1 | 1.405 | 0.75 | 31.8 | 9 | 312.5 |
| JAK2 | 0.052 | 0.75 | 8.5 | 9 | 312.5 |
| JAK3 | 0.031 | 0.75 | 2.9 | 9 | 312.5 |
| Tyk2 | 2.612 | 0.75 | 6.9 | 9 | 312.5 |

Compound concentrations tested were 1496, 499, 175, 49.9, 18.7, 6.2, 2.1, 0.75, 0.24, 0.075, and 0.0125 nM, with 1.25% residual DMSO.

Biological Data

Examples of the instant invention were evaluated in JAK2 and JAK3 in vitro binding assays. The compounds of the present invention have activities such that the JAK3 isoform $IC_{50}$ is less than the $IC_{50}$ of JAK1 and JAK2 isoforms.

The following table tabulates the biological data disclosed for the instant invention as a range of JAK2 and JAK3 $IC_{50}$ values (A: $IC_{50} \leq 10$ nM; B: 10 nM$>IC_{50} \leq 500$ nM C: $IC_{50} > 500$ nM). In certain instances compounds bearing a reactive functionality, such as of the type, but not limited to, general formula IV, covalent binding of the protein is possible. It is generally accepted that the potency and selectivity in these cases is governed by the affinity of initial non-covalent binding (Ki) and the rate of covalent modification ($k_2$) as outlined by Singh, J.; Petter, R. C.; Baillie, T. A. and Whitty, A., *Nature Reviews Drug Discovery* 2011, 307-317. As such, conventional $IC_{50}$ values are provided in these instances to simply demonstrate enzyme inhibition activity.

| Example | JAK3 IC50 (nM) | JAK2 IC50 (nM) |
|---|---|---|
| 1-1 | 5.5 | 91 |
| 1-2 | B | B |
| 1-3 | B | C |
| 1-4 | B | C |
| 1-5 | 7.2 | 273 |
| 1-6 | B | B |
| 1-7 | B | C |
| 1-8 | B | C |
| 1-9 | B | C |
| 1-10 | B | C |
| 1-11 | B | C |
| 1-12 | B | C |
| 1-13 | B | C |
| 1-14 | B | C |
| 1-15 | 5.7 | 134 |
| 1-17 | B | B |
| 1-18 | B | B |
| 1-19 | B | C |
| 1-20 | B | C |
| 1-21 | 3.5 | 73 |
| 1-22 | 4.6 | 78 |
| 1-23 | 6.0 | 62 |
| 1-24 | 7.5 | 125 |
| 1-25 | B | B |
| 1-26 | B | B |
| 1-27 | B | C |
| 1-28 | B | C |
| 1-29 | 8.1 | 339 |
| 1-30 | B | C |
| 1-31 | 4.6 | 91 |
| 1-32 | 8.3 | 215 |
| 1-33 | B | C |
| 1-34 | B | B |
| 1-35 | 5.7 | 134 |
| 1-36 | B | C |
| 1-37 | B | B |
| 1-38 | B | C |
| 1-39 | 8.4 | 145 |
| 1-40 | 8.8 | 186 |
| 1-41 | 7.5 | 168 |
| 1-42 | 9.0 | 121 |
| 1-43 | B | C |
| 1-44 | 4.2 | 47 |
| 1-45 | 5.6 | 127 |
| 1-46 | 7.6 | 143 |
| 1-47 | 3.3 | 90 |
| 1-48 | 3.8 | 66 |
| 1-49 | B | C |
| 1-50 | 4.8 | 54 |
| 1-51 | B | C |
| 1-52 | 3.3 | 62 |
| 1-53 | 1.5 | 35 |
| 1-54 | 4.0 | 61 |
| 1-55 | B | C |
| 1-56 | B | B |
| 1-57 | B | B |
| 1-58 | B | C |
| 1-59 | B | B |
| 1-60 | B | C |
| 1-61 | B | C |
| 1-62 | B | C |
| 1-63 | B | C |
| 1-64 | B | C |
| 1-65 | B | B |
| 1-66 | B | C |
| 1-67 | B | C |
| 1-68 | B | C |
| 1-69 | 6.5 | 98 |
| 1-71 | B | C |
| 1-72 | B | C |
| 1-73 | B | C |
| 1-74 | B | C |
| 1-75 | B | C |
| 1-76 | B | B |
| 1-77 | B | C |
| 1-78 | B | C |
| 1-79 | B | C |
| 1-80 | 2.3 | 53 |
| 1-81 | B | C |
| 1-82 | B | B |
| 1-83 | 9.7 | 137 |
| 1-84 | B | B |
| 1-85 | B | C |
| 1-86 | B | B |
| 1-87 | B | C |
| 1-88 | B | C |
| 1-89 | B | C |
| 1-90 | B | B |
| 1-91 | B | C |
| 1-92 | B | C |
| 1-93 | B | C |
| 1-94 | 7.5 | 121 |
| 1-95 | B | C |
| 1-96 | B | C |
| 1-97 | 6.8 | 348 |
| 1-98 | B | C |
| 1-99 | B | C |
| 1-100 | B | C |
| 1-102 | B | C |
| 1-103 | B | C |
| 1-104 | B | C |
| 1-105 | B | C |
| 1-106 | B | C |
| 1-107 | B | B |
| 2-1 | 9.0 | 153 |
| 2-2 | B | B |
| 3-1 | B | C |
| 3-2 | B | C |
| 4-1 | 0.15 | >1480 |
| 4-2 | 4.0 | >1496 |
| 4-3 | 0.085 | >1496 |
| 4-4 | 0.049 | >1496 |
| 4-5 | 0.040 | 790 |
| 4-6 | 1.6 | 483 |

| Example | JAK3 IC50 (nM) | JAK2 IC50 (nM) |
|---|---|---|
| 4-7 | B | C |
| 4-8 | 0.61 | >1496 |
| 4-9 | 0.013 | >1496 |
| 4-10 | 0.15 | >1496 |
| 4-11 | 0.033 | >1496 |
| 4-12 | 0.19 | >1496 |
| 4-13 | B | C |
| 4-14 | 0.066 | >1496 |
| 4-15 | 0.11 | >1496 |
| 4-16 | 0.070 | >1496 |
| 4-17 | 0.11 | >1496 |
| 4-18 | 0.11 | >1496 |
| 4-19 | 0.050 | >1496 |
| 4-20 | 0.081 | >1496 |
| 4-21 | 2.3 | >1496 |
| 4-22 | B | C |
| 4-23 | 0.34 | >1496 |
| 4-24 | 0.068 | >1496 |
| 4-25 | 0.11 | >1496 |
| 4-26 | 0.19 | >1496 |
| 4-27 | 0.14 | >1496 |
| 4-28 | 1.5 | >1496 |
| 4-29 | 0.087 | >1496 |
| 4-30 | 1.5 | >1496 |
| 4-31 | 0.11 | >1496 |
| 4-32 | 0.68 | >1496 |
| 4-33 | 0.47 | >1496 |
| 4-34 | 1.1 | >1496 |
| 4-35 | 0.049 | >1496 |
| 5-1 | 0.024 | >1496 |
| 5-2 | 0.11 | >1496 |
| 5-3 | 0.072 | >1496 |
| 5-4 | B | B |
| 5-5 | 0.043 | 892 |
| 5-6 | 0.22 | >1496 |
| 5-7 | B | C |
| 5-8 | 2.1 | >1496 |
| 5-9 | 8.3 | >1496 |
| 5-10 | 0.013 | >1496 |
| 5-13 | B | C |
| 5-14 | 5.3 | >1496 |
| 5-15 | B | C |
| 5-16 | 6.6 | 452 |
| 5-17 | 2.0 | >1496 |
| 5-18 | B | C |
| 5-19 | 2.4 | >1496 |
| 5-20 | B | C |
| 5-21 | B | C |
| 5-22 | B | C |
| 5-23 | B | C |
| 5-24 | B | C |
| 5-25 | B | C |
| 5-26 | B | C |
| 5-27 | B | C |
| 5-29 | B | C |
| 5-30 | B | C |
| 5-31 | B | C |
| 5-32 | B | C |
| 5-33 | B | C |
| 5-34 | 1.9 | >1496 |
| 5-35 | B | C |
| 5-36 | 0.14 | >1496 |
| 5-37 | B | C |
| 5-38 | B | C |
| 5-39 | 3.9 | 496 |
| 5-40 | B | C |
| 5-41 | 0.66 | >1496 |
| 5-42 | B | C |
| 5-43 | B | C |
| 5-44 | B | C |
| 5-45 | 0.025 | >1496 |
| 6-1 | 9.2 | 109 |
| 6-2 | B | C |
| 6-3 | B | B |
| 6-4 | B | C |
| 7-1 | B | C |
| 7-2 | B | C |
| 7-3 | B | C |
| 7-4 | B | C |
| 8-1 | B | C |
| 9-1 | B | C |
| 9-2 | B | B |
| 10-1 | 0.037 | >1496 |
| 10-2 | 8.2 | >1496 |
| 10-3 | B | C |
| 11-1 | 0.40 | >1496 |
| 11-2 | 2.0 | >1496 |
| 12-1 | 0.13 | >1496 |
| 13-1 | 0.052 | >1496 |
| 13-2 | A | >1496 |
| 13-3 | A | >1496 |
| 14 | 0.066 | >1496 |
| 15-1 | 0.024 | >1496 |
| 15-2 | 0.020 | >1496 |
| 16 | 0.20 | >1496 |
| 17 | 6.6 | >1496 |
| 18-1 | 0.056 | >1496 |
| 18-2 | B | C |
| 19 | B | C |
| 20-1 | 0.17 | >1496 |
| 20-2 | 0.59 | >1496 |
| 20-3 | 0.96 | >1496 |
| 20-4 | 1.5 | >1496 |
| 20-5 | 1.5 | >1496 |
| 20-6 | 5.2 | >1496 |
| 20-7 | 5.4 | >1496 |
| 20-8 | B | C |
| 20-9 | 0.016 | >1496 |
| 21-1 | B | C |
| 21-2 | 7.5 | >1496 |
| 21-3 | B | C |
| 21-4 | 9.7 | >1496 |
| 21-5 | 5.0 | >1496 |
| 21-6 | 10.3 | >1496 |
| 21-7 | 1.8 | >500 |
| 22 | 8.0 | >1496 |
| 23 | 8.3 | >1496 |
| 24 | C | C |
| 25 | B | C |
| 26 | 2.5 | >1496 |
| 27 | B | C |
| 28 | B | C |
| 29 | B | C |
| 30 | 5.0 | >1496 |
| 31 | B | C |
| 32-1 | B | B |
| 32-2 | B | C |
| 32-3 | 3.1 | 93 |
| 32-4 | B | C |
| 32-5 | B | C |
| 32-6 | B | C |
| 33-1 | 3.4 | 183 |
| 33-2 | 6.9 | >1496 |
| 33-3 | 1.4 | 71 |
| 33-4 | B | B |
| 33-5 | B | C |
| 33-6 | B | B |

What is claimed is:

1. A compound selected from the group consisting of:
ethyl 4-phenyl-7H-pyrrolo[2,3-d]pyrimidine-5-carboxylate;
ethyl 4-(4-chlorophenyl)-7H-pyrrolo[2,3-d]pyrimidine-5-carboxylate;
ethyl 4-(3-aminophenyl)-7H-pyrrolo[2,3-d]pyrimidine-5-carboxylate;
prop-2-en-1-yl 4-(2-methyl-2H-indazol-6-yl)-7H-pyrrolo[2,3-d]pyrimidine-5-carboxylate;
ethyl 4-(2-methyl-2H-indazol-6-yl)-7H-pyrrolo[2,3-d]pyrimidine-5-carboxylate;

ethyl 4-(3-cyanophenyl)-7H-pyrrolo[2,3-d]pyrimidine-5-carboxylate;
ethyl 4-(4-carbamoylphenyl)-7H-pyrrolo[2,3-d]pyrimidine-5-carboxylate;
ethyl 4-[3-(methoxycarbonyl)phenyl]-7H-pyrrolo[2,3-d]pyrimidine-5-carboxylate;
ethyl 4-[4-(methoxycarbonyl)phenyl]-7H-pyrrolo[2,3-d]pyrimidine-5-carboxylate;
ethyl 4-(4-cyanophenyl)-7H-pyrrolo[2,3-d]pyrimidine-5-carboxylate;
ethyl 4-[4-(methylsulfonyl)phenyl]-7H-pyrrolo[2,3-d]pyrimidine-5-carboxylate;
ethyl 4-(3-carbamoylphenyl)-7H-pyrrolo[2,3-d]pyrimidine-5-carboxylate;
ethyl 4-[4-(dimethylcarbamoyl)phenyl]-7H-pyrrolo[2,3-d]pyrimidine-5-carboxylate;
ethyl 4-pyridin-4-yl-7H-pyrrolo[2,3-d]pyrimidine-5-carboxylate;
ethyl 4-(4-methoxyphenyl)-7H-pyrrolo[2,3-d]pyrimidine-5-carboxylate;
3-[5-(ethoxycarbonyl)-7H-pyrrolo[2,3-d]pyrimidin-4-yl]benzoic acid;
ethyl 4-(3-methoxyphenyl)-7H-pyrrolo[2,3-d]pyrimidine-5-carboxylate;
ethyl 4-[1-(tert-butoxycarbonyl)-1,2,3,6-tetrahydropyridin-4-yl]-7H-pyrrolo[2,3-d]pyrimidine-5-carboxylate;
ethyl 4-[1-(tert-butoxycarbonyl)-1,2,5,6-tetrahydropyridin-3-yl]-7H-pyrrolo[2,3-d]pyrimidine-5-carboxylate;
ethyl 4-[1-(tert-butoxycarbonyl)-2,5-dihydro-1H-pyrrol-3-yl]-7H-pyrrolo[2,3-d]pyrimidine-5-carboxylate;
ethyl 4-[3-(2,2,2-trifluoroethoxy)phenyl]-7H-pyrrolo[2,3-d]pyrimidine-5-carboxylate;
ethyl 4-(3-amino-4-methylphenyl)-7H-pyrrolo[2,3-d]pyrimidine-5-carboxylate;
ethyl 4-cyclohex-1-en-1-yl-7H-pyrrolo[2,3-d]pyrimidine-5-carboxylate;
ethyl 4-(3-amino-4-chlorophenyl)-7H-pyrrolo[2,3-d]pyrimidine-5-carboxylate;
ethyl 4-(2-methyl-1,3-benzothiazol-5-yl)-7H-pyrrolo[2,3-d]pyrimidine-5-carboxylate;
ethyl 4-[3-(trifluoromethoxy)phenyl]-7H-pyrrolo[2,3-d]pyrimidine-5-carboxylate;
ethyl 4-(1-methyl-1H-pyrazol-4-yl)-7H-pyrrolo[2,3-d]pyrimidine-5-carboxylate;
ethyl 4-pyridin-3-yl-7H-pyrrolo[2,3-d]pyrimidine-5-carboxylate;
ethyl 4-(3-fluoro-2-methyl-2H-indazol-6-yl)-7H-pyrrolo[2,3-d]pyrimidine-5-carboxylate;
ethyl 4-[3-(dimethylcarbamoyl)-2-methyl-2H-indazol-6-yl]-7H-pyrrolo[2,3-d]pyrimidine-5-carboxylate;
ethyl 4-(2,3-dihydro-1H-indol-6-yl)-7H-pyrrolo[2,3-d]pyrimidine-5-carboxylate;
ethyl 4-[3-amino-4-(hydroxymethyl)phenyl]-7H-pyrrolo[2,3-d]pyrimidine-5-carboxylate;
ethyl 4-[3-amino-4-(methoxymethyl)phenyl]-7H-pyrrolo[2,3-d]pyrimidine-5-carboxylate;
ethyl 4-(4-fluorophenyl)-7H-pyrrolo[2,3-d]pyrimidine-5-carboxylate;
ethyl 4-(4-hydroxyphenyl)-7H-pyrrolo[2,3-d]pyrimidine-5-carboxylate;
ethyl 4-[4-(trifluoromethyl)phenyl]-7H-pyrrolo[2,3-d]pyrimidine-5-carboxylate;
ethyl 4-(4-methylphenyl)-7H-pyrrolo[2,3-d]pyrimidine-5-carboxylate;
ethyl 4-(2-methylphenyl)-7H-pyrrolo[2,3-d]pyrimidine-5-carboxylate;
ethyl 4-(3-chlorophenyl)-7H-pyrrolo[2,3-d]pyrimidine-5-carboxylate;
ethyl 4-naphthalen-2-yl-7H-pyrrolo[2,3-d]pyrimidine-5-carboxylate;
ethyl 4-(2-fluorophenyl)-7H-pyrrolo[2,3-d]pyrimidine-5-carboxylate;
ethyl 4-(3-fluorophenyl)-7H-pyrrolo[2,3-d]pyrimidine-5-carboxylate;
ethyl 4-(2-chlorophenyl)-7H-pyrrolo[2,3-d]pyrimidine-5-carboxylate;
ethyl 4-biphenyl-4-yl-7H-pyrrolo[2,3-d]pyrimidine-5-carboxylate;
ethyl 4-(3-hydroxyphenyl)-7H-pyrrolo[2,3-d]pyrimidine-5-carboxylate;
ethyl 4-(3-methylphenyl)-7H-pyrrolo[2,3-d]pyrimidine-5-carboxylate;
ethyl 4-[4-(dimethylamino)phenyl]-7H-pyrrolo[2,3-d]pyrimidine-5-carboxylate;
ethyl 4-(1,3-benzodioxol-5-yl)-7H-pyrrolo[2,3-d]pyrimidine-5-carboxylate;
ethyl 4-quinolin-6-yl-7H-pyrrolo[2,3-d]pyrimidine-5-carboxylate;
ethyl 4-(1-benzothiophen-2-yl)-7H-pyrrolo[2,3-d]pyrimidine-5-carboxylate;
ethyl 4-(1H-pyrazol-4-yl)-7H-pyrrolo[2,3-d]pyrimidine-5-carboxylate;
ethyl 4[3-(benzyloxy)phenyl]-7H-pyrrolo[2,3-d]pyrimidine-5-carboxylate;
ethyl 4-(1H-indol-5-yl)-7H-pyrrolo[2,3-d]pyrimidine-5-carboxylate;
ethyl 4-(1-benzofuran-2-yl)-7H-pyrrolo[2,3-d]pyrimidine-5-carboxylate;
ethyl 4-(2-aminophenyl)-7H-pyrrolo[2,3-d]pyrimidine-5-carboxylate;
ethyl 4-thiophen-2-yl-7H-pyrrolo[2,3-d]pyrimidine-5-carboxylate;
ethyl 4-thiophen-3-yl-7H-pyrrolo[2,3-d]pyrimidine-5-carboxylate;
ethyl 4-[6-(hydroxymethyl)pyridin-3-yl]-7H-pyrrolo[2,3-d]pyrimidine-5-carboxylate;
ethyl 4-[3-(difluoromethoxy)phenyl]-7H-pyrrolo[2,3-d]pyrimidine-5-carboxylate;
ethyl 4-[2-(hydroxymethyl)pyridin-4-yl]-7H-pyrrolo[2,3-d]pyrimidine-5-carboxylate;
ethyl 4-(1-benzothiophen-7-yl)-7H-pyrrolo[2,3-d]pyrimidine-5-carboxylate;
ethyl 4-(4,5,6,7-tetrahydropyrazolo[1,5-a]pyridin-3-yl)-7H-pyrrolo[2,3-d]pyrimidine-5-carboxylate;
ethyl 4-(1-benzofuran-3-yl)-7H-pyrrolo[2,3-d]pyrimidine-5-carboxylate;
ethyl 4-(1H-indazol-4-yl)-7H-pyrrolo[2,3-d]pyrimidine-5-carboxylate;
ethyl 4-(1-oxo-2,3-dihydro-1H-isoindol-5-yl)-7H-pyrrolo[2,3-d]pyrimidine-5-carboxylate;
ethyl 4-(1,3-dimethyl-2-oxo-2,3-dihydro-1H-benzimidazol-5-yl)-7H-pyrrolo[2,3-d]pyrimidine-5-carboxylate;
ethyl 4-(1-methyl-1H-benzotriazol-6-yl)-7H-pyrrolo[2,3-d]pyrimidine-5-carboxylate;
ethyl 4-(1-oxo-2,3,4,5-tetrahydro-1H-2-benzazepin-6-yl)-7H-pyrrolo[2,3-d]pyrimidine-5-carboxylate;
ethyl 4-(1H-indazol-5-yl)-7H-pyrrolo[2,3-d]pyrimidine-5-carboxylate;
ethyl 4-(1,3-benzodioxol-5-yl)-7H-pyrrolo[2,3-d]pyrimidine-5-carboxylate;
ethyl 4-(1-benzothiophen-3-yl)-7H-pyrrolo[2,3-d]pyrimidine-5-carboxylate;

ethyl 4-[3-(trifluoromethyl)-1H-indazol-5-yl]-7H-pyrrolo[2,3-d]pyrimidine-5-carboxylate;
ethyl 4-(1-oxo-2,3-dihydro-1H-isoindol-4-yl)-7H-pyrrolo[2,3-d]pyrimidine-5-carboxylate;
tert-butyl 6-[5-(ethoxycarbonyl)-7H-pyrrolo[2,3-d]pyrimidin-4-yl]-3,4-dihydroisoquinoline-2(1H)-carboxylate;
ethyl 4-(3-oxo-2,3-dihydro-1H-isoindol-5-yl)-7H-pyrrolo[2,3-d]pyrimidine-5-carboxylate;
ethyl 4-(1H-indazol-6-yl)-7H-pyrrolo[2,3-d]pyrimidine-5-carboxylate;
ethyl 4-[2-(tert-butoxycarbonyl)-1-oxo-2,3-dihydro-1H-isoindol-5-yl]-7H-pyrrolo[2,3-d]pyrimidine-5-carboxylate;
tert-butyl 7-[5-(ethoxycarbonyl)-7H-pyrrolo[2,3-d]pyrimidin-4-yl]-3,4-dihydroisoquinoline-2(1H)-carboxylate;
tert-butyl 7-[5-(ethoxycarbonyl)-7H-pyrrolo[2,3-d]pyrimidin-4-yl]-2,3-dihydro-1,4-benzoxazepine-4(5H)-carboxylate;
ethyl 4-(4-aminophenyl)-7H-pyrrolo[2,3-d]pyrimidine-5-carboxylate;
ethyl 4-(1H-pyrazol-5-yl)-7H-pyrrolo[2,3-d]pyrimidine-5-carboxylate;
ethyl 4-(1,3-benzothiazol-5-yl)-7H-pyrrolo[2,3-d]pyrimidine-5-carboxylate;
ethyl 4-(1H-indol-6-yl)-7H-pyrrolo[2,3-d]pyrimidine-5-carboxylate;
ethyl 4-(1H-pyrrolo[2,3-b]pyridin-5-yl)-7H-pyrrolo[2,3-d]pyrimidine-5-carboxylate;
ethyl 4-[4-(4-methylpiperazin-1-yl)phenyl]-7H-pyrrolo[2,3-d]pyrimidine-5-carboxylate;
ethyl 4-(4-hydroxycyclohex-1-en-1-yl)-7H-pyrrolo[2,3-d]pyrimidine-5-carboxylate;
ethyl 4-[6-(4-methylpiperazin-1-yl)pyridin-3-yl]-7H-pyrrolo[2,3-d]pyrimidine-5-carboxylate;
ethyl 4-(5,6-dihydro-2H-pyran-3-yl)-7H-pyrrolo[2,3-d]pyrimidine-5-carboxylate;
ethyl 4-(2-methoxypyridin-4-yl)-7H-pyrrolo[2,3-d]pyrimidine-5-carboxylate;
ethyl 4-(4-cyanocyclohex-1-en-1-yl)-7H-pyrrolo[2,3-d]pyrimidine-5-carboxylate;
ethyl 4-(2-methoxypyrimidin-5-yl)-7H-pyrrolo[2,3-d]pyrimidine-5-carboxylate;
ethyl 4-{1-[2-(methylsulfonyl)ethyl]-1H-pyrazol-4-yl}-7H-pyrrolo[2,3-d]pyrimidine-5-carboxylate;
ethyl 4-(6-methoxypyridin-3-yl)-7H-pyrrolo[2,3-d]pyrimidine-5-carboxylate;
ethyl 4-[4-(1H-pyrazol-1-yl)phenyl]-7H-pyrrolo[2,3-d]pyrimidine-5-carboxylate;
ethyl 4-[3-(1,1-dioxidothiomorpholin-4-yl)phenyl]-7H-pyrrolo[2,3-d]pyrimidine-5-carboxylate;
ethyl 4-[3-(morpholin-4-ylmethyl)phenyl]-7H-pyrrolo[2,3-d]pyrimidine-5-carboxylate;
ethyl 4-[4-(1,1-dioxidothiomorpholin-4-yl)phenyl]-7H-pyrrolo[2,3-d]pyrimidine-5-carboxylate;
ethyl 4-(3,6-dihydro-2H-pyran-4-yl)-7H-pyrrolo[2,3-d]pyrimidine-5-carboxylate;
ethyl 4-[1-(2-methoxyethyl)-1H-pyrazol-4-yl]-7H-pyrrolo[2,3-d]pyrimidine-5-carboxylate;
ethyl 4-[4-(tetrahydrofuran-3-ylcarbamoyl)phenyl]-7H-pyrrolo[2,3-d]pyrimidine-5-carboxylate;
ethyl 4-(3-oxo-2,3-dihydro-1H-isoindol-5-yl)-7H-pyrrolo[2,3-d]pyrimidine-5-carboxylate;
ethyl 4-{3-[methyl(methylsulfonyl)amino]phenyl}-7H-pyrrolo[2,3-d]pyrimidine-5-carboxylate;
ethyl 4-[3-(1H-pyrazol-1-yl)phenyl]-7H-pyrrolo[2,3-d]pyrimidine-5-carboxylate;
ethyl 4-[6-(cyanomethyl)pyridin-3-yl]-7H-pyrrolo[2,3-d]pyrimidine-5-carboxylate;
ethyl 4-[3-(1-hydroxy-1-methylethyl)phenyl]-7H-pyrrolo[2,3-d]pyrimidine-5-carboxylate;
ethyl 4-[5-(hydroxymethyl)pyridin-3-yl]-7H-pyrrolo[2,3-d]pyrimidine-5-carboxylate;
ethyl 4-[4-(1-hydroxy-1-methylethyl)phenyl]-7H-pyrrolo[2,3-d]pyrimidine-5-carboxylate;
ethyl 4-(3-amino-5-fluorophenyl)-7H-pyrrolo[2,3-d]pyrimidine-5-carboxylate;
ethyl 4-(5-amino-2-fluorophenyl)-7H-pyrrolo[2,3-d]pyrimidine-5-carboxylate;
ethyl 4-(3-amino-4-fluorophenyl)-7H-pyrrolo[2,3-d]pyrimidine-5-carboxylate;
propyl 4-(2-methyl-2H-indazol-6-yl)-7H-pyrrolo[2,3-d]pyrimidine-5-carboxylate;
prop-2-en-1-yl 4-(2-methyl-2H-indazol-6-yl)-7H-pyrrolo[2,3-d]pyrimidine-5-carboxylate;
ethyl 4-{3-[(2,2,2-trifluoroethyl)amino]phenyl}-7H-pyrrolo[2,3-d]pyrimidine-5-carboxylate;
ethyl 4-{4-methyl-3-[(2,2,2-trifluoroethyl)amino]phenyl}-7H-pyrrolo[2,3-d]pyrimidine-5-carboxylate;
ethyl 4-{3-[(2-methylacryloyl)amino]phenyl}-7H-pyrrolo[2,3-d]pyrimidine-5-carboxylate;
ethyl 4-{2-fluoro-3-[(2-methylacryloyl)amino]phenyl}-7H-pyrrolo[2,3-d]pyrimidine-5-carboxylate;
ethyl 4-{5-[(2-methylacryloyl)amino]pyridin-3-yl}-7H-pyrrolo[2,3-d]pyrimidine-5-carboxylate;
ethyl 4-{2-methoxy-6-[(2-methylacryloyl)amino]pyridin-4-yl}-7H-pyrrolo[2,3-d]pyrimidine-5-carboxylate;
ethyl 4-[3-(acryloylamino)phenyl]-7H-pyrrolo[2,3-d]pyrimidine-5-carboxylate;
ethyl 4-{3-[(2E)-but-2-enoylamino]phenyl}-7H-pyrrolo[2,3-d]pyrimidine-5-carboxylate;
ethyl 4-[3-(propanoylamino)phenyl]-7H-pyrrolo[2,3-d]pyrimidine-5-carboxylate;
ethyl 4-{3-[(2-methylidenebutanoyl)amino]phenyl}-7H-pyrrolo[2,3-d]pyrimidine-5-carboxylate;
ethyl 4-{4-chloro-3-[(2-methylacryloyl)amino]phenyl}-7H-pyrrolo[2,3-d]pyrimidine-5-carboxylate;
ethyl 4-{4-methyl-3-[(2-methylacryloyl)amino]phenyl}-7H-pyrrolo[2,3-d]pyrimidine-5-carboxylate;
ethyl 4-[3-(acryloylamino)-4-methylphenyl]-7H-pyrrolo[2,3-d]pyrimidine-5-carboxylate;
ethyl 4-[3-(acryloylamino)-2-methylphenyl]-7H-pyrrolo[2,3-d]pyrimidine-5-carboxylate;
ethyl 4-{2-methyl-3-[(2-methylacryloyl)amino]phenyl}-7H-pyrrolo[2,3-d]pyrimidine-5-carboxylate;
ethyl 4-[3-(acryloylamino)-4-chlorophenyl]-7H-pyrrolo[2,3-d]pyrimidine-5-carboxylate;
ethyl 4-[3-(acryloylamino)-4-methoxyphenyl]-7H-pyrrolo[2,3-d]pyrimidine-5-carboxylate;
ethyl 4-{4-fluoro-3-[(2-methylacryloyl)amino]phenyl}-7H-pyrrolo[2,3-d]pyrimidine-5-carboxylate;
ethyl 4-{4-methoxy-3-[(2-methylacryloyl)amino]phenyl}-7H-pyrrolo[2,3-d]pyrimidine-5-carboxylate;
ethyl 4-{2-fluoro-5-[(2-methylacryloyl)amino]phenyl}-7H-pyrrolo[2,3-d]pyrimidine-5-carboxylate;
ethyl 4-{3-fluoro-5-[(2-methylacryloyl)amino]phenyl}-7H-pyrrolo[2,3-d]pyrimidine-5-carboxylate;
ethyl 4-(1-acryloyl-2,3-dihydro-1H-indol-6-yl)-7H-pyrrolo[2,3-d]pyrimidine-5-carboxylate;
ethyl 4-[1-(2-methylacryloyl)-2,3-dihydro-1H-indol-6-yl]-7H-pyrrolo[2,3-d]pyrimidine-5-carboxylate;

ethyl 4-{2-cyano-5-[(2-methylacryloyl)amino]phenyl}-7H-pyrrolo[2,3-d]pyrimidine-5-carboxylate;
ethyl 4-[1-(2-methylacryloyl)-1H-indol-6-yl]-7H-pyrrolo[2,3-d]pyrimidine-5-carboxylate;
ethyl 4-{3-cyano-5-[(2-methylacryloyl)amino]phenyl}-7H-pyrrolo[2,3-d]pyrimidine-5-carboxylate;
ethyl 4-{4-(hydroxymethyl)-3-[(2-methylacryloyl)amino]phenyl}-7H-pyrrolo[2,3-d]pyrimidine-5-carboxylate;
ethyl 4-{3-methyl-5-[(2-methylacryloyl)amino]phenyl}-7H-pyrrolo[2,3-d]pyrimidine-5-carboxylate;
ethyl 4-{4-cyano-3-[(2-methylacryloyl)amino]phenyl}-7H-pyrrolo[2,3-d]pyrimidine-5-carboxylate;
ethyl 4-{4-(dimethylcarbamoyl)-3-[(2-methylacryloyl)amino]phenyl}-7H-pyrrolo[2,3-d]pyrimidine-5-carboxylate;
ethyl 4-{3-[(2-methylacryloyl)amino]-4-(methylsulfonyl)phenyl}-7H-pyrrolo[2,3-d]pyrimidine-5-carboxylate;
ethyl 4-{4-[(dimethylamino)methyl]-3-[(2-methylacryloyl)amino]phenyl}-7H-pyrrolo[2,3-d]pyrimidine-5-carboxylate;
ethyl 4-{4-hydroxy-3-[(2-methylacryloyl)amino]phenyl}-7H-pyrrolo[2,3-d]pyrimidine-5-carboxylate;
ethyl 4-{6-methoxy-5-[(2-methylacryloyl)amino]pyridin-3-yl}-7H-pyrrolo[2,3-d]pyrimidine-5-carboxylate;
ethyl 4-{5-[(2-methylacryloyl)amino]-6-oxo-1,6-dihydropyridin-3-yl}-7H-pyrrolo[2,3-d]pyrimidine-5-carboxylate;
ethyl 4-{1-methyl-5-[(2-methylacryloyl)amino]-6-oxo-1,6-dihydropyridin-3-yl}-7H-pyrrolo[2,3-d]pyrimidine-5-carboxylate;
ethyl 4-{2-[(2-methylacryloyl)amino]pyridin-4-yl}-7H-pyrrolo[2,3-d]pyrimidine-5-carboxylate;
ethyl 4-{3-[(2-fluoroacryloyl)amino]phenyl}-7H-pyrrolo[2,3-d]pyrimidine-5-carboxylate;
ethyl 4-{2-fluoro-5-[(2-methylacryloyl)amino]phenyl}-7H-pyrrolo[2,3-d]pyrimidine-5-carboxylate;
ethyl 4-[3-(but-2-ynoylamino)phenyl]-7H-pyrrolo[2,3-d]pyrimidine-5-carboxylate;
ethyl 4-{3-[(cyanoacetyl)amino]phenyl}-7H-pyrrolo[2,3-d]pyrimidine-5-carboxylate;
ethyl 4-{3-[(2-bromoacryloyl)amino]phenyl}-7H-pyrrolo[2,3-d]pyrimidine-5-carboxylate;
ethyl 4-{3-[(2-chloroacryloyl)amino]phenyl}-7H-pyrrolo[2,3-d]pyrimidine-5-carboxylate;
ethyl 4-{3-[(4-oxopentanoyl)amino]phenyl}-7H-pyrrolo[2,3-d]pyrimidine-5-carboxylate;
ethyl 4-(3-{[(2E)-4-methoxybut-2-enoyl]amino}phenyl)-7H-pyrrolo[2,3-d]pyrimidine-5-carboxylate;
ethyl 4-{3-[(2Z)-but-2-enoylamino]phenyl}-7H-pyrrolo[2,3-d]pyrimidine-5-carboxylate;
ethyl 4-{4-fluoro-3-[(2-fluoroacryloyl)amino]phenyl}-7H-pyrrolo[2,3-d]pyrimidine-5-carboxylate;
ethyl 4-{3-[(2-fluoroacryloyl)amino]-4-methylphenyl}-7H-pyrrolo[2,3-d]pyrimidine-5-carboxylate;
ethyl 4-{3-fluoro-5-[(2-methylacryloyl)amino]phenyl}-7H-pyrrolo[2,3-d]pyrimidine-5-carboxylate;
ethyl 4-{3-[(5,6-dihydro-1,4-dioxin-2-ylcarbonyl)amino]phenyl}-7H-pyrrolo[2,3-d]pyrimidine-5-carboxylate;
ethyl 4-(3-{[(2E)-4-oxopent-2-enoyl]amino}phenyl)-7H-pyrrolo[2,3-d]pyrimidine-5-carboxylate;
ethyl 4-(3-{[(2E)-3-(1,3,5-trimethyl-1H-pyrazol-4-yl)prop-2-enoyl]amino}phenyl)-7H-pyrrolo[2,3-d]pyrimidine-5-carboxylate;
ethyl 4-(3-{[(2E)-3-pyridin-2-ylprop-2-enoyl]amino}phenyl)-7H-pyrrolo[2,3-d]pyrimidine-5-carboxylate;
ethyl 4-(3-{[(2E)-3-pyridin-4-ylprop-2-enoyl]amino}phenyl)-7H-pyrrolo[2,3-d]pyrimidine-5-carboxylate;
ethyl 4-(3-{[(2,4-dioxo-1,2,3,4-tetrahydropyrimidin-5-yl)carbonyl]amino}phenyl)-7H-pyrrolo[2,3-d]pyrimidine-5-carboxylate;
ethyl 4-(3-{[(2E)-3-(1H-indol-3-yl)prop-2-enoyl]amino}phenyl)-7H-pyrrolo[2,3-d]pyrimidine-5-carboxylate;
ethyl 4-(3-{[(2-oxo-2,3-dihydro-1H-imidazol-4-yl)carbonyl]amino}phenyl)-7H-pyrrolo[2,3-d]pyrimidine-5-carboxylate;
ethyl 4-(3-{[(2E)-3-thiophen-2-ylprop-2-enoyl]amino}phenyl)-7H-pyrrolo[2,3-d]pyrimidine-5-carboxylate;
ethyl 4-(3-{[(2E)-3-furan-3-ylprop-2-enoyl]amino}phenyl)-7H-pyrrolo[2,3-d]pyrimidine-5-carboxylate;
ethyl 4-(3-{[(2Z)-3-(2-methoxyphenyl)prop-2-enoyl]amino}phenyl)-7H-pyrrolo[2,3-d]pyrimidine-5-carboxylate;
ethyl 4-(3-{[(2E)-3-(3-methoxyphenyl)prop-2-enoyl]amino}phenyl)-7H-pyrrolo[2,3-d]pyrimidine-5-carboxylate;
ethyl 4-(3-{[(2E)-2-methylpent-2-enoyl]amino}phenyl)-7H-pyrrolo[2,3-d]pyrimidine-5-carboxylate;
ethyl 4-(3-{[(2Z)-2-fluoro-3-phenylprop-2-enoyl]amino}phenyl)-7H-pyrrolo[2,3-d]pyrimidine-5-carboxylate;
ethyl 4-{3-[(3-methylbut-2-enoyl)amino]phenyl}-7H-pyrrolo[2,3-d]pyrimidine-5-carboxylate;
ethyl 4-(3-{[(2E)-2-methyl-3-phenylprop-2-enoyl]amino}phenyl)-7H-pyrrolo[2,3-d]pyrimidine-5-carboxylate;
ethyl 4-(3-{[(2E)-3-(4-methoxyphenyl)prop-2-enoyl]amino}phenyl)-7H-pyrrolo[2,3-d]pyrimidine-5-carboxylate;
ethyl 4-(3-{[(2E)-3-pyridin-3-ylprop-2-enoyl]amino}phenyl)-7H-pyrrolo[2,3-d]pyrimidine-5-carboxylate;
ethyl 4-(3-{[(2E)-2-methylbut-2-enoyl]amino}phenyl)-7H-pyrrolo[2,3-d]pyrimidine-5-carboxylate;
ethyl 4-(3-{[(2E)-3-furan-2-ylprop-2-enoyl]amino}phenyl)-7H-pyrrolo[2,3-d]pyrimidine-5-carboxylate;
ethyl 4-{3-[(2E)-pent-2-enoylamino]phenyl}-7H-pyrrolo[2,3-d]pyrimidine-5-carboxylate;
ethyl 4-(3-{[(2Z)-4,4,4-trifluoro-3-methylbut-2-enoyl]amino}phenyl)-7H-pyrrolo[2,3-d]pyrimidine-5-carboxylate;
ethyl 4-{3-[(cyclohex-1-en-1-ylcarbonyl)amino]phenyl}-7H-pyrrolo[2,3-d]pyrimidine-5-carboxylate;
ethyl 4-(3-{[(3-oxocyclopent-1-en-1-yl)carbonyl]amino}phenyl)-7H-pyrrolo[2,3-d]pyrimidine-5-carboxylate;
ethyl 4-{3-[(cyclopentylideneacetyl)amino]phenyl}-7H-pyrrolo[2,3-d]pyrimidine-5-carboxylate;
ethyl 4-(3-{[(2E)-2-methoxybut-2-enoyl]amino}phenyl)-7H-pyrrolo[2,3-d]pyrimidine-5-carboxylate;
ethyl 4-(3-{[(2E)-3-(1,3-thiazol-2-yl)prop-2-enoyl]amino}phenyl)-7H-pyrrolo[2,3-d]pyrimidine-5-carboxylate;
ethyl 4-{3-[(4,5-dihydrofuran-3-ylcarbonyl)amino]phenyl}-7H-pyrrolo[2,3-d]pyrimidine-5-carboxylate;
ethyl 4-(3-{[2-(morpholin-4-ylmethyl)acryloyl]amino}phenyl)-7H-pyrrolo[2,3-d]pyrimidine-5-carboxylate;

ethyl 4-(3-{[(2E)-4,4,4-trifluorobut-2-enoyl]amino}phenyl)-7H-pyrrolo[2,3-d]pyrimidine-5-carboxylate;
ethyl 4-(3-{[(2E)-2-methyl-3-phenylprop-2-enoyl]amino}phenyl)-7H-pyrrolo[2,3-d]pyrimidine-5-carboxylate;
ethyl 4-[3-({(2E)-3-[4-(trifluoromethyl)phenyl]prop-2-enoyl}amino)phenyl]-7H-pyrrolo[2,3-d]pyrimidine-5-carboxylate;
ethyl 4-(3-{[2-(methoxymethyl)acryloyl]amino}phenyl)-7H-pyrrolo[2,3-d]pyrimidine-5-carboxylate;
ethyl 4-{3-[(3-chloro-1,2,4-thiadiazol-5-yl)amino]phenyl}-7H-pyrrolo[2,3-d]pyrimidine-5-carboxylate;
ethyl 4-{3-[(3-cyanopyrazin-2-yl)amino]phenyl}-7H-pyrrolo[2,3-d]pyrimidine-5-carboxylate;
ethyl 4-{3-[(4-cyano-1,3,5-triazin-2-yl)amino]phenyl}-7H-pyrrolo[2,3-d]pyrimidine-5-carboxylate;
ethyl 4-{3-[(3-cyano-1,2,4-thiadiazol-5-yl)amino]phenyl}-7H-pyrrolo[2,3-d]pyrimidine-5-carboxylate;
ethyl 4-(3-(2-cyanopyrimidin-4-yl)phenyl)-7H-pyrrolo[2,3-d]pyrimidine-5-carboxylate;
ethyl 4-(3-(3-chloro-1,2,4-thiadiazol-5-yl)phenyl)-7H-pyrrolo[2,3-d]pyrimidine-5-carboxylate;
ethyl 4-(3-(3-bromo-1,2,4-thiadiazol-5-yl)phenyl)-7H-pyrrolo[2,3-d]pyrimidine-5-carboxylate;
ethyl 4-(3-(cyano-1,2,4-thiadiazol-5-yl)phenyl)-7H-pyrrolo[2,3-d]pyrimidine-5-carboxylate;
ethyl 4-(3-(cyanomethylcarbamoyl)phenyl)-7H-pyrrolo[2,3-d]pyrimidine-5-carboxylate;
ethyl 4-(3-(3-(cyanomethyl)ureido)phenyl)-7H-pyrrolo[2,3-d]pyrimidine-5-carboxylate;
ethyl 4-(3-(3-cyanoureido)phenyl)-7H-pyrrolo[2,3-d]pyrimidine-5-carboxylate;
ethyl 4-{3-[(ethenylsulfonyl)amino]phenyl}-7H-pyrrolo[2,3-d]pyrimidine-5-carboxylate;
ethyl 4-(3-{[(1E)-prop-1-en-1-ylsulfonyl]amino}phenyl)-7H-pyrrolo[2,3-d]pyrimidine-5-carboxylate;
ethyl 4-(3-{[(1-methylethenyl)sulfonyl]amino}phenyl)-7H-pyrrolo[2,3-d]pyrimidine-5-carboxylate;
methyl 4-{4-fluoro-3-[(2-methylacryloyl)amino]phenyl}-7H-pyrrolo[2,3-d]pyrimidine-5-carboxylate;
methyl 4-{3-[(2-methylacryloyl)amino]phenyl}-7H-pyrrolo[2,3-d]pyrimidine-5-carboxylate;
ethyl 4-(3-(N-methylacrylamido)phenyl)-7H-pyrrolo[2,3-d]pyrimidine-5-carboxylate;
ethyl 4-(3-(2-(methylsulfonamidomethyl)acrylamido)phenyl)-7H-pyrrolo[2,3-d]pyrimidine-5-carboxylate;
ethyl 4-(3-(2-(aminomethyl)acrylamido)phenyl)-7H-pyrrolo[2,3-d]pyrimidine-5-carboxylate;
ethyl 4-(3-(2-(acetamidomethyl)acrylamido)phenyl)-7H-pyrrolo[2,3-d]pyrimidine-5-carboxylate;
ethyl 4-[3-({2-[(dimethylamino)methyl]acryloyl}amino)phenyl]-7H-pyrrolo[2,3-d]pyrimidine-5-carboxylate;
ethyl 4-(3-{[2-(fluoromethyl)acryloyl]amino}phenyl)-7H-pyrrolo[2,3-d]pyrimidine-5-carboxylate;
ethyl 4-(3-{[2-(hydroxymethyl)acryloyl]amino}phenyl)-7H-pyrrolo[2,3-d]pyrimidine-5-carboxylate;
ethyl 4-(3-{[(2E)-4-(dimethylamino)but-2-enoyl]amino}phenyl)-7H-pyrrolo[2,3-d]pyrimidine-5-carboxylate;
ethyl 4-(3-{[(2E)-4-(dimethylamino)-2-methylbut-2-enoyl]amino}phenyl)-7H-pyrrolo[2,3-d]pyrimidine-5-carboxylate;
ethyl 4-(3-(2-methyloxirane-2-carboxamido)phenyl)-7H-pyrrolo[2,3-d]pyrimidine-5-carboxylate;
ethyl 4-(3-(2,3-dihydroxy-2-methylpropanamido)phenyl)-7H-pyrrolo[2,3-d]pyrimidine-5-carboxylate;
N-(3-{5-[4-(aminomethyl)phenyl]-7H-pyrrolo[2,3-d]pyrimidin-4-yl}phenyl)-2-methylprop-2-enamide;
2-methyl-N-{3-[5-(3-methylphenyl)-7H-pyrrolo[2,3-d]pyrimidin-4-yl]phenyl}prop-2-enamide;
N-{3-[5-(3-fluorophenyl)-7H-pyrrolo[2,3-d]pyrimidin-4-yl]phenyl}-2-methylprop-2-enamide;
N-{3-[5-(2-fluorophenyl)-7H-pyrrolo[2,3-d]pyrimidin-4-yl]phenyl}-2-methylprop-2-enamide;
N-{3-[5-(4-fluorophenyl)-7H-pyrrolo[2,3-d]pyrimidin-4-yl]phenyl}-2-methylprop-2-enamide;
N-{3-[5-(2-chloro-3-fluorophenyl)-7H-pyrrolo[2,3-d]pyrimidin-4-yl]phenyl}-2-methylprop-2-enamide;
2-methyl-N-{3-[5-(2-methylphenyl)-7H-pyrrolo[2,3-d]pyrimidin-4-yl]phenyl}prop-2-enamide;
2-methyl-N-{3-[5-(4-methylphenyl)-7H-pyrrolo[2,3-d]pyrimidin-4-yl]phenyl}prop-2-enamide;
2-methyl-N-{3-[5-(2,4,6-trimethylphenyl)-7H-pyrrolo[2,3-d]pyrimidin-4-yl]phenyl}prop-2-enamide;
N-[3-(5-phenyl-7H-pyrrolo[2,3-d]pyrimidin-4-yl)phenyl]prop-2-enamide;
N-(3-(5-(pyridin-2-yl)-7H-pyrrolo[2,3-d]pyrimidin-4-yl)phenyl)methacrylamide;
N-(3-(5-(1H-imidazol-5-yl)-7H-pyrrolo[2,3-d]pyrimidin-4-yl)phenyl)methacrylamide;
N-(3-(5-(pyridin-4-yl)-7H-pyrrolo[2,3-d]pyrimidin-4-yl)phenyl)methacrylamide;
N-(3-(5-(pyridin-3-yl)-7H-pyrrolo[2,3-d]pyrimidin-4-yl)phenyl)methacrylamide;
N-(3-(5-(3,6-dihydro-2H-pyran-4-yl)-7H-pyrrolo[2,3-d]pyrimidin-4-yl)phenyl)methacrylamide;
N-(3-(5-(2-methylthiazol-5-yl)-7H-pyrrolo[2,3-d]pyrimidin-4-yl)phenyl)methacrylamide;
N-(3-(5-(thiazol-5-yl)-7H-pyrrolo[2,3-d]pyrimidin-4-yl)phenyl)methacrylamide;
N-(3-(5-(oxazol-2-yl)-7H-pyrrolo[2,3-d]pyrimidin-4-yl)phenyl)methacrylamide;
N-(3-(5-(tetrahydro-2H-pyran-4-yl)-7H-pyrrolo[2,3-d]pyrimidin-4-yl)phenyl)methacrylamide;
N-methyl-N-(3-(5-(tetrahydro-2H-pyran-4-yl)-7H-pyrrolo[2,3-d]pyrimidin-4-yl)phenyl)methacrylamide;
N-(3-(5-(tetrahydrofuran-2-yl)-7H-pyrrolo[2,3-d]pyrimidin-4-yl)phenyl)methacrylamide;
N-(3-(5-(5-methyl-1,3,4-oxadiazol-2-yl)-7H-pyrrolo[2,3-d]pyrimidin-4-y1)phenyl)methacrylamide;
N-(3-(5-(5-methyl-1,3,4-thiadiazol-2-yl)-7H-pyrrolo[2,3-d]pyrimidin-4-y1)phenyl)methacrylamide;
N-(3-(5-(5-methyl-4,5-dihydrooxazol-2-yl)-7H-pyrrolo[2,3-d]pyrimidin-4-yl)phenyl)methacrylamide;
N-(3-(5-(4-methyloxazol-2-yl)-7H-pyrrolo[2,3-d]pyrimidin-4-yl)phenyl)methacrylamide;
N-(3-(5-(oxazol-5-yl)-7H-pyrrolo[2,3-d]pyrimidin-4-yl)phenyl)methacrylamide;
N-(3-(5-(thiazol-2-yl)-7H-pyrrolo[2,3-d]pyrimidin-4-yl)phenyl)methacrylamide ;
5-(2-methoxypyridin-3-yl)-4-phenyl-7H-pyrrolo[2,3-c]pyrimidine;
4,5-diphenyl-7H-pyrrolo[2,3-d]pyrimidine;
methyl[4-methoxy-3-(4-phenyl-7H-pyrrolo[2,3-d]pyrimidin-5-yl)phenyl]acetate;
5-(3-methoxyphenyl)-4-phenyl-7H-pyrrolo[2,3-d]pyrimidine;
5-(3-phenoxyphenyl)-4-phenyl-7H-pyrrolo[2,3-d]pyrimidine;
5-[3-(benzyloxy)phenyl]-4-phenyl-7H-pyrrolo[2,3-c]pyrimidine;
5-(2-phenoxyphenyl)-4-phenyl-7H-pyrrolo[2,3-d]pyrimidine;

5-(2-methoxyphenyl)-4-phenyl-7H-pyrrolo[2,3-d]pyrimidine;

5-(2-methoxyphenyl)-4-(2-methyl-2H-indazol-6-yl)-7H-pyrrolo[2,3-d]pyrimidine;

5-(5-fluoro-2-methoxyphenyl)-4-phenyl-7H-pyrrolo[2,3-d]pyrimidine;

5-(2-methoxyphenyl)-4-(3-methoxyphenyl)-7H-pyrrolo[2,3-d]pyrimidine;

3-[5-(2-methoxyphenyl)-7H-pyrrolo[2,3-d]pyrimidin-4-yl]-N,N-dimethylbenzamide; and 5-(2-methoxyphenyl)-4-(1H-pyrazol-4-yl)-7H-pyrrolo[2,3-d]pyrimidine, or a pharmaceutically acceptable salt or a stereoisomer thereof.

2. A pharmaceutical composition comprising a compound of claim 1 or a pharmaceutically acceptable salt thereof and a pharmaceutically acceptable carrier.

3. A method of treating rheumatoid arthritis in a mammal in need thereof, comprising administering a therapeutically effective amount of a compound according to claim 1 or a pharmaceutically acceptable salt thereof.

\* \* \* \* \*